(12) United States Patent
Rosenthal et al.

(10) Patent No.: US 8,540,990 B2
(45) Date of Patent: Sep. 24, 2013

(54) METHODS FOR TREATING OSTEOARTHRITIS PAIN BY ADMINISTERING A NERVE GROWTH FACTOR ANTAGONIST AND COMPOSITIONS CONTAINING THE SAME

(75) Inventors: Arnon Rosenthal, Woodside, CA (US); David Louis Shelton, Alameda, CA (US); Patricia Ann Walicke, Brisbane, CA (US)

(73) Assignee: Rinat Neuroscience Corp., South San Francisco, CA (US)

( * ) Notice: Subject to any disclaimer, the term of this patent is extended or adjusted under 35 U.S.C. 154(b) by 479 days.

(21) Appl. No.: 11/911,305

(22) PCT Filed: Apr. 11, 2006

(86) PCT No.: PCT/US2006/013921
§ 371 (c)(1),
(2), (4) Date: Jul. 15, 2009

(87) PCT Pub. No.: WO2006/110883
PCT Pub. Date: Oct. 19, 2006

(65) Prior Publication Data
US 2011/0033447 A1 Feb. 10, 2011

Related U.S. Application Data

(63) Continuation of application No. 11/104,248, filed on Apr. 11, 2005, now Pat. No. 7,569,364.

(51) Int. Cl.
*A61K 39/395* (2006.01)
*A61P 25/00* (2006.01)

(52) U.S. Cl.
USPC .................. 424/133.1; 424/145.1; 424/158.1

(58) Field of Classification Search
USPC .................. 424/133.1, 145.1, 158.1
See application file for complete search history.

(56) References Cited

U.S. PATENT DOCUMENTS

| 4,389,404 | A | 6/1983 | Zhorov et al. |
| 5,843,942 | A | 12/1998 | Breault et al. |
| 6,022,875 | A | 2/2000 | Zimmer et al. |
| 6,887,861 | B1 | 5/2005 | Hill et al. |
| 7,252,822 | B2 | 8/2007 | Shelton et al. |
| 7,255,860 | B2 | 8/2007 | Shelton et al. |
| 2002/0028779 | A1 | 3/2002 | High et al. |
| 2003/0120044 | A1 | 6/2003 | Huse et al. |
| 2004/0071701 | A1 | 4/2004 | Delafoy et al. |
| 2004/0131615 | A1 | 7/2004 | Shelton et al. |
| 2004/0219144 | A1 | 11/2004 | Shelton |
| 2004/0237124 | A1 | 11/2004 | Pons et al. |
| 2004/0253244 | A1 | 12/2004 | Shelton et al. |
| 2005/0265994 | A1 | 12/2005 | Shelton et al. |
| 2006/0147450 | A1 | 7/2006 | Shelton |

FOREIGN PATENT DOCUMENTS

| WO | WO93/06213 | 4/1993 |
| WO | WO2005/019266 | 3/2005 |
| WO | WO2006/077441 | 7/2006 |

OTHER PUBLICATIONS

Kasai et al. (Neuroscience Letters 272:41-44 (1999).*
Iannone et al, Rhemuatology, 41:1413-1418 (2002).
McMahon, Nature Med., 1:774 (1995).
Ro, Pain, 79:265 (1999).
Brennan, Ilar, 40:129 (1999).
Shelton et al, Pain:, vol. 116, No. 1-2, pp. 8-16 (Jul. 2005).
Hongo et al, Hybridoma, 19(3):215-227 (2000).
Ruberti et al, Cell. Molec. Nuerobiol., 13(5):559-568 (1993).
Debeir et al, Proc. Natl. Acad. Sci. USA, vol. 96, pp. 4067-4072 (1999).
Cattaneo et al, J. of Neurosci., 19(2):9687-9697 (1999(.
Molnar et al, Euro. J. of Neurosci., vol. 10, pp. 3127-3140 (1998).
Shelton et al, Restorative Neuro. and Neurosci., 8:99-100 (1995).
Aloe et al, Growth Factors, vol. 9, pp. 149-155 (1993).
Jongen et al, Neurotrophic Factors and Cancer Pain, Program 52, 2, Abstract, Soc. for Neurosci. (2002).
Bennett et al, Euro. J. of Neurosci., vol. 10, 1282-1291 (1998).
Lane et al, Arthritis & Rheumatism, vol. 52, No. 9, Suppl. S, p. S461 (2005).
Halliday et al, Neurochemical Res., vol. 23, No. 6, p. 921 (1998).
B. Vastag, Nature Biotechnology, vol. 24, No. 6, pp. 595-596 (2006).

* cited by examiner

*Primary Examiner* — Lynn Bristol
(74) *Attorney, Agent, or Firm* — Pfizer Inc.

(57) ABSTRACT

The invention concerns anti-NGF antibodies (such as anti-NGF antagonist antibodies), and polynucleotides encoding the same. The invention further concerns use of such antibodies and/or polynucleotides in the treatment and/or prevention of pain, including post-surgical pain, rheumatoid arthritis pain, and osteoarthritis pain.

38 Claims, 32 Drawing Sheets

FIGURE 1A

CDRs: bold italics = Kabat; underlined = Chothia

1A) HEAVY CHAIN VARIABLE REGION
1 = mouse 911 antibody (CDRs)
2 = VH4-59 human acceptor germline
3 = CDR grafted
4 = 3 + one framework mutation
5 = 4 + affinity maturation H1, H2
6 = 5 + affinity maturation H3 (heavy chain variable region of antibody 3E)

```
        1      5      10     15     20     25     30     35     40     45
1 -                                             GFSLI GYDIN
2 - QVQLQESGPGLVKPSETLSLTCTVSGGSISSYYWSWIRQPPGKGLE
3 - QVQLQESGPGLVKPSETLSLTCTVSGFSLIGYDINWIRQPPGKGLE
4 - QVQLQESGPGLVKPSETLSLTCTVSGFSLIGYDINWIRQPPGKGLE
5 - QVQLQESGPGLVKPSETLSLTCTVSGFSLIGYDLNWIRQPPGKGLE
6 - QVQLQESGPGLVKPSETLSLTCTVSGFSLIGYDLNWIRQPPGKGLE 50     55     60     65     70     75     80     85     90
1 -     MIWGDGTTDYNSALKS
2 - WIGYIYYSGSTNYNPSLKSRVTISVDTSKNQFSLKLSSVTAADTAV
3 - WIGMIWGDGTTDYNSALKSRVTISVDTSKNQFSLKLSSVTAADTAV
4 - WIGMIWGDGTTDYNSALKSRVTISKDTSKNQFSLKLSSVTAADTAV
5 - WIGIIWGDGTTDYNSAVKSRVTISKDTSKNQFSLKLSSVTAADTAV
6 - WIGIIWGDGTTDYNSAVKSRVTISKDTSKNQFSLKLSSVTAADTAV
```

1B) LIGHT CHAIN VARIABLE REGION
1=mouse 911 antibody (CDRs)
2-08 human acceptor germline
3=CDR grafted
4=3 + affinity maturation L1, L2
5=4 + affinity maturation L3 (light chain variable region of antibody 3E)

```
Db.911.3E standard; circular DNA;        ; 1429 BP.
This file is created by Vector NTI
http://www.informaxinc.com/
VNTDATE|285871584|
VNTDBDATE|285873257|
VNTAUTHORNAME|Demo User|
Sequence 1429 BP; 331 A; 440 C; 380 G; 278 t;
atggcaaccg actccagaac ctcctggctg ctgacagtgt ccctgctgtg totgctgtgg       60
ccacaggagg ccagcgtca gtgcagctg caggagtctg gcccaggact ggtgaagcct       120
tccgagaccc tgtccctcac ctgcactgtc tctgttctt cacttatcgg ctatgatctt       180
aactggatcc gacagcctcc agggaagga ctggagtgga ttgggattat ctgggtgat       240
ggaacacacg actataattc agtctgtaaa tccggtgtca ccatctcaaa agacacctca       300
aagaaccagt tctccctgaa gctgagctct gtgaccgccg cggacacggc cgtgtattac       360
tgtgcgagag gaggttattg gtacgcaact agtactact ttgactactg gggccagggc       420
accctggtca ccgtctcctc agcctccacc aagggcccat ctgtcttccc cctggccca       480
tgctccgga gcacctccga gagcacagcc gccctgggct gcctggtcaa ggactacttc       540
ccagaacctg tgaccgtgtc ctggaactct ggcgctgtga ccagcggcgt gcacaccttc       600
ccagctgtcc tgcagtcctc agtctctac tccctcagca gcgtggtgac cgtgccatcc       660
agcaacttcg gcacccagac ctacacctgc aacgtagatc acaagccaag caacaccaag       720
gtggacaaga cgtggagag aaagtgttgt gtggagtgtc cacctgtcc agcccctcca       780
gtgcccgac catccgtgtt cctgttccct ccaaagccaa aggacacect gatgatctcc       840
agaacccag agttgacctg tgtggtgtg gacgtgtccc acgaggaccc agaggtgcag       900
ttcaactggt atgtggacgg agtgagtgg cacaacgca agacaaagcc acgagaggag       960
cagttcaact ccacctteaact agatataagtg agtgctgacg gtgctgacca ggactgctg     1020
aacgaaaggg gacacctcca agccaag acaaggac tgccatccag tgtataccct gcaccatcc    1080
accatctcca agaccaagg ccagtgtcc ccagccaaa ggacacctgt cctgtgaag gccatccac     1140
agagggga tgaccaagaa ccagtggagtg gagtcaaa ggatccttc ttcctgtatt ccaaggcac     1200
tccgacatcg ccgtggagtg gagactccga cggatccttc ttcctgtatt ccaagctgac cgtggacaag     1260
cctccaatgc agcaggaaa agcagggaaa gtgttctct ccaagaagt   taagacc         1320
tccaagagca agaagagcc ccggatccttc ttcctgtatt ccaagctgag ctccaagctg aggtgaaga      1380
cactataccc agaagagcc gctgctgcct ccaggaagt aattctaga                1429
```

FIGURE 3

Eb.911.3E standard; circular DNA;     ; 729 BP.
This file is created by Vector NTI
http://www.informaxinc.com/
VNTDATE|285871514|
VNTDBDATE|285872959|
VNTAUTHORNAME|Demo User|
Sequence 729 BP; 182 A; 231 C; 161 G; 154 t; 1 other;

```
atggcaacg actccagaac ctcctggctg ctgacagtgt ccctgctgtg tctgctgtgg      60
ccaggagg ccagcgtga tatccagatg acacagtccc catcctccct gtctgcctct       120
gtgggtgacc ggtcaccat cacctgcgc gcatctcagt ccattagcaa taatctgaac      180
tggtatcagc agaagccagg caaagcccca aaactcctga totactacac ctcacgcttc    240
cactcaggtg tcccatcacg cttcagtggc agtggctctg gtacagattt cacctcacc    300
attagcagcc tgcaaccaga agatattgcc acttattact gccaacagga gcatacccttt  360
ccatatacct tcggtcaagg caccaagctg gagatcaaac gtaactgtgg tgcaccatct   420
gtcttcatct ttcctccatc tgatgagcag ttgaaatccg gaactgcctc tgttgtgtgc   480
ctgctgaata acttctatcc acgcgaggcc aaagtacagt ggaaggtgga taacgcccta   540
caatccggta actccagga gagtgtcaca gagcaggaca gcaaggacag cacctacagc   600
ctcagcagca cccctgaccct gagcaaagca gactacgaga aacaaaagt ctacgcctgc   660
gaagtcaccc atcagggcct gagttctcca gtcacaaaga gttcaaccg gttgagtgc    720
taattctag                                                            729
```

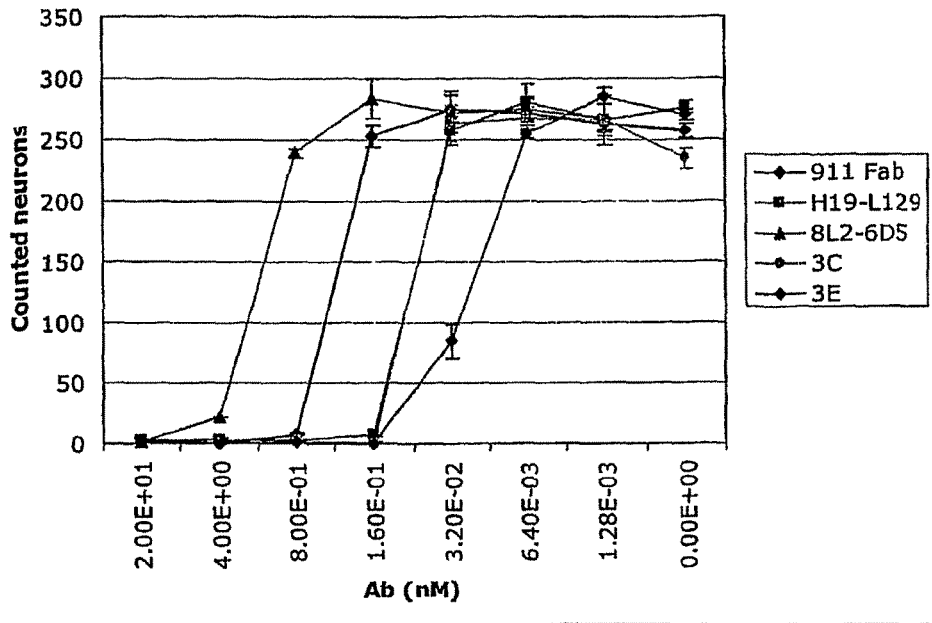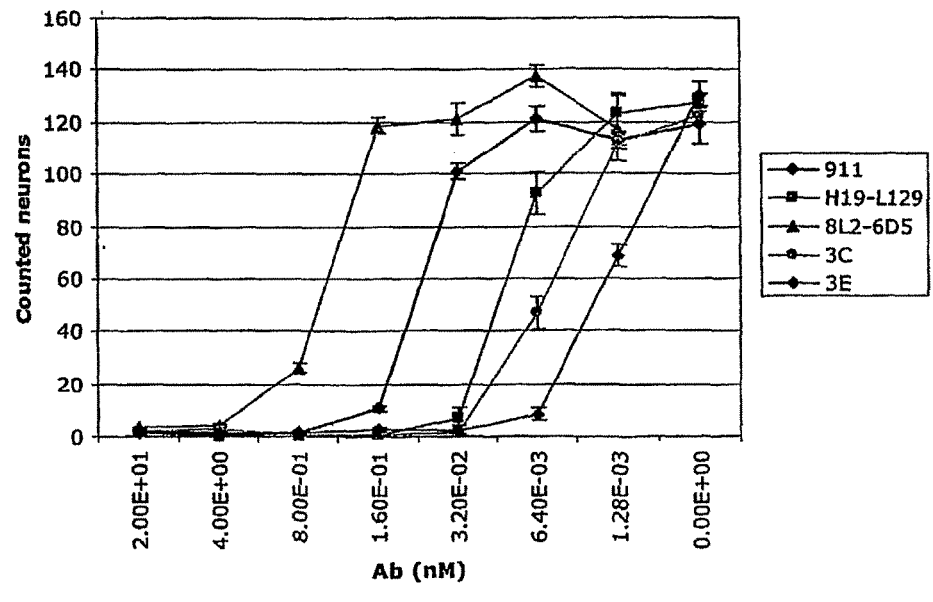
FIGURE 5

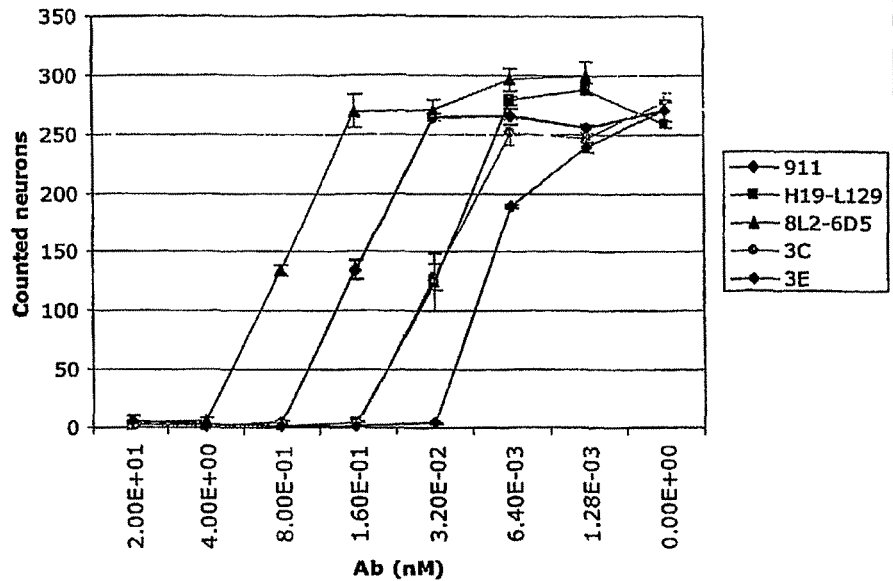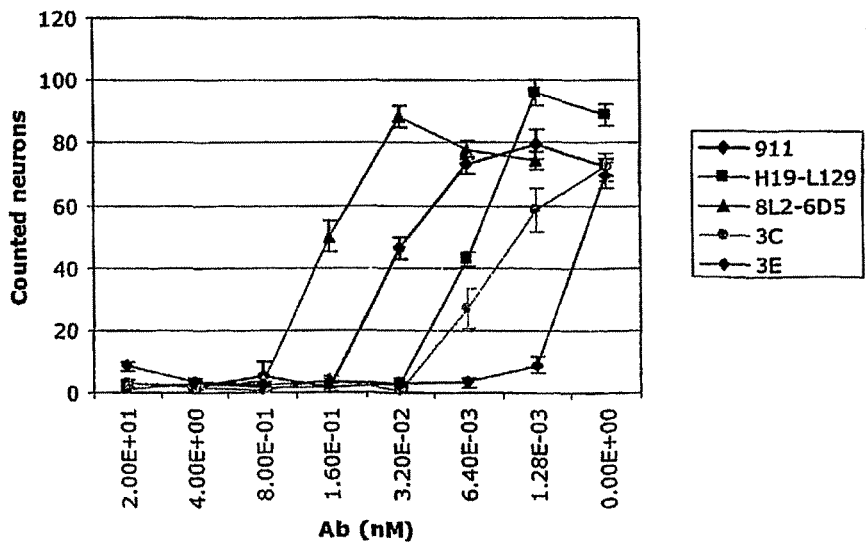
FIGURE 6

FIGURE 23A
3E HEAVY CHAIN VARIABLE DOMAIN NUMBERING
A-     PROTEIN SEQUENTIAL NUMBERING
B-     KABAT NUMBERING
C-     CHOTHIA NUMBERING

BOXES: CDR AS KABAT, UNDERLINED=CDR AS CHOTHIA

| | | | | | | | | | | | | |
|---|---|---|---|---|---|---|---|---|---|---|---|---|
| A-1 | 2 | 3 | 4 | 5 | 6 | 7 | 8 | 9 | 10 | 11 | 12 | 13 |
| B-1 | 2 | 3 | 4 | 5 | 6 | 7 | 8 | 9 | 10 | 11 | 12 | 13 |
| C-1 | 2 | 3 | 4 | 5 | 6 | 7 | 8 | 9 | 10 | 11 | 12 | 13 |
| Q | V | Q | L | Q | E | S | G | P | G | L | V | K |

| | | | | | | | | | | | | |
|---|---|---|---|---|---|---|---|---|---|---|---|---|
| 14 | 15 | 16 | 17 | 18 | 19 | 20 | 21 | 22 | 23 | 24 | 25 | 26 |
| 14 | 15 | 16 | 17 | 18 | 19 | 20 | 21 | 22 | 23 | 24 | 25 | 26 |
| 14 | 15 | 16 | 17 | 18 | 19 | 20 | 21 | 22 | 23 | 24 | 25 | 26 |
| P | S | E | T | L | S | L | T | C | T | V | S | <u>G</u> |

H1

| | | | | | | | | | | | | |
|---|---|---|---|---|---|---|---|---|---|---|---|---|
| 27 | 28 | 29 | 30 | 31 | 32 | 33 | 34 | 35 | 36 | 37 | 38 | 39 |
| 27 | 28 | 29 | 30 | 31 | 32 | 33 | 34 | 35 | 36 | 37 | 38 | 39 |
| 27 | 28 | 29 | 30 | 31 | 32 | 33 | 34 | 35 | 36 | 37 | 38 | 39 |
| <u>F</u> | <u>S</u> | <u>L</u> | <u>I</u> | [G | Y | D | L | N | W] | I | R | Q |

| | | | | | | | | | | | | |
|---|---|---|---|---|---|---|---|---|---|---|---|---|
| 40 | 41 | 42 | 43 | 44 | 45 | 46 | 47 | 48 | 49 | 50 | 51 | 52 |
| 40 | 41 | 42 | 43 | 44 | 45 | 46 | 47 | 48 | 49 | 50 | 51 | 52 |
| 40 | 41 | 42 | 43 | 44 | 45 | 46 | 47 | 48 | 49 | 50 | 51 | 52 |
| P | P | G | K | G | L | E | W | I | G | [I | <u>I</u> | <u>W</u> |

H2

| | | | | | | | | | | | | |
|---|---|---|---|---|---|---|---|---|---|---|---|---|
| 53 | 54 | 55 | 56 | 57 | 58 | 59 | 60 | 61 | 62 | 63 | 64 | 65 |
| 53 | 54 | 55 | 56 | 57 | 58 | 59 | 60 | 61 | 62 | 63 | 64 | 65 |
| 53 | 54 | 55 | 56 | 57 | 58 | 59 | 60 | 61 | 62 | 63 | 64 | 65 |
| <u>G</u> | <u>D</u> | <u>G</u> | <u>T</u> | T | D | Y | N | S | A | V | K | S] |

| | | | | | | | | | | | | |
|---|---|---|---|---|---|---|---|---|---|---|---|---|
| 66 | 67 | 68 | 69 | 70 | 71 | 72 | 73 | 74 | 75 | 76 | 77 | 78 |
| 66 | 67 | 68 | 69 | 70 | 71 | 72 | 73 | 74 | 75 | 76 | 77 | 78 |
| 66 | 67 | 68 | 69 | 70 | 71 | 72 | 73 | 74 | 75 | 76 | 77 | 78 |
| R | V | T | I | S | K | D | T | S | K | N | Q | F |

| | | | | | | | | | | | |
|---|---|---|---|---|---|---|---|---|---|---|---|
| 79 | 80 | 81 | 82 | 83 | 84 | 85 | 86 | 87 | 88 | 89 | 90 | 91 |
| 79 | 80 | 81 | 82 | 82A | 82B | 82C | 83 | 84 | 85 | 86 | 87 | 88 |
| 79 | 80 | 81 | 82 | 82A | 82B | 82C | 83 | 84 | 85 | 86 | 87 | 88 |
| S | L | K | L | S | S | V | T | A | A | D | T | A |

FIGURE 23A (continued)

|  |  |  |  |  |  |  |  |  | H3 |  |  |
|---|---|---|---|---|---|---|---|---|---|---|---|
| 92 | 93 | 94 | 95 | 96 | 97 | 98 | 99 | 100 | 101 | 102 | 103 | 104 |
| 89 | 90 | 91 | 92 | 93 | 94 | 95 | 96 | 97 | 98 | 99 | 100 | 100A |
| 89 | 90 | 91 | 92 | 93 | 94 | 95 | 96 | 97 | 98 | 99 | 100 | 100A |
| V | Y | Y | C | A | R | G | G | Y | W | Y | A | T |

| 105 | 106 | 107 | 108 | 109 | 109 | 110 | 111 | 112 | 113 | 114 | 115 | 116 |
|---|---|---|---|---|---|---|---|---|---|---|---|---|
| 100B | 100C | 100D | 100E | 101 | 102 | 103 | 104 | 105 | 106 | 107 | 108 | 109 |
| 100B | 100C | 100D | 100E | 101 | 102 | 103 | 104 | 105 | 106 | 107 | 108 | 109 |
| S | Y | Y | F | D | Y | W | G | Q | G | T | L | V |

| 117 | 118 | 119 |
|---|---|---|
| 110 | 111 | 112 |
| 110 | 111 | 112 |
| T | V | S |

FIGURE 23B
3E LIGHT CHAIN VARIABLE DOMAIN NUMBERING
A-    PROTEIN SEQUENTIAL NUMBERING
B-    Kabat numbering
C-    Chothia numbering

BOXES: CDR AS KABAT, UNDERLINED=CDR AS CHOTHIA

| | | | | | | | | | | | | |
|---|---|---|---|---|---|---|---|---|---|---|---|---|
| A-1 | 2 | 3 | 4 | 5 | 6 | 7 | 8 | 9 | 10 | 11 | 12 | 13 |
| B-1 | 2 | 3 | 4 | 5 | 6 | 7 | 8 | 9 | 10 | 11 | 12 | 13 |
| C-1 | 2 | 3 | 4 | 5 | 6 | 7 | 8 | 9 | 10 | 11 | 12 | 13 |
| D | I | Q | M | T | Q | S | P | S | S | L | S | A |

L1
| | | | | | | | | | | | | |
|---|---|---|---|---|---|---|---|---|---|---|---|---|
| 14 | 15 | 16 | 17 | 18 | 19 | 20 | 21 | 22 | 23 | 24 | 25 | 26 |
| 14 | 15 | 16 | 17 | 18 | 19 | 20 | 21 | 22 | 23 | 24 | 25 | 26 |
| 14 | 15 | 16 | 17 | 18 | 19 | 20 | 21 | 22 | 23 | <u>24</u> | <u>25</u> | <u>26</u> |
| S | V | G | D | R | V | T | I | T | C | [R | A | S] |

| | | | | | | | | | | | | | |
|---|---|---|---|---|---|---|---|---|---|---|---|---|---|
| 27 | 28 | 29 | 30 | 31 | 32 | 33 | 34 | 35 | 36 | 37 | 38 | 39 | |
| 27 | 28 | 29 | 30 | 31 | 32 | 33 | 34 | 35 | 36 | 37 | 38 | 39 | 27 |
| <u>28</u> | <u>29</u> | <u>30</u> | <u>31</u> | <u>32</u> | <u>33</u> | <u>34</u> | <u>35</u> | 36 | 37 | 38 | 39 | | |
| [Q | S | I | S | N | N | L | N] | W | Y | Q | Q | K | |

L2
| | | | | | | | | | | | | |
|---|---|---|---|---|---|---|---|---|---|---|---|---|
| 40 | 41 | 42 | 43 | 44 | 45 | 46 | 47 | 48 | 49 | 50 | 51 | 52 |
| 40 | 41 | 42 | 43 | 44 | 45 | 46 | 47 | 48 | 49 | 50 | 51 | 52 |
| 40 | 41 | 42 | 43 | 44 | 45 | 46 | 47 | 48 | 49 | <u>50</u> | <u>51</u> | <u>52</u> |
| P | G | K | A | P | K | L | L | I | Y | [Y | T | S] |

| | | | | | | | | | | | | |
|---|---|---|---|---|---|---|---|---|---|---|---|---|
| 53 | 54 | 55 | 56 | 57 | 58 | 59 | 60 | 61 | 62 | 63 | 64 | 65 |
| 53 | 54 | 55 | 56 | 57 | 58 | 59 | 60 | 61 | 62 | 63 | 64 | 65 |
| 53 | 54 | 55 | 56 | 57 | 58 | 59 | 60 | 61 | 62 | 63 | 64 | 65 |
| [R | F | H | S] | G | V | P | S | R | F | S | G | S |

| | | | | | | | | | | | | | |
|---|---|---|---|---|---|---|---|---|---|---|---|---|---|
| 66 | 67 | 68 | 69 | 70 | 71 | 72 | 73 | 74 | 75 | 76 | 77 | 78 | |
| 66 | 67 | 68 | 69 | 70 | 71 | 72 | 73 | 74 | 75 | 76 | 77 | 78 | 66 |
| 67 | 68 | 69 | 70 | 71 | 72 | 73 | 74 | 75 | 76 | 77 | 78 | | |
| G | S | G | T | D | F | T | F | T | I | S | S | L | |

L3
| | | | | | | | | | | | | |
|---|---|---|---|---|---|---|---|---|---|---|---|---|
| 79 | 80 | 81 | 82 | 83 | 84 | 85 | 86 | 87 | 88 | 89 | 90 | 91 |
| 79 | 80 | 81 | 82 | 83 | 84 | 85 | 86 | 87 | 88 | 89 | 90 | 91 |
| 79 | 80 | 81 | 82 | 83 | 84 | 85 | 86 | 87 | 88 | <u>89</u> | <u>90</u> | <u>91</u> |
| Q | P | E | D | I | A | T | Y | Y | C | [Q | Q | E] |

| | | | | | | | | | | | | |
|---|---|---|---|---|---|---|---|---|---|---|---|---|
| 92 | 93 | 94 | 95 | 96 | 97 | 98 | 99 | 100 | 101 | 102 | 103 | 104 |
| [H | T | L | P | Y | T] | F | G | Q | G | T | K | L |

SEQUENCE LISTING

<160> NUMBER OF SEQ ID NOS: 77

<210> SEQ ID NO 1
<211> LENGTH: 120
<212> TYPE: PRT
<213> ORGANISM: Artificial Sequence
<220> FEATURE:
<223> OTHER INFORMATION: Synthetic Construct

<400> SEQUENCE: 1

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
        35                  40                  45

Gly Ile Ile Trp Gly Asp Gly Thr Thr Asp Tyr Asn Ser Ala Val Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser
        115                 120
```

<210> SEQ ID NO 2
<211> LENGTH: 109
<212> TYPE: PRT
<213> ORGANISM: Artificial Sequence
<220> FEATURE:
<223> OTHER INFORMATION: Synthetic Construct

<400> SEQUENCE: 2

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr
            100                 105
```

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Gly Phe Ser Leu Ile Gly Tyr Asp Leu Asn

```
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct

<400> SEQUENCE: 4

Ile Ile Trp Gly Asp Gly Thr Thr Asp Tyr Asn Ser Ala Val Lys Ser
1               5                   10                  15

<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

Gly Gly Tyr Trp Tyr Ala Thr Ser Tyr Tyr Phe Asp Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Construct

<400> SEQUENCE: 6

Arg Ala Ser Gln Ser Ile Ser Asn Asn Leu Asn
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Tyr Thr Ser Arg Phe His Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Gln Gln Glu His Thr Leu Pro Tyr Thr
1               5

<210> SEQ ID NO 9
<211> LENGTH: 10
<212> TYPE: PRT
<213> ORGANISM: Mus musculus

<400> SEQUENCE: 9

Gly Phe Ser Leu Ile Gly Tyr Asp Ile Asn
1               5                   10

<210> SEQ ID NO 10
```

<211> LENGTH: 16
<212> TYPE: PRT
<213> ORGANISM: Mus musculus

<400> SEQUENCE: 10

Met Ile Trp Gly Asp Gly Thr Thr Asp Tyr Asn Ser Ala Leu Lys Ser
1               5                   10                  15

<210> SEQ ID NO 11
<211> LENGTH: 13
<212> TYPE: PRT
<213> ORGANISM: Mus musculus

<400> SEQUENCE: 11

Gly Gly Tyr Tyr Tyr Gly Thr Ser Tyr Tyr Phe Asp Tyr
1               5                   10

<210> SEQ ID NO 12
<211> LENGTH: 11
<212> TYPE: PRT
<213> ORGANISM: Mus musculus

<400> SEQUENCE: 12

Arg Ala Ser Gln Asp Ile Ser Asn His Leu Asn
1               5                   10

<210> SEQ ID NO 13
<211> LENGTH: 7
<212> TYPE: PRT
<213> ORGANISM: Mus musculus

<400> SEQUENCE: 13

Tyr Ile Ser Arg Phe His Ser
1               5

<210> SEQ ID NO 14
<211> LENGTH: 9
<212> TYPE: PRT
<213> ORGANISM: Mus musculus

<400> SEQUENCE: 14

Gln Gln Ser Lys Thr Leu Pro Tyr Thr
1               5

<210> SEQ ID NO 15
<211> LENGTH: 15
<212> TYPE: PRT
<213> ORGANISM: Artificial Sequence
<220> FEATURE:
<223> OTHER INFORMATION: Synthetic Construct

<400> SEQUENCE: 15

Gly Gly Gly Gly Ser Gly Gly Gly Gly Ser Gly Gly Gly Gly Ser
1               5                   10                  15

<210> SEQ ID NO 16
<211> LENGTH: 447
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr

-continued

```
                 20                  25                  30
Asp Leu Asn Trp Ile Arg Gln Pro Gly Lys Gly Leu Glu Trp Ile
         35                  40                  45
Gly Ile Ile Trp Gly Asp Gly Thr Thr Asp Tyr Asn Ser Ala Val Lys
 50                  55                  60
Ser Arg Val Thr Ile Ser Lys Asp Thr Ser Lys Asn Gln Phe Ser Leu
 65                  70                  75                  80
Lys Leu Ser Ser Val Thr Ala Ala Asp Thr Ala Val Tyr Tyr Cys Ala
                 85                  90                  95
Arg Gly Gly Tyr Trp Tyr Ala Thr Ser Tyr Tyr Phe Asp Tyr Trp Gly
         100                 105                 110
Gln Gly Thr Leu Val Thr Val Ser Ser Ala Ser Thr Lys Gly Pro Ser
         115                 120                 125
Val Phe Pro Leu Ala Pro Cys Ser Arg Ser Thr Ser Glu Ser Thr Ala
         130                 135                 140
Ala Leu Gly Cys Leu Val Lys Asp Tyr Phe Pro Glu Pro Val Thr Val
 145                 150                 155                 160
Ser Trp Asn Ser Gly Ala Leu Thr Ser Gly Val His Thr Phe Pro Ala
                 165                 170                 175
Val Leu Gln Ser Ser Gly Leu Tyr Ser Leu Ser Ser Val Val Thr Val
         180                 185                 190
Pro Ser Ser Asn Phe Gly Thr Gln Thr Tyr Thr Cys Asn Val Asp His
         195                 200                 205
Lys Pro Ser Asn Thr Lys Val Asp Lys Thr Val Glu Arg Lys Cys Cys
 210                 215                 220
Val Glu Cys Pro Pro Cys Pro Ala Pro Pro Val Ala Gly Pro Ser Val
 225                 230                 235                 240
Phe Leu Phe Pro Pro Lys Pro Lys Asp Thr Leu Met Ile Ser Arg Thr
                 245                 250                 255
Pro Glu Val Thr Cys Val Val Val Asp Val Ser His Glu Asp Pro Glu
         260                 265                 270
Val Gln Phe Asn Trp Tyr Val Asp Gly Val Glu Val His Asn Ala Lys
         275                 280                 285
Thr Lys Pro Arg Glu Glu Gln Phe Asn Ser Thr Phe Arg Val Val Ser
 290                 295                 300
Val Leu Thr Val Val His Gln Asp Trp Leu Asn Gly Lys Glu Tyr Lys
 305                 310                 315                 320
Cys Lys Val Ser Asn Lys Gly Leu Pro Ser Ser Ile Glu Lys Thr Ile
                 325                 330                 335
Ser Lys Thr Lys Gly Gln Pro Arg Glu Pro Gln Val Tyr Thr Leu Pro
         340                 345                 350
Pro Ser Arg Glu Glu Met Thr Lys Asn Gln Val Ser Leu Thr Cys Leu
         355                 360                 365
Val Lys Gly Phe Tyr Pro Ser Asp Ile Ala Val Glu Trp Glu Ser Asn
         370                 375                 380
Gly Gln Pro Glu Asn Asn Tyr Lys Thr Thr Pro Pro Met Leu Asp Ser
 385                 390                 395                 400
Asp Gly Ser Phe Phe Leu Tyr Ser Lys Leu Thr Val Asp Lys Ser Arg
                 405                 410                 415
Trp Gln Gln Gly Asn Val Phe Ser Cys Ser Val Met His Glu Ala Leu
         420                 425                 430
His Asn His Tyr Thr Gln Lys Ser Leu Ser Leu Ser Pro Gly Lys
         435                 440                 445
```

```
<210> SEQ ID NO 17
<211> LENGTH: 214
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (190)..(190)
<223> OTHER INFORMATION: Xaa = Any Amino Acid

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Xaa Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Arg Ala Ser Gln Ser Ile Ser Asn Asn Leu Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct

<400> SEQUENCE: 19

Tyr Thr Ser Arg Phe His Ser
```

```
<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Arg Ala Ser Gln Tyr Ile Ser Asn His Leu Asn
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Tyr Thr Ser Arg Phe His Ser
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

Arg Ala Ser Gln Ser Ile Ser Asn Gln Leu Asn
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Tyr Val Ser Arg Phe His Ser
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Arg Ala Phe Gln Ala Ile Ser Asn Gln Leu Asn
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Tyr Ile Ser Arg Phe His Thr
1               5
```

```
<210> SEQ ID NO 26
<211> LENGTH: 11
<212> TYPE: PRT
<213> ORGANISM: Artificial Sequence
<220> FEATURE:
<223> OTHER INFORMATION: Synthetic Construct

<400> SEQUENCE: 26

Arg Ala Phe Gln Ser Ile Ser Asn Gln Leu Asn
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic Construct

<400> SEQUENCE: 27

Tyr Ala Ser Arg Phe His Ser
1               5

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

Gly Phe Ser Leu Ile Gly Tyr Asp Ser Asn
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic Construct

<400> SEQUENCE: 29

Ile Ile Trp Gly Asp Gly Thr Thr Asp Tyr Asn Ser Ala Leu
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Gly Phe Ser Leu Ile Gly Tyr Asp Leu Asn
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic Construct

<400> SEQUENCE: 31

Ile Ile Trp Gly Asp Gly Thr Thr Asp Tyr Asn Ser Ala Val
1               5                   10

<210> SEQ ID NO 32
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Gly Phe Ser Leu Ile Gly Tyr Asp Val Thr
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic Construct

<400> SEQUENCE: 33

Gly Ile Trp Gly Asp Gly Thr Thr Asp Tyr Asn Ser Ala Val
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

Gly Phe Ser Leu Ile Gly Tyr Asp Val Thr
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic Construct

<400> SEQUENCE: 35

Gly Ile Trp Gly Asp Gly Thr Thr Asp Tyr Asn Ser Ser Val
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Gly Phe Ser Leu Ile Gly Tyr Asp Ala Thr
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic Construct

<400> SEQUENCE: 37

Gly Ile Trp Gly Asp Gly Thr Thr Asp Tyr Asn Ser Ala Val
1               5                   10

<210> SEQ ID NO 38
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 38

Gly Phe Ser Leu Ile Gly Tyr Asp Val Ser
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic Construct

<400> SEQUENCE: 39

Ile Ile Trp Gly Asp Gly Thr Thr Asp Tyr Asn Ser Ser Val
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic Construct

<400> SEQUENCE: 40

Gly Phe Ser Leu Ile Gly Tyr Asp Ile Ser
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic Construct

<400> SEQUENCE: 41

Gln Ile Trp Gly Asp Gly Thr Thr Asp Tyr Asn Ser Ser Val
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Gly Phe Ser Leu Ile Gly Tyr Asp Ala Ser
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Synthetic Construct

<400> SEQUENCE: 43

Gly Ile Trp Gly Asp Gly Thr Thr Asp Tyr Asn Ser Ser Val
1               5                   10

<210> SEQ ID NO 44
<211> LENGTH: 10
<212> TYPE: PRT
<213> ORGANISM: Artificial Sequence
<220> FEATURE:
```

<223> OTHER INFORMATION: Synthetic Construct

<400> SEQUENCE: 44

Gly Phe Ser Leu Ile Gly Tyr Asp Ser Thr
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Synthetic Construct

<400> SEQUENCE: 45

Ser Ile Trp Gly Asp Gly Thr Thr Asp Tyr Asn Ser Ala Leu
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic Construct

<400> SEQUENCE: 46

Gly Gly Tyr Trp Tyr Gly Thr Ser Tyr Tyr Phe Asp Tyr
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic Construct

<400> SEQUENCE: 47

Gly Gly Tyr Tyr Tyr Gly Thr Ala Tyr Tyr Phe Asp Tyr
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic Construct

<400> SEQUENCE: 48

Gly Gly Tyr Tyr Tyr Gly Thr Thr Tyr Tyr Phe Asp Tyr
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic Construct

<400> SEQUENCE: 49

Gly Gly Tyr Tyr Tyr Ala Thr Ser Tyr Tyr Phe Asp Tyr
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 50

Gln Gln Glu Lys Thr Leu Pro Tyr Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic Construct

<400> SEQUENCE: 51

Gln Gln Glu Ala Thr Leu Pro Tyr Thr
1               5

<210> SEQ ID NO 52
<211> LENGTH: 13
<212> TYPE: PRT
<213> ORGANISM: Artificial Sequence
<220> FEATURE:
<223> OTHER INFORMATION: Synthetic Construct

<400> SEQUENCE: 52

Gly Gly Tyr Trp Tyr Ala Thr Ser Tyr Tyr Phe Asp Tyr
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Synthetic Construct

<400> SEQUENCE: 53

Gln Gln Glu Arg Thr Leu Pro Tyr Thr
1               5

<210> SEQ ID NO 54
<211> LENGTH: 13
<212> TYPE: PRT
<213> ORGANISM: Artificial Sequence
<220> FEATURE:
<223> OTHER INFORMATION: Synthetic Construct

<400> SEQUENCE: 54

Gly Gly Tyr Trp Tyr Ala Thr Ser Tyr Tyr Phe Asp Tyr
1               5                   10

<210> SEQ ID NO 55
<211> LENGTH: 9
<212> TYPE: PRT
<213> ORGANISM: Artificial Sequence
<220> FEATURE:
<223> OTHER INFORMATION: Synthetic Construct

<400> SEQUENCE: 55

Gln Gln Glu His Thr Leu Pro Tyr Thr
1               5

<210> SEQ ID NO 56
<211> LENGTH: 13
<212> TYPE: PRT
<213> ORGANISM: Artificial Sequence
<220> FEATURE:
<223> OTHER INFORMATION: Synthetic Construct

<400> SEQUENCE: 56
```

Gly Gly Tyr Trp Tyr Ala Thr Ser Tyr Phe Asp Tyr
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Synthetic Construct

<400> SEQUENCE: 57

Gln Gln Glu Ser Thr Leu Pro Tyr Thr
1               5

<210> SEQ ID NO 58
<211> LENGTH: 13
<212> TYPE: PRT
<213> ORGANISM: Artificial Sequence
<220> FEATURE:
<223> OTHER INFORMATION: Synthetic Construct

<400> SEQUENCE: 58

Gly Gly Tyr Trp Tyr Ser Thr Ser Tyr Tyr Phe Asp Tyr
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Synthetic Construct

<400> SEQUENCE: 59

Gln Gln Glu Lys Thr Leu Pro Tyr Thr
1               5

<210> SEQ ID NO 60
<211> LENGTH: 13
<212> TYPE: PRT
<213> ORGANISM: Artificial Sequence
<220> FEATURE:
<223> OTHER INFORMATION: Synthetic Construct

<400> SEQUENCE: 60

Gly Gly Tyr Tyr Tyr Ala Thr Ser Tyr Tyr Phe Asp Tyr
1               5                   10

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct

<400> SEQUENCE: 61

Gln Gln Glu Arg Thr Leu Pro Tyr Thr
1               5

<210> SEQ ID NO 62
<211> LENGTH: 13
<212> TYPE: PRT
<213> ORGANISM: Artificial Sequence
<220> FEATURE:
<223> OTHER INFORMATION: Synthetic Construct

<400> SEQUENCE: 62

Gly Gly Tyr Trp Tyr Ala Thr Ser Tyr Tyr Phe Asp Tyr
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Synthetic Construct

<400> SEQUENCE: 63

Gln Gln Glu Arg Thr Leu Pro Tyr Thr
1               5

<210> SEQ ID NO 64
<211> LENGTH: 13
<212> TYPE: PRT
<213> ORGANISM: Artificial Sequence
<220> FEATURE:
<223> OTHER INFORMATION: Synthetic Construct

<400> SEQUENCE: 64

Gly Gly Tyr Tyr Tyr Ala Thr Ser Tyr Tyr Phe Asp Tyr
1               5                   10

<210> SEQ ID NO 65
<211> LENGTH: 1344
<212> TYPE: DNA
<213> ORGANISM: Artificial Sequence
<220> FEATURE:
<223> OTHER INFORMATION: Synthetic Construct

<400> SEQUENCE: 65
caggtgcagc tgcaggagtc tggcccagga ctggtgaagc cttccgagac cctgtccctc     60
acctgcactg tctctgggtt ctcacttatc ggctatgatc ttaactggat ccgacagcct    120
ccagggaagg gactggagtg gattgggatt atctggggtg atggaaccac agactataat    180
tcagctgtca atcccgcgt caccatctca aagacacct ccaagaacca gttctccctg    240
aagctgagct ctgtgaccgc cgcggacacg gccgtgtatt actgtgcgag aggaggttat    300
tggtacgcca ctagctacta cttgactac tggggccagg gcaccctggt caccgtctcc    360
tcagcctcca ccaagggccc atctgtcttc ccactggccc catgctcccg cagcacctcc    420
gagagcacag ccgccctggg ctgcctggtc aaggactact cccagaacc tgtgaccgtg    480 tcctggaact ctggcgctct gaccagcggc gtgcacacct cccagctgt cctgcagtcc    540 tcaggtctct actccctcag cagcgtggtg accgtgccat ccagcaactt cggcacccag    600
acctacacct gcaacgtaga tcacaagcca agcaacacca aggtcgacaa gaccgtggag    660
agaaagtgtt gtgtggagtg tccaccttgt ccagccctc cagtggccgg accatcgtg    720 ttcctgttcc ctccaaagcc aaaggacacc ctgatgatct ccagaacccc agaggtgacc    780
tgtgtggtgg tggacgtgtc ccacgaggac ccagaggtgc agttcaactg gtatgtggac    840
ggagtggagg tgcacaacgc caagaccaag ccaagagagg agcagttcaa ctccaccttc    900
agagtggtga gcgtgctgac cgtggtgcac caggactggc tgaacggaaa ggagtataag    960
tgtaaggtgt ccaacaaggg actgccatcc agcatcgaga gaccatctc caagaccaag   1020 ggacagccaa gagagccaca ggtgtatacc ctgccaccat ccagagagga tgaccaag    1080 aaccaggtgt ccctgacctg tctggtgaag ggattctatc catccgacat cgccgtggag   1140
tgggagtcca acggacagcc agagaacaac tataagacca cccctccaat gctggactcc    1200
gacggatcct tcttcctgta ttccaagctg accgtggaca gtccagatg gcagcaggga    1260 aacgtgttct cttgttccgt gatgcacgag gccctgcaca accactatac ccagaagagc   1320

```
ctgtccctgt ctccaggaaa gtaa                                          1344

<210> SEQ ID NO 66
<211> LENGTH: 363
<212> TYPE: DNA
<213> ORGANISM: Artificial Sequence
<220> FEATURE:
<223> OTHER INFORMATION: Synthetic Construct

<400> SEQUENCE: 66
caggtgcagc tgcaggagtc tgggcccagga ctggtgaagc cttccgagac cctgtccctc      60
acctgcactg tctctgggtt ctcacttatc ggctatgatc ttaactggat ccgacagcct     120
ccagggaagg gactggagtg gattgggatt atctggggtg atggaaccac agactataat     180
tcagctgtca atcccgcgt caccatctca aaagacacct ccaagaacca gttctccctg     240
aagctgagct ctgtgaccgc cgcggacacg gccgtgtatt actgtgcgag aggaggttat     300
tggtacgcca ctagctacta ctttgactac tggggccagg gcaccctggt caccgtctcc     360
tca                                                                   363

<210> SEQ ID NO 67
<211> LENGTH: 645
<212> TYPE: DNA
<213> ORGANISM: Artificial Sequence
<220> FEATURE:
<223> OTHER INFORMATION: Synthetic Construct

<400> SEQUENCE: 67
gatatccaga tgacacagtc cccatcctcc ctgtctgcct ctgtgggtga ccgcgtcacc      60
atcacctgcc gcgcatctca gtccattagc aataatctga actggtatca gcagaagcca     120
ggcaaagccc caaaactcct gatctactac acctcacgct tccactcagg tgtcccatca     180
cgcttcagtg gcagtggctc tggtacagat ttcaccttca ccattagcag cctgcaacca     240
gaagatattg ccacttatta ctgccaacag gagcataccc ttccatatac cttcggtcaa     300
ggcaccaagc tggagatcaa acgcactgtg gctgcaccat ctgtcttcat ctttcctcca     360
tctgatgagc agttgaaatc cggaactgcc tctgttgtgt gcctgctgaa taacttctat     420
ccacgcgagg ccaaagtaca gtggaaggtg gataacgccc tccaatccgg taactcccag     480
gagagtgtca cagagcagga cagcaaggac agcacctaca gcctcagcag caccctgacc     540
ctgagcaaag cagactacga gaaacacmaa gtctacgcct cgaagtcac ccatcagggc     600 ctgagttctc cagtcacaaa gagcttcaac cgcggtgagt gctaa                     645

<210> SEQ ID NO 68
<211> LENGTH: 324
<212> TYPE: DNA
<213> ORGANISM: Artificial Sequence
<220> FEATURE:
<223> OTHER INFORMATION: Synthetic Construct

<400> SEQUENCE: 68
gatatccaga tgacacagtc cccatcctcc ctgtctgcct ctgtgggtga ccgcgtcacc      60
atcacctgcc gcgcatctca gtccattagc aataatctga actggtatca gcagaagcca     120
ggcaaagccc caaaactcct gatctactac acctcacgct tccactcagg tgtcccatca     180
cgcttcagtg gcagtggctc tggtacagat ttcaccttca ccattagcag cctgcaacca     240
gaagatattg ccacttatta ctgccaacag gagcataccc ttccatatac cttcggtcaa     300
ggcaccaagc tggagatcaa acgc                                            324
```

<210> SEQ ID NO 69
<211> LENGTH: 98
<212> TYPE: PRT
<213> ORGANISM: Homo sapiens

<400> SEQUENCE: 69

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly

<210> SEQ ID NO 70
<211> LENGTH: 120
<212> TYPE: PRT
<213> ORGANISM: Artificial Sequence
<220> FEATURE:
<223> OTHER INFORMATION: Synthetic Construct

<400> SEQUENCE: 70

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Ile Asn Trp Ile Arg Gln Pro Pro Gly Lys Gly Leu Glu Trp Ile
        35                  40                  45

Gly Met Ile Trp Gly Asp Gly Thr Thr Asp Tyr Asn Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Tyr Tyr Gly Thr Ser Tyr Tyr Phe Asp Tyr Trp Gly
            100                 105                 110

Gln Gly Thr Leu Val Thr Val Ser
        115                 120

<210> SEQ ID NO 71
<211> LENGTH: 120
<212> TYPE: PRT
<213> ORGANISM: Artificial Sequence
<220> FEATURE:
<223> OTHER INFORMATION: Synthetic Construct

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Ile Asn Trp Ile Arg Gln Pro Pro Gly Lys Gly Leu Glu Trp Ile

-continued

```
                35                  40                  45
Gly Met Ile Trp Gly Asp Gly Thr Thr Asp Tyr Asn Ser Ala Leu Lys
 50                  55                  60

Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Gly Tyr Tyr Tyr Gly Thr Ser Tyr Tyr Phe Asp Tyr Trp Gly
                100                 105                 110

Gln Gly Thr Leu Val Thr Val Ser
            115                 120

<210> SEQ ID NO 72
<211> LENGTH: 120
<212> TYPE: PRT
<213> ORGANISM: Artificial Sequence
<220> FEATURE:
<223> OTHER INFORMATION: Synthetic Construct

<400> SEQUENCE: 72

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ile Gly Tyr
                20                  25                  30

Asp Leu Asn Trp Ile Arg Gln Pro Pro Gly Lys Gly Leu Glu Trp Ile
                35                  40                  45

Gly Ile Ile Trp Gly Asp Gly Thr Thr Asp Tyr Asn Ser Ala Val Lys
 50                  55                  60

Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Gly Tyr Tyr Tyr Gly Thr Ser Tyr Tyr Phe Asp Tyr Trp Gly
                100                 105                 110

Gln Gly Thr Leu Val Thr Val Ser
            115                 120

<210> SEQ ID NO 73
<211> LENGTH: 95
<212> TYPE: PRT
<213> ORGANISM: Homo sapiens

<400> SEQUENCE: 73

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
                35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro
                 85                  90                  95

<210> SEQ ID NO 74
<211> LENGTH: 109
```

```
<212> TYPE: PRT
<213> ORGANISM: Artificial Sequence
<220> FEATURE:
<223> OTHER INFORMATION: Synthetic Construct

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn His
            20                  25                  30

Leu Asn Trp Tyr Gln Gln Lys Pro Gly Lys Ala Pro Lys Leu Leu Ile
        35                  40                  45

Tyr Tyr Ile Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Lys Thr Leu Pro Tyr
                85                  90                  95

Thr Phe Gly Gln Gly Thr Lys Leu Glu Ile Lys Arg Thr
            100                 105

<210> SEQ ID NO 75
<211> LENGTH: 109
<212> TYPE: PRT
<213> ORGANISM: Artificial Sequence
<220> FEATURE:
<223> OTHER INFORMATION: Synthetic Construct

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Lys Thr Leu Pro Tyr
                85                  90                  95

Thr Phe Gly Gln Gly Thr Lys Leu Glu Ile Lys Arg Thr
            100                 105

<210> SEQ ID NO 76
<211> LENGTH: 1429
<212> TYPE: DNA
<213> ORGANISM: Artificial Sequence
<220> FEATURE:
<223> OTHER INFORMATION: Synthetic construct

<400> SEQUENCE: 76
atggccaccg actccagaac ctcctggctg ctgacagtgt ccctgctgtg tctgctgtgg      60
ccacaggagg ccagcgctca ggtgcagctg caggagtctg gcccaggact ggtgaagcct     120
tccgagaccc tgtccctcac ctgcactgtc tctgggttct cacttatcgg ctatgatctt     180
aactggatcc gacagcctcc agggaaggga ctggagtgga ttgggattat ctggggtgat     240
ggaaccacag actataattc agctgtcaaa tcccgcgtca ccatctcaaa agacacctcc     300
aagaaccagt tctccctgaa gctgagctct gtgaccgccg cggacacggc cgtgtattac     360
```

| | |
|---|---|
| tgtgcgagag gaggttattg gtacgccact agctactact ttgactactg gggccagggc | 420 |
| accctggtca ccgtctcctc agcctccacc aagggcccat ctgtcttccc actggcccca | 480 |
| tgctcccgca gcacctccga gagcacagcc gccctgggct gcctggtcaa ggactacttc | 540 |
| ccagaacctg tgaccgtgtc ctggaactct ggcgctctga ccagcggcgt gcacaccttc | 600 |
| ccagctgtcc tgcagtcctc aggtctctac tccctcagca gcgtggtgac cgtgccatcc | 660 |
| agcaacttcg gcacccagac ctacacctgc aacgtagatc acaagccaag caacaccaag | 720 |
| gtcgacaaga ccgtggagag aaagtgttgt gtggagtgtc caccttgtcc agcccctcca | 780 |
| gtggccggac catccgtgtt cctgttccct ccaaagccaa aggacaccct gatgatctcc | 840 |
| agaaccccag aggtgacctg tgtggtggtg gacgtgtccc acgaggaccc agaggtgcag | 900 |
| ttcaactggt atgtggacgg agtggaggtg cacaacgcca gaccaagcc aagagaggag | 960 |
| cagttcaact ccaccttcag agtggtgagc gtgctgaccg tggtgcacca ggactggctg | 1020 |
| aacggaaagg agtataagtg taaggtgtcc aacaaggac tgccatccag catcgagaag | 1080 |
| accatctcca agaccaaggg acagccaaga gagccacagg tgtataccct gccaccatcc | 1140 |
| agagaggaga tgaccaagaa ccaggtgtcc ctgacctgtc tggtgaaggg attctatcca | 1200 |
| tccgacatcg ccgtggagtg ggagtccaac ggacagccag agaacaacta taagaccacc | 1260 |
| cctccaatgc tggactccga cggatccttc ttcctgtatt ccaagctgac cgtggacaag | 1320 |
| tccagatggc agcagggaaa cgtgttctct tgttccgtga tgcacgaggc cctgcacaac | 1380 |
| cactataccc agaagagcct gtccctgtct ccaggaaagt aattctaga | 1429 |

<210> SEQ ID NO 77
<211> LENGTH: 729
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (646)..(646)
<223> OTHER INFORMATION: m = A or C

<400> SEQUENCE: 77

| | |
|---|---|
| atggccaccg actccagaac ctcctggctg ctgacagtgt ccctgctgtg tctgctgtgg | 60 |
| ccacaggagg ccagcgctga tatccagatg acacagtccc catcctccct gtctgcctct | 120 |
| gtgggtgacc gcgtcaccat cacctgccgc gcatctcagt ccattagcaa taatctgaac | 180 |
| tggtatcagc agaagccagg caaagcccca aaactcctga tctactacac ctcacgcttc | 240 |
| cactcaggtg tcccatcacg cttcagtggc agtggctctg gtacagattt caccttcacc | 300 |
| attagcagcc tgcaaccaga agatattgcc acttattact gccaacagga gcataccctt | 360 |
| ccatataccc tcggtcaagg caccaagctg gagatcaaac gcactgtggc tgcaccatct | 420 |
| gtcttcatct ttcctccatc tgatgagcag ttgaaatccg gaactgcctc tgttgtgtgc | 480 |
| ctgctgaata acttctatcc acgcgaggcc aaagtacagt ggaaggtgga taacgccctc | 540 |
| caatccggta actcccagga gagtgtcaca gagcaggaca gcaaggacag cacctacagc | 600 |
| ctcagcagca ccctgaccct gagcaaagca gactacgaga acacmaagt ctacgcctgc | 660 |
| gaagtcaccc atcagggcct gagttctcca gtcacaaaga gcttcaaccg cggtgagtgc | 720 |
| taattctag | 729 |

METHODS FOR TREATING OSTEOARTHRITIS PAIN BY ADMINISTERING A NERVE GROWTH FACTOR ANTAGONIST AND COMPOSITIONS CONTAINING THE SAME

CROSS-REFERENCE TO RELATED APPLICATIONS

This application claims the priority benefit of U.S. patent application Ser. No. 11/104,248, filed Apr. 11, 2005, which is incorporated herein by reference in its entirety.

REFERENCE TO SEQUENCE LISTING

This application was filed electronically via EFS-Web and includes an electronically submitted sequence listing in .txt format. The .txt file contains a sequence listing entitled "PC19615A_SequenceListing.txt" created on Jul. 17, 2013 and having a size of 35 KB. The sequence listing contained in this .txt file is part of the specification and is herein incorporated by reference in its entirety.

FIELD OF THE INVENTION

The invention concerns anti-NGF antibodies (such as anti-NGF antagonist antibodies). The invention further concerns use of antagonists such as antibodies in the treatment and/or prevention of pain, including post-surgical pain, rheumatoid arthritis pain, and osteoarthritis pain.

BACKGROUND OF THE INVENTION

Nerve growth factor (NGF) was the first neurotrophin to be identified, and its role in the development and survival of both peripheral and central neurons has been well characterized. NGF has been shown to be a critical survival and maintenance factor in the development of peripheral sympathetic and embryonic sensory neurons and of basal forebrain cholinergic neurons. Smeyne et al., Nature 368:246-249 (1994) and Crowley et-al., Cell 76:1001-1011 (1994). NGF up-regulates expression of neuropeptides in sensory neurons (Lindsay and Harmer, Nature 337:362-364 (1989)) and its activity is mediated through two different membrane-bound receptors, the TrkA tyrosine kinase receptor and the p75 common neurotrophin receptor (sometimes termed "high affinity" and "low affinity" NGF receptors, respectively). Chao et al., Science 232:518-521 (1986). The p75 receptor is structurally related to other members of the tumor necrosis factor receptor family (Chao, et al., Science 232:518-521 (1986)). For review on NGF, see Huang et al., Annu. Rev. Neurosci. 24:677-736 (2001); Bibel et al., Genes Dev. 14:2919-2937 (2000). The crystal structure of NGF and NGF in complex with the trkA receptor have been determined. See Nature 254:411 (1991); Nature 401:184-188 (1996).

In addition to its effects in the nervous system, NGF has been increasingly implicated in processes outside of the nervous system. For example, NGF has been shown to enhance vascular permeability (Otten, et al., Eur J Pharmacol. 106: 199-201 (1984)), enhance T- and B-cell immune responses (Otten, et al., Proc. Natl. Acad. Sci. USA 86:10059-10063 (1989)), induce lymphocyte differentiation and mast cell proliferation and cause the release of soluble biological signals from mast cells (Matsuda, et al., Proc. Natl. Acad. Sci. USA 85:6508-6512 (1988); Pearce, et al., J. Physiol. 372:379-393 (1986); Bischoff, et al., Blood 79:2662-2669 (1992); Horigome, et al., J. Biol. Chem. 268:14881-14887 (1993)). Although exogenously added NGF has been shown to be capable of having all of these effects, it is important to note that it has only rarely been shown that endogenous NGF is important in any of these processes in vivo (Torcia, et al., Cell. 85(3):345-56 (1996)). Therefore, it is not clear what that effect might be, if any, of inhibiting the bioactivity of endogenous NGF.

NGF is produced by a number of cell types including mast cells (Leon, et al., Proc. Natl. Acad Sci. USA 91:3739-3743 (1994)), B-lymphocytes (Torcia, et al., Cell 85:345-356 (1996), keratinocytes (Di Marco, et al., J. Biol. Chem. 268: 22838-22846)), smooth muscle cells (Ueyama, et al., J. Hypertens. 11:1061-1065 (1993)), fibroblasts (Lindholm, et al., Eur. J. Neurosci. 2:795-801 (1990)), bronchial epithelial cells (Kassel, et al., Clin. Exp. Allergy 31:1432-40 (2001)), renal mesangial cells (Steiner, et al., Am. J. Physiol. 261: F792-798 (1991)) and skeletal muscle myotubes (Schwartz, et al., J Photochem. Photobiol. B66:195-200 (2002)). NGF receptors have been found on a variety of cell types outside of the nervous system. For example, TrkA has been found on human monocytes, T- and B-lymphocytes and mast cells.

An association between increased NGF levels and a variety of inflammatory conditions has been observed in human patients as well as in several animal models. These include systemic lupus erythematosus (Bracci-Laudiero, et al., Neuroreport 4:563-565 (1993)), multiple sclerosis (Bracci-Laudiero, et al., Neurosci. Lett. 147:9-12 (1992)), psoriasis (Raychaudhuri, et al., Acta Derm. l'enereol. 78:84-86 (1998)), arthritis (Falcim, et al., Ann. Rheum. Dis. 55:745-748 (1996)), interstitital cystitis (Okragly, et al., J. Urology 161:438-441 (1999)) and asthma (Braun, et al., Eur. J. Immunol. 28:3240-3251 (1998)).

Consistently, an elevated level of NGF in peripheral tissues is associated with hyperalgesia and inflammation and has been observed in a number of forms of arthritis. The synovium of patients affected by rheumatoid arthritis expresses high levels of NGF while in non-inflamed synovium NGF has been reported to be undetectable (Aloe, et al., Arch. Rheum. 35:351-355 (1992)). Similar results were seen in rats with experimentally induced rheumatoid arthritis (Aloe, et al., Clin. Exp. Rheumatol. 10:203-204 (1992)). Elevated levels of NGF have been reported in transgenic arthritic mice along with an increase in the number of mast cells (Aloe, et al., Int. J. Tissue Reactions-Exp. Clin. Aspects 15:139-143 (1993)). PCT Publication No. WO 02/096458 discloses use of anti-NGF antibodies of certain properties in treating various NGF related disorders such as inflammatory condition (e.g., rheumatoid arthritis). It has been reported that a purified anti-NGF antibody injected into arthritic transgenic mice carrying the human tumor necrosis factor-α (TNF-α) gene caused reduction in the number of mast cells, as well as a decrease in histamine and substance P levels within the synovium of arthritis mice (Aloe et al., Rheumatol. Int. 14: 249-252 (1995)). It has been shown that exogenous administration of a NGF antibody reduced the enhanced level of TNF-α occurring in arthritic mice (Manni et al., Rheumatol. Int. 18: 97-102 (1998)).

Also, increased expression of NGF and high affinity NGF receptor (TrkA) was observed in human osteoarthritis chondrocytes (Iannone et al., Rheumatology 41:1413-1418 (2002)).

Rodent anti-NGF antagonist antibodies have been reported. See, e.g., Hongo et al, Hybridoma (2000) 19(3): 215-227; Ruberti et Al. (1993) Cell. Molec. Neurobiol. 13(5): 559-568. However, when rodent antibodies are used therapeutically in humans, a human anti-murine antibody response develops in significant numbers of treated individuals. In addition, effector functions of mouse antibodies have proven to be less efficient in the human context. Thus, there is a serious need for anti-NGF antagonist antibodies, including humanized anti-NGF antagonist antibodies.

All references, publications, and patent applications disclosed herein are hereby incorporated by reference in their entirety.

BRIEF SUMMARY OF THE INVENTION

The invention disclosed herein concerns antibodies to nerve growth factor.

In another aspect, the invention is a humanized and affinity matured antibody, E3, which specifically binds human and rodent nerve growth factor ("NGF"). The amino acid sequences of the heavy chain and light chain variable regions of E3 are shown in FIGS. 1A (SEQ ID NO:1) and 1B (SEQ ID NO:2), respectively. The CDR portions of antibody E3 (including Chothia and Kabat CDRs) are diagrammatically depicted in FIGS. 1A and 1B. The amino acid sequences of E3 heavy and, light chains, and of the individual extended CDRs are also shown below (See, "antibody sequences", below).

In another aspect, the invention is an antibody comprising a fragment or a region of the antibody E3 (interchangeably termed "E3" herein). In one embodiment, the fragment is a light chain of the antibody E3 as shown in FIG. 1B. In another embodiment, the fragment is a heavy chain of the antibody E3 as shown in FIG. 1A. In yet another embodiment, the fragment contains one or more variable regions from a light chain and/or a heavy chain of the antibody E3. In yet another embodiment, the fragment contains one or more complementarity determining regions (CDRs) from a light chain and/or a heavy chain of the antibody E3 as shown in FIGS. 1A and 1B.

In another aspect, the invention is an antibody comprising a light chain that is encoded by a polynucleotide that is produced by a host cell with a deposit number of ATCC No. PTA-4893 or ATCC No. PTA-4894. In another aspect, the invention is an antibody comprising a heavy chain that is encoded by a polynucleotide that is produced by a host cell with a deposit number of ATCC No. PTA-4895. In another aspect, the invention is an antibody comprising (a) a light chain that is encoded by a polynucleotide that is produced by a host cell with a deposit number of ATCC No. PTA-4894 or ATCC No. PTA-4893; and (b) a heavy chain that is encoded by a polynucleotide that is produced by a host cell with a deposit number of ATCC No. PTA-4895 (for convenience herein, the polynucleotide(s) produced by a deposited host cell are referred to as having a deposit number of ATCC NOs PTA-4894, PTA-4893 and PTA-4895). In another aspect, the invention is an antibody comprising a light chain variable region of a light chain that is encoded by a polynucleotide that is produced by a host cell with a deposit number of ATCC No. PTA-4894 or ATCC No. PTA-4893. In another aspect, the invention is an antibody comprising a heavy chain variable region of a heavy chain that that is encoded by a polynucleotide that is produced by a host cell with a deposit number of ATCC No. PTA-4895. In another aspect, the invention is an antibody comprising (a) a light chain variable region of a light chain that is encoded by a polynucleotide that is produced by a host cell with a deposit number of ATCC No. PTA-4894 or ATCC No. PTA-4893, and (b) a heavy chain variable region of a heavy chain that that is encoded by a polynucleotide that is produced by a host cell with a deposit number of ATCC No. PTA-4895. In still another aspect, the invention is an antibody comprising one or more CDR(s) encoded by (a) a polynucleotide that is produced by a host cell with a deposit number of ATCC No. PTA-4894; and/or (b) a heavy chain that is encoded by a polynucleotide that is produced by a host cell with a deposit number of ATCC No. PTA-4895.

In some embodiments, the antibody comprises the human heavy chain IgG2a constant region. In some embodiments the antibody comprises the human light chain kappa constant region. In some embodiments, the antibody comprises a modified constant region, such as a constant region that is immunologically inert, e.g., does not trigger complement mediated lysis, or does not stimulate antibody-dependent cell mediated cytotoxicity (ADCC). In other embodiments, the constant region is modified as described in *Eur. J. Immunol.* (1999) 29:2613-2624; PCT Application No. PCT/GB99/01441; and/or UK Patent Application No. 9809951.8. In still other embodiments, the antibody comprises a human heavy chain IgG2a constant region comprising the following mutations: A330P331 to S330S331 (amino acid numbering with reference to the wildtype IgG2a sequence). *Eur. J. Immunol.* (1999) 29:2613-2624.

In another aspect, the invention provides polypeptides (which may or may not be an antibody) comprising any one or more of the following: a) one or more CDR(s) of antibody E3 shown in FIGS. 1A and 1B; b) CDR H3 from the heavy chain of antibody E3 shown in FIG. 1A; c) CDR L3 from the light chain of antibody E3 shown in FIG. 1B; d) three CDRs from the light chain of antibody E3 shown in FIG. 1B; e) three CDRs from the heavy chain of antibody E3 shown in FIG. 1A; and f) three CDRs from the light chain and three CDRs from the heavy chain, of antibody E3 shown in FIGS. 1A and 1B. The invention further provides polypeptides (which may or may not be an antibody) comprising any one or more of the following: a) one or more (one, two, three, four, five, or six) CDR(s) derived from antibody E3 shown in FIGS. 1A and 1B; b) a CDR derived from CDR H3 from the heavy chain of antibody E3 shown in FIG. 1A; and/or c) a CDR derived from CDR L3 from the light chain of antibody E3 shown in FIG. 1B. In some embodiments, the CDRs may be Kabat CDRs, Chothia CDRs, or a combination of Kabat and Chothia CDRs (termed "extended" or "combined" CDRs herein). In some embodiments, polypeptides (such as an antibody) bind NGF (such as human NGF). In some embodiments, the polypeptides comprise any of the CDF configurations (including combinations, variants, etc.) described herein.

In one aspect; the invention provides polypeptides (such as an antibody), which comprise a heavy chain variable region comprising SEQ ID NO:9, wherein I34 is S, L, V A, or I; and N35 is substituted with N, T or S. For convenience herein, "substituted" or "is" in this context or reference to an amino acid refers to choices of amino acid(s) for a given position. As is clear, the substitution, or choice, may be the amino acid depicted in a SEQ ID or Figure.

In another aspect, the invention provides polypeptides (such as an antibody) which comprise a heavy chain variable, region comprising SEQ ID NO:10, wherein M50 is M, I, G, Q, S, or L; A62 is A, or S; and L63 is L or V.

In another aspect, the invention provides polypeptides (such as an antibody) which comprises a heavy chain variable region comprising SEQ ID NO:11, wherein Y100 is Y, L, or R; wherein Y101 is Y or W; wherein G103 is G, A, or S; wherein. T104 is T or S; wherein S105 is S, A, or T; wherein Y106 is Y, R, T, or M; wherein Y107 is Y or F; wherein F108 is F or W; wherein D109 is D, N, or G; and wherein Y110 is Y, K, S, R or T.

In another aspect, the invention provides polypeptides (such as an antibody) which comprise a heavy chain variable region comprising SEQ ID NO:11, wherein Y100 is Y, L, or R; wherein Y101 is Y or W; wherein G103 is G, A, or S;

wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid.

In another aspect, the invention provides polypeptides (such as an antibody) which comprise a heavy chain variable region comprising SEQ ID NO: 11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid.

In another aspect, the invention provides polypeptides (such as an antibody) which comprise a light chain variable region comprising SEQ ID NO:12, wherein S26 is S or F; D28 is D, S, A, or Y; and H32 is H, N, or Q.

In another aspect, the invention provides polypeptides (such as an antibody) which comprise a light chain variable region comprising SEQ ID NO: 13, wherein I51 is I, T, V or A; and S56 is S or T.

In another aspect, the invention provides polypeptides (such as an antibody) which comprise a light chain variable region comprising SEQ ID NO:14, wherein S91 is S or E; K92 is K, H, R, or S; and wherein Y96 is Y or R.

In another aspect, the invention provides polypeptides (such as an antibody) which comprise a light chain variable region comprising SEQ ID NO:14, wherein S91 is S or E; K92 is any amino acid; T93 is any amino acid; and wherein Y96 is Y or R.

In one aspect, the invention provides polypeptides (such as an antibody), which comprise an amino acid sequence shown in SEQ ID NO:9, wherein I34 is S, L, V A, or I; and N35 is N, T or S.

In another aspect, the invention provides polypeptides (such as an antibody) which comprise an amino acid sequence shown in SEQ ID NO:10, wherein M50 is M, I, G, Q, S, or L; A62 is A, or S; and L63 is L or V.

In another aspect, the invention provides polypeptides (such as an antibody) which comprise an amino acid sequence shown in SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; and wherein Y110 is Y, K, S, R or T.

In another aspect, the invention provides polypeptides (such as an antibody) which comprise an amino acid sequence shown in SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid.

In another aspect, the invention provides polypeptides (such as an antibody) which comprise an amino acid sequence shown in SEQ ID NO:11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein 5105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid.

In another aspect, the invention provides polypeptides (such as an antibody) which comprise an amino acid sequence shown in SEQ ID NO:12, wherein S26 is S or F; D28 is D, S, A, or Y; and H32 is H, N, or Q.

In another aspect, the invention provides polypeptides (such as an antibody) which comprise an amino acid sequence shown in SEQ ID NO: 13, wherein I51 is I, T, V or A; and S56 is S or T.

In another aspect, the invention provides polypeptides (such as an antibody) which comprise an amino acid sequence shown in SEQ ID NO:14, wherein S91 is S or E; K92 is K, H, R, or S; and wherein Y96 is Y or R.

In another aspect, the invention provides polypeptides (such as an antibody) which comprise an amino acid sequence shown in SEQ ID NO:14, wherein S91 is S or E; K92 is any amino acid; T93 is any amino acid; and wherein Y96 is Y or R.

In another aspect, the invention provides polypeptides (such an antibodies, including humanized antibodies) which comprise a heavy chain variable region comprising the CDR1 region of SEQ ID NO:9, wherein I34 is S, L, V A, or I; and N35 is N, T or S; the CDR2 region of SEQ ID NO:10, wherein M50 is M, I, G, Q, S, or L; A62 is A, or S; and L63 is L or V; and the CDR3 region of SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; wherein Y110 is Y, K, S, R or T. In some embodiments, the heavy chain variable region comprises the CDR3 region of SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; wherein Y110 is any amino acid. In other embodiments, the heavy chain variable region comprises the CDR3 region of SEQ ID NO:11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is For W; wherein D109 is S, A, C, G, D, N, T, or G; and wherein Y110 is any amino acid. In some embodiments, the polypeptide (such as an antibody) further comprises an antibody light chain variable region.

In another aspect, the invention provides polypeptides (such as an antibody) which comprise a light chain variable region comprising the CDR1 region of SEQ ID NO:12, wherein S26 is S or F; D28 is D, S, A, or Y; and H32 is H, N, or Q; the CDR2 region of SEQ ID NO:13, wherein I51 is I, T, V or A; and S56 is S or T; and the CDR3 region of SEQ ID NO:14, wherein S91 is S or E; K92 is K, H, R, or S; and wherein Y96 is Y or R. In some embodiments, the light chain variable region comprises the CDR3 region of SEQ ID NO:14, wherein S91 is S or E; K92 is any amino acid; T93 is any amino acid; and wherein Y96 is Y or R. In some embodiments, the polypeptide (such as an antibody) further comprises an antibody heavy chain.

In another aspect, the invention provides polypeptides (such as an antibody) which comprise (a) a heavy chain variable region comprising the CDR1 region of SEQ ID NO:9, wherein I34 is S, L, V A, or I; and N35 is N, T or S; the CDR2 region of SEQ ID NO:10, wherein M50 is M, I, G, Q, S, or L; A62 is A, or S; and L63 is L or V; and the CDR3 region of SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; wherein Y110 is Y, K, S, R or T; and (b) a light chain variable region comprising the CDR1 region of SEQ ID NO:12, wherein S26 is S or F; D28 is D, S, A, or Y;

and H32 is H, N, or Q; the CDR2 region of SEQ ID NO:13, wherein I51 is I, T, V or A; and S56 is S or T; and the CDR3 region of SEQ ID NO:14, wherein S91 is S or E; K92 is K, H, R, or S; and wherein Y96 is Y or R. In some embodiments, the light chain variable region comprises the CDR3 region of SEQ ID NO:14, wherein S91 is S or E; K92 is any amino acid; T93 is any amino acid; and wherein Y96 is Y or R. In some embodiments, the heavy chain variable region comprises the CDR3 region of SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; wherein Y110 is any amino acid. In other embodiments, the heavy chain variable region comprises the CDR3 region of SEQ ID NO:11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid. In some embodiments, the polypeptide further comprises an antibody light chain.

In another aspect, the invention provides polypeptides (such an antibody, including a humanized antibody) which comprise an amino acid sequence shown in SEQ ID NO:9, wherein I34 is S, L, V A, or I; and N35 is N, T or S; an amino acid sequence shown in SEQ ID NO:10, wherein M50 is M, I, G, Q, S, or L; A62 is A, or S; and L63 is L or V; and an amino acid sequence shown in SEQ ID NO: 11, wherein Y100 is Y, L, or R; wherein Y101 is Y or W; wherein G103 is G, A, or S; wherein T104 is T or S; wherein 5105 is S, A, or T; wherein Y106 is Y, R, T, or M; wherein Y107 is Y or F; wherein F108 is F or W; wherein D109 is D, N, or G; wherein Y110 is Y, K, S, R or T. In some embodiments, the polypeptide comprises an amino acid sequence shown in SEQ ID NO:11, wherein Y100 is Y, L, or R; and wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid. In other embodiments, the polypeptide comprises an amino acid sequence shown in SEQ ID NO:11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid. In some embodiments, the polypeptide (such as an antibody) further comprises an antibody light chain variable region.

In another aspect, the invention provides polypeptides (such as an antibody) which comprise an amino acid sequence shown in SEQ ID NO:12, wherein S26 is S or F; D28 is D, S, A, or Y; and H32 is H, N, or Q; an amino acid sequence shown in SEQ ID NO:13, wherein I51 is I, T, V or A; and S56 is S or T; and an amino acid sequence shown in SEQ ID NO:14, wherein S91 is S or E; K92 is K, H, R, or S; and wherein Y96 is Y or R. In some embodiments, the polypeptide comprises an amino acid sequence shown in SEQ ID NO:14, wherein S91 is S or E; K92 is any amino acid; T93 is any amino acid; and wherein Y96 is Y or R. In some embodiments, the polypeptide (such as an antibody) further comprises an antibody heavy chain variable region.

In another aspect, the invention provides polypeptides (such as an antibody) which comprise (a) an amino acid sequence shown in SEQ ID NO:9, wherein I34 is S, L, V A, or I; and N35 is N, T or S; an amino acid sequence shown in SEQ ID NO:10, wherein M50 is M, I, G, Q, S, or L; A62 is A, or S; and L63 is L or V; and an amino acid sequence shown in SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108, is F or W; wherein D109 is D, N, or G; and wherein Y110 is Y, K, S, R or T; and (b) an amino acid sequence shown in SEQ ID NO:12, wherein S26 is S or F; D28 is D, S, A, or Y; and H32 is H, N, or Q; an amino acid sequence shown in SEQ ID NO:13, wherein I51 is I, T, V or A; and S56 is S or T; and an amino acid sequence shown in SEQ ID NO:14, wherein S91 is S or E; K92 is K, H, R, or S; and wherein Y96 is Y or R. In some embodiments, the polypeptide comprises an amino acid sequence shown in SEQ ID NO:14, wherein S91 is S or E; K92 is any amino acid; T93 is any amino acid; and wherein Y96 is Y or R. In some embodiments, the polypeptide comprises an amino acid sequence shown in SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; wherein Y110 is any amino acid. In other embodiments, the polypeptide comprises an amino acid sequence shown in SEQ ID NO:11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid. In some embodiments, the polypeptide further comprises an antibody light chain variable region.

In another aspect, the invention provides polypeptide (such as antibodies) comprising a heavy chain variable region comprising: (a) a CDR1 region of SEQ ID NO:9, wherein I34 is S, L, V A, or I; and N35 is substituted with N, T or S; (b) a CDR2 region of SEQ ID NO:10, wherein M50 is I, G, Q, S, or L; A62 is A, or S; and L63 is L or V; and (c) a CDR3 region of SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; and wherein Y110 is Y, K, S, R or T; wherein the antibody binds NGF.

In another aspect, the invention provides polypeptides (such as antibodies) comprising a light chain variable region comprising: (a) a CDR1 region of SEQ ID NO:12, wherein S26 is S or F; D28 is D, S, A, or Y; and H32 is H, N, or Q; (b) a CDR2 region of SEQ ID NO: 13, wherein I51 is I, T, V or A; and S56 is S or T; and (c) a CDR3 region of SEQ ID NO:14, wherein K92 is K, H, R, or S; and wherein Y96 is Y or R; wherein the antibody binds NGF.

In another aspect, the invention provides polypeptides (such as antibodies) comprising (a) a heavy chain variable region comprising: (i) a CDR1 region of SEQ ID NO:9, wherein I34 is substituted with S, L, V A, or I; and N35 is substituted with N, T or S; (ii) a CDR2 region of SEQ ID NO:10, wherein M50 is I, G, Q, S, or L; A62 is A, or S; and L63 is L or V; and (iii) a CDR3 region of SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; wherein Y110 is Y, K, 5, R or T; and (b) a light chain variable region comprising: (i) a CDR1 region of SEQ ID NO:12, wherein S26 is S or F; D28 is D, S, A, or Y; and H32 is H, N, or Q; (ii) a CDR2 region of SEQ ID NO: 13, wherein I51 is I, T, V or A; and S56 is S or T; and (iii) a CDR3 region of SEQ ID NO:14, wherein S91 is S or E; K92 is K, H, R, or S; and wherein Y96 is Y or R; wherein the antibody binds NGF.

Unless otherwise noted, choice (e.g., substitution) of an amino acid in one location is independently selected from selection of an amino acid in any other location.

In some embodiments, polynucleotides (such as an antibody) bind NGF (such as human NGF). In some embodiments, the polypeptides comprise any of the CDR configurations (including combinations, variations, etc.) described herein.

As is evident from the description herein, the variable region numbering used herein is sequential numbering. One of skill in the art readily understands that a number of antibody numbering systems exist (such as Kabat and Chothia numbering), and how to convert sequential numbering into another numbering system, such as Kabat numbering or Chothia numbering.

In another aspect, the invention provides a polypeptide (such as an antibody) comprising an amino acid sequence (such as a CDR3 sequence) selected from SEQ ID NO:46 or 50. In still other embodiments, the polypeptide further comprises one or more of the amino acid sequences shown in SEQ ID NOS:3, 4, 5, 6, 7, and 8. In still other embodiments, the polypeptide further comprises one of more of the amino acid sequences shown in SEQ ID NOS:9, 10, 11, 12, 13, 14, and 15.

In another aspect, the invention provides a polypeptide (such as an antibody) comprising an amino acid sequence (such as a CDR region, such as a CDRH1 and/or CDR H2 region) selected from (a) SEQ ID NOS:28 and/or 29; (b) SEQ ID NOS:30 and/or 31; (c) SEQ ID NOS:32 and/or 33; (d) SEQ ID NOS:34 and/or 35; (e) SEQ ID NOS:36 and/or 37; (f) SEQ ID NOS:38 and/or 39; and (g) SEQ ID NOS:40 and 41. In some embodiments, the polypeptide comprises an amino acid sequence (such as a CDR H1 region) selected from SEQ ID NOS:28, 30, 32, 34, 36, 38, and 40. In some embodiments, the polypeptide comprises an amino acid sequence (such as a CDR H2 region) selected from SEQ ID NOS:29, 31, 33, 35, 37, 39 and 41. In still other embodiments, the polypeptide further comprises one or more of the amino acid sequences shown in SEQ ID NOS:3, 4, 5, 6, 7, and 8. In still other embodiments, the polypeptide further comprises one of more of the amino acid sequences shown in SEQ ID NOS:9, 10, 11, 12, 13, 14, and 15.

In another aspect, the invention provides a polypeptide (such as an antibody) comprising an amino acid sequence (such as a CDR region, such as a CDRL1 and/or CDR L2 region) selected from (a) SEQ ID NOS:18 and/or 19; (b) SEQ ID NOS:20 and/or 21; and (c) SEQ ID NOS:22 and/or 23. In some embodiments, the polypeptide comprises an amino acid sequence (such as a CDR L1 region) selected from SEQ ID NOS:18, 20, and 22. In some embodiments, the polypeptide comprises an amino acid sequence (such as a CDR L2 region) selected from SEQ ID NOS:19, 21, and 23. In still other embodiments, the polypeptide further comprises one or more of the amino acid sequences shown in SEQ ID NOS:3, 4, 5, 6, 7, 8. In still other embodiments, the polypeptide further comprises one of more of the amino acid sequences shown in SEQ ID NOS:9, 10, 11, 12, 13, 14, and 15.

In another aspect, the invention provides a polypeptide (such as an antibody) comprising an amino acid sequence (such as a CDR region, such as a CDRL3 and/or CDR H3 region) selected from (a) SEQ ID NOS:51 and/or 52; (b) SEQ ID NOS:55 and/or 56; (c) SEQ ID NOS:57 and/or 58; (c) SEQ ID NOS:59 and/or 60; (d) SEQ ID NOS:61 and/or 62; (e) SEQ ID NOS:63 and/or 64. In some embodiments, the polypeptide comprises an amino acid sequence (such as a CDR L3 region) selected from SEQ ID NOS:51, 55, 57, 59, 61, and 63. In some embodiments, the polypeptide comprises an amino acid sequence (such as a CDR H3 region) selected from SEQ ID NOS:52, 56, 58, 60, 62, and 64. In still other embodiments, the polypeptide further comprises an amino acid sequence shown in one or more of SEQ ID NOS:18, 19, 30 and 31. In still other embodiments, the polypeptide further comprises one or more of the amino acid sequences shown in SEQ ID NOS:3, 4, 5, 6, 7, and 8. In still other embodiments, the polypeptide further comprises one of more of the amino acid sequences shown in SEQ ID NOS:9, 10, 11, 12, 13, 14, and 15.

In another aspect, the invention provides a polypeptide (such as an antibody) comprising one or more of an amino acid sequence (such as a CDR region) shown in SEQ ID NOS:61, 63, 18, 19, 30 and 31.

In one aspect, the invention provides an anti-NGF antibody (such as an antagonist antibody) that binds NGF (such as human NGF) with a high affinity. In some embodiments, high affinity is (a) binding NGF with a $K_D$ of less than about 2 nM (such as any of about 1 nM, 800 pM, 600 pM, 400 pM, 200 pM, 100 pM, 90 pM, 80 pM, 70 pM, 60 pM, 50 pM, or less), and/or a $k_{off}$ of slower than about $6 \times 10^{-5}$ $s^{-1}$); and/or (b) inhibiting (reducing, and/or blocking) human NGF-dependent survival of mouse E13.5 trigeminal neurons with an IC50 (in the presence of about 15 pM of NGF) of about any of 200 pM, 150 pM, 100 pM, 80 pM, 60 pM, 40 pM, 20 pM, 10 pM, or less; and/or (c) inhibiting (reducing, and/or blocking) human NGF-dependent survival of mouse E13.5 trigeminal neurons with an IC50 (in the presence of about 1.5 pM of NGF) of about any of 50 pM, 40 pM, 30 pM, 10 pM, 20 pM, 10 pM, 5 pM, 2 pM, 1 pM, or less; and/or (d) inhibiting (reducing, and/or blocking) rat NGF-dependent survival of mouse E13.5 trigeminal neurons with an IC50 (in the presence of about 15 pM of NGF) of about any of 150 pM, 125 pM, 100 pM, 80 pM, 60 pM, 40 pM, 30 pM, 20 pM, 10 pM, 5 pM, or less; and/or (e) inhibiting (reducing, and/or blocking) rat NGF-dependent survival of mouse E13.5 trigeminal neurons with an IC50 (in the presence of about 1.5 pM of NGF) of about any of 30 pM, 25 pM, 20 pM, 15 pM, 10 pM, 5 pM, 4 pM, 3 pM, 2 pM, 1 pM, or less; and/or (f) and/or bind NGF with higher affinity than does the trkA receptor.

In another aspect, the invention provides polypeptides (such as an antibody), wherein the polypeptides (a) bind NGF (such as human NGF) with a $K_D$ of less than about 2 nM (such as any of about 1 nM, 800 pM, 600 pM, 400 pM, 200 pM, 100 pM, 90 pM, 80 pM, 70 pM, 60 pM, 50 pM, or less), and/or a $k_{off}$ of slower than about $6 \times 10^{-5}$ $s^{-1}$); and/or (b) inhibit human NGF-dependent survival of mouse E13.5 trigeminal neurons with an IC50 (in the presence of about 15 pM of NGF) of about any of 200 pM, 150 pM, 100 pM, 80 pM, 60 pM, 40 pM, 20 pM, 10 pM, or less; and/or (c) inhibit human NGF-dependent survival of mouse E13.5 trigeminal neurons with an IC50 (in the presence of about 1.5 pM of NGF) of about any of 50 pM, 40 pM, 30 pM, 10 pM, 20 pM, 10 pM, 5 pM, 2 pM, 1 pM, or less; and/or bind NGF with higher affinity than does the trkA receptor. In some embodiments, the polypeptides (a) bind NGF with a $K_D$ of less than about 2 nM; and/or (b) inhibit human NGF-dependent survival of mouse E13.5 trigeminal neurons with an IC50 of about 100 pM or less, wherein the IC50 is measured in the presence of about 15 pM NGF; and/or (c) inhibit human NGF-dependent survival of mouse E13.5 trigeminal neurons with an IC50 of about 10 pM or less, wherein the IC50 is measured in the presence of about 1.5 pM of NGF, wherein the IC50 is measured in the presence of about 15 pM NGF. In some embodiments, the polypeptides (a) bind NGF with a $K_D$ of less than about 100 pM; and/or (b) inhibit human NGF-dependent survival of mouse E13.5 trigeminal neurons with an IC50 of about 20 pM or less, wherein the IC50 is measured in the presence of about 15 pM NGF; and/or (c) inhibit human NGF-dependent survival of mouse E13.5 trigeminal neurons with an IC50 of about 2 pM or less, wherein the IC50 is measured in the presence of about 1.5 pM of NGF.

As is evident from the description herein, specifically excluded from the invention are polypeptide embodiments consisting of the identical amino acid sequence to an amino acid sequence of mouse monoclonal antibody, 911. The extended CDR sequences of Mab 911 are shown in FIGS. 1A and 1B, and in SEQ ID NOS:9-14.

In some embodiments, the invention provides any of the above polypeptides or antibodies, further wherein the polypeptide (such as an antibody) is isolated. In some embodiments, the polypeptide (such as an antibody) is substantially purified. In still other embodiments, the polypeptide (such as an antibody) is affinity natured. In other embodiments, the antibody is an antagonist antibody. In some embodiments, the polypeptide (such as an antibody) comprises human framework sequences. In still other embodiments, the polypeptide (such as an antibody) comprises one or more non-human framework residues. In some embodiments, the polypeptide (such as an antibody) binds NGF (such as human NGF) with a $K_D$ of 2 nM or less. In some embodiments, the polypeptide comprises one or more (such as 2, 3, 4, 5, 6, 7, 8, or more) human amino acid substitutions relative to a non-human amino acid sequence (such as a variable region sequence, such as a CDR sequence, such as a framework sequence). In some embodiments the polypeptide comprises at least 1, at least 2, or more such as at least 3, 4, 5, 6, or more amino acid substitutions relative to a parent polypeptide amino acid sequence (such as an antibody 911 amino acid sequence, such as any one or more of SEQ ID NOs 9-14). In some embodiments, the binding affinity of the antibody has been altered (in some embodiments, increased) relative to a parent antibody (such as Mab 911) affinity. In still other embodiments, the binding affinity of the antibody is lower than the binding affinity of trkA receptor for NGF (such as human NGF). In some embodiments, the polypeptides may be antibodies. In some embodiments, the antibodies are human antibodies. In other embodiments, the antibodies are humanized antibodies. In still other embodiments, the antibodies are monoclonal antibodies. In some embodiments, the antibody is an affinity matured antibody.

The invention provides polynucleotides (including isolated polynucleotide) comprising polynucleotides encoding any of the embodiments above.

In another aspect, the invention provides an isolated polynucleotide comprising a polynucleotide encoding a fragment or a region of the antibody E3 (interchangeably termed "E3" herein). In one embodiment, the fragment is a light chain of the antibody E3 as shown in FIG. 1B. In another embodiment, the fragment is a heavy chain of the antibody E3 as shown in FIG. 1A. In yet another embodiment, the fragment contains one or more variable regions from a light chain and/or a heavy chain of the antibody E3. In yet another embodiment, the fragment contains one or more complementarity determining regions (CDRs) from a light chain and/or a heavy chain of the antibody E3 as shown in FIGS. 1A and 1B.

In another aspect, the invention is an isolated polynucleotide comprising a polynucleotide that encodes for antibody E3. In some embodiments, the polynucleotide comprises either or both of the polynucleotide shown in FIGS. 2 and 3.

In another aspect, the invention is an isolated polynucleotide that encodes for an E3 light chain with a deposit number of ATCC No. PTA-4893 or ATCC No. PTA-4894. In another aspect, the invention is an isolated polynucleotide that encodes for an E3 heavy chain with a deposit number of ATCC No. PTA-4895. In yet another aspect, the invention is an isolated polynucleotide comprising (a) a variable region encoded in the polynucleotide with a deposit number of ATCC No. PTA-4893 or PTA-4894 and (b) a variable region encoded in the polynucleotide with a deposit number of ATCC No. PTA-4895. In another aspect, the invention is an isolated polynucleotide comprising (a) one or more CDR encoded in the polynucleotide with a deposit number of ATCC No. PTA-4893 or PTA-4894; and/or (b) one or more CDR encoded in the polynucleotide with a deposit number of ATCC No. PTA-4895.

In another aspect, the invention provides polynucleotides encoding any of the antibodies (including antibody fragments) or polypeptides described herein.

In another aspect, the invention provides vectors (including expression and cloning vectors) and host cells comprising any of the polynucleotide disclosed herein.

As is evident from the description herein, specifically included from the invention are polynucleotide embodiments consisting of the identical polynucleotide sequence to a polynucleotide sequence of mouse monoclonal antibody, 911. The extended CDR sequences of Mab 911 are shown in FIGS. 1A and 1B, and in SEQ ID NOS:9-14.

In another aspect, the invention is a host cell comprising a polynucleotide encoding E3 light chain and a polynucleotide encoding E3 heavy chain, wherein the polynucleotide(s) encoding E3 light chain has a deposit number of ATCC No. PTA-4893 and/or ATCC No. PTA-4894, and the polynucleotide encoding E3 heavy chain has a deposit number of ATCC No. PTA-4895. In some embodiments, the host cell comprises polynucleotide comprising (a) a variable region encoded in the polynucleotide with a deposit number of ATCC No. PTA-4893 or PTA-4894 and/or (b) a variable region encoded in the polynucleotide with a deposit number of ATCC No. PTA-4895. In some embodiments, the host cell comprises a polynucleotide encoding (a) one or more CDR encoded in the polynucleotide with a deposit number of ATCC No. PTA-4893 or PTA-4894; and/or (b) one or more CDR encoded in the polynucleotide with a deposit number of ATCC No. PTA-4895. In some embodiments, the host cell is a mammalian cell.

In another aspect, the invention is a complex of NGF bound by antibody E3. In another aspect, the complex is isolated. In another aspect, the complex is substantially purified.

In another aspect, the invention is a complex of NGF bound by any of the antibodies or polypeptides described herein. In another aspect, the complex is isolated. In another aspect, the complex is substantially purified.

In another aspect, the invention is a pharmaceutical composition comprising any of the polypeptides (including antibodies such as antibody E3) or polynucleotides described herein, such as pharmaceutical compositions comprising the antibody E3 or an antibody comprising a fragment of the antibody E3, and a pharmaceutically acceptable excipient.

In another aspect, the invention is a method of generating antibody E3 comprising preparing a host cell comprising an expression vector that encodes for antibody E3; culturing the host cell or progeny thereof under conditions that allow production of antibody E3; and purifying the antibody E3. In some embodiments, the expression vector comprises one or both of the polynucleotide sequences shown in FIGS. 2 and 3.

In another aspect, the invention is a method of generating antibody E3 comprising expressing a polynucleotide encoding E3 light chain and a polynucleotide encoding E3 heavy chain in a suitable cell, wherein the polynucleotide encoding E3 light chain has a deposit number of ATCC No. PTA-4893 and/or ATCC No. PTA-4894, and the polynucleotide encoding E3 heavy chain has a deposit number of ATCC No. PTA-4895; generally followed by recovering and/or isolating the antibody.

In another aspect, the invention provides methods of generating any of the polypeptides (such as antibodies) described herein by expressing one or more polynucleotides encoding the antibody (which may be separately expressed as a single light or heavy chain, or both a light and a heavy chain may be expressed from one vector) in a suitable cell, generally followed by recovering and/or isolating the antibody or polypeptides of interest.

In another aspect, the invention is a method of antagonizing NGF (such as human NGF) biological activity using any of the polypeptides (including antibodies such as antibody E3) disclosed herein. In one embodiment, the method comprises contacting human nerve growth factor with any of the polypeptides (including antibody E3) described herein, whereby NGF activity (such as human nerve growth factor activity) is antagonized, reduced, blocked, or suppressed.

In another aspect, the invention is a method of detecting NGF using any of the polypeptides (including antibodies, such as the antibody E3) described herein. The presence of NGF is detected by detecting a complex between NGF and any of the polypeptides described herein (such as antibody E3). The term "detection" as used herein includes qualitative and/or quantitative detection (Measuring levels) with or without reference to a control.

In another aspect, the invention is a method of treating pain by administering an effective amount of a composition comprising the antibody E3 or any of the polypeptide (including antibody) or polynucleotide embodiments described herein. In some embodiments, the pain is post-surgical pain.

In another aspect, the invention is a method for preventing or treating rheumatoid arthritis pain in an individual by administering an effective amount of anti-NGF antagonist antibody to the individual. It has been shown in accordance with the invention that an anti-NGF antagonist antibody is capable of inhibiting or blocking the pain associated with rheumatoid arthritis. In some embodiments, the pain is alleviated within about 24 hours after administering the anti-NGF antagonist antibody. In some embodiments, the pain is alleviated within about 4 days after administering the anti-NGF antagonist antibody. In some embodiments, the pain is alleviated before observing or in the absence of an indication of improvement of the inflammatory condition in the individual.

In another aspect, the invention provides methods for reducing incidence of rheumatoid arthritis pain, ameliorating rheumatoid arthritis pain, suppressing rheumatoid arthritis pain, palliating rheumatoid arthritis pain, and/or delaying the onset, development, or progression of rheumatoid arthritis pain in an individual, said method comprising administering an effective amount of anti-NGF antagonist antibody to the individual.

In another aspect, the invention provides methods for treating inflammatory cachexia (weight loss) associated with rheumatoid arthritis in an individual comprising administering an effective amount of an anti-NGF antagonist antibody.

In another aspect, the invention is a method for preventing or treating osteoarthritis pain in an individual by administering an effective amount of an antagonist of nerve growth factor (such as an anti-NGF antagonist antibody) to the individual.

In another aspect, the invention provides methods for reducing incidence of osteoarthritis pain, ameliorating osteoarthritis pain, suppressing osteoarthritis pain, palliating osteoarthritis pain, and/or delaying the onset, development, or progression of osteoarthritis pain in an individual, said method comprising administering an effective amount of an antagonist of NGF (such as anti-NGF antagonist antibody) to the individual.

In another aspect, the invention provides methods for improving physical function in an individual having osteoarthritis, said method comprising administering an effective amount of an antagonist of NGF (such as anti-NGF antagonist antibody) to the individual.

In another aspect, the invention provides methods for improving stiffness in an individual having osteoarthritis, said method comprising administering an effective amount of an antagonist of NGF (such as anti-NGF antagonist antibody) to the individual.

In some embodiments, the individual is a human. In some embodiments, for treating osteoarthritis pain, dosing frequency of anti-NGF antagonist antibody is between once every week and once every 10 weeks, or less frequent.

In another aspect, the invention provides kits and compositions comprising any one or more of the compositions described herein. These kits, generally in suitable packaging and provided with appropriate instructions, are useful for any of the methods described herein. The invention also provides pharmaceutical compositions for use in any of the methods described herein, which compositions comprise an effective amount of an NGF antagonist (such as an anti-NGF antibody) and a pharmaceutically acceptable carrier.

The invention also provides any of the compositions and kits described for any use described herein whether in the context of use as medicament and/or use for manufacture of a medicament.

BRIEF DESCRIPTION OF THE FIGURES

FIG. 1A: shows the amino acid sequence of the heavy chain variable region of the E3 antibody (labeled "6" and "5+ affinity maturation H3). The Chothia CDRs and Kabat CDRs are depicted by underlined text and bold and italicized text, respectively. FIG. 1A also shows the alignment of the following heavy chain variable region amino acid sequences; (2) VH4-59 human germline acceptor sequence (labeled "VH4-59" or "2") (SEQ ID NO:69); (3) the acceptor sequences grafted with the extended CDRs of the mouse antibody 911 (labeled "CDR grafted" or "3") (SEQ ID NO:70); (4) the CDR grafted acceptor sequences including the V71K substitution (labeled ""3+ one framework mutation" or "4") (SEQ ID NO:71); (5) the clone containing affinity matured CDRs H1 and H2 (labeled "5" or "4+ affinity maturation H1, H2") (SEQ ID NO:72); and antibody E3 (as described above).

FIG. 1B: shows the amino acid sequence of the light chain variable region of the E3 antibody (labeled. "5" or "4+ affinity maturation L3). The Chothia CDRs and Kabat CDRs are depicted by underlined text and bold and italicized text, respectively. FIG. 1B also shows the alignment of the following light chain variable region amino acid sequences: (2) O8 human germline acceptor sequence (labeled "O8" or "2") (SEQ ID NO:73); (3) the acceptor sequences grafted with the extended CDRs of the mouse antibody 911 (labeled "CDR grafted" or "3") (SEQ ID NO:74); (4) the CDR grafted acceptor sequences (labeled ""3+ affinity maturation L1, L2" or "4") (SEQ ID NO:75); (5) the clone containing affinity matured CDRs L1 and L2 (labeled "5" or "4+ affinity maturation L3"); and antibody E3 (as described above).

FIG. 2: shows a polynucleotide comprising a polynucleotide sequence encoding the heavy chain variable region of antibody E3 (SEQ ID NO:76).

FIG. 3: shows a polynucleotide comprising a polynucleotide sequence encoding the light chain variable region of antibody E3 (SEQ ID NO:77).

FIG. 5: is a graph comparing the NGF blocking effect of various Fabs in the presence of either 0.04 ng/ml of human NGF (approximately 1.5 pM; shown in lower panel) or 0.4 ng/ml human NGF (approximately 15 pM; shown in upper panel). Survival of E13.5 mouse trigeminal neurons in various concentrations of Fab E3; murine 911 Fab; and Fab H19-L129 and Fab 8L2-6D5 was assessed. The IC50 (in pM) was calculated for each Fab at each NGF concentration, and is shown in Table 9. Fab E3 strongly blocked human NGF-dependent trigeminal neuron survival, with an IC50 of approximately 21 pM in the presence of 15 pM human NGF, and an IC50 of approximately 1.2 pM in the presence of 1.5 pM human NGF. Fabs 3C and H19-L129 also strongly blocked human NGF-dependent trigeminal neuron survival. In both panels, the X axis corresponds to antibody concentration (nM) and the Y axis corresponds to counted neurons. 1.5 pM of NGF was around the IC50, while 15 pM represented a saturating concentration of NGF.

FIG. 6: is a graph comparing the NGF blocking effect of various Fabs in the presence of either 0.04 ng/ml of rat NGF (approximately 1.5 pM; shown in lower panel) or 0.4 ng/ml rat NGF (approximately 15 pM; shown in upper panel). Survival of E13.5 mouse trigeminal neurons in various concentrations of Fab E3; murine Fab 911; and Fab H19-L129 and 8L2-6D5 was assessed as described above. The IC50 (in pM) was calculated for each Fab at each NGF concentration, and is shown in Table 9. Fab E3 strongly blocked human NGF-dependent trigeminal neuron survival, with an IC50 of approximately 31.6 pM in the presence of 15 pM rat NGF, and an IC50 of approximately 1.3 pM in the presence of 1.5 pM rat NGF. Fabs 3C and H19-L129 also strongly blocked rat NGF-dependent trigeminal neuron survival. 1.5 pM of NGF was around the IC50, while 15 pM represented a saturating concentration of NGF. In both panels, the X axis corresponds to antibody concentration (nM) and the Y axis corresponds to counted neurons.

FIG. 23: depicts the E3 heavy chain variable region amino acid sequence (FIG. 23A) and light chain variable region amino acid sequence (FIG. 23B), as numbered using sequential numbering, Kabat numbering, and Chothia numbering.

DETAILED DESCRIPTION OF THE INVENTION

Figure 4:
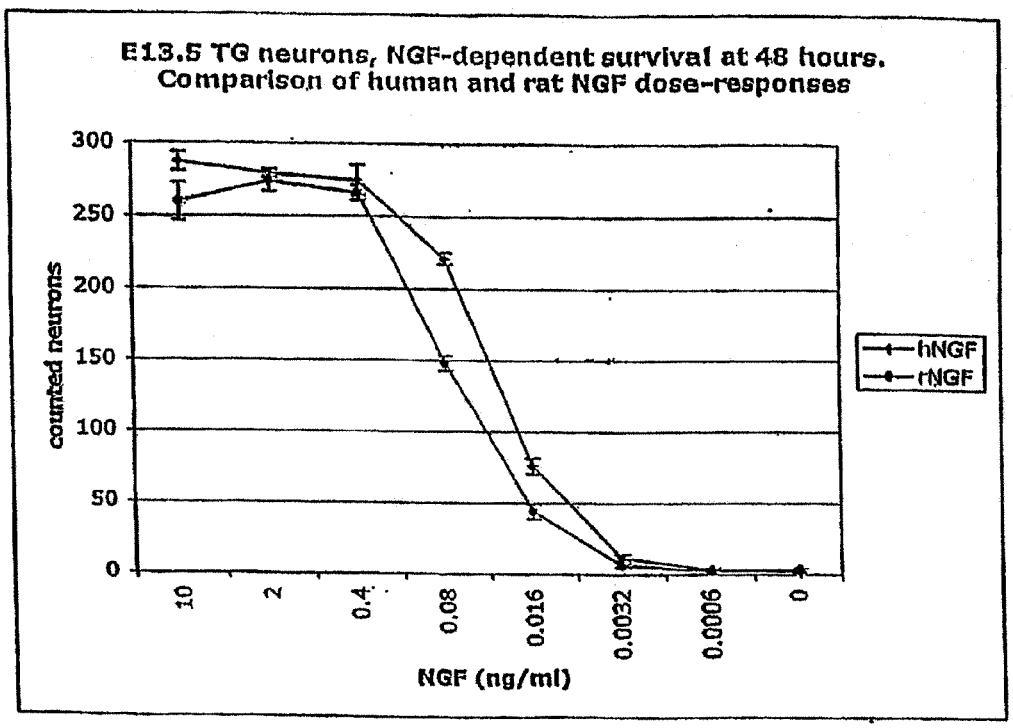
FIG. 4: is a graph depicting NGF-dependent survival of E13.5 neurons in the presence of varying concentration of human and rat NGF. The X axis corresponds to NGF concentration (ng/ml) and the Y axis corresponds to counted neurons.

The invention disclosed herein provides anti-NGF antagonist antibodies that bind NGF (such as human NGF) with high affinity. The invention further provides antibodies and polypeptides derived from E3 that bind NGF, and methods of making and using these antibodies. In some embodiments, the invention provides a humanized antibody, E3, which binds to nerve growth factor ("NGF"), and methods of making and using this antibody. The invention also provides E3 polypeptides (including antibodies) that bind NGF, and polynucleotides encoding E3 antibody and/or polypeptide.

The invention disclosed herein also provides methods for preventing and/or treating rheumatoid arthritis pain in an individual by administration of a therapeutically effective amount of an anti-NGF antagonist antibody.

The invention disclosed herein also provides methods for preventing and/or treating osteoarthritis pain in an individual by administration of a therapeutically effective amount of an antagonist of NGF (such as an anti-NGF antagonist antibody).

The invention also provides methods for adjusting the affinity of an antibody and methods for characterizing a CDR region.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989) Cold Spring Harbor Press; Oligonucleotide Synthesis (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-1998) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

DEFINITIONS

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known "Fv" is an antibody fragment that contains a complete antigen-recognition and -binding site. In a two-chain Fv species, this region consists of a dimer of one heavy and one light chain variable domain in tight, non-covalent association. In a single-chain Fv species, one heavy and one light chain variable domain can be covalently linked by a flexible peptide linker such that the light and heavy chains can associate in a dimeric structure analogous to that in a two-chain Fv species. It is in this configuration that the three CDRs of each variable domain interact to define an antigen-binding specificity on the surface of the VH-VL dimer. However, even a single variable domain (or half of a Fv comprising only 3 CDRs specific for an antigen) has the ability to recognize and bind antigen, although generally at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge regions.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies is highly specific, being directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, *Nature Biotechnology*, 14:309-314; Sheets et al., 1998, *PNAS*, (USA) 95:6157-6162; Hoogenboom and Winter, 1991, *J. Mol. Biol.*, 227:381; Marks et al., 1991, *J. Mol. Biol.*, 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., *Monoclonal Antibodies and Cancer Therapy*, Alan R. Liss, p. 77 (1985); Boerner et al., 1991, *J. Immunol.*, 147 (1):86-95; and U.S. Pat. No. 5,750,373.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

A "functional Fc region" possesses at least one effector function of a native sequence Fc region. Exemplary "effector functions" include C1q binding; complement dependent cytotoxicity (CDC); Fc receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in a animal model such as that disclosed in Clynes et al., 1998, *PNAS* (USA), 95:652-656.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, *Ann. Rev. Immunol.*, 9:457-92; Capel et al., 1994, *Immunomethods*, 4:25-34; and de Haas et al., 1995, *J. Lab. Clin. Med.*, 126:330-41. "FcR" also includes the neonatal receptor, FcRn, which is responsible for the transfer of maternal IgGs to the fetus (Guyer et al., 1976, *J. Immunol.*, 117:587; and Kim et al., 1994, *J. Immunol.*, 24:249).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202:163 (1996), may be performed.

Figures 1A, 1B:
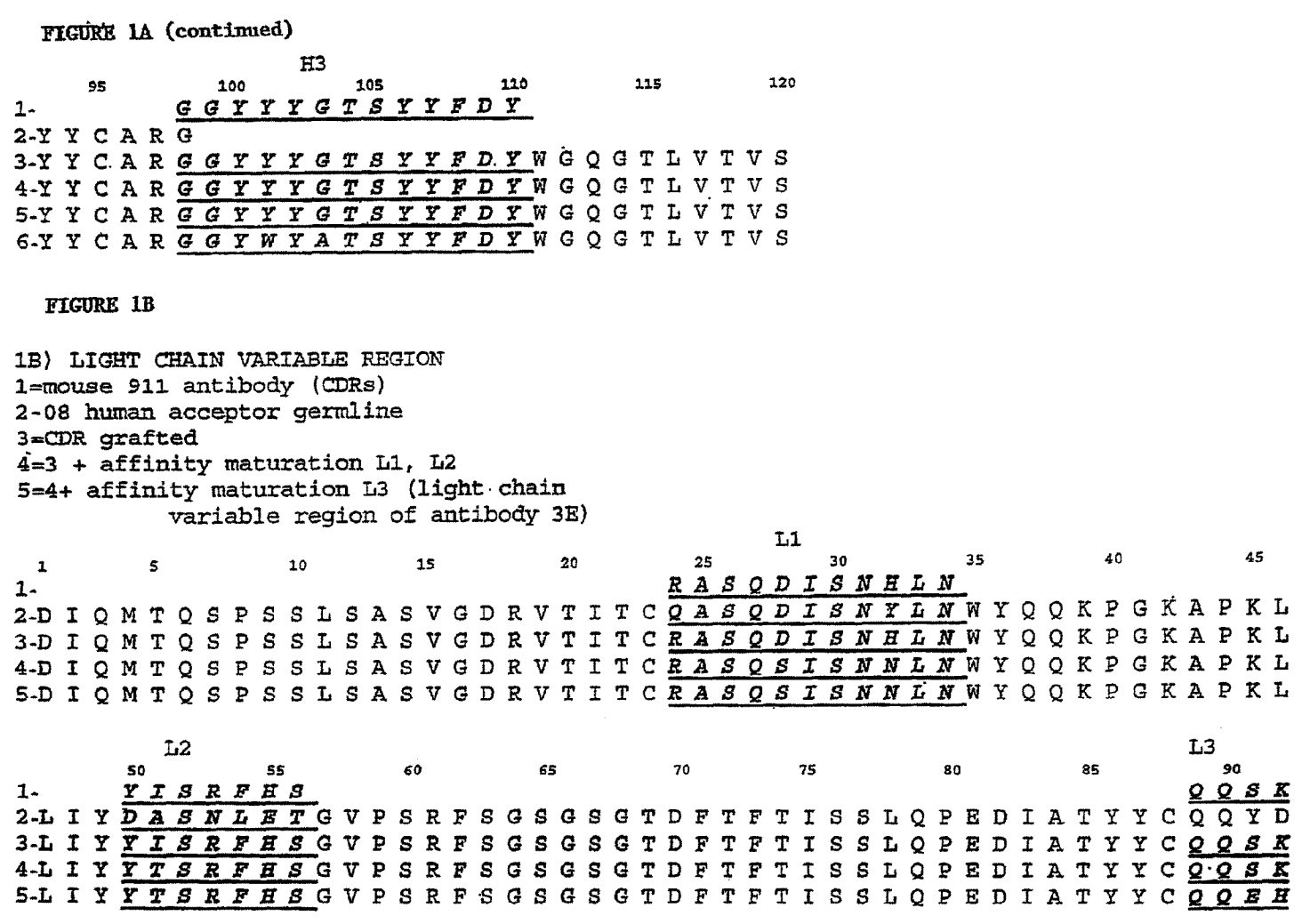

As used herein, the terms "E3", "3E", and "antibody E3" are used interchangeably to refer to an antibody comprising the amino acid sequence of the heavy chain and light chain variable regions shown in FIGS. 1A (SEQ ID NO:1) and 1B (SEQ ID NO:2), respectively. The CDR portions of antibody E3 (including Chothia and Kabat CDRs) are diagrammatically depicted in FIGS. 1A and 1B. FIGS. 2 and 3 show polynucleotides encoding heavy and light chains, respectively, comprising the heavy and light chain variable regions shown in FIGS. 1A and 1B, respectively. The generation and characterization of E3 is described in the Examples. Different biological functions are associated with E3, including, but not limited to, ability to bind to NGF and inhibit NGF biological activity and/or downstream pathway(s) mediated by NGF signaling; and ability to inhibit NGF-dependent survival of mouse E13.5 trigeminal neurons. As discussed herein, antibodies of the invention may have any one or more of these characteristics. In some embodiments, the term "E3" refers to immunoglobulin encoded by (a) a polynucleotide encoding E3 light chain that has a deposit number of ATCC No. PTA-4893 or ATCC No. PTA-4894, and (b) a polynucleotide encoding E3 heavy chain that has a deposit number of ATCC No. PTA-4895.

As used herein, "immunospecific" binding of antibodies refers to the antigen specific binding interaction that occurs between the antigen-combining site of an antibody and the specific antigen recognized by that antibody (i.e., the antibody reacts with the protein in an ELISA or other immunoassay, and does not react detectably with unrelated proteins).

An epitope that "specifically binds", or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an NGF epitope is an antibody that binds this epitope with greater affinity, avidity, more readily, and/or with greater duration than it binds to other NGF epitopes or non-NGF epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2% azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence Variability (i.e., Kabat et al. *Sequences of Proteins of Immunological Interest*, (5th ed., 1991, National Institutes of Health, Bethesda Md.)); and (2) an approach based on crystallographic studies of antigen-antibody complexes (Chothia et al. (1989) *Nature* 342:877; Al-lazikani et al (1997) *J. Molec. Biol.* 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

As used herein, the term "nerve growth factor" and "NGF" refers to nerve growth factor and variants thereof that retain at least part of the biological activity of NGF. As used herein, NGF includes all mammalian species of native sequence NGF, including human, canine, feline, equine, or bovine.

"NGF receptor" refers to a polypeptide that is bound by or activated by NGF. NGF receptors include the TrkA receptor and the p75 receptor of any mammalian species, including, but are not limited to, human, canine, feline, equine, primate, or bovine.

As used herein, an "anti-NGF antagonist antibody" (interchangeably termed "anti-NGF antibody") refers to an antibody which is able to bind to NGF and inhibit NGF biological activity and/or downstream pathway(s) mediated by NGF signaling. An anti-NGF antagonist antibody encompasses antibodies that block, antagonize, suppress or reduce (including significantly) NGF biological activity, including downstream pathways mediated by NGF signaling, such as receptor binding and/or elicitation of a cellular response to NGF. For purpose of the present invention, it will be explicitly understood that the term "anti-NGF antagonist antibody" encompass all the previously identified terms, titles, and functional states and characteristics whereby the NGF itself, an NGF biological activity (including but not limited to its ability to ability to mediate any aspect of post-surgical pain), or the consequences of the biological activity, are substantially nullified, decreased, or neutralized in any meaningful degree. In some embodiments, an anti-NGF antagonist antibody binds NGF and prevent NGF dimerization and/or binding to an NGF receptor (such as p75 and/or trkA). In other embodiments, an anti-NGF antibody binds NGF and prevents trkA receptor dimerization and/or trkA autophosphorylation. Examples of anti-NGF antagonist antibodies are provided herein.

"Biological activity" of NGF generally refers to the ability to bind NGF receptors and/or activate NGF receptor signaling pathways. Without limitation, a biological activity includes any one or more of the following: the ability to bind an NGF receptor (such as p75 and/or trkA); the ability to promote trkA receptor dimerization and/or autophosphorylation; the ability to activate an NGF receptor signaling pathway; the ability to promote cell differentiation, proliferation, survival, growth and other changes in cell physiology, including (in the case of neurons, including peripheral and central neuron) change in neuronal morphology, synaptogenesis, synaptic function, neurotransmitter and/or neuropeptide release and regeneration following damage; the ability to promote survival of mouse E13.5 trigeminal neurons; and the ability to mediate pain, including post-surgical pain.

As used herein, "substantially pure" refers to material which is at least 50% pure (i.e., free from contaminants), more preferably at least 90% pure, more preferably at least 95% pure, more preferably at least 98% pure, more preferably at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "treatment" is an approach for obtaining beneficial or desired clinical results. For purposes of this invention, beneficial or desired clinical results include, but are not limited to, one or more of the following: improvement or alleviation of any aspect of pain, including acute, chronic, inflammatory, neuropathic, post-surgical pain, rheumatoid arthritis pain, or osteoarthritis pain. For purposes of this invention, beneficial or desired clinical results include, but are not limited to, one or more of the following: including lessening severity, alleviation of one or more symptoms associated with pain including any aspect of pain (such as shortening duration of pain, reduction of pain sensitivity or sensation).

An "effective amount" of drug, compound, or pharmaceutical composition is an amount sufficient to effect beneficial or desired results including clinical results such as alleviation or reduction in pain sensation. An effective amount can be administered in one or more administrations. For purposes of this invention, an effective amount of drug, compound, or pharmaceutical composition is an amount sufficient to treat, ameliorate, reduce the intensity of and/or prevent pain, including post-surgical pain, rheumatoid arthritis pain, and/or osteoarthritis pain. In some embodiments, the "effective amount" may reduce pain at rest (resting pain) or mechanically-induced pain (including pain following movement), or both, and it may be administered before, during or after an incision, cut, tear or injury and/or before, during or after painful stimulus. As is understood in the clinical context, an effective amount of a drug, compound, or pharmaceutical composition may or may not be achieved in conjunction with another drug, compound; or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

"Reducing incidence" of pain means any of reducing severity (which can include reducing need for and/or amount of (e.g., exposure to) other drugs and/or therapies generally used for this conditions, including, for example, opiates), duration, and/or frequency (including, for example, delaying or increasing time to post-surgical pain in an individual). As is understood by those skilled in the art, individuals may vary in terms of their response to treatment, and, as such, for example, a "method of reducing incidence of rheumatoid arthritis pain or osteoarthritis pain in an individual" reflects administering the anti-NGF antagonist antibody based on a reasonable expectation that such administration may likely cause such a reduction in incidence in that particular individual.

"Ameliorating" a pain or one or more symptoms of a pain (such as rheumatoid arthritis pain or osteoarthritis pain) means a lessening or improvement of one or more symptoms of a pain as compared to not administering an anti-NGF antagonist antibody. "Ameliorating" also includes shortening or reduction in duration of a symptom.

"Palliating" a pain or one or more symptoms of a pain (such as rheumatoid arthritis pain or osteoarthritis pain) means lessening the extent of one or more undesirable clinical manifestations of post-surgical pain in an individual or population of individuals treated with an anti-NGF antagonist antibody in accordance with the invention.

As used therein, "delaying" the development of pain means to defer, hinder, slow, retard, stabilize, and/or postpone progression of pain, such as post-surgical pain, rheumatoid arthritis pain, or osteoarthritis pain. This delay can be of varying lengths of time, depending on the history of the disease and/or individuals being treated. As is evident to one skilled in the art, a sufficient or significant delay can, in effect, encompass prevention, in that the individual does not develop pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Pain" as used herein refers to pain of any etiology, including acute and chronic pain, and any pain with an inflammatory component. Examples of pain include post-surgical pain, post-operative pain (including dental pain), migraine, headache and trigeminal neuralgia, pain associated with burn, wound or kidney stone, pain associated with trauma (including traumatic head injury), neuropathic pain, pain associated with musculo-skeletal disorders such as rheumatoid arthritis, osteoarthritis, ankylosing spondylitis, sero-negative (non-rheumatoid) arthropathies, non-articular rheumatism and peri-articular disorders, and pain associated with cancer (including "break-through pain" and pain associated with terminal cancer), peripheral neuropathy and post-herpetic neuralgia. Examples of pain with an inflammatory component (in addition to some of those described above) include rheumatic pain, pain associated with mucositis, and dysmenorrhea.

"Post-surgical pain" (interchangeably termed "post-incisional" or "post-traumatic pain") refers to pain arising or resulting from an external trauma such as a cut, puncture, incision, tear, or wound into tissue of an individual (including that that arises from all surgical procedures, whether invasive or non-invasive). As used herein, post-surgical pain does not include pain that occurs (arises or originates) without an external physical trauma. In some embodiments, post-surgical pain is internal or external (including peripheral) pain, and the wound, cut, trauma, tear or incision may occur accidentally (as with a traumatic wound) or deliberately (as with a surgical incision). As used herein, "pain" includes nociception and the sensation of pain, and pain can be assessed objectively and subjectively, using pain scores and other methods well-known in the art. Post-surgical pain, as used herein, includes allodynia (i.e., increased response to a normally non-noxious stimulus) and hyperalgesia (i.e., increased response to a normally noxious or unpleasant stimulus), which can in turn, be thermal or mechanical (tactile) in nature. In some embodiments, the pain is characterized by thermal sensitivity, mechanical sensitivity and/or resting pain. In some embodiments, the post-surgical pain comprises mechanically-induced pain or resting pain. In other embodiments, the post-surgical pain comprises resting pain. The pain can be primary or secondary pain, as is well-known in the art.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals (such as cows), sport animals, pets (such as cats, dogs and horses), primates, mice and rats.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" includes any material which, when combined with an active ingredient, allows the ingredient to retain biological activity and is non-reactive with the subject's immune system.

Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$K_{off}$", as used herein, is intended to refer to the off rate constant for dissociation of an antibody from the antibody/antigen complex.

The term "Kd", as used herein, is intended to refer to the dissociation constant of an antibody-antigen interaction.

Antibody E3, E3-Derived Antibodies, Compositions, And Methods of Use

E3 Compositions, E3 Derived Compositions, and Methods of Making the Compositions This invention encompasses compositions, including pharmaceutical compositions, comprising an E3 antibody or polypeptide; and polynucleotides comprising sequences encoding an E3 antibody or polypeptide. As used herein, compositions comprise one or more antibodies or polypeptides (which may or may not be an antibody) that bind to NGF, and/or one or more polynucleotides comprising sequences encoding one or more antibodies or polypeptides that bind to NGF. These compositions may further comprise suitable excipients, such as pharmaceutically acceptable excipients including buffers, which are well known in the art.

The invention also encompasses isolated antibody, polypeptide and polynucleotide embodiments. The invention also encompasses substantially pure antibody, polypeptide and polynucleotide embodiments.

The antibodies and polypeptides of the invention are characterized by any (one or more) of the following characteristics: (a) ability to bind to NGF; (b) ability to reduce and/or inhibit NGF biological activity and/or downstream pathway(s) mediated by NGF signaling; (c) ability to reduce and/or inhibit NGF-dependent survival of mouse E13.5 trigeminal neurons; (d) absence of any significant cross-reactivity to NT3, NT4/5, and/or BDNF; (e) ability to treat and/or prevent pain (including post-surgical pain); (f) ability to increase clearance of NGF; (g) ability to reduce or inhibit activation of trkA receptor, as detected, for example, using kinase receptor activation assay (KIRA) (see U.S. Pat. No. 6,027,927).

The binding properties of antibody E3, which binds human NGF with high affinity and slow dissociation kinetics, compared with parent murine anti-NGF monoclonal antibody 911, are summarized below. E3 binds human NGF with an approximately 50-fold higher binding affinity than parent mouse antibody 911.

| antibody | $k_D$ | $K_{off}$ | $K_{on}$ |
|---|---|---|---|
| 911 (Fab) | 3.7 nM | $9 \times 10^{-5}$ s$^{-1}$ | $2.2 \times 10^4$ M$^{-1}$s$^{-1}$ |
| E3 (Fab) | 0.07 nM | $<4 \times 10^{-5}$ s$^{-1}$ | $6 \times 10^5$ M$^{-1}$s$^{-1}$ |

The E3 antibody and related antibodies also exhibit a strong capacity to antagonize human NGF, as assessed by in vitro assays (see Examples 2 and 3). For example, antibody E3 antagonizes the NGF-dependent survival of mouse E13 trigeminal neurons at an IC50 of about 21 pM in the presence of 15 pM of human NGF, and about 1.2 pM in the presence of 1.5 pM of human NGF.

Accordingly, in another aspect, the antibodies and polypeptides of the invention are further identified and characterized by: (h) high affinity binding to human NGF with low dissociation kinetics (in some embodiments, with a $K_D$ of less than about 2 nM, and/or a koff of slower than about $6 \times 10^{-5}$ s$-1$) and/or (i) ability to inhibit (block) NGF-dependent survival of mouse E13.5 trigeminal neurons with an IC50 of about 100 pM or less at about 15 pM of NGF (in some embodiments, human NGF) and/or an IC50 of about 20 pM or less at about 1.5 pM of NGF.

In some embodiments, the antibody binds human NGF, and does not significantly bind an NGF from another vertebrate species (in some embodiment, mammalian). In some embodiments, the antibody binds human NGF as well as one or more NGF from another vertebrate species (in some embodiments, mammalian). In still other embodiments, the antibody binds NGF and does not significantly cross-react with other neurotrophins (such as the related neurotrophins, NT3, NT4/5, and/or BDNF). In some embodiments, the antibody binds NGF as well as at least one other neurotrophin. In some embodiments, the antibody binds to a mammalian species of NGF, such as horse or dog, but does not significantly bind to NGF from anther mammalian species.

In some embodiments, the invention is an antibody comprising a light chain that is encoded by a polynucleotide that is produced by a host cell with a deposit number of ATCC No. PTA-4893 or ATCC No. PTA-4894. In another aspect, the invention is an antibody comprising a heavy chain that is encoded by a polynucleotide that is produced by a host cell with a deposit number of ATCC No. PTA-4895. The present invention also encompasses various formulations of E3 and equivalent antibody fragments (e.g., Fab, Fab', F(ab')$_2$, Fv, Fc, etc.), single chain (ScFv), mutants thereof, fusion proteins comprising an antibody portion, and any other modified configuration of E3 that comprises an antigen (NGF) recognition site of the required specificity. The equivalent antibodies of E3, including antibody and polypeptide fragments (which may or may not be antibodies) of E3, and polypeptides comprising polypeptide fragments of E3 are identified and characterized by any (one or more) of the criteria described above.

Accordingly, the invention provides any of the following, or compositions (including pharmaceutical compositions) comprising any of the following: (a) antibody E3; (b) a fragment or a region of the antibody E3; (c) a light chain of the antibody E3 as shown in FIG. 1B; (c) a heavy chain of the antibody E3 as shown in FIG. 1A; (d) one or more variable region(s) from a light chain and/or a heavy chain of the antibody E3; (e) one or more CDR(s) (one, two, three, four, five or six CDRs) of antibody E3 shown in FIGS. 1A and 1B; (f) CDR H3 from the heavy chain of antibody E3 shown in FIG. 1A; (g) CDR L3 from the light chain of antibody E3 shown in FIG. 1B; (h) three CDRs from the light chain of antibody E3 shown in FIG. 1B; (i) three CDRs from the heavy chain of antibody E3 shown in FIG. 1A; (j) three CDRs from the light chain and three CDRs from the heavy chain, of antibody E3 shown in FIGS. 1A and 1B; and (k) an antibody comprising any one of (b) through (j): As is evident from the description herein, specifically excluded from the invention are polypeptide embodiments consisting of the identical amino acid sequence to an amino acid sequence of mouse monoclonal antibody, 911. The extended CDR sequences of Mab 911 are shown in FIGS. 1A and 1B, and in SEQ ID NOS:9-14.

The CDR portions of antibody E3 (including Chothia and Kabat CDRs) are diagrammatically depicted in FIGS. 1A and 1B, and consist of the following amino acid sequences: (a) heavy chain CDR 1 ("CDR H1") GFSLIGYDLN (SEQ ID NO:3); (b) heavy chain CDR 2 ("CDR H2") IIWGDGTT-DYNSAVKS (SEQ ID NO:4); (c) heavy chain CDR 3 ("CDR H3") GGYWYATSYYFDY (SEQ ID NO:5); (d) light chain CDR 1 ("CDR L1") RASQSISNNLN (SEQ ID NO:6); (e) light chain CDR 2 ("CDR L2") YTSRFHS (SEQ ID NO:7); and (f) light chain CDR 3 ("CDR L3") QQEHTLPYT (SEQ ID NO:8). Determination of CDR regions is well within the skill of the art. It is understood that in some embodiments, CDRs can be a combination of the Kabat and Chothia CDR (also termed "combined CDRs" or "extended CDRs"). In some embodiments, the CDRs comprise the Kabat CDR. In other embodiments, the CDRs are the Chothia CDR.

In some embodiments, the invention provides an antibody which comprises at least one CDR that is substantially homologous to at least one CDR, at least two, at least three, at least four, at least 5 CDRs of E3 (or, in some embodiments substantially homologous to all 6 CDRs of E3, or derived from E3). Other embodiments include antibodies which have at least two, three, four, five, or six CDR(s) that are substantially homologous to at least two, three, four, five or six CDRs of E3 or derived from E3. It is understood that, for purposes of this invention, binding specificity and/or overall activity (which may be in terms of treating and/or preventing pain or inhibiting NGF-dependent survival of E13.5 mouse trigeminal neurons) is generally retained, although the extent of activity may vary compared to E3 (may be greater or lesser).

The invention also provides a polypeptide (which may or may not be an antibody) which comprises an amino acid sequence of E3 (shown in FIGS. 1A and 1B) that has any of the following: at least 5 contiguous amino acids, at least 8 contiguous amino acids, at least about 10 contiguous amino acids, at least about 15 contiguous amino acids, at least about 20 contiguous amino acids, at least about 25 contiguous amino acids, at least about 30 contiguous amino acids of a sequence of E3, wherein at least 3 of the amino acids are from a variable region of E3, with the understanding that embodiments that consist of the identical amino acid sequence to an amino acid sequence of mouse monoclonal antibody, 911, are specifically excluded. The extended CDR sequences of Mab 911 are shown in FIGS. 1A and 1B, and in SEQ ID NOS:9-14. In one embodiment, the variable region is from a light chain of E3. In another embodiment, the variable region is from a heavy chain of E3. In another embodiment, the 5 (or more) contiguous amino acids are from a complementarity determining region (CDR) of E3 shown in FIGS. 1A and 1B.

In another embodiment, the invention provides a polypeptide which comprises an amino acid sequence of E3 that has any of the following: at least 5 contiguous amino acids, at least 8 contiguous amino acids, at least about 10 contiguous amino acids, at least about 15 contiguous amino acids, at least about 20 contiguous amino acids, at least about 25 contiguous amino acids, at least about 30 contiguous amino acids of a sequence of E3, wherein the E3 sequence comprises any one or more of: amino acid residue L29 of CDRH1, I50 of CDRH2, W101 of CDRH3, and/or A103 of CDRH3; and/or amino acid residue S28 of CDRL1, N32 of CDRL1, T51 of CDRL2, 91E of CDRL3 and/or H92 of CDRL3, with the understanding that embodiments that consist of the identical amino acid sequence to an amino acid sequence of mouse monoclonal antibody, 911, are specifically excluded.

As is evident, throughout this disclosure, a sequential amino acid numbering scheme is used to refer to amino acid residues in the variable regions (that is, the amino acid residues in each variable region are numbered in sequence). As is well known in the art, the Kabat and/or Chothia numbering systems, are useful when comparing two antibodies or polypeptides, such as an E3 antibody and an E3 variant (or polypeptide suspected of being an E3 variant). It is well understood in the art how to convert sequential numbering to Chothia and/or Kabat numbering, if desired, for example, for use in making comparisons between E3 and another polypeptide. FIG. 23 depicts the E3 variable regions numbered using sequential, Chothia and Kabat numbering. In addition, to facilitate comparison, generally it is understood that framework residues generally, but not always, have approximately the same number of residues. However, the CDRs may vary in size (i.e., it is possible to have insertions and/or deletions of one or more amino acid residues). When comparing an E3 antibody and a candidate E3 variant (for example, in the case of a CDR region from a candidate sequence which is longer in the sequence in antibody E3 to which is aligned), one may follow the following steps (though other methods are known in the art). The candidate antibody sequence is aligned with E3 antibody heavy chain and light chain variable regions. Alignment may be done by hand, or by computer using commonly accepted computer programs. Alignment may be facilitated by using some amino acid residues which are common to most Fab sequences. For example, the light and heavy chains each typically have two cysteines, which are often found at a conserved position. It is understood that the amino acid sequence of a candidate variant antibody may be longer (i.e. have inserted amino acid residues) or shorter (have deleted amino acid residues). Suffixes may be added to the residue number to indicate the insertion of additional residues, e.g., residue 34 abc. For candidate sequences which, for example, align with a E3 sequence for, e.g., residues 33 and 35, but have no residue between them to align with residue 35, the residue 35 is simply not assigned to a residue. In another approach, it is generally well known that comparison may be made between structural equivalent (e.g., same position in the antigen-antibody complex) amino acids when comparing CDRs of different lengths. For example, the Chothia numbering (Al-Lazikani et al, supra) generally (but not in all cases), places insertions and deletions at the structurally correct positions. Structural equivalence may also be deduced or demonstrated using X-ray crystallography or double mutant cycle analysis (see Pons et al. (1999) Prot. Sci. 8:958-968).

The binding affinity of an anti-NGF antibody to NGF (such as hNGF) can be about 0.10 to about 0.80 nM, about 0.15 to about 0.75 nM and about 0.18 to about 0.72 nM. In some embodiments, the binding affinity is about 2 pM, about 5 pM, about 10 pM, about 15 pM, about 20 pM, about 40 pM, or greater than about 40 pM. In one embodiment, the binding affinity is between about 2 pM and 22 pM. In other embodiments, the binding affinity is less than about 10 nM, about 5 nM, about 4 nM, about 3.5 nM, about 3 nM, about 2.5 nM, about 2 nM, about 1.5 nM, about 1 nM, about 900 pM, about 800 pM, about 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM. In some embodiments, the binding affinity is about 10 nM. In other embodiments, the binding affinity is less than about 10 nM. In other embodiments, the binding affinity is about 0.1 nM or about 0.07 nM. In other embodiments, the binding affinity is less than about 0.1 nM or less than about 0.07 nM. In other embodiments, the binding affinity is any of about 10 nM, about 5 nM, about 4 nM, about 3.5 nM, about 3 nM, about 2.5 nM, about 2 nM, about 1.5 nM, about 1 nM, about 900 pM, about 800 pM, bout 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM to any of about 2 pM, about 5 pM, about 10 pM, about 15 pM, about 20 pM, or about 40 pM. In some embodiments, the binding affinity is any of about 10 nM, about 5 nM, about 4 nM, about 3.5 nM, about 3 nM, about 2.5 nM, about 2 nM, about 1.5 nM, about 1 nM, about 900 pM, about 800 pM, bout 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM. In still other embodiments, the binding affinity is about 2 pM, about 5 pM, about 10 pM, about 15 pM, about 20 pM, about 40 pM, or greater than about 40 pM.

The binding affinity of the antibody to NGF can be determined using methods well known in the art. One way of determining binding affinity of antibodies to NGF is by measuring affinity of monofunctional Fab fragments of the antibody, as described in the Examples. To obtain monofunctional Fab fragments, an antibody (for example, IgG) can be cleaved with papain or expressed recombinantly. The affinity of an anti-NGF Fab fragment of an antibody can be determined by surface plasmon resonance (BIAcore3000™ surface plasmon resonance (SPR) system, BIAcore, INC, Piscataway N.J.), as described in the Examples. This protocol is suitable for use in determining binding affinity of an antibody to NGF of any species, including human NGF, NGF of another vertebrate (in some embodiments, mammalian) (such as mouse NGF, rat NGF, primate NGF), as well as for use with other neurotrophins, such as the related neurotrophins NT3, NT4/5, and/or BDNF.

In some embodiments, the antibodies or peptides of the invention may inhibit (reduce, and/or block) human NGF-dependent survival of mouse E13.5 trigeminal neurons with an IC50 (in the presence of about 15 pM of NGF) of about any of 200 pM, 150 pM, 100 pM, 80 pM, 60 pM, 40 pM, 20 pM, 10 pM, or less. In some embodiments, the antibodies or peptides of the invention may inhibit (reduce, and/or block) human NGF-dependent survival of mouse E13.5 trigeminal neurons with an IC50 (in the presence of about 1.5 pM of NGF) of about any of 50 pM, 40 pM, 30 pM, 10 pM, 20 pM, 10 pM, 5 pM, 2 pM, 1 pM, or less. In some embodiments, the antibodies or peptides of the invention may inhibit (reduce, and/or block) rat NGF-dependent survival of mouse E13.5 trigeminal neurons with an IC50 (in the presence of about 15 pM of NGF) of about any of 150 pM, 125 pM, 100 pM, 80 pM, 60 pM, 40 pM, 30 pM, 20 pM, 10 pM, 5 pM, or less. In some embodiments, the antibodies or peptides of the invention may inhibit (reduce, and/or block) rat NGF-dependent survival of mouse E13.5 trigeminal neurons with an IC50 (in the presence of about 1.5 pM of NGF) of about any of 30 pM, 25 pM, 20 pM, 15 pM, 10 pM, 5 pM, 4 pM, 3 pM, 2 pM, 1 pM, or less. Methods for measurement of the NGF-dependent survival of mouse E13 trigeminal neurons are known in the art, and described, e.g., in Example 2.

The invention also provides methods of making any of these antibodies or polypeptides. The antibodies of this invention can be made by procedures known in the art, some of which are illustrated in the Examples. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, a E3 antibody could be produced by an automated polypeptide synthesizer employing the solid phase method. See also, U.S. Pat. Nos. 5,807,715; 4,816,567; and 6,331,415. Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

In another alternative, the antibodies can be made recombinantly using procedures that are well known in the art. In one embodiment, a polynucleotide comprising a sequence encoding the variable and light chain regions of antibody E3 (shown in FIGS. 1A and 1B) is cloned into a vector for expression or propagation in a host cell (e.g., CHO cells). In another embodiment, the polynucleotide sequences shown in FIGS. 2 and 3 are cloned into one or more vectors for expression or propagation. The sequence encoding the antibody of interest may be maintained in a vector in a host cell and the host cell can then be expanded and frozen for future use. Vectors (including expression vectors) and host cells are further described herein. Methods for expressing antibodies recombinantly in plants or milk have been disclosed. See, for example, Peeters et al. (2001) Vaccine 19:2756; Lonberg, N. and D. Huszar (1995) Int. Rev. Immunol 13:65; and Pollock et al. (1999) J Immunol Methods 231:147. Methods for making derivatives of antibodies, e.g., humanized, single chain, etc. are known in the art.

The invention also encompasses single chain variable region fragments ("scFv") of antibodies of this invention, such as E3. Single chain variable region fragments are made by linking light and/or heavy chain variable regions by using a short linking peptide. Bird et al. (1988) Science 242:423-426. An example of a linking peptide is (GGGGS)3 (SEQ ID NO:15), which bridges approximately 3.5 nm between the carboxy terminus of one variable region and the amino terminus of the other variable region. Linkers of other sequences have been designed and used (Bird et al. (1988)). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

Other forms of single chain antibodies, such as diabodies are also encompassed. Diabodies are bivalent, bispecific antibodies in which VH and VL domains are expressed on a single polypeptide chain but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

The antibody may be a bispecific antibody, a monoclonal antibody that has binding specificities for at least two different antigens. A bispecific antibody can be prepared using the antibodies disclosed herein. Methods for making bispecific antibodies are known in the art (see, e.g., Suresh et al., 1986, Methods in Enzymology 121:210). Traditionally, the recombinant production of bispecific antibodies was based on the coexpression of two immunoglobulin heavy chain-light chain pairs, with the two heavy chains having different specificities (Milstein and Cuello, 1983, Nature 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690, published Mar. 3, 1994.

Heteroconjugate antibodies; comprising two covalently joined antibodies, are also within the scope of the invention. Such antibodies have been used to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

The antibody may be a humanized antibody, for example, as known in the art, and as described herein.

Antibodies may be modified as described in PCT Publication No. WO 99/58572, published Nov. 18, 1999. These antibodies comprise, in addition to a binding domain directed at the target molecule, an effector domain having an amino acid sequence substantially homologous to all, or part of a constant domain of a human immunoglobulin heavy chain. These antibodies are capable of binding the target molecule without triggering significant complement dependent lysis, or cell-mediated destruction of the target. Preferably, the effector domain is capable of specifically binding FcRn and/or FcγRIIb. These are typically based on chimeric domains derived from two or more human immunoglobulin heavy chain CH2 domains. Antibodies modified in this manner are preferred for use in chronic antibody therapy, to avoid inflammatory and other adverse reactions to conventional antibody therapy.

The invention encompasses modifications to antibody E3, including functionally equivalent antibodies which do not significantly affect their properties and variants which have enhanced or decreased activity. Modification of polypeptides is routine practice in the art and is further exemplified in the Examples. Examples of modified polypeptides include polypeptides with substitutions (including conservative substitutions) of amino acid residues, one or more deletions or additions of amino acids which do not significantly deleteriously change the functional activity, or use of chemical analogs.

A polypeptide "variant," as used herein, is a polypeptide that differs from a native protein in one or more substitutions, deletions, additions and/or insertions, such that the immunoreactivity of the polypeptide is not substantially diminished. In other words, the ability of a variant to specifically bind antigen may be enhanced or unchanged, relative to the native protein, or may be diminished by less than 50%, and preferably less than 20%, relative to the native protein. Polypeptide variants preferably exhibit at least about 80%, more preferably at least about 90% and most preferably at least about 95% identity (determined as described herein) to the identified polypeptides.

Amino acid sequence variants of the antibodies may be prepared by introducing appropriate nucleotide changes into the antibody DNA, or by peptide synthesis. Such variants include, for example, deletions from, and/or insertions into and/or substitutions of, residues within the amino acid sequences of SEQ ID NO:1 or 2 described herein. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis or modification is called "alanine scanning mutagenesis," and is described by Cunningham and Wells, 1989, Science, 244:1081-1085. A residue or group of target residues is identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity. Library scanning mutagenesis, as described herein, may also be used to identify locations in an antibody that are suitable for mutagenesis or modification.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 1 under the heading of "conservative substitutions". If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
  (1) Hydrophobic: Norleucine, Met, Ala, Val, Leu, Ile;
  (2) Neutral hydrophilic: Cys, Ser, Thr;
  (3) Acidic: Asp, Glu;
  (4) Basic: Asn, Gln, His, Lys, Arg;
  (5) Residues that influence chain orientation: Gly, Pro; and
  (6) Aromatic: Trp, Tyr, Phe.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiment, no more than one to five conservative amino acid substitutions are made within a CDR domain. In other embodiments, no more than one to three conservative amino acid substitutions are made within a CDR3 domain. In still other embodiments, the CDR domain is CDRH3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Hefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycdsylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H). In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified E3 polypeptides are made using established procedures in the art and can be screened using standard assays known in the art, some of which are described below and in the Examples.

Other antibody modifications include antibodies that have been modified as described in PCT Publication No. WO 99/58572, published Nov. 18, 1999. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

The invention also encompasses fusion proteins comprising one or more fragments or regions from the antibodies (such as E3) or polypeptides of this invention. In one embodiment, a fusion polypeptide is provided that comprises at least 10 contiguous amino acids of the variable light chain region shown in FIG. 1B and/or at least 10 amino acids of the variable heavy chain region shown in FIG. 1A. In another embodiment, the fusion polypeptide comprises a light chain variable region and/or a heavy chain variable region of E3, as shown in FIGS. 1A and 1B. In another embodiment, the fusion polypeptide comprises one or more CDR(s) of E3. In still other embodiments, the fusion polypeptide comprises CDR H3 and/or CDR L3 of antibody E3. In another embodiment, the fusion polypeptide comprises any one or more of: amino acid residue L29 of CDRH1, I50 of CDRH2, W101 of CDRH3, and/or A103 of CDRH3; and/or amino acid residue S28 of CDRL1, N32 of CDRL1, T51 of CDRL2; 91E of CDRL3 and/or H92 of CDRL3. For purposes of this invention, a E3 fusion protein contains one or more E3 antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

A E3 fusion polypeptide can be created by methods known in the art, for example, synthetically or recombinantly. Typically, the E3 fusion proteins of this invention are made by preparing an expressing a polynucleotide encoding them using recombinant methods described herein, although they may also be prepared by other means known in the art, including, for example, chemical synthesis.

This invention also provides compositions comprising E3 antibodies or polypeptides conjugated (for example, linked) to an agent that facilitate coupling to a solid support (such as biotin or avidin). For simplicity, reference will be made generally to E3 or antibodies with the understanding that these methods apply to any of the NGF binding embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

An antibody or polypeptide of this invention may be linked to a labeling agent (alternatively termed "label") such as a fluorescent molecule, a radioactive molecule or any others labels known in the art. Labels are known in the art which generally provide (either directly or indirectly) a signal. Accordingly, the invention includes labeled antibodies and polypeptides.

The ability of the antibodies and polypeptides of this invention, such as binding NGF; reducing or inhibiting a NGF biological activity; reducing and/or blocking NGF-induced survival of E13.5 mouse trigeminal neurons, may be tested using methods known in the art, some of which are described in the Examples.

The invention also provides compositions (including pharmaceutical compositions) and kits comprising antibody E3, and, as this disclosure makes clear, any or all of the antibodies and/or polypeptides described herein.

Polynucleotides, Vectors and Host Cells

The invention also provides isolated polynucleotides encoding the antibodies and polypeptides of the invention (including an antibody comprising the polypeptide sequences of the light chain and heavy chain variable regions shown in FIGS. 1A and 1B), and vectors and host cells comprising the polynucleotide.

Accordingly, the invention provides polynucleotides (or compositions, including pharmaceutical compositions), comprising polynucleotides encoding any of the following: (a) antibody E3; (b) a fragment or a region of the antibody E3; (c) a light chain of the antibody E3 as shown in FIG. 1B; (d) a heavy chain of the antibody E3 as shown in FIG. 1A; (e) one or more variable region(s) from a light chain and/or a heavy chain of the antibody E3; (f) one or more CDR(s) (one, two, three, four, five or six CDRs) of antibody E3 shown in FIGS. 1A and 1B; (g) CDR H3 from the heavy chain of antibody E3 shown in FIG. 1A; (h) CDR L3 from the light chain of antibody E3 shown in FIG. 1B; (i) three CDRs from the light chain of antibody E3 shown in FIG. 1B; (j) three CDRs from the heavy chain of antibody E3 shown in FIG. 1A; (k) three CDRs from the light chain and three CDRs from the heavy chain, of antibody E3 shown in FIGS. 1A and 1B; or (l) an antibody comprising any of (b) to (k). In some embodiments, the polynucleotide comprises either or both of the polynucleotide(s) shown in FIGS. 2 and 3.

In another aspect, the invention is an isolated polynucleotide that encodes for an E3 light chain with a deposit number of ATCC No. PTA-4893 or ATCC No. PTA-4894. In another aspect, the invention is an isolated polynucleotide that encodes for an E3 heavy chain with a deposit number of ATCC No. PTA-4895. In yet another aspect, the invention is an isolated polynucleotide comprising (a) a variable region encoded in the polynucleotide with a deposit number of ATCC No. PTA-4894 and (b) a variable region encoded in the polynucleotide with a deposit number of ATCC No. PTA-4895. In another aspect, the invention is an isolated polynucleotide comprising (a) one or more CDR encoded in the polynucleotide with a deposit number of ATCC No. PTA-4894; and/or (b) one or more CDR encoded in the polynucleotide with a deposit number of ATCC No. PTA-4895.

In another aspect, the invention provides polynucleotides encoding any of the antibodies (including antibody fragments) and polypeptides described herein. Polynucleotides can be made by procedures known in the art In another aspect, the invention provides compositions (such as a pharmaceutical compositions) comprising any of the polynucleotides of the invention. In some embodiments, the composition comprises an expression vector comprising a polynucleotide encoding the E3 antibody as described herein. In other embodiment, the composition comprises an expression vector comprising a polynucleotide encoding any of the antibodies or polypeptides described herein. In still other embodiments, the composition comprises either or both of the polynucleotides shown in FIGS. 2 and 3. Expression vectors, and administration of polynucleotide compositions are further described herein.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably at least about 80% identity and most preferably at least about 90% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include pre-washing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp 18, mp 19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae*, *S. pombe*; or *K. lactis*). Preferably, the host cells express the cDNAs at a level of about 5 fold higher, more preferably 10 fold higher, even more preferably 20 fold higher than that of the corresponding endogenous antibody or protein of interest, if present, in the host cells. Screening the host cells for a specific binding to NGF is effected by an immunoassay or FACS. A cell overexpressing the antibody or protein of interest can be identified.

Methods Using E3 and E3 Derived Antibodies

Antibody E3 which binds NGF may be used to identify or detect the presence or absence of NGF. For simplicity, reference will be made generally to E3 or antibodies with the understanding that these methods apply to any of the NGF binding embodiments (such as polypeptides) described herein. Detection generally involves contacting a biological sample with an antibody described herein that binds to NGF and the formation of a complex between NGF and an antibody (e.g., E3) which binds specifically to NGF. The formation of such a complex can be in vitro or in vivo. The term "detection" as used herein includes qualitative and/or quantitative detection (measuring levels) with or without reference to a control.

Any of a variety of known methods can be used for detection, including, but not limited to, immunoassay, using antibody that binds the polypeptide, e.g. by enzyme-linked immunosorbent assay (ELISA), radioimmunoassay (RIA) and the like; and functional assay for the encoded polypeptide, e.g. binding activity or enzymatic assay. In some embodiments, the antibody is detectably labeled.

Diagnostic Uses of the E3 and Derivatives

Antibodies and polypeptides of the invention can be used in the detection, diagnosis and monitoring of a disease, condition, or disorder associated with altered or aberrant NGF expression (in some embodiments, increased or decreased NGF expression (relative to a normal sample), and/or inappropriate expression, such as presence of expression in tissue(s) and/or cell(s) that normally lack NGF expression, or absence of NGF expression in tissue(s) or cell(s) that normally possess NGF expression). The antibodies and polypeptides of the invention are further useful for detection of NGF expression, for example, in a disease associated with altered or aberrant sensitivity or responsiveness to NGF. In some embodiments, NGF expression is detected in a sample from an individual suspected of having a disease, disorder featuring or associated with an altered or aberrant sensitivity or responsiveness to NGF expression (e.g., a cancer in which NGF promotes growth and/or metastasis).

Thus, in some embodiments, the invention provides methods comprising contacting a specimen (sample) of an individual suspected of having altered or aberrant NGF expression with an antibody or polypeptide of the invention and determining whether the level of NGF differs from that of a control or comparison specimen. In some embodiments, the individual has a cardiac arrhythmia, Alzheimer's disease, and/or autonomic dysfunction.

In other embodiments, the invention provides methods comprises contacting a specimen (sample) of an individual and determining level of NGF expression. In some embodiments, the individual is suspected of having a disease, disorder featuring or associated with an altered or aberrant sensitivity or responsiveness to NGF expression. In some embodiments, the individual has small cell lung cancer, breast cancer, pancreatic cancer, prostate cancer, ovarian carcinoma, hepatocellular carcinoma, or melanoma.

For diagnostic applications, the antibody typically will be labeled with a detectable moiety including but not limited to radioisotopes, fluorescent labels, and various enzyme-substrate labels. Methods of conjugating labels to an antibody are known in the art. In other embodiments of the invention, antibodies of the invention need not be labeled, and the presence thereof can be detected using a labeled antibody which binds to the antibodies of the invention.

The antibodies of the present invention may be employed in any known assay method, such competitive binding assays, direct and indirect sandwich assays, and immunoprecipitation assays. Zola, Monoclonal Antibodies: A Manual of Techniques, pp. 147-158 (CRC Press, Inc. 1987).

The antibodies may also be used for in vivo diagnostic assays, such as in vivo imaging. Generally, the antibody is labeled with a radionuclide (such as 111In, 99Tc, 14C, 131I, 125I, or 3H) so that the cells or tissue of interest can be localized using immunoscintiography.

The antibody may also be used as staining reagent in pathology, following techniques well known in the art.

Methods of Using E3 and Derivatives for Therapeutic Purposes

Antibody E3 is useful for reducing and/or blocking the biological activity of NGF. This antagonistic activity is believed to be useful in the treatment of pathological conditions associated with endogenous NGF production, such as pain. Generally, in these embodiments an effective amount is administered to an individual. Accordingly, in one aspect, the invention provides a method of antagonizing human NGF biological activity using any of the polypeptides (including antibodies such as antibody E3) disclosed herein. In one embodiment, the method comprises contacting human nerve growth factor with any of the polypeptides (including antibody E3) described herein, whereby human nerve growth factor activity is antagonized, reduced, blocked, or suppressed. In yet another embodiment, an individual with pain (such as post-surgical pain, or rheumatoid arthritis pain) is given treatment with E3.

For simplicity, reference will be made generally to E3 or antibody with the understanding that these methods apply to any of the E3 variant antibodies and polypeptides described herein.

Various formulations of E3 or fragments of E3 (e.g., Fab, Fab', F(ab')2, Fv, Fc, etc.), such as single chain (ScFv), mutants thereof, fusion proteins comprising an antibody portion, and any other modified configuration of E3 that comprises an antigen NGF recognition site of the required specificity, may be used for administration. In some embodiments, E3 antibodies or various formulations of E3 thereof may be administered neat. In other embodiments, E3 or various formulations of E3 (including any composition embodiment described herein) thereof and a pharmaceutically acceptable excipient are administered, and may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing (2000).

In some embodiments, these agents are formulated for administration by injection (e.g., intraperitoneally, intravenously, subcutaneously, intramuscularly, etc.), although other forms of administration (e.g., oral, mucosal, via inhalation, sublingually, etc) can be also used. Accordingly, E3 antibody and equivalents thereof are preferably combined with pharmaceutically acceptable vehicles such as saline, Ringer's solution, dextrose solution, and the like. The particular dosage regimen, i.e., dose, timing and repetition, will depend on the particular individual and that individual's medical history. Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 ug/kg body weight; at least about 100 µg/kg body weight; at least about 50 µg/kg body weight; at least about 10 ug/kg body weight; at least about 1 µg/kg body weight, or less, is administered. For repeated administrations over several days or longer, depending on the condition, the treatment is sustained until a desired suppression of disease symptoms occurs. An exemplary dosing regimen comprises administering an initial dose of about 2 mg/kg, followed by a weekly maintenance dose of about 1 mg/kg of the anti-NGF antibody, or followed by a maintenance dose of about 1 mg/kg every other week. However, other dosage regimens may be useful, depending on the pattern of pharmacokinetic decay that the practitioner wishes to achieve. Empirical considerations, such as the half-life, generally will contribute to determination of the dosage. The progress of this therapy is easily monitored by conventional techniques and assays.

In some individuals, more than one dose may be required. Frequency of administration may be determined and adjusted over the course of therapy. For example, frequency of administration may be determined or adjusted based on the type and severity of the pain to be treated, whether the agent is administered for preventive or therapeutic purposes, previous therapy, the patient's clinical history and response to the agent, and the discretion of the attending physician. Typically the clinician will administer an anti-NGF antagonist antibody (such as E3), until a dosage is reached that achieves the desired result. In some cases, sustained continuous release formulations of E3 antibodies may be appropriate. Various formulations and devices for achieving sustained release are known in the art.

In one embodiment, dosages for E3 antibodies (or polypeptides) may be determined empirically in individuals who have been given one or more administration(s). Individuals are given incremental dosages of E3. To assess efficacy of E3 or other equivalent antibody, markers of the disease symptoms (such as pain) can be monitored.

Administration of an antibody (such as E3) or polypeptide in accordance with the method in the present invention can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing pain, before, during, before and after, during and after, or before, during, and after developing pain. Administration can be before, during and/or after wound, incision, trauma, surgery, and any other event likely to give rise to post-surgical pain.

Other formulations include suitable delivery forms known in the art including, but not limited to, carriers such as liposomes. See, for example, Mahato et al. (1997) *Pharm. Res.* 14:853-859. Liposomal preparations include, but are not limited to, cytofectins, multilamellar vesicles and unilamellar vesicles.

In some embodiments, more than one antibody or polypeptide may be present. The antibodies can be monoclonal or polyclonal. Such compositions may contain at least one, at least two, at least three, at least four, at least five different antibodies. A mixture of antibodies, as they are often denoted in the art, may be particularly useful in treating a broader range of population of individuals.

A polynucleotide encoding any of the antibodies or polypeptides of the invention (such as antibody E3) may also be used for delivery and expression of any of the antibodies or polypeptides of the invention (such as antibody E3) in a desired cell. It is apparent that an expression vector can be used to direct expression of an E3 antibody or polypeptide. The expression vector can be administered by any means known in the art, such as intraperitoneally, intravenously, intramuscularly, subcutaneously, intrathecally, intraventricularly, orally, enterally, parenterally, intranasally, dermally, sublingually, or by inhalation. For example, administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions comprising a polynucleotide encoding any of the antibodies or polypeptides of the invention (such as antibody E3) can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci.* (USA) (1990) 87:3655; Wu et al., *J. Biol. Chem.* (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740; 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:16985); eukaryotic cell-delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent NO. 0 524 968. Additional approaches are described in Philip, Mol. Cell. Biol. (1994) 14:2411 and in Woffendin, Proc. Natl. Mad. Sci. (1994) 91:1581.

With respect to all methods described herein, reference to anti-NGF antagonist antibodies also include compositions comprising one or more of these agents. These compositions may further comprise suitable excipients, such as pharmaceutically acceptable excipients including buffers, which are well known in the art. The present invention can be used alone or in combination with other conventional methods of treatment.

Methods of Using Anti-NGF Antagonist Antibody for Treating or Preventing Rheumatoid Arthritis Pain In some aspects, the invention provides methods for treating and/or preventing rheumatoid arthritis pain in individuals including mammals, both human and non-human. Accordingly, in one aspect, the invention provides methods of treating rheumatoid arthritis pain in an individual comprising administering an effective amount of an anti-NGF antagonist antibody. Anti-NGF antagonist antibodies are known in the art and described herein.

In another aspect, the invention provides methods for reducing incidence of, ameliorating, suppressing, palliating, and/or delaying the onset, the development or the progression of rheumatoid arthritis pain in an individual. Thus, in some embodiments, the anti-NGF antagonist antibody is administered prior to development of pain or a pain episode in an individual having rheumatoid arthritis.

In another aspect, the invention provides methods for treating inflammatory cachexia (weight loss) associated with rheumatoid arthritis in an individual comprising administering an effective amount of an anti-NGF antagonist antibody (Roubenoff et al., *Arthritis Rheum.* 40(3): 534-9 (1997); Roubenoff et al., *J. Clin. Invest.* 93(6):2379-86 (1994)).

Diagnosis or assessment of rheumatoid arthritis pain is well-established in the art. Assessment may be performed based on measures known in the art, such as patient characterization of pain using various pain scales. See, e.g., Katz et al, *Surg Clin North Am.* (1999) 79 (2):231-52; Caraceni et al. *J Pain Symptom Manage* (2002) 23(3):239-55. There are also commonly used scales to measure disease state such as the American College of Rheumatology (ACR) (Felson, et al., *Arthritis and Rheumatism* (1993) 36(6):729-740), the Health Assessment Questionnaire (HAQ) (Fries, et al., (1982) *J. Rheumatol.* 9: 789-793), the Paulus Scale (Paulus, et al., *Arthritis and Rheumatism* (1990) 33: 477-484), and the Arthritis Impact Measure Scale (AIMS) (Meenam, et al., *Arthritis and Rheumatology* (1982) 25: 1048-1053). Anti-NGF antagonist antibody may be administered to an individual via any suitable route. Examples of different administration route are described herein.

Pain relief may be characterized by time course of relief. Accordingly, in some embodiments, pain relief is observed within about 24 hours after administration of anti-NGF antagonist antibody. In other embodiments, pain relief is observed within about 36, 48, 60, 72 hours or 4 days after administration of anti-NGF antagonist antibody. In still other embodiments, pain relief is observed before observing an indication of improvement of the inflammatory condition associated with rheumatoid arthritis. In some embodiments, frequency and/or intensity of pain is diminished, and/or quality of life of those suffering the disease is increased.

Making and using NGF antagonists (including anti-NGF antibodies) for these methods are described in sections below ("NGF antagonists", "Anti-NGF antagonist antibody"; "Other NGF antagonists"; "Identification of NGF antagonists (such as anti-NGF antagonist antibodies)"; "Compositions for use in the methods of the invention"; "Administration of an NGF antagonist (such as an anti-NGF antagonist antibody)").

Methods of Using Anti-NGF Antagonist Antibody for Treating or preventing Osteoarthritis Pain In some aspects, the invention provides methods for treating and/or preventing osteoarthritis pain in individuals including mammals, both human and non-human. Accordingly, in one aspect, the invention provides methods of treating osteoarthritis pain in an individual comprising administering an effective amount of an NGF antagonist (such as an anti-NGF antagonist antibody). NGF antagonists, including anti-NGF antagonist antibodies, are known in the art and described herein.

In another aspect, the invention provides methods for reducing incidence of, ameliorating, suppressing, palliating, and/or delaying the onset, the development or the progression of osteoarthritis pain in an individual comprising administering an effective amount of an NGF antagonist (such as an anti-NGF antagonist antibody). Thus, in some embodiments, the NGF antagonist (such as anti-NGF antagonist antibody) is administered prior to development of pain or a pain episode in an individual having osteoarthritis.

Diagnosis or assessment of osteoarthritis pain is well-established in the art. Assessment may be performed based on measures known in the art, such as patient characterization of pain using various pain scales. See, e.g., Katz et al, *Surg Clin North Am.* (1999) 79 (2):231-52; Caraceni et al. *J Pain Symptom Manage* (2002) 23(3):239-55. For example, WOMAC Ambulation Pain Scale (including pain, stiffness, and physical function) and 100 mm Visual Analogue Scale (VAS) may be employed to assess pain and evaluate response to the treatment.

NGF antagonists (such as an anti-NGF antagonist antibody) may be administered to an individual via any suitable route. Examples of different administration route are described herein.

In some embodiments, the NGF antagonist (such as the anti-NGF antagonist antibody) is administered once every week, once every two weeks, once every three weeks, once every four weeks, once every five weeks, once every six weeks, once every seven weeks, once every eight weeks, once every nine weeks, once every ten weeks, once every fifteen weeks, once every twenty weeks, once every twenty five weeks, or once every twenty six weeks. In some embodiments, the NGF antagonist (such as the anti-NGF antagonist antibody) is administered once every month, once every two months, once every three months, once every four months, once every five months, or once every six months.

Pain relief may be characterized by time course of relief. Accordingly, in some embodiments, pain relief is observed within about 24 hours after administration of an NGF antagonist (such as an anti-NGF antagonist antibody). In other embodiments, pain relief is observed within about 36, 48, 60, 72 hours or 4 days after administration of the NGF antagonist (such as the anti-NGF antagonist antibody). In some embodiments, frequency and/or intensity of pain is diminished, and/or quality of life of those suffering the disease is increased. In some embodiments, pain relief for osteoarthritis is provided for duration of at least about 7 days, at least about 14 days, at least about 21 days, at least about 28 days, at least about 35 days, at least about 42 days, at least about 49 days, at least about 56 days, at least about 63 days, at least about 70 days, at least about 77 days, at least about 84 days, at least about 180 days, or longer after a single dose of the NGF antagonist (such as the anti-NGF antagonist antibody).

Making and using NGF antagonists (including anti-NGF antibodies) for these methods are described in sections below ("NGF antagonists", "Anti-NGF antagonist antibody"; "Other NGF antagonists"; "Identification of NGF antagonists (such as anti-NGF antagonist antibodies)"; "Compositions for use in the methods of the invention"; "Administration of an NGF antagonist (such as an anti-NGF antagonist antibody)").

NGF Antagonists

The methods of the invention (pertaining to rheumatoid arthritis pain and osteoarthritis pain) use an NGF antagonist, which refers to any molecule that blocks, suppresses or reduces (including significantly) NGF biological activity, including downstream pathways mediated by NGF signaling, such as receptor binding and/or elicitation of a cellular response to NGF. The term "antagonist" implies no specific mechanism of biological action whatsoever, and is deemed to expressly include and encompass all possible pharmacological, physiological, and biochemical interactions with NGF and its consequences which can be achieved by a variety of different, and chemically divergent, compositions. Exemplary NGF antagonists include, but are not limited to, an anti-NGF antibody, an anti-sense molecule directed to NGF (including an anti-sense molecule directed to a nucleic acid encoding NGF), an anti-sense molecule directed to an NGF receptor (such as TrkA receptor and/or p75 receptor) (including an anti-sense molecule directed to a nucleic acid encoding TrkA and/or p75), an NGF inhibitory compound, an NGF structural analog, a dominant-negative mutation of a TrkA receptor that binds an NGF, a TrkA immunoadhesin, an anti-TrkA antibody, a dominant-negative mutation of a p75 receptor that binds an NGF, an anti-p75 antibody, and a kinase inhibitor. For purpose of the present invention, it will be explicitly understood that the term "antagonist" encompasses all the previously identified terms, titles, and functional states and characteristics whereby the NGF itself, an NGF biological activity (including but not limited to its ability to mediate any aspect of pain), or the consequences of the biological activity, are substantially nullified, decreased, or neutralized in any meaningful degree. In some embodiments, an NGF antagonist (e.g., an antibody) binds (physically interact with) NGF, binds to an NGF receptor (such as TrkA receptor and/or p75 receptor), and/or reduces (impedes and/or blocks) downstream NGF receptor signaling. Accordingly, in some embodiments, an NGF antagonist binds (physically interacts with) NGF. In some embodiments, the NGF antagonist is a polypeptide which binds to NGF. In some embodiments, the NGF antagonist is a peptide or a modified peptide (such as NGF binding peptide fused to a Fc domain) described in PCT WO 2004/026329. In other embodiment, an NGF antagonist binds to an NGF receptor (such as trkA receptor or p75). In other embodiments, an NGF antagonist reduces (impedes and/or blocks) downstream NGF receptor signaling (e.g., inhibitors of kinase signaling). In other embodiments, an NGF antagonist inhibits (reduces) NGF synthesis and/or release. In another embodiment, the NGF antagonist is an NGF antagonist that is not a TrkA immunoadhesin (i.e., is other than a TrkA immunoadhesin). In another embodiment, the NGF antagonist is other than an anti-NGF antibody. In other embodiment, the NGF antagonist is other than a TrkA immunoadhesin and other than an anti-NGF antibody. In some embodiment, the NGF antagonist binds NGF (such as hNGF) and does not significantly bind to related neurotrophins, such as NT-3, NT4/5, and/or BDNF. In some embodiments, the NGF antagonist is not associated with an adverse immune response. In other embodiments, the NGF antagonist is an anti-NGF antibody. In still other embodiments, the anti-NGF antibody is humanized (such as antibody E3 described herein). In some embodiments, the anti-NGF antibody is antibody E3 (as described herein). In other embodiments, the anti-NGF antibody comprises one or more CDR(s) of antibody E3 (such as one, two, three, four, five, or, in some embodiments, all six CDRs from E3). In other embodiments, the antibody is human. In still other embodiments, the anti-NGF antibody comprises the amino acid sequence of the heavy chain variable region shown in FIG. 1A (SEQ ID NO:1) and the amino acid sequence of the light chain variable region shown in FIG. 1B (SEQ ID NO:2). In still other embodiments, the antibody comprises a modified constant region, such as a constant region that is immunologically inert, e.g., does not trigger complement mediated lysis, or does not stimulate antibody-dependent cell mediated cytotoxicity (ADCC). In other embodiments, the constant region is modified as described in Eur. J. Immunol. (1999) 29:2613-2624; PCT Application No. PCT/GB99/01441; and/or UK Patent Application No. 9809951.8.

Anti-NGF Antagonist Antibody

The methods of the invention (pertaining to rheumatoid arthritis pain and osteoarthritis pain) use an anti-NGF antagonist antibody, which refers to any antibody molecule that blocks, suppresses or reduces (including significantly) NGF biological activity, including downstream pathways mediated by NGF signaling, such as receptor binding and/or elicitation of a cellular response to NGF.

An anti-NGF antagonist antibody should exhibit any one or more of the following characteristics: (a) bind to NGF and inhibit NGF biological activity or downstream pathways mediated by NGF signaling function; (b) prevent, ameliorate, or treat any aspect of rheumatoid arthritis pain or osteoarthritis pain; (c) block or decrease NGF receptor activation (including TrkA receptor dimerization and/or autophosphorylation); (d) increase clearance of NGF; (e) inhibit (reduce) NGF synthesis, production or release. Anti-NGF antagonist antibodies are known in the art; see, e.g., PCT Publication Nos. WO 01/78698, WO 01/64247, U.S. Pat. Nos. 5,844,092, 5,877,016, and 6,153,189; Hongo et al., Hybridoma, 19:215-227 (2000); Cell. Molec. Biol. 13:559-568 (1993); GenBank Accession Nos. U39608, U39609, L17078, or L17077. Anti-NGF antagonist antibodies and polypeptides are also described in PCT WO 2005/019266.

For purposes of this invention, the antibody reacts with NGF in a manner that inhibits NGF and/or downstream pathways mediated by the NGF signaling function. In some embodiments, the anti-NGF antagonist antibody recognizes human NGF. In yet other embodiments, the anti-NGF antagonist antibody specifically binds human NGF. In some embodiment, the anti-NGF antagonist antibody does not significantly bind to related neurotrophins, such as NT-3, NT4/5, and/or BDNF. In still other embodiments, the anti-NGF antibody is capable of binding NGF and effectively inhibiting the binding of NGF to its TrkA and/or p75 receptor in vivo and/or effectively inhibiting NGF from activating its TrkA and/or p75 receptor. In still other embodiments, the anti-NGF antagonist antibody is a monoclonal antibody. In still other embodiments, the anti-NGF antibody is humanized (such as antibody E3 described herein). In some embodiments, the anti-NGF antibody is human. See, e.g., WO 2005/019266. In one embodiment, the antibody is a human antibody which recognizes one or more epitopes on human NGF. In another embodiment, the antibody is a mouse or rat antibody which recognizes one or more epitopes on human NGF. In another embodiment, the antibody recognizes one or more epitopes on an NGF selected from the group consisting of: primate, canine, feline, equine, and bovine. In still further embodiments, the anti-NGF antagonist antibody binds essentially the same NGF epitope 6 as an antibody selected from any one or more of the following: MAb 911, MAb 912 and MAb 938 (See Hongo, et al., Hybridoma 19:215-227 (2000)). In other embodiments, the antibody binds the same epitope as Mab 911. In another embodiment, the antibody comprises a constant region that is immunologically inert (e.g., does not trigger complement mediated lysis or antibody dependent cell mediated cytotoxicity (ADCC)). ADCC activity can be assessed using methods disclosed in U.S. Pat. No. 5,500,362. In some embodiments, the constant region is modified as described in Eur. J. Immunol. (1999) 29:2613-2624; PCT Application No. PCT/GB99/01441; and/or UK Patent Application No. 9809951.8.

In some embodiments, the anti-NGF antagonist antibody is a humanized mouse anti-NGF monoclonal antibody termed antibody "E3", any of the E3 related antibodies described herein, or any fragments thereof, which are NGF antagonists.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

The binding affinity of an anti-NGF antagonist antibody to NGF (such as hNGF) can be about 0.10 to about 0.80 nM, about 0.15 to about 0.75 nM and about 0.18 to about 0.72 nM. In one embodiment, the binding affinity is between about 2 pM and 22 pM. In one embodiment, the binding affinity is between about 23 pM and about 100 pM. In some embodiment, the binding affinity is about 10 nM. In other embodiments, the binding affinity is less than about 10 nM. In other embodiments, the binding affinity is about 0.1 nM or about 0.07 nM. In other embodiments, the binding affinity is less than about 0.1 nM or less than about 0.07 nM. In other embodiments, the binding affinity is any of about 100 nM, about 50 nM, about 10 nM, about 1 nM, about 500 pM, about 100 pM, or about 50 pM to any of about 2 pM, about 5 pM, about 10 pM, about 15 pM, about 20 pM, or about 40 pM. In some embodiments, the binding affinity is any of about 100 nM, about 50 nM, about 10 nM, about 1 nM, about 500 pM, about 100 pM, or about 50 pM, or less than about 50 pM. In some embodiments, the binding affinity is less than any of about 100 nM, about 50 nM, about 10 nM, about 1 nM, about 500 pM, about 100 pM, or about 50 pM. In still other embodiments, the binding affinity is about 2 pM, about 5 pM, about 10 pM, about 15 pM, about 20 pM, about 40 pM, or greater than about 40 pM.

One way of determining binding affinity of antibodies to NGF is by measuring binding affinity of monofunctional Fab fragments of the antibody. To obtain monofunctional Fab fragments, an antibody (for example, IgG) can be cleaved with papain or expressed recombinantly. The affinity of an anti-NGF Fab fragment of an antibody can be determined by surface plasmon resonance (BIAcore3000™ surface plasmon resonance (SPR) system, BIAcore, INC, Piscaway N.J.). CM5 chips can be activated with N-ethyl-N'-(3-dimethylaminopropyl)-carbodiimide hydrochloride (EDC) and N-hydroxysuccinimide (NHS) according to the supplier's instructions. Human NGF (or any other NGF) can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. The chip can be blocked with ethanolamine. Regeneration studies have shown that a mixture of Pierce elution buffer (Product No. 21004, Pierce Biotechnology, Rockford Ill.) and 4 M NaCl (2:1) effectively removes the bound Fab while keeping the activity of hNGF on the chip for over 200 injections. HBS-EP buffer (0.01M HEPES, pH 7.4, 0.15 NaCl, 3 mM EDTA, 0.005% Surfactant P29) is used as running buffer for the BIAcore assays. Serial dilutions (0.1-10× estimated $K_D$) of purified Fab samples are injected for 1 min at 100 µL/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates (kon) and dissociation rates (koff) are obtained simultaneously by fitting the data to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any NGF, including human NGF, NGF of another vertebrate (in some embodiments, mammalian) (such as mouse NGF, rat NGF, primate NGF), as well as for use with other neurotrophins, such as the related neurotrophins NT3, NT4/5, and/or BDNF.

In some embodiments, the antibody binds human NGF, and does not significantly bind an NGF from another vertebrate species (in some embodiment, mammalian). In some embodiments, the antibody binds human NGF as well as one or more NGF from another vertebrate species (in some embodiments, mammalian). In still other embodiments, the antibody binds NGF and does not significantly cross-react with other neurotrophins (such as the related neurotrophins, NT3, NT4/5, and/or BDNF). In some embodiments, the antibody binds NGF as well as at least one other neurotrophin. In some embodiments, the antibody binds to a mammalian species of NGF, such as horse or dog, but does not significantly bind to NGF from anther mammalian species.

The epitope(s) can be continuous or discontinuous. In one embodiment, the antibody binds essentially the same hNGF epitopes as an antibody selected from the group consisting of MAb 911, MAb 912, and MAb 938 as described in Hongo et al., Hybridoma, 19:215-227 (2000). In another embodiment, the antibody binds essentially the same hNGF epitope as MAb 911. In still another embodiment, the antibody binds essentially the same epitope as MAb 909. Hongo et al., supra. For example, the epitope may comprise one or more of residues K32, K34 and E35 within variable region 1 (amino acids 23-35) of hNGF; residues F79 and T81 within variable region 4 (amino acids 81-88) of hNGF; residues H84 and K88 within variable region 4; residue R103 between variable region 5 (amino acids 94-98) of hNGF and the C-terminus (amino acids 111-118) of hNGF; residue E11 within pre-variable region 1 (amino acids 10-23) of hNGF; Y52 between variable region 2 (amino acids 40-49) of hNGF and variable region 3 (amino acids 59-66) of hNGF; residues L112 and S113 within the C-terminus of hNGF; residues R59 and R69 within variable region 3 of hNGF; or residues V18, V20, and G23 within pre-variable region 1 of hNGF. In addition, an epitope can comprise one or more of the variable region 1, variable region 3, variable region 4, variable region 5, the N-terminus region, and for the C-terminus of hNGF. In still another embodiment, the antibody significantly reduces the solvent accessibility of residue R103 of hNGF. It is understood that although the epitopes described above relate to human NGF, one of ordinary skill can align the structures of human NGF with the NGF of other species and identify likely counterparts to these epitopes.

In one aspect, antibodies (e.g., human, humanized, mouse, chimeric) that can inhibit NGF may be made by using immunogens that express full length or partial sequence of NGF. In another aspect, an immunogen comprising a cell that overexpresses NGF may be used. Another example of an immunization that can be used is NGF protein that contains full-length NGF or a portion of the NGF protein.

The anti-NGF antagonist antibodies may be made by any method known in the art. The route and schedule of immunization of the host animal are generally in keeping with established and conventional techniques for antibody stimulation and production, as further described herein. General techniques for production of human and mouse antibodies are known in the art and are described herein.

It is contemplated that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975)

Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-NGF monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for NGF, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a human NGF, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaradehyde, succinic anhydride, SOCl2, or R1N=C=NR, where R and R1 are different alkyl groups, can yield a population of antibodies (e.g., monoclonal antibodies).

If desired, the anti-NGF antagonist antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to NGF and greater efficacy in inhibiting NGF. It will be apparent to one of skill in the art that one or more polynucleotide changes can be made to the anti-NGF antagonist antibody and still maintain its binding ability to NGF.

There are four general steps to humanize a monoclonal antibody. These are: (1) determining the nucleotide and predicted amino acid sequence of the starting antibody light and heavy variable domains (2) designing the humanized antibody, i.e.: deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530, 101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. Nature 349:293-299 (1991), Lobuglio et al. Proc. Nat. Acad. Sci. USA 86:4220-4224 (1989), Shaw et al. J. Immunol. 138:4534-4538 (1987), and Brown et al. Cancer Res. 47:3577-3583 (1987). Other references describe rodent CDRs grafted into a human supporting framework region (FR) prior to fusion with an appropriate human antibody constant domain. See, for example, Riechmann et al. Nature 332:323-327 (1988), Verhoeyen et al. Science 239:1534-1536 (1988), and Jones et al. Nature 321:522-525 (1986). Another reference describes rodent CDRs supported by recombinantly veneered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., Nucl. Acids Res. 19:2471-2476 (1991) and in U.S. Pat. Nos. 6,180,377; 6,054, 297; 5,997,867; 5,866,692; 6,210,671; and 6,350,861; and in PCT Publication No. WO 01/27160.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565, 332; 5,580,717; 5,733,743; and 6,265,150; and Winter et al., Annu. Rev. Immunol. 12:433-455 (1994). Alternatively, the phage display technology (McCafferty et al., *Nature* 348: 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., *Current Opinion in Structural Biology* 3:564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., *J. Mol. Biol.* 222:581-597 (1991), or Griffith et al., *EMBO J.* 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., *Bio/ Technol.* 10:779-783 (1992)). In this Method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., *Nucl. Acids Res.* 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213, published Apr. 1, 1993). Unlike traditional humanization of rodent antibodies by CDR grafting, this technique provides completely human antibodies, which have no framework or CDR residues of rodent origin.

It is apparent that although the above discussion pertains to humanized antibodies, the general principles discussed are applicable to customizing antibodies for use, for example, in dogs, cats, primate, equines and bovines. It is further apparent that one or more aspects of humanizing an antibody described herein may be combined, e.g., CDR grafting, framework mutation and CDR mutation.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756 (2001); Lonberg, N. and D. Huszar Int. Rev. Immunol 13:65 (1995); and Pollock, et al., J Immunol Methods 231:147 (1999). Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for NGF.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat. Acad. Sci. 81:6851 (1984), or by covalently joining to the immunoglobulin coding sequence all or part of the coding sequence for a non-immunoglobulin polypeptide. In that mariner, "chimeric" or "hybrid" antibodies are prepared that have the binding specificity of an anti-NGF monoclonal antibody herein.

Anti-NGF antagonist antibodies may be characterized using methods well known in the art. For example, one method into identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an anti-NGF antagonist antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an anti-NGF antagonist antibody. In another example, the epitope to which the anti-NGF antagonist antibody binds can be determined in a systematic screening by using overlapping peptides derived from the NGF sequence and determining binding by the anti-NGF antagonist antibody. According to the gene fragment expression assays, the open reading frame encoding NGF is fragmented either randomly or by specific genetic constructions and the reactivity of the expressed fragments of NGF with the antibody to be tested is determined.

The gene fragments may, for example, be produced by PCR and then transcribed and translated into protein in vitro, in the presence of radioactive amino acids. The binding of the antibody to the radioactively labeled NGF fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant NGF in which various fragments of the NGF polypeptide have been replaced (swapped) with sequences from a closely related, but antigenically distinct protein (such as another member of the neurotrophin protein family). By assessing binding of the antibody to the mutant NGF, the importance of the particular NGF fragment to antibody binding can be assessed.

Yet another method which can be used to characterize an anti-NGF antagonist antibody is to use competition assays with other antibodies known to bind to the same antigen, i.e., various fragments on NGF, to determine if the anti-NGF antagonist antibody binds to the same epitope as other antibodies. Competition assays are well known to those of skill in the art. Example of antibodies that can be used in the competition assays for the present invention include MAb 911, 912, 938, as described in Hongo, et al., Hybridoma 19:215-227 (2000).

An expression vector can be used to direct expression of an anti-NGF antagonist antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventricle, or pericardium.

Targeted delivery of therapeutic compositions containing an expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, *Mol. Cell. Biol.* (1994) 14:2411, and in Woffendin, *Proc. Natl. Acad. Sci.* (1994) 91:1581.

Other NGF Antagonists

NGF antagonists other than anti-NGF antibodies may be used (pertaining to rheumatoid arthritis pain and osteoarthritis pain). In some embodiments of the invention, the NGF antagonist comprises at least one antisense molecule capable of blocking or decreasing the expression of a functional NGF. Nucleotide sequences of the NGF are known and are readily available from publicly available databases. See, e.g., Borsani et al., *Nuc. Acids Res.* 1990, 18, 4020; Accession Number NM 002506; Ullrich et al., *Nature* 303:821-825 (1983). It is routine to prepare antisense oligonucleotide molecules that will specifically bind NGF mRNA without cross-reacting with other polynucleotides. Exemplary sites of targeting include, but are not limited to, the initiation codon, the 5' regulatory regions, the coding sequence and the 3' untranslated region. In some embodiments, the oligonucleotides are about 10 to 100 nucleotides in length, about 15 to 50 nucleotides in length, about 18 to 25 nucleotides in length, or more. The oligonucleotides can comprise backbone modifications such as, for example, phosphorothioate linkages, and 2'-O sugar modifications well know in the art. Exemplary antisense molecules include the NGF antisense molecules described in U.S. Publication No. 20010046959; see also http://www.rna-tec.com/repair.htm.

In other embodiments, the NGF antagonist comprises at least one antisense molecule capable of blocking or decreasing the expression of a functional NGF receptor (such as TrkA and/or p75). Woolf et al., J. Neurosci. (2001) 21(3):1047-55; Taglialetela et al, J Neurochem (1996) 66(5): 1826-35. Nucleotide sequences of TrkA and p75 are known and are readily available from publicly available databases.

Alternatively, NGF expression and/or release and/or NGF receptor expression can be decreased using gene knockdown, morpholino oligonucleotides, RNAi, or ribozymes, methods that are well-known in the art. See http://www.macalester.edu/~montgomery/RNAi.html; http://pub32.ezboard.com/fmorpholinosfrm19.showMessage?topicID=6.topic; http://www.highveld.com/ribozyme.html.

In other embodiments, the NGF antagonist comprises at least one NGF inhibitory compound. As used herein, "NGF inhibitory compound" refers to a compound other than an anti-NGF antibody that directly or indirectly reduces, inhibits, neutralizes, or abolishes NGF biological activity. An NGF inhibitory compound should exhibit any one or more of the following characteristics: (a) bind to NGF and inhibit NGF biological activity and/or downstream pathways mediated by NGF signaling function; (b) prevent, ameliorate, or treat any aspect of pain (such as osteoarthritis pain); (c) block or decrease NGF receptor activation (including TrkA receptor dimerization and/or autophosphorylation); (d) increase clearance of NGF; (e) inhibit (reduce) NGF synthesis, production or release. Exemplary NGF inhibitory compounds include the small molecule NGF inhibitors described in U.S. Publication No. 20010046959; the compounds that inhibit NGF's binding to p75, as described in PCT Publication No. WO 00/69829; and PD90780 [7-(benzolylamino)-4,9-dihydro-4-methyl-9-oxo-pyrazolo[5,1-b]quinazoline-2-carboxylic acid] as described by Colquhoun et al., *J. Pharmacol. Exp. Ther.* 310(2):505-11 (2004); the compounds that inhibit NGF's binding to TrkA and/or p75, as described in PCT Publication No. WO 98/17278. Additional examples of NGF inhibitory compounds include the compounds described in PCT Publication Nos. WO 02/17914 and WO 02/20479, and in U.S. Pat. Nos. 5,342,942; 6,127,401; and 6,359,130. Further exemplary NGF inhibitory compounds are compounds that are competitive inhibitors of NGF. See U.S. Pat. No. 6,291,247. Furthermore, one skilled in the art can prepare other small molecules NGF inhibitory compounds.

In some embodiments, an NGF inhibitory compound binds NGF. Exemplary sites of targeting (binding) include, but are not limited to, the portion of the NGF that binds to the TrkA receptor and/or p75 receptor, and those portions of the NGF that are adjacent to the receptor-binding region and which are responsible, in part, for the correct three-dimensional shape of the receptor-binding portion. In another embodiment, an NGF inhibitory compound binds an NGF receptor (such as TrkA and/or p75) and inhibits an NGF biological activity. Exemplary sites of targeting include those portions of TrkA and/or p75 that bind to NGF.

In embodiments comprising small molecules, a small molecule can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In general, when the NGF-antagonist according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

In other embodiments, the NGF antagonist comprises at least one NGF structural analog. "NGF structural analogs" in the present invention refer to compounds that have a similar 3-dimensional structure as part of that of NGF and which bind to an NGF receptor under physiological conditions in vitro or in vivo, wherein the binding at least partially inhibits an NGF biological activity. In one embodiment, the NGF structural analog binds to a TrkA and/or a p75 receptor. Exemplary NGF structural analogs include, but are not limited to, the bicyclic peptides described in PCT Publication No. WO 97/15593; the bicyclic peptides described in U.S. Pat. No. 6,291,247; the cyclic compounds described in U.S. Pat. No. 6,017,878; and NGF-derived peptides described in PCT Publication No. WO 89/09225. Suitable NGF structural analogs can also be designed and synthesized through molecular modeling of NGF-receptor binding, for example by the method described in PCT Publication No. WO 98/06048. The NGF structural analogs can be monomers or dimers/oligomers in any desired combination of the same or different structures to obtain improved affinities and biological effects.

In other embodiments, the invention provides an NGF antagonist comprising at least one dominant-negative mutant of the TrkA receptor and/or p75 receptor. One skilled in the art can prepare dominant-negative mutants of, e.g., the TrkA receptor such that the receptor will bind the NGF and, thus, act as a "sink" to capture NGFs. The dominant-negative mutants, however, will not have the normal bioactivity of the TrkA receptor upon binding to NGF. Exemplary dominant-negative mutants include, but are not limited to, the mutants described in the following references: Li et al., Proc. Natl. Acad. Sci. USA 1998, 95, 10884; Eide et al., J. Neurosci. 1996, 16, 3123; Liu et al., J. Neurosci 1997, 17, 8749; Klein et al., Cell 1990, 61, 647; Valenzuela et al., Neuron 1993, 10, 963; Tsoulfas et al., Neuron 1993, 10, 975; and Lamballe et al., EMBO J. 1993, 12, 3083, each of which is incorporated herein by reference in its entirety. The dominant negative mutants can be administered in protein form or in the form of an expression vector such that the dominant negative mutant, e.g., mutant TrkA receptor, is expressed in vivo. The protein or expression vector can be administered using any means known in the art, such as intraperitoneally, intravenously, intramuscularly, subcutaneously, intrathecally, intraventricularly, orally, enterally, parenterally, intranasally, dermally, or by inhalation. For example, administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol. The therapeutic polynucleotides and polypeptides of the present invention can be delivered using gene delivery vehicles. The gene delivery vehicle can be of viral or non-viral origin (see generally, Jolly, Cancer Gene Therapy (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

It is also apparent that an expression vector can be used to direct expression of any of the protein-based NGF antagonists described herein (e.g., anti-NGF antibody, TrkA immunoadhesin, etc.). For example, other TrkA receptor fragments that are capable of blocking (from partial to complete blocking) NGF and/or an NGF biological activity are known in the art.

In another embodiment, the NGF antagonist comprises at least one TrkA immunoadhesin. TrkA immunoadhesins as used herein refer to soluble chimeric molecules comprising the extracellular domain of a TrkA receptor and an immunoglobulin sequence, which retains the binding specificity of the TrkA receptor (substantially retains the binding specificity of the trkA receptor) and is capable of binding to NGF.

TrkA immunoadhesins are known in the art, and have been found to block the binding of NGF to the TrkA receptor. See, e.g., U.S. Pat. No. 6,153,189. Brennan et al. report administration of TrkA immunoadhesin in a rat model of post-surgical pain. See Society for Neuroscience Abstracts 24 (1-2) 880 (1998). In one embodiment, the TrkA immunoadhesin comprises a fusion of a TrkA receptor amino acid sequence (or a portion thereof) from TrkA extracellular domain capable of binding NGF (in some embodiments, an amino acid sequence that substantially retains the binding specificity of the trkA receptor) and an immunoglobulin sequence. In some embodiments, the TrkA receptor is a human TrkA receptor sequence, and the fusion is with an immunoglobulin constant domain sequence. In other embodiments, the immunoglobulin constant domain sequence is an immunoglobulin heavy chain constant domain sequence. In other embodiments, the association of two TrkA receptor-immunoglobulin heavy chain fusions (e.g., via covalent linkage by disulfide bond(s)) results in a homodimeric immunoglobulin-like structure. An immunoglobulin light chain can further be associated with one or both of the TrkA receptor-immunoglobulin chimeras in the disulfide-bonded dimer to yield a homotrimeric or homotetrameric structure. Examples of suitable TrkA immunoadhesins include those described in U.S. Pat. No. 6,153, 189.

In another embodiment, the NGF antagonist comprises at least one anti-TrkA antibody capable of blocking, suppressing, altering, and/or reducing NGF physical interaction with the TrkA receptor and/or downstream signaling, whereby an NGF biological activity is reduced and/or blocked. Anti-TrkA antibodies are known in the art. Exemplary anti-TrkA antibodies include those described in PCT Publication Nos. WO 97/21732, WO 00/73344, WO 02/15924, and U.S. Publication No. 20010046959.

In another embodiment, the NGF antagonist comprises at least one anti-p75 antibody capable of blocking, suppressing and/or reducing NGF physical interaction with the p75 receptor and/or downstream signaling, whereby an NGF biological activity is reduced and/or blocked.

In another embodiment, the NGF antagonist comprises at least one kinase inhibitor capable of inhibiting downstream kinase signaling associated with TrkA and/or p75 receptor activity. An exemplary kinase inhibitor is K252a or K252b, which is known in the art and described in Knusel et al., J. Neurochem. 59:715-722 (1992); Knusel et al., J. Neurochemistry 57:955-962 (1991); Koizumi et al., J. Neuroscience 8:715-721 (1988); Hirata et al., Chemical Abstracts 111:728, XP00204135, see abstract and 12th Collective Chemical Substance Index, p. 34237, c. 3 (5-7), 55-60, 66-69), p. 34238, c.1 (41-44), c.2 (25-27, 32-33), p. 3423, c.3 (48-50, 52-53); and U.S. Pat. No. 6,306,849.

It is expected that a number of other categories of NGF antagonists will be identified if sought for by the clinician. Identification of NGF Antagonists (Such as Anti-NGF Antagonist Antibodies)

NGF antagonists, including anti-NGF antagonist antibodies, can be identified or characterized using methods known in the art, whereby reduction, amelioration, or neutralization of an NGF biological activity is detected and/or measured. Methods described in PCT WO 04/065560 can be used. Another method, for example, a kinase receptor activation (KIRA) assay described in U.S. Pat. Nos. 5,766,863 and 5,891,650, can be used to identify anti-NGF agents. This ELISA-type assay is suitable for qualitative or quantitative measurement of kinase activation by measuring the autophosphorylation of the kinase domain of a receptor protein tyrosine kinase (hereinafter "rPTK"), e.g. TrkA receptor, as well as for identification and characterization of potential antagonists of a selected rPTK, e.g., TrkA. The first stage of the assay involves phosphorylation of the kinase domain of a kinase receptor, for example, a TrkA receptor, wherein the receptor is present in the cell membrane of an eukaryotic cell. The receptor may be an endogenous receptor or nucleic acid encoding the receptor, or a receptor, construct, may be transformed into the cell. Typically, a first solid phase (e.g., a well of a first assay plate) is coated with a substantially homogeneous population of such cells (usually a mammalian cell line) so that the cells adhere to the solid phase. Often, the cells are adherent and thereby adhere naturally to the first solid phase. If a "receptor construct" is used, it usually comprises a fusion of a kinase receptor and a flag polypeptide. The flag polypeptide is recognized by the capture agent, often a capture antibody, in the ELISA part of the assay. An analyte, such as a candidate NGF antagonist (including anti-NGF antagonist antibody) is then added together with NGF to the wells having the adherent cells, such that the tyrosine kinase receptor (e.g. TrkA receptor) is exposed to (or contacted with) NGF and the analyte. This assay enables identification of antagonists (including antibodies) that inhibit activation of TrkA by its ligand NGF. Following exposure to NGF and the analyte, the adhering cells are solubilized using a lysis buffer (which has a solubilizing detergent therein) and gentle agitation, thereby releasing cell lysate which can be subjected to the ELISA part of the assay directly, without the need for concentration or clarification of the cell lysate.

The cell lysate thus prepared is then ready to be subjected to the ELISA stage of the assay. As a first step in the ELISA stage, a second solid phase (usually a well of an ELISA microliter plate) is coated with a capture agent (often a capture antibody) which binds specifically to the tyrosine kinase receptor, or, in the case of a receptor construct, to the flag polypeptide. Coating of the second solid phase is carried out so that the capture agent adheres to the second solid phase. The capture agent is generally a monoclonal antibody, but, as is described in the examples herein, polyclonal antibodies may also be used. The cell lysate obtained is then exposed to, or contacted with, the adhering capture agent so that the receptor or receptor construct adheres to (or is captured in) the second solid phase. A washing step is then carried out, so as to remove unbound cell lysate, leaving the captured receptor or receptor construct. The adhering or captured receptor or receptor construct is then exposed to, or contacted with, an anti-phosphotyrosine antibody which identifies phosphorylated tyrosine residues in the tyrosine kinase receptor. In one embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule. Finally, binding of the anti-phosphotyrosine antibody to the captured receptor or receptor construct is measured, e.g., by a color change in the color reagent.

NGF antagonists (such as anti-NGF antagonist antibody) can also be identified by incubating a candidate agent with NGF and monitoring any one or more of the following characteristics: (a) binding to NGF and inhibiting NGF biological activity or downstream pathways mediated by NGF signaling function; (b) inhibiting, blocking or decreasing NGF receptor activation (including TrkA dimerization and/or autophosphorylation); (c) increasing clearance of NGF; (d) treating or preventing any aspect of rheumatoid arthritis pain or osteoarthritis pain; (e) inhibiting (reducing) NGF synthesis, production or release. In some embodiments, an NGF antagonist (e.g., an anti-NGF antagonist antibody) is identified by incubating an candidate agent with NGF and monitoring binding and/or attendant reduction or neutralization of a biological activity of NGF. The binding assay may be performed with purified NGF polypeptide(s), or with cells naturally expressing, or transfected to express, NGF polypeptide(s). In one embodiment, the binding assay is a competitive binding assay, where the ability of a candidate agent (such as an antibody) to compete with a known anti-NGF antagonist antibody for NGF binding is evaluated. The assay may be performed in various formats, including the ELISA format. In other embodiments, an NGF antagonist (such as anti-NGF antagonist antibody) is identified by incubating a candidate agent with NGF and monitoring binding and attendant inhibition of trkA receptor dimerization and/or autophosphorylation.

Following initial identification, the activity of a candidate anti-NGF antagonist (such as an anti-NGF antagonist antibody) can be further confirmed and refined by bioassays, known to test the targeted biological activities. Alternatively, bioassays can be used to screen candidates directly. For example, NGF promotes a number of morphologically recognizable changes in responsive cells. These include, but are not limited to, promoting the differentiation of PC12 cells and enhancing the growth of neurites from these cells (Greene et al., Proc Natl Acad Sci USA. 73(7):2424-8, 1976), promoting neurite outgrowth from explants of responsive sensory and sympathetic ganglia (Levi-Montalcini, R. and Angeletti, P. Nerve growth factor. Physiol. Rev. 48:534-569, 1968) and promoting the survival of NGF dependent neurons such as embryonic dorsal root ganglion, trigeminal ganglion, or sympathetic ganglion neurons (e.g., Chun & Patterson, Dev. Biol. 75:705-711, (1977); Buchman & Davies, Development 118: 989-1001 (1993). Thus, the assay for inhibition of NGF biological activity entail culturing NGF responsive cells with NGF plus an analyte, such as a candidate NGF antagonist (including anti-NGF antagonist antibody). After an appropriate time the cell response will be assayed (cell differentiation, neurite outgrowth or cell survival).

The ability of a candidate NGF antagonist (including anti-NGF antagonist antibody) to block or neutralize a biological activity of NGF can also be assessed by monitoring the ability of the candidate agent to inhibit NGF mediated survival in the embryonic rat dorsal root ganglia survival bioassay as described in Hongo et al., Hybridoma 19:215-227 (2000).

Compositions for Use in the Methods of the Invention

The compositions used in the methods of the invention (pertaining to rheumatoid arthritis pain and osteoarthritis pain) comprise an effective amount of an NGF antagonist (such as an anti-NGF antibody), and, in some embodiments, further comprise a pharmaceutically acceptable excipient. In some embodiments, the composition is for use in any of the methods described herein. Examples of such compositions, as well as how to formulate, are also described in an earlier section and below. In one embodiment, the composition comprises an NGF antagonist. In another embodiment, the composition comprises one or more NGF antagonists. In another embodiment, the composition comprises one or more NGF antagonists selected from any one or more of the following: an antagonist (e.g., an antibody) that binds (physically interacts with) NGF, an antagonist that binds to an NGF receptor (such as a TrkA and/or p75 receptor), and an antagonist that reduces (impedes and/or blocks) downstream NGF receptor signaling. In still other embodiments, the composition comprises any NGF antagonist that is not a TrkA immunoadhesin (i.e., is other than a TrkA immunoadhesin). In other embodiments, the composition comprises any NGF antagonist that is other than an anti-NGF antibody. In still other embodiments, the composition comprises any NGF antagonist that is other than a TrkA immunoadhesin and other than an anti-NGF antibody. In other embodiments, an NGF antagonist inhibits (reduces) NGF synthesis, production or release. In some embodiments, the NGF antagonist binds NGF and does not significantly cross-react with related neurotrophins (such as NT3, NT4/5, and/or BDNF). In some embodiments, the NGF antagonist is not associated with an adverse immune response. In some embodiments, the NGF antagonist is selected from the group consisting of an anti-NGF antibody, an anti-sense molecule directed to an NGF (including an anti-sense molecule directed to a nucleic acid encoding NGF), an anti-sense molecule directed to an NGF receptor (such as TrkA and/or p75), an NGF inhibitory compound, an NGF structural analog, a dominant-negative mutation of a TrkA receptor that binds an NGF, a TrkA immunoadhesin, an anti-TrkA antibody, an anti-p75 antibody and a kinase inhibitor. In another embodiment, the NGF antagonist is an anti-NGF antibody. In other embodiments, the anti-NGF antibody recognizes human NGF. In some embodiments, the anti-NGF antibody is human. In still other embodiments, the anti-NGF antibody is humanized (such as antibody E3 described herein). In still other embodiment, the anti-NGF antibody comprises a constant region that does not trigger an unwanted or undesirable immune response, such as antibody-mediated lysis or ADCC. In other embodiments, the anti-NGF antibody comprises one or more CDR(s) of antibody E3 (such as one, two, three, four, five, or, in some embodiments, all six CDRs from E3).

It is understood that the compositions can comprise more than one NGF antagonist. For example, a composition can comprise more than one member of a class of NGF antagonist (e.g., a mixture of anti-NGF antibodies that recognize different epitopes of NGF), as well as members of different classes of NGF antagonists (e.g., an anti-NGF antibody and an NGF inhibitory compound). Other exemplary compositions comprise more than one anti-NGF antibodies that recognize the same epitope(s), different species of anti-NGF antibodies that bind to different epitopes of NGF, or different NGF inhibitory compounds.

The composition used in the present invention can further comprise pharmaceutically acceptable carriers, excipients, or stabilizers (*Remington: The Science and Practice of Pharmacy* 20th Ed. (2000) Lippincott Williams and Wilkins, Ed. K. E. Hoover), in the form of lyophilized formulations or aqueous solutions. Pharmaceutically acceptable excipients are further described herein.

The NGF antagonist and compositions thereof can also be used in conjunction with other agents that serve to enhance and/or complement the effectiveness of the agents. For osteoarthritis pain, NGF antagonist may be administered in conjunction with one or more other analgesics, NSAIDS, or steroids. Analgesics include, but are not limited to, acetaminophen, tramadol, capsaicin (topical). Examples of NSAIDS are acetylated salicylates including aspirin; nonacetylated salicylates including salsalate, diflunisal; acetic acids including etodolac, diclofenac, indomethacin, ketorolac, nabumetone; propionic acids including fenoprofen, flurbiprofen, ibuprofen, ketoprofen, naproxen, naproxen sodium, oxaprozin; fenamates including meclofenamate, mefenamic acid; phenylbutazone, piroxicam; COX-2 inhibitors including celecoxib, etoricoxib, valdecoxib, rofecoxib, lumiracoxib. An example of steroids is intraarticular corticosteroids (IACs).

For treating rheumatoid arthritis pain, NGF antagonist may be administered in conjunction with one or more other analgesics, NSAIDS, corticosteroids (e.g., prednisone), or other disease modifying anti-rheumatic drugs. Examples of disease modifying anti-rheumatic drugs are methotrexate, hydroxychloroquine, sulfasalazine, leflunomide, TNF inhibitors, soluble interleukin-1 receptor, gold-conjugates, cytotoxic agents (azathiprine, cyclophosphamide, cyclosporine A).

Administration of an NGF Antagonist (Such as an Anti-NGF Antagonist Antibody)

The NGF antagonist (such as anti-NGF antagonist antibody) can be administered to an individual (for rheumatoid arthritis and osteoarthritis) via any suitable route. It should be apparent to a person skilled in the art that the examples described herein are not intended to be limiting but to be illustrative of the techniques available. Accordingly, in some embodiments, the NGF antagonist (such as anti-NGF antagonist antibody) is administered to an individual in accord with known methods, such as intravenous administration, e.g., as a bolus or by continuous infusion over a period of time, by intramuscular, intraperitoneal, intracerebrospinal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, NGF antagonist (such as anti-NGF antagonist antibody) can be aerosolized using a fluorocarbon formulation and a metered dose inhaler, or inhaled as a lyophilized and milled powder.

In one embodiment, an NGF antagonist (such as an anti-NGF antagonist antibody) is administered via site-specific or targeted local delivery techniques. Examples of site-specific or targeted local delivery techniques include various implantable depot sources of the NGF antagonist (such as anti-NGF antagonist antibody) or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of an NGF antagonist (such as an anti-NGF antagonist antibody) may be used for administration. In some embodiments, the NGF antagonist (e.g., anti-NGF antagonist antibody) may be administered neat. In some embodiments, NGF antagonist (e.g., anti-NGF antagonist antibody) and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing (2000).

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

An anti-NGF antibody can be administered using any suitable method, including by injection (e.g., intraperitoneally, intravenously, subcutaneously, intramuscularly, etc.). Anti-NGF antibodies can also be administered via inhalation, as described herein. Generally, for administration of anti-NGF antibodies, an initial candidate dosage can be about 2 mg/kg. For the purpose of the present invention, a typical daily dosage might range from about any of 0.1 µg/kg to 1 µg/kg to 3 µg/kg to 30 µg/kg to 300 µg/kg to 3 mg/kg, to 30 mg/kg to 100 mg/kg or more, depending on the factors mentioned above. For example, an anti-NGF antibody may be administered at about 1 µg/kg, about 10 µg/kg, about 20 µg/kg, about 50 µg/kg, about 100 µg/kg, about 200 µg/kg, about 500 µg/kg, about 1 mg/kg, or about 2 mg/kg. For repeated administrations over several days or longer, depending on the condition, the treatment is sustained until a desired suppression of symptoms occurs or until sufficient therapeutic levels are achieved to reduce pain. An exemplary dosing regimen comprises administering an initial dose of about 2 mg/kg, followed by a weekly maintenance dose of about 1 mg/kg of the anti-NGF antibody, or followed by a maintenance dose of about 1 mg/kg every other week. However, other dosage regimens may be useful, depending on the pattern of pharmacokinetic decay that the practitioner wishes to achieve. For example, in some embodiments, dosing from one-four times a week is contemplated. Even less frequent dosing may be used. In some embodiments, the anti-NGF antibody is administered once every 2 weeks, every 3 weeks, every 4 weeks, every 5 weeks, every 6 weeks, every 7 weeks, every 8 weeks, every 9 weeks, every 10 weeks, every 15 weeks, every 20 weeks, every 25 weeks, or longer. In some embodiments, the anti-NGF antibody is administered once every 1 month, every 2 months, every 3 months, every 4 months, every 5 months, every 6 months, or longer. The progress of this therapy is easily monitored by conventional techniques and assays. The dosing regimen (including the NGF antagonist(s) used) can vary over time.

Figure 24:
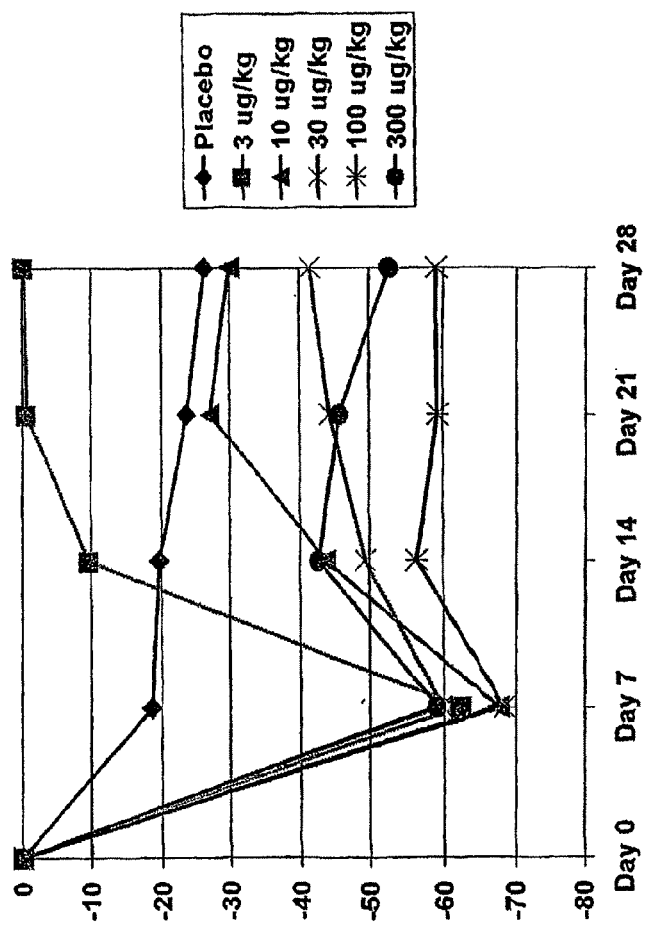
FIG. 24 depicts the changes in mean daily pain intensity after administration of anti-NGF antibody E3 as compared to baseline on day 0. Y axis corresponds to reduction in mean daily pain intensity (VAS score) as compared to mean daily pain intensity on day 0. X axis corresponds to days after administration of anti-NGF antibody E3.
Figure 25:
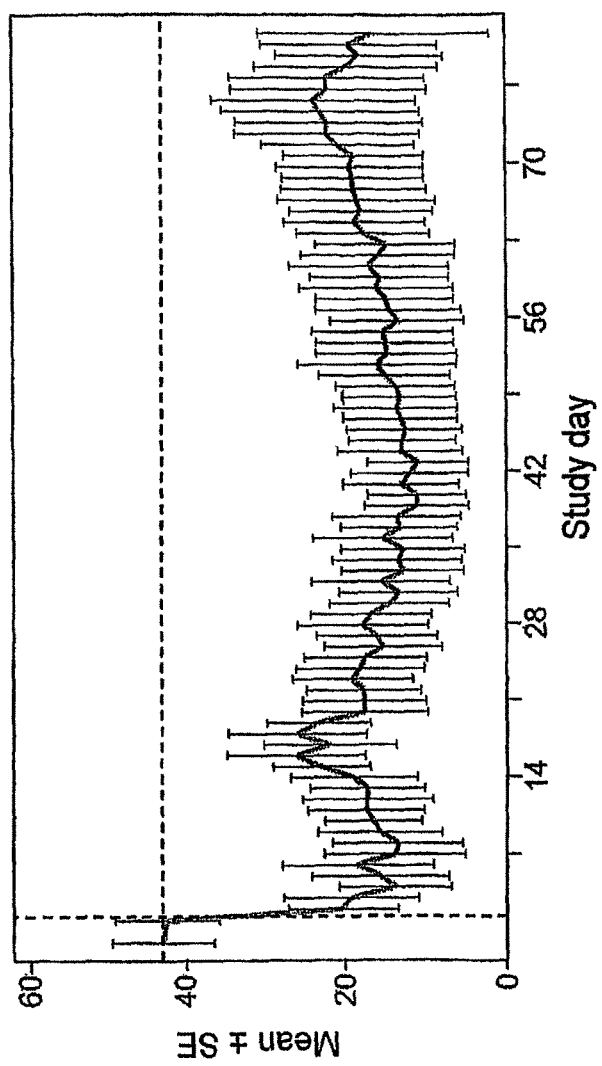
FIG. 25 depicts mean VAS score after administration of anti-NGF antibody E3. "SE" refers to standard error.

Studies carried out in patients with moderate to severe pain from osteoarthritis of the knee (summarized in Example 9) demonstrated that dosages in the range of 3 to 300 µg/kg provided pain relief for varying durations. All dosages tested (3, 10, 30, 100, and 300 µg/kg) produced a reduction in pain for at least 7 days; higher dosages resulted in prolonged pain relief of at least 28 days (FIG. 24). A dose of 100 µg/kg produced pain relief for at least 80 days (FIG. 25).

In general, when it is not an antibody, an NGF antagonist may (in some embodiments) be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present invention, the appropriate dosage of an NGF antagonist (including an anti-NGF antagonist antibody) will depend on the NGF antagonist (or compositions thereof) employed, the type and severity of the pain to be treated, whether the agent is administered for preventive or therapeutic purposes, previous therapy, the patient's clinical history and response to the agent, and the discretion of the attending physician. Typically the clinician will administer an NGF antagonist (e.g., anti-NGF antagonist antibody), until a dosage is reached that achieves the desired result. Dose and/or frequency can vary over course of treatment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of pain. Alternatively, sustained continuous release formulations of NGF antagonists (e.g., anti-NGF antagonist antibodies) may be appropriate. Various formulations and devices for achieving sustained release are known in the art.

In one embodiment, dosages for an NGF antagonist (e.g., anti-NGF antagonist antibody) may be determined empirically in individuals who have been given one or more administration(s) of an NGF antagonist. Individuals are given incremental dosages of an NGF antagonist (e.g., an anti-NGF antagonist antibody). To assess efficacy of an NGF antagonist (e.g., anti-NGF antagonist antibody), an indicator of pain can be followed.

Administration of an NGF antagonist (e.g., an anti-NGF antagonist antibody) in accordance with the method in the present invention can be continuous or intermittent, depending, for example, upon the recipient's physiological condition, whether the purpose of the administration is therapeutic or prophylactic, and other factors known to skilled practitioners. The administration of an NGF antagonist (e.g., an anti-NGF antagonist antibody) may be essentially continuous over a preselected period of time or may be in a series of spaced dose, e.g., either before, during, or after developing pain; before; during; before and after; during and after; before and during; or before, during, and after developing pain.

In some embodiments, more than one NGF antagonist, such as an anti-NGF antagonist antibody, may be present. At least one, at least two, at least three, at least four, at least five different, or more NGF antagonist (e.g., anti-NGF antagonist antibodies) can be present. Generally, those NGF antagonists (such as anti-NGF antagonist antibodies) have complementary activities that do not adversely affect each other. NGF antagonists can also be used in conjunction with other agents that serve to enhance and/or complement the effectiveness of the agents.

Therapeutic formulations of the NGF antagonist (e.g., anti-NGF antagonist antibody) used in accordance with the present invention are prepared for storage by mixing an NGF antagonist (e.g., an antibody) having the desired degree of purity with optional pharmaceutically acceptable carriers, excipients or stabilizers (Remington, The Science and Practice of Pharmacy 20th Ed. Mack Publishing (2000)), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosacchandes, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the NGF antagonist (such as anti-NGF antagonist antibody) are prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antagonist (such as the antibody), which matrices are in the form of shaped articles, e.g. films, or microcapsules. Examples of sustained-release matrices include polyesters, hydrogels (for example, poly(2-hydroxyethyl-methacrylate), or poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−))-3-hydroxybutyric acid.

The formulations to be used for in vivo administration must be sterile. This is readily accomplished by, for example, filtration through sterile filtration membranes. Therapeutic NGF antagonist (e.g., anti-NGF antagonist antibody) compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .μm, particularly 0.1 and 0.5 .μm, and have a pH in the range of 5.5 to 8.0.

The emulsion compositions can be those prepared by mixing an NGF antagonist (such as a nerve growth factor antibody) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Treatment efficacy can be assessed by methods well-known in the art.

Kits Comprising Antibodies and Polynucleotides of the Invention

The invention also provides kits comprising antibodies or polypeptides for use in detection and/or therapy. Accordingly, in some embodiments, the kits comprise an antibody E3. In some embodiments, the kit comprises any antibody or polypeptide described herein.

In other aspects, the kits may be used for any of the methods described herein, including, for example, to treat an individual with pain (including post-surgical pain, rheumatoid arthritis pain, and osteoarthritis pain). The kits of this invention are in suitable packaging, and may optionally provide additional components such as, buffers and instructions for use of the antibody in any of the methods described herein. In some embodiments, the kits include instructions for treating pain. In some embodiments, the kit comprises an anti-NGF antagonist antibody described herein and instructions for treating and/or preventing rheumatoid arthritis pain in an individual. In other embodiments, the kit comprises an NGF antagonist (such as an anti-NGF antagonist antibody) described herein and instructions for treating and/or preventing osteoarthritis pain in an individual. In some of the embodiments, the anti-NGF antagonist antibody is antibody E3.

In another aspect, the invention provides kits comprising a polynucleotide encoding an E3 polypeptide as described herein. In some embodiments, the kits further comprise instructions for use of the polynucleotide in any of the methods described herein.

Methods for Adjusting the Affinity of an Antibody and Methods for Characterizing a CDR We have developed a novel method for characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide, and candidates with increased, the same, decreased or no binding are identified. Methods for determining binding affinity are well-known in the art. In some embodiments, binding affinity is determined using BIAcore surface plasmon resonance analysis, which detects differences in binding affinity of about 2-fold or greater. BIAcore is particularly useful when the starting antibody already binds with a relatively high affinity, for example a $K_D$ of about 10 nM or lower. Screening using BIAcore surface plasmon resonance is described in the Examples, herein.

In other embodiments, binding affinity is determined using Kinexa Biocensor, scintillation proximity assays, ELISA, ORIGEN immunoassay (IGEN), fluorescence quenching, fluorescence transfer, and/or yeast display. In other embodiments, binding affinity is screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, in some embodiments, the library comprises substitutions in two or more positions in one CDR. In other embodiments, the library comprises substitution in two or more positions in two or more CDRs. In still other embodiments, the library comprises substitution in 3, 4, 5, or more positions, said positions found in two, three, four, five or six CDRs. In some embodiments, the substitution is prepared using low redundancy codons. See, e.g., Table 2 of Balint et al., (1993) Gene 137(1):109-18).

In some embodiments, the CDR is CDRH3 and/or CDRL3. In other embodiments, the CDR is one or more of CDRL1, CDRL2, CDRL3, CDRH1, CDRH2, and/or CDRH3. In some embodiments, the CDR is a Kabat CDR, a Chothia CDR, or an extended CDR.

Candidates with improved binding may be sequenced, thereby identifying a CDR substitution mutant which results in improved affinity (also termed an "improved" substitution). For example, as demonstrated in Example 1, use of this method permitted identification of a single substitution which improved binding, even when an estimated 18 other substitutions at the same amino acid position resulted in no binding (i.e., loss of antibody function). Candidates that bind may also be sequenced, thereby identifying a CDR substitution which retains binding.

In some embodiments, multiple rounds of screening are conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acid (including all 20 amino acids), and positions in the CDRs which cannot be changed or which can only be changed to a few amino acids. This aspect is discussed and exemplified in Example 1.

In some embodiments, candidates with improved affinity are combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. In some embodiments, the library also comprises substitution at positions that did not show improved affinity in the first round of screening.

The second library is screened or selected for library members with improved and/or altered binding affinity using any method known in the art, including screening using BIAcore surface plasmon resonance analysis, and selection using any method known in the art for selection, including phage display, yeast display, and ribosome display.

Advantages of the Methods for Adjusting the Affinity of an Antibody and Characterizing a CDR The methods are useful for pre-screening CDR amino acid positions in order to identify amino acid substitutions that improve binding or retain binding. Pre-identification of important residues, substitution that improve binding and/or substitutions that retain antibody function permits efficient design and screening of an affinity maturation library.

The present method is also useful for characterizing a CDR, and provides comprehensive information regarding the importance of each amino acid position in a CDR for binding to antigen. The present method may also be used to identify substitutions that improve binding.

The use of small libraries, in which each position may be randomized (in some embodiments, one at a time), permits screening of substitution mutants using sensitive methods such as BIAcore which provide detailed kinetic information. Screening methods are generally impractical when larger libraries are screened. Instead, selection methods, such as phage display, yeast display, and ribosome display, are commonly used to identify clones that retain binding. Phage display and ELISA assays may depend heavily on the concentration of the protein sample prepared from the clone, and thus tend to be heavily biased towards clones that have increased expression, increased stability, or decreased toxicity, rather than identifying clones with increased binding affinity. In addition, differences in expression level of the clones may mask small improvements in binding affinity. These disadvantages are particularly acute when an antibody with high binding affinity is used as the starting material, because very low levels of antigen must be used in order for screening to be sufficiently stringent.

By contrast, the methods of the invention, such as randomization at each position (in some embodiments, one position at a time), permits introduction and characterization of the effect of the substitution of, for example, all 20 amino acids at a given position. This analysis provides information as to how many substitutions at a given position are tolerated (i.e., retain antibody binding), which in turn, provides information relating to the importance of each amino acid for antibody function. Further, substitutions that result in improved binding can be identified, even under circumstances in which many or most of the substitutions at a given position yield non-functional (non-binding) antibodies. By contrast, alanine-scanning mutagenesis, which is commonly used to identify important CDR positions, provides information relating to whether the substitution of alanine permits or prevents binding. Generally, positions at which an alanine substitution prevents binding are removed from the affinity maturation library. In many cases, however, alanine may be a poor substitute at the CDR position.

The present methods also permit identification and characterization of the effect of single CDR mutations. By contrast, methods such as phage display introduce and select many mutations simultaneously, and thus potentially increase the risk that positive mutations will be masked by the presence of a detrimental mutation present in a particular clone.

The present methods are also useful for improving affinity while retaining the binding specificity of the original (starting) antibody, insofar as the present methods permit identification of small numbers of mutations (e.g., 1, 2, 3, 4, or 5 mutations in a single CDR) that result in improved binding affinity. By contrast, methods such as phage display typically improve binding affinity using multiple mutations at once, which may result in shifting specificity of the antibody and/or increasing undesirable cross-reactivity.

The following examples are provided to illustrate, but not to limit, the invention.

EXAMPLES

Example 1

Humanization and Affinity Maturation of Mouse Antagonist Anti-NGF Antibody 911

A. General Methods

The following general methods were used in this example.
Library Generation

Libraries were generated by PCR cassette mutagenesis with degenerate oligonucleotides as described in Kay et al. (1996), *Phage display of peptides and proteins: a laboratory manual*, San Diego, Academic Press (see, pages pp. 277-291). The doping codon NNK was used to randomize one amino acid position to include 20 possible amino acids. To randomize one amino acid position to include only a subset of amino acids with specific properties, doping codons were used as described in Balint et al, (1993) *Gene* 137(1):109-18). Site directed mutagenesis was performed using recombinant PCR as described in Innis et al, (1990) PCR protocols: A guide to methods and applications (see, pp. 177-183).
Small Scale Fab Preparation Small scale expression in 96 wells plates was optimized for screening Fab libraries. Starting from *E. coli* transformed with a Fab library, colonies were picked to inoculate both a master plate (agar LB+Ampicillin (50 µg/ml)+2% Glucose) and a working plate (2 ml/well, 96 well/plate containing 1.5 mL of LB+Ampicillin (50 µg/ml)+2% Glucose). Both plates were grown at 30° C. for 8-12 hours. The master plate was stored at 4° C. and the cells from the working plate were pelleted at 5000 rpm and resuspended with 1 mL of LB+Ampicillin (50 µg/ml)+1 mM IPTG to induce expression of Fabs. Cells were harvested by centrifugation after 5 h expression time at 30° C., then resuspended in 500 µL of buffer HBS-EP (100 mM HEPES buffer pH 7.4, 150 mM NaCl, 0.005% P20, 3 mM EDTA). Lysis of HBS-EP resuspended cells was attained by one cycle of freezing (−80° C.) then thawing at 37° C. Cell lysates were centrifuged at 5000 rpm for 30 min to separate cell debris from supernatants containing Fabs. The supernatants were then injected into the BIAcore plasmon resonance apparatus to obtain affinity information for each Fab. Clones expressing Fabs were rescued from the master plate to sequence the DNA and for large scale Fab production and detailed characterization as described below.
Large Scale Fab Preparation To obtain detailed kinetic parameters, Fabs were expressed and purified from large cultures. Erlenmeyer flasks containing 200 mL of LB+Ampicillin (50 µg/ml)+2% Glucose were inoculated with 5 mL of over night culture from a selected Fab-expressing *E. coli* clone. Clones were incubated at 30° C. until an $OD_{550nm}$ of 1.0 was attained and then induced by replacing the media for 200 ml, of LB+Ampicillin (50 µg/ml)+1 mM IPTG. After 5 h expression time at 30° C., cells were pelleted by centrifugation, then resuspended in 10 mL PBS (pH 8). Lysis of the cells was obtained by two cycles of freeze/thaw (at −80° C. and 37° C., respectively). Supernatant of the cell lysates were loaded onto Ni-NTA superflow sepharose (Qiagen, Valencia. CA) columns equilibrated with PBS, pH 8, then washed with 5 column volumes of PBS, pH 8. Individual Fabs eluted in different fractions with PBS (pH 8)+300 mM Imidazol. Fractions containing Fabs were pooled and dialized in PBS, then quantified by ELISA prior to affinity characterization.

Full Antibody Preparation

For expression of full antibodies, heavy and light chain variable regions were cloned in 2 mammalian expression vectors (Eb.911.E3 or Eb.pur.911.3E for light chain and Db.911.3E for heavy chain; described herein) and transfected using lipofectemine into HEK 293 cells for transient expression. Antibodies were purified using protein A using standard methods.

Biacore Assay

Affinities of anti-NGF Fabs and monoclonal antibodies were determined using the BIAcore3000™ surface plasmon resonance (SPR) system (BIAcore, INC, Piscaway N.J.). CM5 chips were activated with N-ethyl-N-(3-dimethylaminopropyl)-carbodiinide hydrochloride (EDC) and N-hydroxysuccinimide (NHS) according to the supplier's instructions. Human NGF was diluted into 10 mM sodium acetate pH 4.0 and injected over the activated chip at a concentration of 0.005 mg/mL. Using variable flow time across the individual chip channels, two ranges of antigen density were achieved: 100-200 response units (RU) for detailed kinetic studies and 500-600 RU for screening assays. The chip was blocked with ethanolamine. Regeneration studies showed that a mixture of Pierce elution buffer (Product No. 21004, Pierce Biotechnology, Rockford, Ill.) and 4 M NaCl (2:1) effectively removed the bound Fab while keeping the activity of hNGF on the chip for over 200 injections. HBS-EP buffer (0.01M HEPES, pH 7.4, 0.15 NaCl, 3 mM EDTA, 0.005% Surfactant P29) was used as running buffer for all the BIAcore assays.

Screening Assay

A screening BIAcore assay was optimized to determine the affinity of Fab clones from libraries. Supernatants of small culture lysates were injected at 50 µl/min for 2 min. Dissociation times of 10 to 15 minutes were used for determination of a single exponential dissociation rate ($k_{off}$) using BIAevaluation software. Samples that showed $k_{off}$ rates in the same range as the template used to create the library (clone 8L2-6D5, $k_{off}$ 1×10$^{-3}$ s$^{-1}$) were injected for confirmation and dissociation times of up to 45 min were allowed to obtain better $k_{off}$ values. Clones showing improved (slower) $k_{off}$ values were expressed at large scale and full kinetic parameters, $k_{on}$ and $k_{off}$, were determined on purified protein. The assay was capable of detecting differences in affinity that were approximately 2-fold or larger.

Affinity Determination Assay

Serial dilutions (0.1-10× estimated $K_D$) of purified Fab samples were injected for 1 min at 100 µL/min and dissociation times of up to 2 h were allowed. The concentrations of the Fab proteins were determined by ELISA and/or SDS-PAGE electrophoresis using as a standard a Fab of known concentration (as determined by amino acid analysis). Kinetic association rates ($k_{on}$) and dissociation rates ($k_{off}$) were obtained simultaneously by fitting the data to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values were calculated as $k_{off}/k_{on}$.

B. Humanization and Affinity Maturation of Mouse Antagonist Anti-NGF Antibody 911

The mouse antagonist anti-NGF antibody, 911 (see Hongo et al, (2000) Hybridoma 19(3):215-227) was selected for humanization and affinity maturation. Mab 911 binds human and rat NGF with high affinity and exhibits no significant cross-reactivity with the neurotrophins NT3, NT4/5 or BDNF. See Hongo, id. The affinity of the papain-cleaved Fab fragment of mouse Mab 911 was determined using BIAcore analysis as described above. The papain-cleaved Fab fragment of mouse Mab 911 bound human NGF with a $K_D$ of approximately 10 nM.

Humanization and affinity maturation was conducted in several steps, as follows:

(1) Preparation of CDR-Grafted Template.

The light chain extended CDRs of antibody 911 (i.e., including both the Kabat and Chothia CDR regions) were grafted into the human germline acceptor sequences O8 with JK2 and the heavy chain extended CDRs of antibody 911 were grafted in to human germline acceptor sequence VH4-59 with JH4. The amino acid sequences of the human germline acceptor sequences are shown in FIGS. 1A and 1B. Amino acid numbering is sequential. Using the protein frameworks noted above, DNA sequences were designed for synthetic genes encoding human framework with the murine CDRs. These humanized heavy and light variable domains were termed hVH and hVL respectively. Codons were optimized for E. coli and hamster usage. Several overlapping oligonucleotides (69-90 bases in length) extending the full length of the hVL and hVH with two short flanking primers for each chain were used to separately synthesize the two genes by recursive PCR essentially as described in Prodromou et al, (1992) Protein Eng 5(8): 827-9. Resulting DNA fragments of the correct length were gel purified and then cloned into an E. coli bicistronic expression plasmid (ampicillin resistant). Expression of the antibodies was under control of an IPTG inducible lacZ promoter similar to that described in Barbas (2001) Phage display: a laboratory manual, Cold Spring Harbor, N.Y., Cold Spring Harbor Laboratory Press (see Vector pComb3X, at pg 2.10), however, modifications included addition and expression of the following additional domains: the human Kappa light chain constant domain (see GenBank Accession No. CAA09181) and the CHI constant domain of IgG2a human immunoglobulin (GenBank Accession No. P01859).

The amino acid sequences of the variable regions of the CDR-grafted antibody (also termed the "template"), termed 8L2-4D5, are also shown in FIGS. 1A and 1B. The affinity of 8L2-4D5 was determined using BIAcore analysis as described above. 8L2-4D5 bound human NGF with a $K_D$ of approximately 38 nM.

(2) Introduction of a Point Mutation into the Framework Sequence.

The V71K substitution was introduced into the CDR-grafted heavy chain using recombinant PCR site directed mutagenesis as described in Innis et al, (1995) PCR strategies, San Diego, Academic Press. This substitution replaced the human framework residue with the corresponding mouse framework residue. The resulting antibody was termed 8L2-6D5, and the amino acid sequence of the heavy chain variable region of 8L2-6D5 is shown in FIG. 1A. The affinity of 8L2-6D5 was determined using BIAcore analysis as described above. The Fab fragment of 8L2-6D5 bound human NGF with a Kd of approximately 15 nM. 8L2-6D5 was chosen as template for affinity maturation.

(3) Humanization and Affinity Maturation of CDRs L1, L2, H1 and H2. CDRs L1, L2, H1 and H2 were subjected to humanization and affinity maturation. Amino acid positions in CDRs L1, L2, H1, and H2 were identified that are not essential for the structure of the CDRs based on the Chothia canonical structure (see Al-Lazikani et al (1997) J. Mol. Biol. 273(4):927-48); and subjected to randomization as follows. Two libraries were prepared containing the light chain mutations or heavy chain mutations shown in Table 2, and the grafted (mouse) CDR L3 or CDR H3, respectively, using PCR cassette mutagenesis with degenerate oligonucleotides as described in Kay et al. (1996), *Phage display of peptides and proteins: a laboratory manual*, San Diego, Academic Press, using doping codons as described in Balint et al, (1993) *Gene* 137(1):109-18). Generally, the amino acid residues were altered to residues that are more common in human antibodies, based on alignments of antibody 911 light chain and heavy chain amino acid sequences with human germline antibody sequences. The wildtype (unsubstituted) amino acid residue was also represented in the library with the exception of CDR H2 residue 50, a methionine, in which the wildtype methionine was not represented in the library. Methionine residues are subject to oxidation; thus, replacement of that residue was expected to improve stability of the resulting antibody. The libraries of Fabs were cloned into vector pComb3X plus the human CH1 and Cκ regions, as described above.

TABLE 2

1. Heavy chain H1/H2 library:
CDR-H1

I34 was changed to F, L, V, S, P, T, A, or I
N35 was changed to N, T, S, or Y
CDR-H2

M50 was changed to all 20 natural amino acids
A62 was changed to A or S
L63 was changed to L or V TABLE 2-continued 2. Light chain L1/L2 library

CDR-L1

S26 was changed to S, A, V, or F
D28 was changed to D, A, S, or Y
H32 was changed to H, N, K, D, E, Q, or Y
CDR-L2

Y50 was changed to Y, D, A, or S
I51 was changed to I, T, A, or V
F54 was changed to F or L
S56 was changed to S and T For affinity screening experiments, each library was further paired with the corresponding CDR-grafted light or heavy chain (for example, the H1/H2 library was paired with CDR-grafted light chain), the antibody was expressed, and affinity to human NGF of the individual clones was screened using the BIACORE surface plasmon resonance (SPR) system (BIAcore, Inc. Piscataway, N.J.) according to the manufacturer's instructions and as described above. $k_{off}$, $k_{on}$ and $K_D$ were determined. Antibody clones were ranked based on $k_{off}$ rates, since generally most variation in affinity is seen in $K_{off}$ rates, and further because $k_{off}$ rates are independent of antibody concentration.

The sequence of clones that bound was determined and the sequence of clones that bound is shown in table 3.

TABLE 3

L1 and L2 amino acid sequences, H1 and H2 amino acid sequences, and kinetic data for clones that bound following affinity screening of H1/H2 or L1/L2 library clones.

| CDR 1-2 mutants kinetic data Light chain library clones Paired with 8L2 heavy chain | CDRL1 AA sequence | CDRL2 AA sequence | $k_{off}$ (s-1) | *$K_D$ (nM) |
|---|---|---|---|---|
| 8L2-6D5 (control) | RASQDISNHLN (SEQ ID NO: 12) | YISRFHS (SEQ ID NO: 13) | **1e-3 | 25 |
| L129 | RASQSISNNLN (SEQ ID NO: 18) | YTSRFHS (SEQ ID NO: 19) | 4.5e-4 | 11 |
| L208 | RASQYISNHLN (SEQ ID NO: 20) | YTSRFHS (SEQ ID NO: 21) | 4.6e-4 | 11 |
| L97 | RASQSISNQLN (SEQ ID NO: 22) | YVSRFHS (SEQ ID NO: 23) | 5.6e-4 | 14 |
| L81 | RAFQAISNQLN (SEQ ID NO: 24) | YISRFHT (SEQ ID NO: 25) | 7.4e-4 | 18 |
| L6 | RAFQSISNQLN (SEQ ID NO: 26) | YASRFHS (SEQ ID NO: 27) | 8.2e-4 | 20 |
| Heavy chain library clones Paired with 6D5 Light chain | CDRH1 AA sequence | CDRH2 AA sequence | $k_{off}$ (s-1) | *$K_D$ (nM) |
| 8L2-6D5 (control) | GFSLIGYDIN (SEQ ID NO: 9) | MIWGDGTTDYNSAL (SEQ ID NO: 10) | 1e-3 | 25 |
| H109 | GFSLIGYDSN (SEQ ID NO: 28) | IIWGDGTTDYNSAL (SEQ ID NO: 29) | 1.6e-4 | 4 |
| H19 | GFSLIGYDLN (SEQ ID NO: 30) | IIWGDGTTDYNSAV (SEQ ID NO: 31) | 2.4e-4 | 6 |

TABLE 3-continued

L1 and L2 amino acid sequences, H1 and H2 amino acid sequences, and kinetic data for clones that bound following affinity screening of H1/H2 or L1/L2 library clones.

| | | | | |
|---|---|---|---|---|
| H222 | GFSLIGYDVT (SEQ ID NO: 32) | GIWGDGTTDYNSAV (SEQ ID NO: 33) | 3.8e-4 | 9.5 |
| H225 | GFSLIGYDVT (SEQ ID NO: 34) | GIWGDGTTDYNSSV (SEQ ID NO: 35) | 3.8e-4 | 9.5 |
| H18 | GFSLIGYDAT (SEQ ID NO: 36) | GIWGDGTTDYNSAV (SEQ ID NO: 37) | 4.2e-4 | 10.5 |
| H9 | GFSLIGYDVS (SEQ ID NO: 38) | IIWGDGTTDYNSSV (SEQ ID NO: 39) | 4.1e-4 | 10.2 |
| H227 | GFSLIGYDIS (SEQ ID NO: 40) | QIWGDGTTDYNSSV (SEQ ID NO: 41) | 5.4e-4 | 13.5 |
| H17 | GFSLIGYDAS (SEQ ID NO: 42) | GIWGDGTTDYNSSV (SEQ ID NO: 43) | 6.1e-4 | 15.2 |
| H28 | GFSLIGYDST (SEQ ID NO: 44) | SIWGDGTTDYNSAL (SEQ ID NO: 45) | 7.5e-4 | 18.7 |

AA in bold were randomized as indicated above
*KD calculated using $k_{on}$ 4e4 $M^{-1}s^{-1}$
**For convenience, "e" as used herein denotes "x10." Thus, 4e4 interchangeably means $4 \times 10^4$.

CDRs containing the following substitutions retained binding:
CDR-H1
I34: S, L, V, I and A bound.
N35: N, T and S bound.
CDR-H2
M50: M, I, G, Q, S, L bound.
A62: A and S bound.
L63: L and V bound.
CDR-L1
S26: S, and F bound.
D28: D, S, A, Y bound.
H32: H, N, Q bound.
CDR-L2
Y50: Y bound.
I51: I, T, V, A, bound.
F54: F bound
S56: S and T bound CDRs containing the following substitutions were selected generally based on binding affinity and combined into a single clone, termed H19-L129:
CDR-H1: I34L; N35N (no change)
CDR-H2: M50I; A62A (no change); L63V
CDR-L1: S26S (no change); D28S; H32N
CDR-L2: Y50Y (no change); I51T; F54F (no change); S56S (no change)

These mutations were combined (by amplifying the H and L chains by PCR, cutting the PCR products and vector (pRN8) with restriction enzyme and performing a 3 fragment ligation) into a single clone, termed H19-L129, which also included the grafted H3 and L3 CDRs. The sequence of the heavy chain and light chain variable regions of H19-L129 is shown in FIGS. 1A and 1B, and Table 4 shows the amino acid sequence of CDRs L1, L2, H1 and H2. H19-L129 bound NGF with a KD of approximately 1 nM, as determined using BIAcore analysis as described herein.

TABLE 4

Amino acid sequence of CDRs H1, H2, L1 and L2 and kinetic data for combined clone H19-L129.

| Combination clone: mutations in CDRs H1, H2, L1, L2 | CDRL1 CDRH1 AA sequence | CDRL2 CDRH2 AA sequence | $k^{off}$ (s-1) | $*K_D$ (nM) |
|---|---|---|---|---|
| H19-L129 | CDR-L1: RASQSISNNLN (SEQ ID NO: 18) CDR H1: GFSLIGYDLN (SEQ ID NO: 30) | CDRL2: YTSRFHS (SEQ ID NO: 19) CDR-H2: IIWGDGTTDYNSAV (SEQ ID NO: 31) | 1.1e-4 | 3.5 |

*KD calculated using $k_{on}$ 4e4 $M^{-1}s^{-1}$ (4) Affinity maturation of H3 and L3 CDRs. Affinity maturation of the H3 and L3 CDRs was carried out in two steps. First, in a process termed "library scanning mutagenesis", each amino acid residue in H3 and L3 was individually pre-screened in order to identify amino acid positions at which a mutation resulted in increased binding affinity to human NGF. Based on the results of the library scanning mutagenesis (also termed "small library randomization analysis"), a subset of amino acid positions in H3 and L3 were selected for preparation of the affinity maturation library, and the affinity maturation library was screened for affinity to human NGF using BIAcore analysis as described herein. It is appreciated that these techniques can be generally applied.
(a) Library Scanning Mutagenesis
Each amino acid position in the H3 and L3 CDRs was individually pre-screened for substitutions which resulted in increased binding affinity to human NGF. The frequency of amino acid substitutions at any given position that resulted in improved binding, the same binding, worse binding or no binding provided information relating to relating to positions in the CDRs that can be changed to many different amino acid (including all 20 amino acids), and positions in the CDRs which cannot be changed or which can only be changed to a few amino acids. Amino acid substitutions resulting in increased binding affinity were also identified. Based on the results of this screening, a subset of amino acid positions in CDRs H3 and L3 were selected for preparation of an affinity maturation library.

Individual Fab libraries were prepared in which each amino acid of L3 and H3 CDRs was randomized to all 20 amino acids, one at a time, resulting in several (5 libraries for the light chain and 13 libraries for the heavy chain) small libraries, each with a complexity of 20 amino acid possibilities at each amino acid position. In all cases, the native (i.e., unchanged) amino acid was represented in the library. Libraries were prepared by PCR cassette mutagenesis with degenerate oligonucleotides as described in Kay et al. (1996), *Phage display of Peptides and Proteins: a laboratory manual*, San Diego, Academic Press, using the doping codon NNK to randomize one amino acid position to include 20 possible amino acids. The 8L2-6D5 (the CDR grafted antibody, having the framework mutation V71K) served as the template for library construction because the lower affinity of the CDR grafted antibody permitted easier detection of differences in affinity in H3 and L3 mutants during screening. Thus, each member of a library contained a CDR3 (either H3 or L3) with one amino acid substitution, and 5 grafted CDRs.

20-80 clones from each small library were screened using BIAcore analysis as described herein. Samples were simultaneously analyzed by BIAcore for binding affinity to NGF in one channel of the BIAcore chip and for presence of Fab by binding to a penta-histag antibody in another channel of the sensor chip, to detect the his tag at the C terminus of the heavy chain. Clones that expressed protein were classified as having the same affinity, worse affinity, better affinity or no binding, using koff to classify: The results of this analysis are shown in Table 5.

TABLE 5

Clones that expressed protein were classified as having the same affinity, worse affinity, better affinity or no binding, based on koff.

| mutation | better 1e-3< | same ≥1e-3, 2e-3< | Worse ≥2e-3 | no bind | Percentage of AAs that retain binding capacity |
|---|---|---|---|---|---|
| Light chain | | | | | |
| L_S91X | 13% | 40% | 20% | 26% | 50% |
| L_K92X | | 100% | | | ~100% |
| L_T93X | | 93% | 7% | | 93% |
| L_L94X | | 40% | 60% | | 40% |
| L_Y96X | | 13% | 80% | 7% | 13% |
| Heavy chain | | | | | |
| H_G98X | | 50% | 37% | 13% | 50% |
| H_G99X | | 46% | 54% | | 46% |
| HY100X | | 26% | | 73% | 26% |
| HY101X | 6% | | 12% | 82% | 6% |
| H_Y102X | | 7% | 25 | 68% | 7% |
| H_G103X | 4% | 21% | 16% | 58% | 25% |
| H_T104X | | 20% | 30% | 50% | 20% |
| H_S105X | 10% | 25% | 26% | 39% | 35% |
| H_Y106X | | 75% | 25% | | 75% |
| H_Y107X | | 8% | 46% | 46% | 8% |
| H_F108X | | 23% | 27% | 50% | 23% |
| H_D109X | | 29% | 46% | 25% | 29% |
| H_Y110X | | 90% | 5% | 5% | 90% |

The sequence of all clones with improved affinity was determined, revealing the frequency and identity of amino acid substitutions that resulted in increased affinity. In addition, a few clones that retained an affinity similar to the 8l2-6D5 clone were selected from each library, in order to ascertain amino acid sequence substitutions that were permitted at a given position, even though the substitution did not necessarily increase binding affinity. The results of this analysis are summarized in Table 6.

TABLE 6

| | $k_{off}$(s-1) 1E-3 | $K_D$* (nM) 25 |
|---|---|---|
| CDR H3 mutations (8L2-6D5 template, including antibody 911 CDR-H3 amino acid sequence: GGYYYGTSYYFDY (SEQ ID NO: 11) | | |
| Y100L | 1.2E-3 | 30 |
| Y100R | 1.1E-3 | 27 |
| Y101W | 5.6E-4 | 14 |
| G103A | 1.6E-4 | 4 |
| T104S | 2.2E-3 | 55 |
| S105A | 5.1E-4 | 13 |
| S105T | 6.4E-4 | 16 |
| Y106R | 1.6E-3 | 40 |
| Y106T | 2.0E-3 | 50 |
| Y106M | 2.7E-3 | 67 |
| Y107F | 1.4E-3 | 35 |
| F108W | 1.22E-3 | 30 |
| D109N | 1.5E-3 | 37 |
| D109G | 1E-3 | 25 |
| Y110K | 1.4E-3 | 35 |
| Y110S | 1.5E-3 | 37 |
| Y110R | 1.6E-3 | 40 |
| Y110T | 1.7E-3 | 42 |
| CDR L3 mutations (8L2-6D5 template, including wildtype (unsubstituted) CDR-L3 amino acid sequence: QQSKTLPYT (SEQ ID NO: _14) | | |
| S91E | 2.5E-4 | 6 |
| Y96R | 1.7E-3 | 42 |

*KD calculated using $k_{on}$ 4e4 $M^{-1}s^{-1}$

Several mutations resulted in increased binding affinity. At least the following mutations resulted in significantly increased binding affinity as compared with the 8L2-6D5 template: (H_Y101W (CDR sequence GGYWYGTSYYFDY (SEQ ID NO:46)); H_S105A (CDR sequence GGYYYGTAYYFbY (SEQ ID NO:47)); H_S105T (CDR sequence GGYYYGTTYYFDY (SEQ ID NO:48)); H_G103A (CDR sequence GGYYYATSYYFDY (SEQ ID NO:49); and L_S91E (CDR sequence QQEKTLPYT (SEQ ID NO:50)).

The results of this experiment were used to guide selection of amino acid positions for generation of the affinity maturation libraries.

This experiment also provided information regarding the frequency of amino acid substitutions at any given position that resulted in improved binding, the same binding, worse binding or no binding, as shown in Table 5. This information permitted identification of amino acid positions in the CDRs that could be changed to many different amino acid (including all 20 amino acids), and positions in the CDRs which could be changed to a few amino acids or a very few amino acids (in some embodiments, no amino acids). These results also demonstrated amino acid substitutions that increased binding affinity.

(b) Affinity Maturation

Next, the results of the small library randomization analysis (above) were used to select residues for production of the H3 and L3 libraries for affinity maturation of the H3 and L3 CDRs. Residues Y101 and G103 of CDR H3 and residues S91 and K92 of CDR L3 were selected for production of the H3 and L3 libraries for affinity maturation of the H3 and L3 CDRs.

This library combined mutations in H3 and L3 at the same time in CDR-grafted clone 8L2-6D5, and separately in the background of H19-L129, and had a diversity of 80 different clones. Table 7 shows the amino acid residues selected for substitution and the amino acids that were substituted at each position.

TABLE 7

Amino acid residues in H3 and L3 selected for substitution and the amino acids that were substituted at each position

CDR-H3:

Y101 was changed to Y and W, C. (Note that C was included because use of codon TRS in one degenerated oligonucleotide also generated codon C). G103 was changed to A, P, S
CDR-L3:

S91 was changed to E.
K92 was changed to all twenty amino acids. A, R, K, and H bound.

Each polypeptide was expressed as a Fab, and affinity to human NGF of 96 individual clones was screened for each library using BIACORE analysis according to the manufacturer's instructions and described above. The results of this analysis are shown in Table 8.

TABLE 8

| CDR L3 H3 COMBINATION mutations (8L2-6D5 template) | $k_{off}$ (s-1) 1E-3 | $K_D$* (nM) 25 |
|---|---|---|
| L_S91E; L_K92A (CDR sequence QQEATLPYT (SEQ ID NO: 51)) | 5.5E-4 | 13 |
| H_Y101W; H_G103A (CDR sequence GGYWYATSYYFDY (SEQ ID NO: 52)) | | |
| L_S91E; L_K92R (CDR sequence QQERTLPYT (SEQ ID NO: 53)) | 1.0E-4 | 25 |
| H_Y101W; H_G103A (CDR sequence GGYWYATSYYFDY (SEQ ID NO: 54)) | | |
| CDR L3 H3 COMBINATION mutations (H19-L129 template, H1H2L1L2 matured) | $k_{off}$(s-1) 1.1e-4 | $K_D$* (nM) |
| L_S91E; L_K92H (CDR sequence QQEHTLPYT (SEQ ID NO: 55)) | 1.2E-5 | 0.3 |
| H_Y101W; H_G103A (CDR sequence GGYWYATSYYFDY (SEQ ID NO: 56)) (CLONE E3) | | |
| L_S91E; L_K92S (CDR sequence QQESTLPYT (SEQ ID NO: 57)) | 4.7E-5 | 1.1 |
| H_Y101W; H_G103S (CDR sequence GGYWYSTSYYFDY (SEQ ID NO: 58)) | | |

TABLE 8-continued

| | | |
|---|---|---|
| L_S91E; L_K92K (CDR sequence QQEKTLPYT (SEQ ID NO: 59)) | 2E-5 | 0.5 |
| H_Y101Y; H_G103A (CDR sequence GGYYYATSYYFDY (SEQ ID NO: 60)) | | |
| L_S91E; L_K92R (CDR sequence QQERTLPYT (SEQ ID NO: 61)) | 1.4E-5 | 0.35 |
| H_Y101W; H_G103A (CDR sequence GGYWYATSYYFDY (SEQ ID NO: 62)) (CLONE 3C) | | |
| L_S91E; L_K92R (CDR sequence QQERTLPYT (SEQ ID NO: 63)) | 1.5E-5 | 0.37 |
| H_Y101Y; H_G103A (CDR sequence GGYYYATSYYFDY (SEQ ID NO: 64)) | | |

*KD calculated using $k_{on}$ 4e4 $M^{-1}s^{-1}$

Based on binding affinity, the best clones, E3 (interchangeably termed "3E") and 3C, were selected for further characterization. E3 comprised the following CDR substitutions: CDR-H3: Y101W, G103A; and CDR-L3: S91E, K92H, which were combined into a single clone which also included the following L1, L2, H1 and H2 mutations:
CDR-H1: I34L;
CDR-H2: M50I; L63V;
CDR-L1: D28S; H32N;
CDR-L2: I51T.
The sequence of the heavy chain and light chain variable regions of E3 is shown in FIGS. 1A and 1B. 3C comprised the following CDR substitutions: CDR-L3: S91E; K92R; CDRH3:Y101W; G103A, which were combined into a single clone which also included the L1, L2, H1 and H2 mutations described for clone 3E.

3E and 3C sequences were cloned into mammalian expression vectors for production of Fab and full antibody, and expressed in HEK293 cells and purified using Ni-NTA or protein A chromatography. Pure protein was accurately quantified by amino acid analysis.

Figure 9:
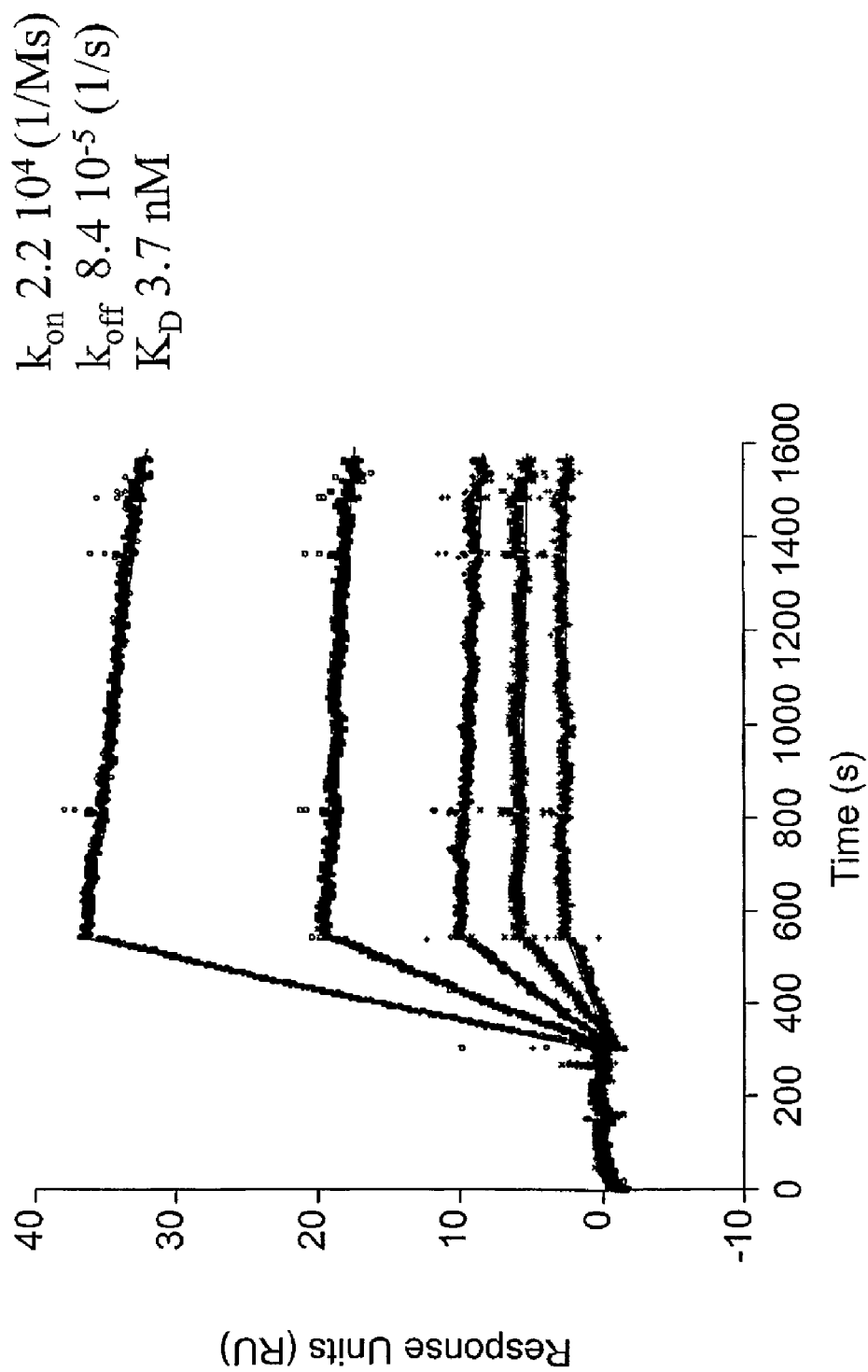
FIG. 9: is a graph showing the results of BIAcore analysis of the binding affinity to human NGF of mouse antibody 911 (Fab). Mouse antibody 911 bound NGF with a KD of 3.7 nM, koff of $8.4 \times 10^{-5}$ s$^{-1}$ and kon of $2.2 \times 10^4$ Ms$^{-1}$.
Figure 10:
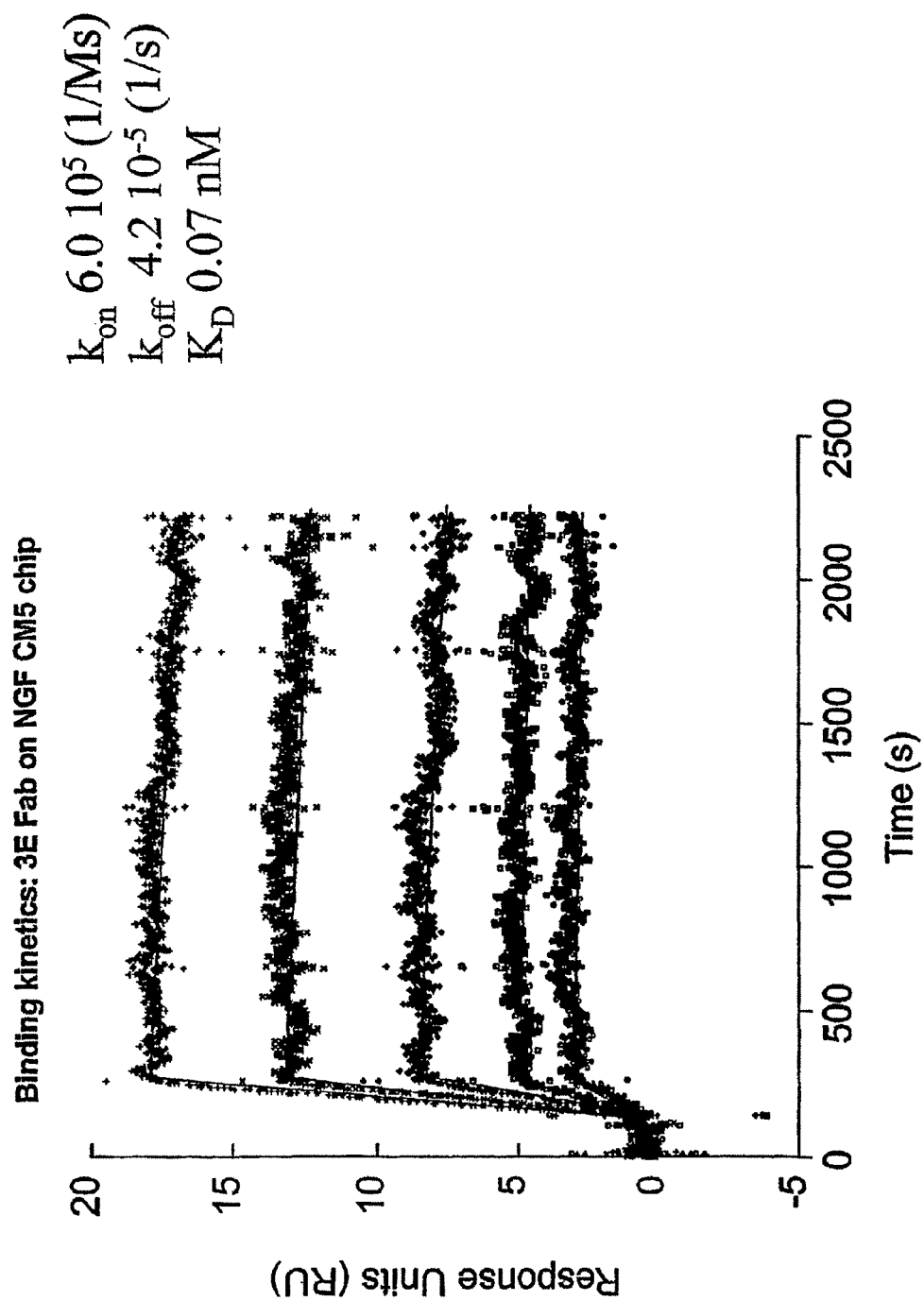
FIG. 10: is a graph showing the results of BIAcore analysis of the binding affinity to human NGF of antibody E3 (Fab) (referred to as "3E Fab"). E3 bound human NGF with a KD of approximately 0.07 nM (and with a kon of about $6.0 \times 10^5$ M$^{-1}$ s$^{-}$, and a $k_{off}$ of about $4.2 \times 10^{-5}$ s$^{-1}$).

The binding affinities to human NGF of Fabs E3 and 3C were measured using BIAcore analysis according to the manufacturer's instructions and as described above, except that 100 RU NGF was used on chip to prevent a rebinding effect. Briefly, several concentrations of antibodies (Fabs) were injected for 2 minutes onto a CM5 chip with 100 RU of immobilized human NGF on it, and permitted to dissociate for 1800 seconds. Mouse antibody 911 (Fab) was analyzed as a control. Data was analyzed using BIAevaluation software following the manufacturer's instructions. The results of the analysis of antibody E3 and 911 are shown in FIGS. 9 and 10. E3 bound human NGF with a KD of approximately 0.07 nM (and with a kon of about 6.0e5 M−1s−1, and a $k_{off}$ of about 4.2e−5 s−1). 3C bound human NGF with a KD of approximately 0.35 nM (with a $k_{off}$ of about 1.4E-5). By contrast, mouse antibody 911 bound NGF with a KD of 3.7 nM, $k_{off}$ of $8.4 \times 10^{-5}$ s$^{-1}$ and $k_{on}$ of $2.2 \times 10^4$ Ms$^{-1}$.

Figure 11:
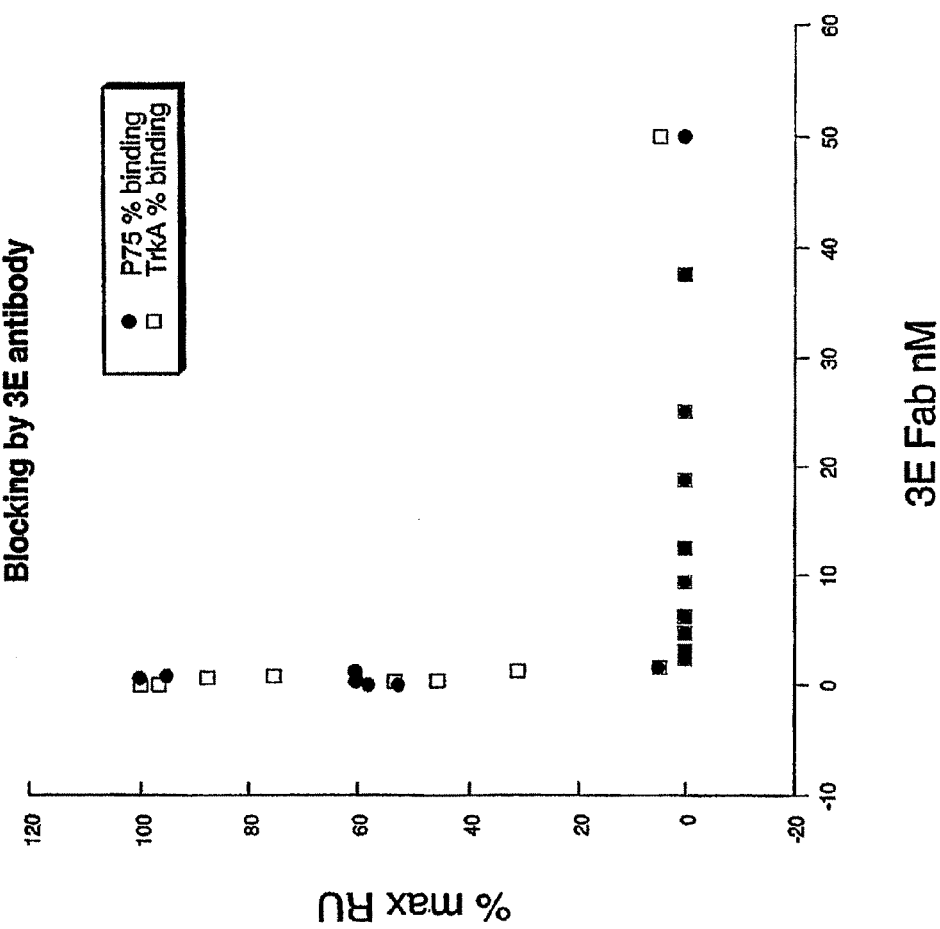
FIG. 11: is a graph depicting that antibody E3 blocks the interaction of NGF with its receptors, trkA and p75, as assessed by percent binding detected between NGF and trkA (shown in black circles) and NGF and p75 (shown as hollow squares). The X axis corresponds to concentration of antibody 3E (Fab) and the Y axis corresponds to NGF binding (percent maximum RU). Increased concentrations of Fab E3 blocked the interaction of NGF with both p75 and trkA, as shown by decreased signal (measured in RU). When antibody E3 (Fab) concentration equaled NGF concentration, no NGF binding was observed (as shown by a signal of zero).

Antibody E3 (interchangeably termed 3E) was selected for further analysis based on the high binding affinity. To test the ability of E3 to prevent the interaction of NGF with the NGF receptors trkA and p75, 2.5 nM of human NGF was premixed and incubated for one hour with 0 to 50 nM of antibody E3 (Fab). After the incubation, samples were injected at 10 ul/minute on a BIAcore CM5 chip containing 260 RU of p75 (channel 2) and 600 RU of trkA (channel 3), and percent binding was determined. The results of this analysis are shown in FIG. 11. Increased concentrations of Fab E3 blocked the interaction of NGF with both p75 and trkA, as shown by decreased signal (measured in RU), indicating that Fab E3 blocks the interaction of human NGF with both trkA and p75. When antibody E3 (Fab) concentration equaled NGF concentration (at about 2.5 nM NGF concentration), no NGF binding was observed (as shown by a signal of zero). The fact that zero percent NGF-receptor binding occurred when concentration of NGF was equal to antibody 3E concentration suggested that 2.5 nM NGF was at least ten-fold higher than the kD of E3 for NGF and at equilibrium.

Example 2

Evaluation of NGF-Blocking Ability of Anti-NGF Antibodies Using Mouse E13.5 Trigeminal Neuron Survival Assay The ability of Fab E3 or full antibody E3 to block NGF activity was evaluated by measurement of the capacity of the antibody to inhibit NGF-dependent survival of mouse E13.5 trigeminal neurons in vitro. The trigeminal ganglion is comprised of cutaneous sensory neurons that innervate the facial region. The survival of mouse E13.5 trigeminal neurons is a sensitive assay to evaluate the NGF-blocking activity of anti-NGF antagonist antibodies because NGF is required to support survival of these neurons. For example, at saturating concentrations of NGF, the survival is close to 100% by 48 hours in culture. By contrast, less than 5% of the neurons survive by 48 hours in absence of NGF.

The survival assay was conducted as follows: time-mated pregnant Swiss Webster female mice were euthanised by CO2 inhalation. The uterine horns were removed and the embryos at embryonic stage E13.5 were extracted and decapitated. The trigeminal ganglia were dissected using electrolytically sharpened tungsten needles. The ganglia were then trypsinized, mechanically dissociated and plated at a density of 200-300 cells per well in defined, serum-free medium in 96-well plates coated with poly-L-ornithine and laminin.

The blocking activity of anti-NGF Fabs or antibodies was assessed by adding to the trigeminal neurons varying doses of anti-NGF antibodies Mab 911 (Fab), 8L2-6D5; H19-L129; E3 and 3C; and human or rat NGF at the following concentrations: 0.4 ng/ml (~15 pM; this concentration represented a saturating concentration of NGF for survival) and 0.04 ng/ml (~1.5 pM; this concentration is around the IC50). After 48 hours in culture, the cells were subjected to an automated immunocytochemistry protocol performed on a Biomek FX liquid handling workstation (Beckman Coulter) as follows: fixation using 4% formaldehyde, 5% sucrose, and PBS; permeabilization using 0.3% Triton X-100 in PBS); blocking of unspecific binding sites using 5% normal goat serum, 0.11% BSA in PBS; and sequential incubation with a primary and secondary antibodies to detect neurons. The primary antibody was rabbit polyclonal antibody against the protein gene product 89.5 (PGP9.5, Chemicon), an established neuronal phenotypic marker. The secondary antibody was Alexa Fluor 488 goat anti-rabbit (Molecular Probes), together with the nuclear dye. Hoechst 33342 (Molecular Probes) to label the nuclei of all the cells present in the culture. Image acquisition and image analysis were performed on a Discovery-I/GenII Imager (Universal Imaging Corporation). Images were automatically acquired at two wavelengths for Alexa Fluor 488 and Hoechst 33342, with the nuclear staining being used as reference point for the image-based auto-focus system of the Imager, since nuclear staining is present in all of the wells. Appropriate objectives and number of sites imaged per well were selected to cover the entire surface of each well. Automated image analysis was set up to count the number of neurons present in each well after 48 hours in culture based on their specific staining with the anti-PGP9.5 antibody. Careful thresholding of the image and application of morphology and fluorescence intensity based selectivity filter resulted in an accurate count of neurons per well.

The results of this experiment demonstrated that Fab E3 blocked NGF activity with a high affinity. The results are shown in FIGS. 4-6, and Table 9.

FIG. 4 is a graph showing NGF-dependent survival of E13.5 neurons in the presence of varying concentration of human and rat NGF.

FIG. 5 is a graph comparing the NGF blocking effect of various Fabs in the presence of either 0.04 ng/ml of human NGF (approximately 1.5 pM; shown in the lower panel) or 0.4 ng/ml human NGF (approximately 15 pM; shown in the upper panel). 1.5 pM of NGF was around the EC50 of NGF promoting survival, while 15 pM represented a saturating concentration of NGF. Survival of E13.5 mouse trigeminal neurons in various concentrations of Fab E3; murine 911 Fab; and Fab H19-L129 and Fab 8L2-6D5 was assessed as described above. The IC50 (in pM) was calculated for each Fab at each NGF concentration, and is shown in Table 9. Fab E3 strongly blocked human NGF-dependent trigeminal neuron survival, with an IC50 of approximately 21 pM in the presence of 15 pM human NGF, and an IC50 of approximately 1.2 pM in the presence of 1.5 pM human NGF. Fabs 3C and H19-L129 also strongly blocked human NGF-dependent trigeminal neuron survival.

FIG. 6 is a graph comparing the NGF blocking effect of various Fabs in the presence of either 0.04 ng/ml of rat NGF (approximately 1.5 pM; shown in the lower panel) or 0.4 ng/ml rat NGF (approximately 15 pM; shown in the upper panel). 1.5 pM of NGF was around the EC50, while 15 pM represented a saturating concentration of NGF. Survival of E13.5 mouse trigeminal neurons in various concentrations of Fab E3; murine Fab 911; and Fab H19-L129 and 8L2-6D5 was assessed as described above. The EC50 (in pM) was calculated for each Fab at each NGF concentration, and is shown in Table 9. Fab E3 strongly blocked human NGF-dependent trigeminal neuron survival, with an IC50 of approximately 31.6 pM in the presence of 15 pM rat NGF, and an IC50 of approximately 1.3 pM in the presence of 1.5 pM rat NGF. Fabs 3C and H19-L129 also strongly blocked rat NGF-dependent trigeminal neuron survival.

TABLE 9

| Human NGF | IC50 (in the presence of 15 pM NGF) pM | IC50 (in the presence of 1.5 pM NGF) pM |
| --- | --- | --- |
| 8L2-6D5 Fab | 1580.5 | 461.8 |
| H19-L129 Fab | 60.1 | 9.6 |
| 3E Fab | <21.0 | <1.2 |
| 3C Fab | 80.9 | 5.6 |
| 911 Fab | 322.3 | 63.5 |

TABLE 9-continued

| Rat NGF | IC50 (15 pM NGF) pM | IC50 (1.5 pM NGF) pM |
|---|---|---|
| 8L2-6D5 Fab | 730.3 | 169.4 |
| H19-L129 Fab | 31.0 | 6.0 |
| 3E Fab | <8.3 | <1.3 |
| 3C Fab | 31.6 | 6.0 |
| 911 Fab | 161.0 | 34.6 |

Figure 12:
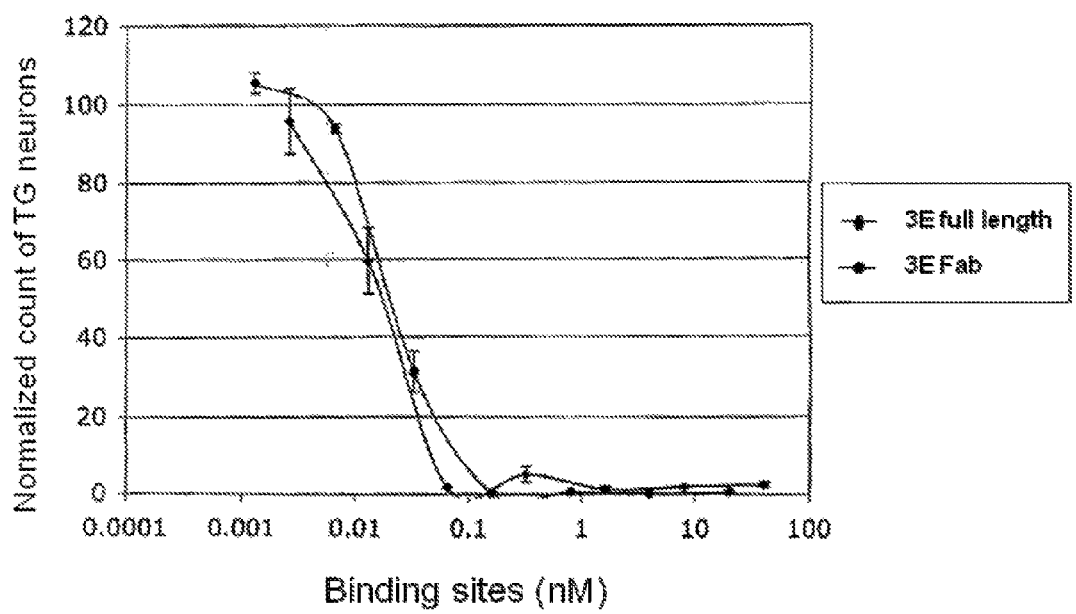
FIG. 12: is a graph depicting the human NGF blocking ability of full antibody E3 and Fab E3. Survival of E13.5 mouse trigeminal neurons in the presence of human NGF and various concentrations of Fab E3 and antibody E3 was assessed. The X axis corresponds to NGF binding sites (nM) and the Y axis corresponds to normalized count of trigeminal (TG) neurons. Full antibody E3 and Fab 3E showed similar levels of inhibition of NGF-dependent survival of trigeminal neurons when the concentration of whole antibody and Fab were normalized to the number of NGF binding sites (Fab has one binding site and whole antibody has two binding sites).

In a different experiment, we compared the ability of full antibody E3 and Fab 3E to inhibit NGF-dependent survival of E13.5 neurons in the presence of 0.4 ng/ml (saturating concentration) of human NGF. The results of the analysis are shown in FIG. 12. Full antibody E3 and Fab 3E showed similar levels of inhibition of NGF-dependent survival when the concentration of whole antibody and Fab were normalized to the number of NGF binding sites (Fab has one binding site and whole antibody has two binding sites). These results demonstrated that there was no avidity effect due to the binding of a full antibody to the NGF dimer.

Figure 13:
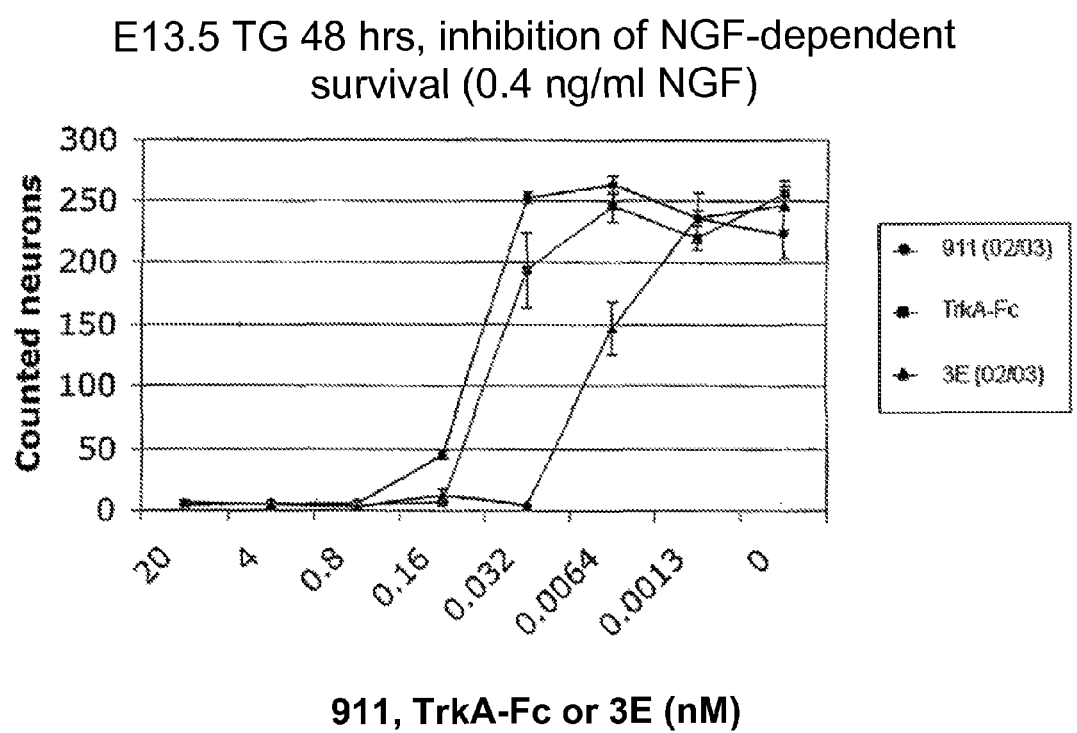
FIG. 13: is a graph depicting the ability of various concentrations (20, 4, 0.8, 0.16, 0.032, 0.0064, 0.00128, and 0.0 nM) of antibody E3 (solid triangles; referred to as "3E"), antibody 911 (solid circles), and a trkA receptor immunoadhesin (shaded squares; referred as "trkA-Fc) to inhibit NGF-dependent survival of E13.5 trigeminal neurons in the presence of 0.4 ng/ml human NGF (saturating conditions). The X axis corresponds to concentration of antibody (nM) and the Y concentration corresponds to counted neurons. These results demonstrated that antibody E3 blocked NGF significantly better than either mouse monoclonal anti-NGF antibody 911 or the trkA immunoadhesin.

In another experiments, we compared the ability of various concentrations (20, 4, 0.8, 0.16, 0.032, 0.0064, 0.00128, and 0.0 nM) of antibody E3, antibody 911, and a trkA receptor immunoadhesin (consisting of the extracellular domain of the NGF receptor trkA fused with the immunoglobulin Fc domain, CH2-CH3) to inhibit NGF-dependent survival of E13.5 neurons in the presence of 0.4 ng/ml (saturating conditions). These results are shown in FIG. 13. These results demonstrated that antibody E3 blocked NGF better than either antibody 911 or the trkA immunoadhesin.

Example 3

Evaluation of the Specificity of Anti-NGF Antibody E3 Using Mouse Trigeminal and Nodose Neuron Survival Assays The ability of antibody E3 to specifically block NGF activity was evaluated by measurement of the capacity of the antibody to inhibit survival of mouse E17/18 trigeminal neurons in vitro in the presence of saturating concentrations of NGF, the NGF-related neurotrophin NT3, or the NGF-unrelated neurotrophic factor, macrophage stimulating protein (MSP). The survival of mouse E17/18 trigeminal neurons is a sensitive assay to evaluate the NGF-blocking activity of anti-NGF antagonist antibodies because NGF is required to support survival of these neurons at higher concentrations than the level of NGF required to support survival of E13.5 TG neurons). Survival of these neurons is also supported by NT3 or MSP; therefore, the survival of these neurons is also a sensitive assay to evaluate whether the anti-NGF antagonist antibody also blocked NT3 or MSP.

The ability of antibody E3 to specifically block NGF activity was also evaluated by measurement of the capacity of the antibody to inhibit survival of mouse nodose E17 neurons in the presence of saturating concentrations of BDNF or NT4/5. Survival of nodose neurons is supported by BDNF or NT4/5; therefore, survival of these neurons is a sensitive assay to evaluate the BDNF or NT4/5-blocking ability of the anti-NGF antagonist antibody.

The survival assay was conducted as follows: time mated pregnant Swiss Webster female mice were euthanised by CO2 inhalation. The uterine horns were removed and the embryos (at embryonic day 17 or 18) were extracted and decapitated. The trigeminal and nodose ganglia were dissected and cleaned. The ganglia were then trypsinised, mechanically dissociated and plated at a density of 100-300 cells per well in defined, serum-free medium in 4-well plates (Greiner) coated with poly-L-ornithine and laminin.

E17/18 trigeminal neurons were grown either without added neurotrophic factors (negative control) or in the presence of saturating concentrations of human NGF (400 pM and 15 pM) (positive control); NT3 (400 pM); or MSP (600 pM). Duplicate cultures were set up that included varying concentrations of E3 and 911 Fabs and full antibodies. Concentration of Fab and full antibodies was indicated per binding site (e.g., a full antibody contains two binding sites, while a Fab contains one binding site).

E17 nodose neurons were grown either in the absence of added neurotrophic factors (negative control), or with saturating concentrations of BDNF (400 pM) (positive control) or NT4/5 (400 pM) or NGF unrelated growth factor ILF (interleukin inhibitory factor). High concentrations of neurotrophins were used, as the goal of this experiment was to test specificity of the antibodies. Duplicate cultures were set up that included varying again with and without the addition of antibodies E3 and 911. After 48 hours in culture the total number of neurons surviving in each well under each condition was ascertained by manual counting using a phase-contrast microscope.

The results of these experiments demonstrated that E3 and 911 antibodies completely blocked the survival promoting effects of NGF on E18 trigeminal neurons. By contrast, E3 and 911 antibodies had no effect on survival of trigeminal neurons promoted by NT3 or MSP, or survival of nodose neurons promoted by BDNF or NT4/5 or LIF. These results demonstrated that antibody E3 possessed selective specificity for NGF, as there was no detected interaction between these antibodies and other NGF related neurotrophins (NT3, NT4/5, BDNF) at concentrations 1000-fold to 10,000-fold higher than effective concentration for NGF blocking. Further, these results demonstrated that the neuronal death seen in NGF-supplemented cultures of NGF-dependent neurons on addition of antibody or Fab E3 was due to a specific interaction between these antibodies and NGF and was not due to a generalized toxic effect. Mouse anti-NGF antagonist antibody 911 was also tested, and similar results were observed. Note that due to the high concentrations of neurotrophins used, both antibody E3 and 911 are very close to their titration conditions and were expected to bind NGF at similar levels because the differences in binding affinity of these antibodies to NGF would to be less apparent under these conditions.

Figure 14:
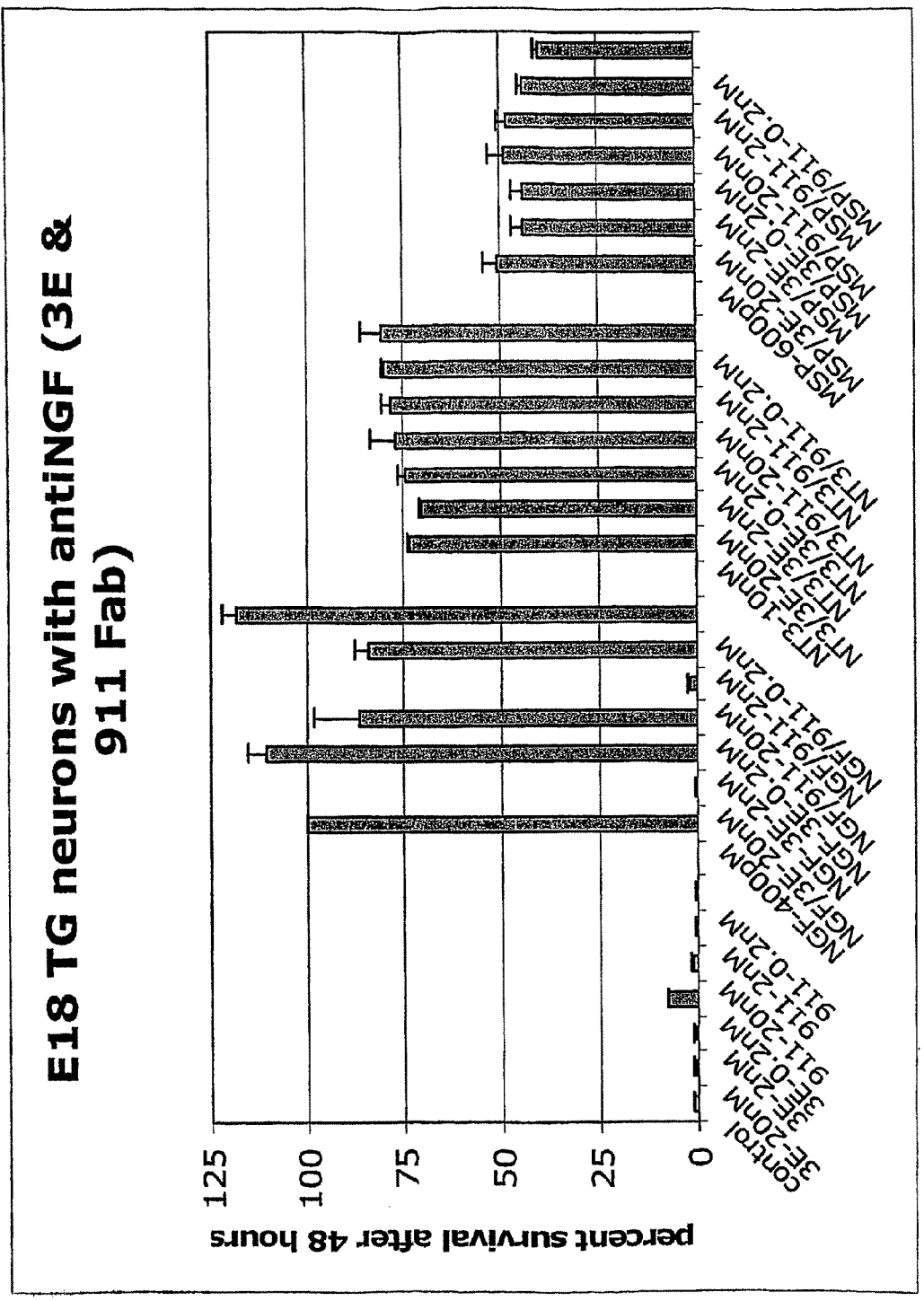
FIG. 14: is a graph depicting that anti-NGF antagonist antibody E3 (termed "3E in the figure") or Fab 911 did not inhibit the neuronal survival promoted by NT3, NT4/5 and MSP, even at antibody concentrations as high as 200 nM. The data represented mean percent survival after 48 hours in culture (±standard error of mean, n=3 for each data point) relative to the survival observed in the positive control for each experiment (100% survival of trigeminal neurons grown in the presence of saturating NGF concentration). Various concentrations (20 nM, 2 nM, or 0.2 nM) of E3 Fab (termed "3E" in the figure) and mouse antibody 911 Fab were used in the presence of no added neurotrophin (termed "control"), 400 pM NGF (termed "NGF-400 pM), 10 nM NT3 (termed "NT3-10 nM) or 600 pM MSP (termed "MSP-600 pM).
Figure 15:
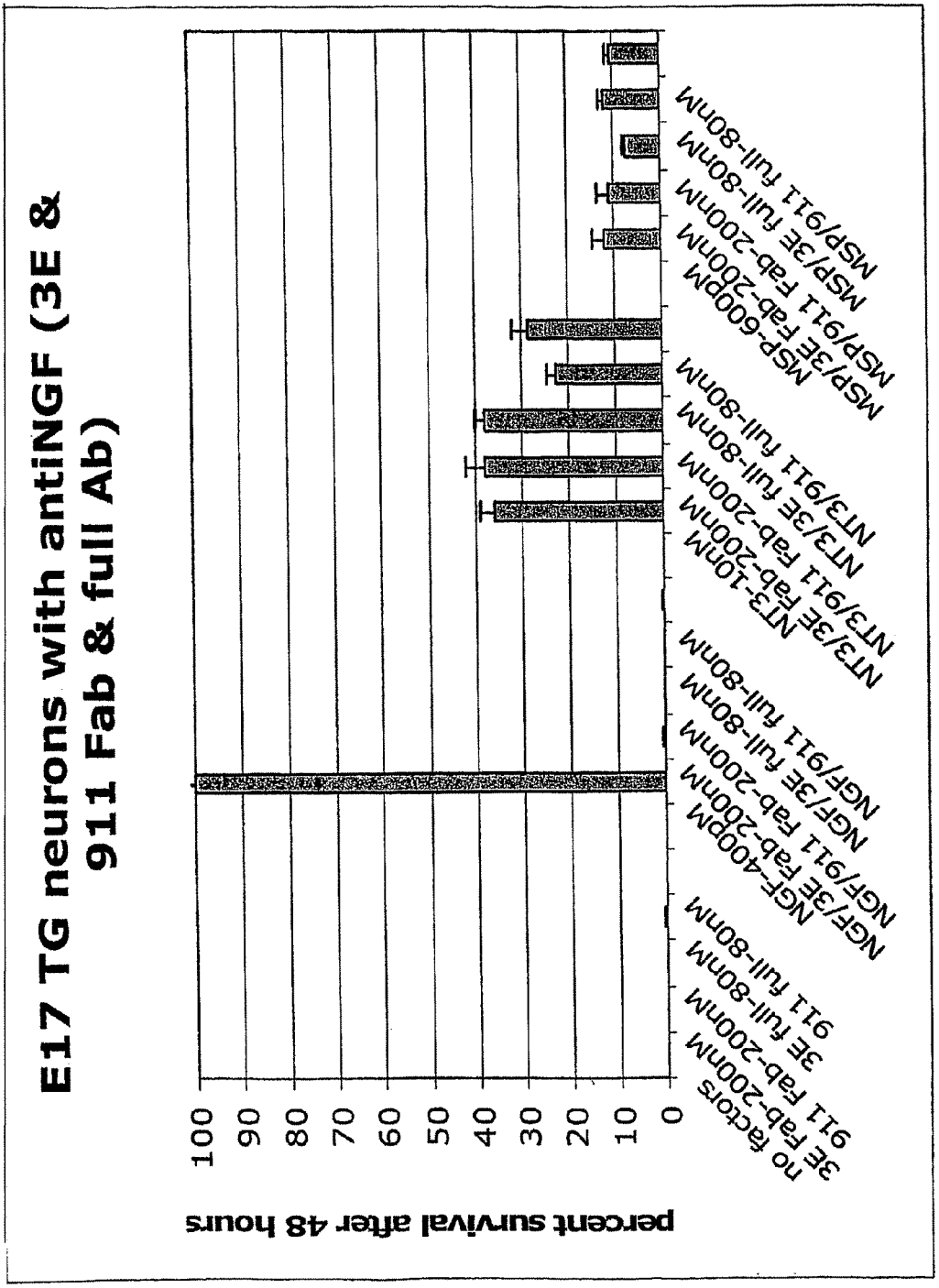
FIG. 15: is a graph depicting that anti-NGF antagonist antibody E3 (Fab or full antibody) (termed "3E in the figure") or mouse antibody 911 (Fab or full antibody) did not inhibit the neuronal survival promoted by NT3, NT4/5 and MSP, even at antibody concentrations as high as 200 nM Various concentrations (200 nM and 80 nM) of E3 Fab and full antibody and mouse antibody 911 full antibody and Fab were used in the presence of no added neurotrophins (termed "no factor"), 400 pM NGF (termed "NGF-400 pM), 10 nM NT3 (termed "NT3-10 nM) or 600 pM MSP (termed "MSP-600 pM).

The results of these experiments are shown in FIGS. 14, 15, 16, and 17. The data showed mean percent survival after 48 hours in culture (±standard error of mean, n=3 for each data point) relative to the survival seen in the positive control for each experiment (e.g., 100% survival of trigeminal neurons grown in the presence of saturating NGF concentration, and 100% survival of nodose neurons grown in the presence of saturating BDNF concentration, respectively). FIGS. 14-15 are graphs showing that anti-NGF antagonist antibody E3 or Fab E3 did not inhibit the survival promoted by NT3, and MSP, even at antibody concentrations as high as 200 nM. By contrast, 20 nM of antibody E3 or Fab 3E and Fab 911 totally blocked NGF-elicited survival. Mouse anti-NGF antagonist antibody 911 was also tested, and similar results were observed. Specifically, FIG. 14 is a graph showing comparison of the effect of various concentrations (20 nM, 2 nM, or 0.2 nM) of E3 Fab (termed "3E" in the figure) and mouse antibody 911 Fab on survival of E18 trigeminal neurons in the presence of no added neurotrophin (termed "control"), 400 pM NGF (termed "NGF-400 pM), 10 nM NT3 (termed "NT3-10 nM) or 600 pM MSP (termed "MSP-600 pM). FIG.

15 is a graph depicting comparison of the effect of various concentrations (200 nM and 80 nM) of E3 Fab and full antibody and mouse antibody 911 full antibody and Fab of survival of E17 trigeminal neurons in the presence of no added neurotrophins (termed "no factor"), 400 pM NGF (termed "NGF-400 pM), 10 nM NT3 (termed "NT3-10 nM) or 600 pM MSP (termed "MSP-600 pM).

Figure 16:
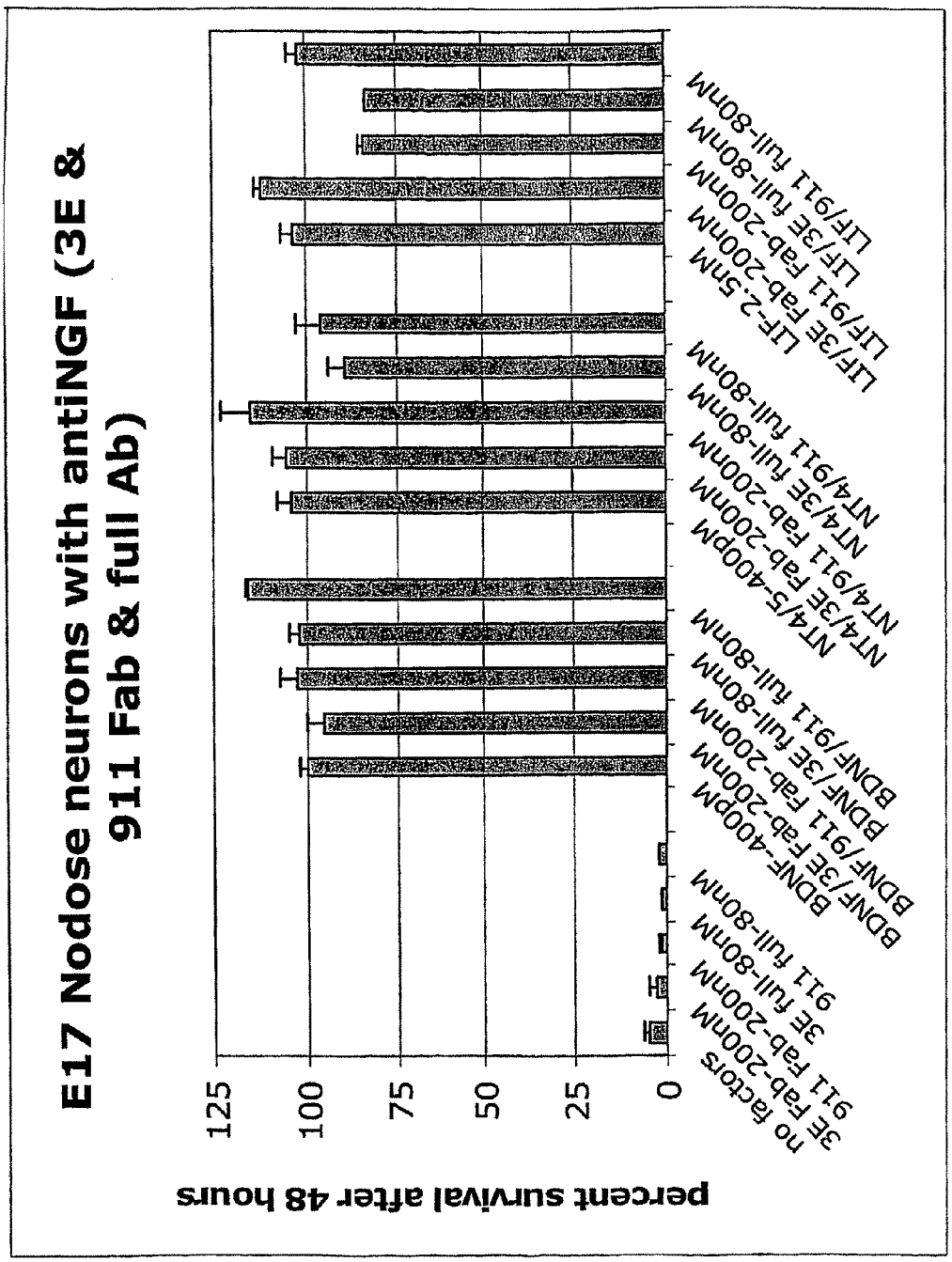
FIG. 16: is a graph depicting that anti-NGF antagonist antibody E3 or Fab E3 did not inhibit survival of E17 nodose neurons promoted by BDNF, NT4/5 or LIF. Mouse anti-NGF antagonist antibody 911 was also tested, and similar results were observed. Various concentrations (200 nM or 80 nM) of full antibody E3 (termed "3E in the figure"), Fab E3, full antibody 911, or Fab 911 were tested in the presence of no added neurotrophins (termed "no factors"), 400 pM BDNF (termed "BDNF-400 pM), 400 pM NT4/5 (termed "NT4/5-400 pM), or 2.5 nM LIF (termed "LIF-2.5 nM).
Figure 17:
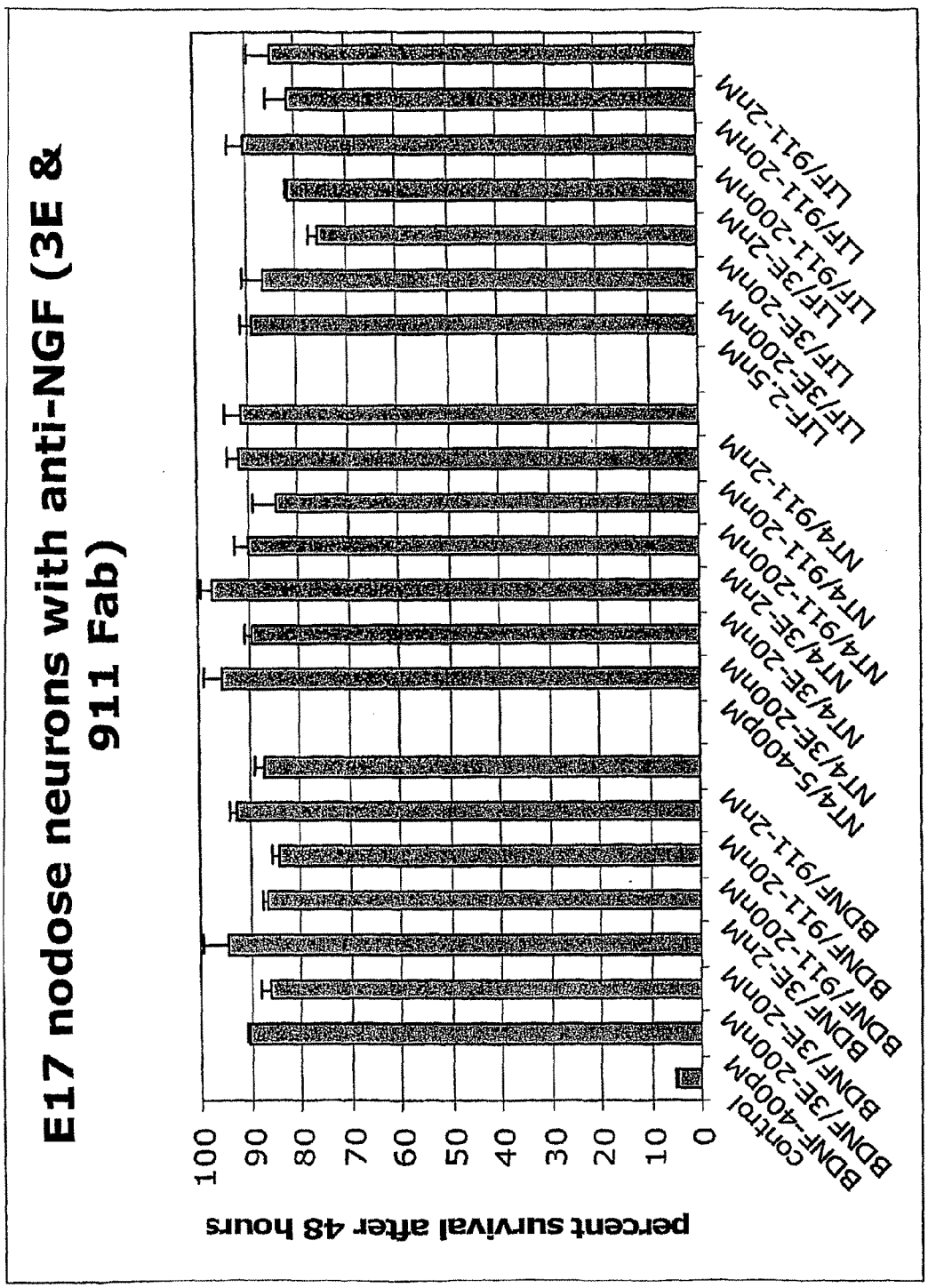
FIG. 17: is a graph depicting that anti-NGF antagonist antibody E3 or Fab E3 did not inhibit survival of E17 nodose neurons promoted by BDNF, NT4/5 or LIF. Various concentrations (200 nM, 20 nM, 2 nM) of Fab E3 (termed "3E in the figure"), or Fab 911 were tested in the presence of no added neurotrophins (termed "control"), 400 pM BDNF (termed "BDNF-400 pM), 400 pM NT4/5 (termed "NT4/5-400 pM), or 2.5 nM LIF (termed "LIP-2.5 nM).

FIG. 16-17 are graphs showing that anti-NGF antagonist antibody E3 or Fab E3 did not inhibit survival of E17 nodose neurons promoted by BDNF, NT4/5 or LIF. Mouse anti-NGF antagonist antibody 911 was also tested, and similar results were observed. Specifically, FIG. 16 is a graph showing comparison of the effect of various concentrations (200 nM or 80 nM) of full antibody E3 (termed "3E in the figure"), Fab E3, full antibody 911, or Fab 911 on the survival of E17 nodose neurons in the presence of no added neurotrophins (termed "no factors"), 400 pM BDNF (termed "BDNF-400 pM), 400 pM NT4/5 (termed "NT4/5-400 pM), or 2.5 nM LIF (termed "LIP-2.5 nM). FIG. 17 is a graph showing comparison of the effect of various concentrations (200 nM, 20 nM, 2 nM) of Fab E3 (termed "3E in the figure"), or Fab 911 on the survival of E17 nodose neurons in the presence of no added neurotrophins (termed "control"), 400 pM BDNF (termed "BDNF-400 pM), 400 pM NT4/5 (termed "NT4/5-400 pM), or 2.5 nM LIF (termed "LIP-2.5 nM).

Example 4

Preparation of Mammalian Expression Vectors and Expression of Antibody E3 in Mammalian Cells Three mammalian expression vectors were designed and constructed for use in the expression of antibody E3 in mammalian cells.

Vector Db.911.3E is an expression vector comprising the heavy chain variable region of the E3 antibody and the human IgG2a constant region, and is suitable for transient or stable expression of the heavy chain. Db.911.3E consists of nucleotide sequences corresponding to the following regions: the murine cytomegalovirus promoter region (nucleotides 1-612); a synthetic intron (nucleotides 619-1507); the DHFR coding region (nucleotides 707-1267); human growth hormone signal peptide (nucleotides 1525-1602); antibody 3E heavy chain variable region (nucleotides 1603-1965); human heavy chain IgG2a constant region containing the following mutations: A330P331 to S330S331 (amino acid numbering with reference to the wildtype IgG2a sequence; see Eur. J. Immunol. (1999) 29:2613-2624); SV40 late polyadenylation signal (nucleotides 2974-3217); SV40 enhancer region (nucleotides 3218-3463); phage f1 region (nucleotides 3551-4006) and beta lactamase (AmpR) coding region (nucleotides 4443-5300). Db.911.3E was deposited at the ATCC on Jan. 8, 2003, and was assigned ATCC Accession No. PTA-4895.

Vector Eb.911.3E is an expression vector comprising the light chain variable region of the E3 antibody and the human kappa chain constant region, and is suitable for transient expression of the light chain. Eb.911.3E consists of nucleotide sequences corresponding to the following regions: the murine cytomegalovirus promoter region (nucleotides 1-612); human EF-1 intron (nucleotides 619-1142); human growth hormone signal peptide (nucleotides 1173-1150); antibody E3 light chain variable region (nucleotides 1251-1571); human kappa chain constant region (nucleotides 1572-1892); SV40 late polyadenylation signal (nucleotides 1910-2153); SV40 enhancer region (nucleotides 2154-2399); phage f1 region (nucleotides 2487-2942) and beta lactamase (AmpR) coding region (nucleotides 3379-4236). Eb.911.3E was deposited at the ATCC on Jan. 8, 2003, and was assigned ATCC Accession No. PTA-4893.

Vector Eb.pur.911.3E is an expression vector comprising the light chain variable region of the E3 antibody and the human kappa constant region, and is suitable for stable expression of the light chain. Eb.pur.911.3E consists of nucleotide sequences corresponding to the following regions: the murine cytomegalovirus promoter region (nucleotides 1-612); human EF-1 intron (nucleotides 619-1758); pac gene (puromycinR) coding region (nucleotides 739-1235); human hsp70 5'UTR region (nucleotides 1771-1973); human growth hormone signal peptide (nucleotides 1985-2062); antibody E3 light chain variable region (nucleotides 2063-2383); human kappa chain constant region (nucleotides 23842704); SV40 late polyadenylation signal (nucleotides 2722-2965); SV40 enhancer region (nucleotides 2966-3211); phage f1 region (nucleotides 3299-3654) and beta lactamase (AmpR) coding region (nucleotides 4191-5048). Eb.pur.911.E3 was deposited at the ATCC on Jan. 8, 2003, and was assigned ATCC Accession No. PTA-4894.

Transient cell expression was performed as follows: CHO and HEK293T cells in 150 mm dishes were transiently co-transfected with 25 ug of each plasmid (i.e., one plasmid containing the heavy chain and one plasmid containing the light chain). DNA was mixed with 100 ul lipofectamine 2000 (Invitrogen) according to the manufacturer's instructions. The DNA-lipid complexes were allowed to contact the cells in DMEM/F12 medium without serum or antibiotics for 5 hours. Following this incubation, the media was changed for expression to Opti-MEM (Invitrogen) without any additives for two days. Cell supernatants containing antibody were harvested sequentially up to four times with subsequent media replacement. Supernatants were purified by affinity chromatography using MapSelect Protein A resin (Amersham biosciences 17-5199-02). Antibody was bound to the protein A resin in 0.3M glycine, 0.6M NaCl buffer at pH 8, then eluted with 0.1 M citrate buffer at pH 3. Fractions containing antibody were immediately neutralized with 1M Tris buffer at pH 8.0, Antibody fractions were then dialyzed and concentrated in PBS.

Example 5

Anti-NGF Antibody E3 is Effective in Treating Post-Surgical Pain

We used a pain model that mimics post surgical pain to assess the efficacy of treatment with antibody E3. Antibody E3 comprised the human heavy chain IgG2a constant region containing the following mutations: A330P331 to S330S331 (amino acid numbering with reference to the wildtype IgG2a sequence; see Eur. J. Immunol. (1999) 29:2613-2624); the human light chain kappa constant region; and the heavy and light chain variable regions shown in Tables 1A and 1B.

Animals. Male Sprague Dawley rats weighting between 220-240 grams were purchased from Harlan (Wisconsin) and acclimated to the animal facility for one week prior to surgery.

Surgery. The surgery was based on the procedure described by Brennan, et al. Pain 64:493-501 (1996). Animals were anesthetized with a 2% isoflurane in air mixture that was maintained during surgery via a nose cone. The plantar surface of the right hind paw was prepared with a povidone-iodine pad, and a 1-cm central longitudinal incision was made through skin and fascia, starting 0.5 cm from the edge of the heel and extending toward the toes. Measurements were made with a ruler with the foot held in a flexed position. The plantaris muscle was elevated using curved forceps and incised longitudinally. The muscle was incised through its full depth, between the origin and insertion. Bleeding was controlled throughout surgery by pressure applied through a gauze pad. The wound was closed with two mattress sutures (5-0 ethilon black monofilament). These sutures were knotted 5-6 times, with the first knot loosely tied. The wound site was swabbed with bacitracin solution. Animals were allowed to recover and rest in clean cages for two hours or more before behavioral testing began.

Figure 1B:
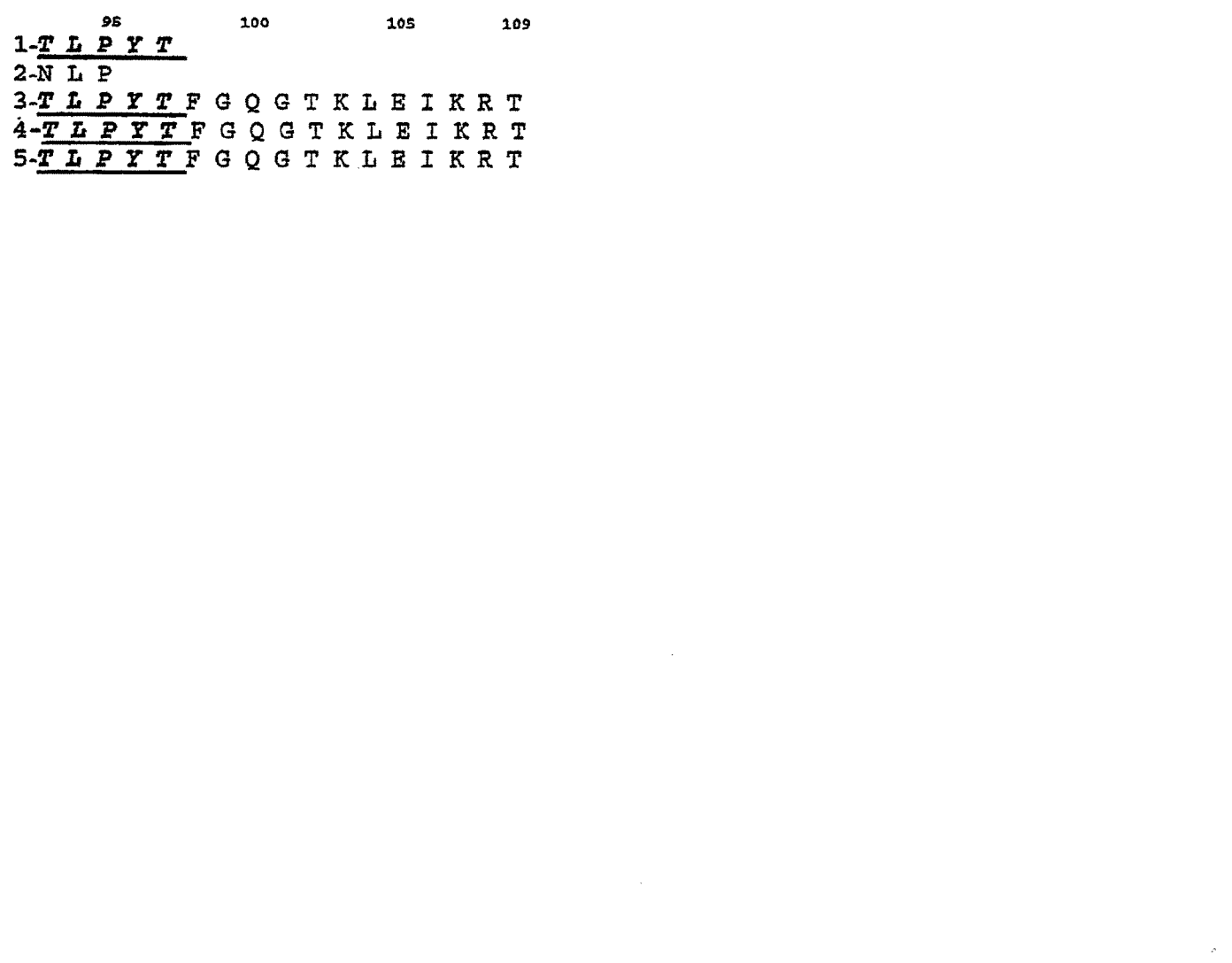

Evaluating resting pain. A cumulative pain score was used to assess pain related to weight bearing. Animals were placed on a plastic mesh (grid: 8 mm$^2$) in clear plastic cages that were elevated on a platform (h: 18") allowing inspection of the underside of their paws. After a 20 minute acclimation period, weight bearing was assessed on a scale of 0 to 2. A score of 0 was given if the paw was blanched or pressed against the mesh, indicating full weight bearing. A score of 1 was given if the paw was favored with the skin just touching the mesh, with no blanching or indentation of the skin. A score of 2 was given if the paw was held completely off the mesh. Flinching the paw was considered a 2 if the rat was still at rest. Each animal was observed for 1 minute every 5 minutes for 30 minutes. The sum of 6 scores (0-12) obtained during ½-hour was used to assess pain in the incised foot. Frequency of scores of 2 was also calculated and used to assess the incidence of severe pain or total guarding of the paw by the animal. Each animal was tested 24 hours before surgery (baseline), and 2 h, 24 h, 48 h, and 72 h postoperatively. The results of this experiment are shown in FIG. 1, which depicts the cumulative resting pain score observed in animals treated with 35 mg/kg of anti-NGF mouse antibody 911. These results demonstrated that treatment with anti-NGF antibody significantly reduced post-surgical resting pain. Weight bearing was a good correlate of how willing the animal was to use the limb, and therefore was an effective measure of pain relief.

The E3 antibody was injected intra peritoneal (i.p.) at various concentrations of the antibody (0.004, 0.01, 0.02, 0.1, 0.6, and 1 mg per kilogram of animal weight) at 15 hours pre-incision. The negative control group received no antibody but was injected i.p. with a saline solution. Fentanyl at 0.01 mg/kg was injected i.p. as a positive control 30 minutes before testing at 24 hours post-surgery. Each experiment involved 8 animals (n=8 per group) for each condition, and the control group had 56 animals. Surgery was performed and a cumulative pain score was measured as described above. Resting pain was evaluated twenty-four hours after the surgery.

Figure 7:
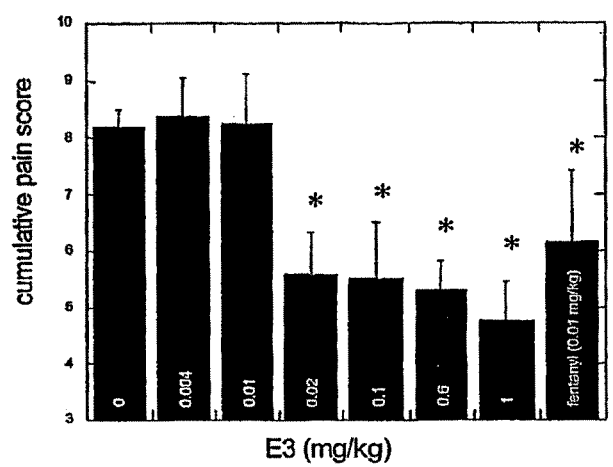
FIG. 7: is a graph depicting resting pain assessed 24 hours after surgery and showing that treatment with 0.02 mg/kg, 0.1 mg/kg, 0.6 mg/kg, or 1 mg/kg of anti-NGF antibody E3 reduced pain. "*" indicates a statistically significant difference ($p<0.5$) from the negative control.

As shown in FIG. 7, humanized anti-NGF antibody E3 significantly reduced resting pain (p<0.05) after surgery when administered at 0.02 mg/kg to 1 mg/kg dosage. A "*" denotes a significantly significant difference from control (p<0.05). Treatment with 0.02 mg/kg alleviated pain behavior at least as effectively as treatment with 0.01 mg/kg fentanyl. This dose of fentanyl is 10 times the normal human dose of this potent opioid.

Figure 8:
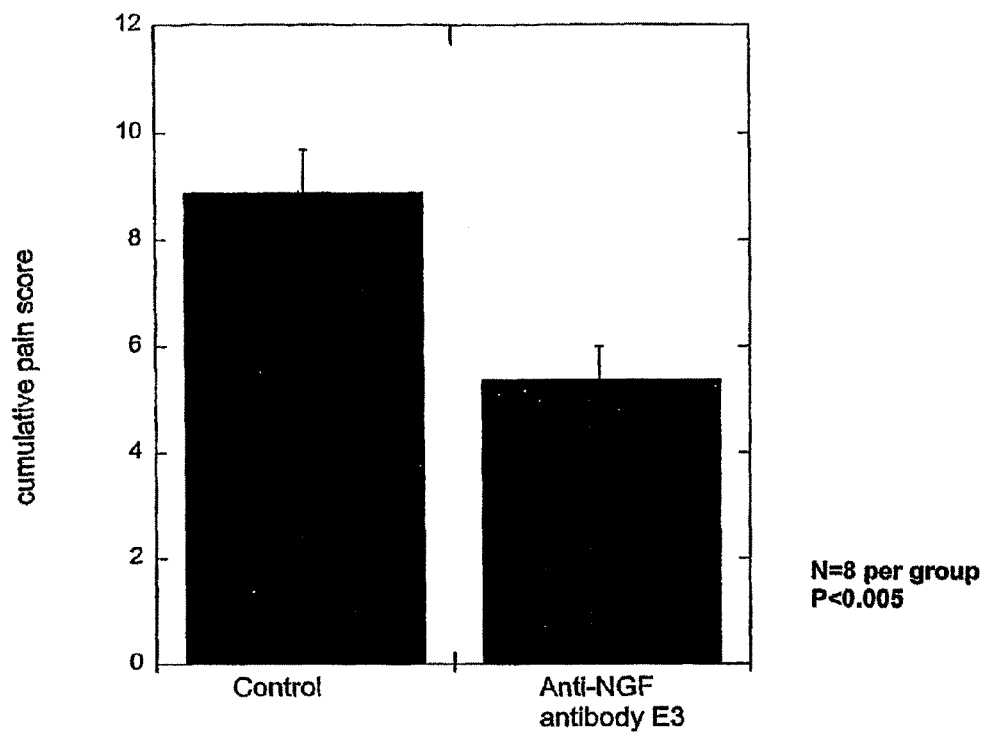
FIG. 8: is a graph depicting resting pain assessed 24 hours after surgery and showing that treatment with 0.5 mg/kg of anti-NGF antibody E3 significantly ($p<0.005$) reduced resting pain when injected two hours after surgery.

In another experiment, the efficacy of the E3 antibody in reducing post-surgical pain when administered post-surgically was tested. Antibody E3 (0.5 mg/kg) were injected intravenously (i.v.) two hours after surgery. The control group received no antibody but was injected i.v. with a saline solution. Surgery was performed and resting pain expressed as a cumulative pain score was assessed 24 hours after surgery. As shown in FIG. 8, treatment with anti-NGF antibody significantly (p<0.05) reduced resting pain at twenty-four hours after incision when the antibody was administered 2 hours post-incision. These results demonstrated that E3 antibody effectively alleviated post-surgical pain when administered after surgery.

Example 6

Assessment of Analgesic Effects of Anti-NGF Antagonist Antibody 911 in a Rat Model of Rheumatoid Arthritis The analgesic effects of anti-NGF antibody, 911 (see Hongo et al., Hybridoma 19(3):215-227 (2000)) in complete Freund's adjuvant (CFA)-induced chronic arthritis in rats were investigated using the vocalization test, in comparison with indomethacine used as reference substance.

Fifty (50) male Lewis rats (LEWIS LEW/Crl Ico) (Charles River Belgium) weighing 150 g to 220 g at the beginning of the experimental phase were included in this study. All animals were kept for at least 5 days before the experiment, and were housed in a temperature (19.5-24.5° C.), relative humidity (45-65%) and 12-h light/dark cycle-controlled room with ad libitum access to filtered tap-water and standard pelleted laboratory chow (U.A.R., France) throughout the study. Animals were individually identified on the tail.

On day 0 (D0), arthritis was induced in rats by intradermal injection into the tail of 0.05 ml of a *Mycobacterium butyricum* (Difco, USA) suspension in mineral oil (10 mg/ml). On day 14 (D14), arthritic rats were included in the study according to their ability to vocalize upon gentle flexion of the hindpaw and by their arthritis index, evaluated using an inflammation score for each hind and forepaw (see Kuzuna et al., *Chem. Pharm. Bull.* (Tokyo) 23:1184-1191 (1975); Pearson et al., *Arthritis Rheum.* 2:440-459 (1959)). Animals were scored based on the following criteria: Score 0: normal aspect; Score 1: erythema; Score 2: erythema with slight edema; Score 3: strong inflammation without ankylosis; Score 4: ankylosis. Only animals able to vocalize upon gentle flexion and presenting a score of 2 or 3 were included in the study.

Four groups of 10 rats each were included in the study. For group 1 (vehicle), on day 14 (D14), after selection, rats were intravenously administered by vehicle (saline). On day 18 (D18), the nociceptive intensity was evaluated by gentle flexion of the hindpaw and the intensity of the level of vocalization was recorded for each animal. For group 2 (4 days), on D14, after selection, rats were intravenously administered 911 (10 mg/kg). On day 18 (D18), the nociceptive intensity was evaluated by gentle flexion of the hindpaw and the intensity of the level of vocalization was recorded for each animal. For group 3 (24 hours), on day 17 after injection of CFA, rats were intravenously administered 911 (10 mg/kg). The nociceptive intensity was evaluated by gentle flexion of the hindpaw 24 hours later, and the intensity of the level of vocalization was recorded for each animal. For group 4 (indomethacin), on day 18 (D18), the nociceptive intensity was evaluated by gentle flexion of the hindpaw one hour after oral administration of indomethacin (10 mg/kg). The intensity of the level of vocalization was also recorded for each animal. The test substances were administered in a blind and random manner by intravenous route under a volume of 5 ml/kg, whereas indomethacin was administered by oral route under a volume of 10 ml/kg.

The analgesic effects of anti-NGF antibody 911 are shown in Table 10. The results were expressed for each group as the nociceptive intensity evaluated the intensity of the level of vocalization recorded for each animal in mV (mean±SEM), and the percentage of variation of the nociceptive intensity calculated from the mean value of the vehicle-treated group. Statistical significance between the treated groups and the vehicle group was determined with a Dunnett's test using the residual variance after a one-way analysis of variance (P<0.05).

TABLE 10

Analgesic effects of 911 in complete freund's adjuvant-induced chronic arthritis in rats

| | Substances (Day of dosing) | | | |
|---|---|---|---|---|
| | Vehicle (D14) | 911 (D14) | 911 (D17) | Indomethacin (D18) |
| Dose (mg/kg) | | 10 | 10 | 10 |
| Nociceptive intensity (mV) | 971.0 ± 116.2 | 234.7 ± 34.4* | 247.2 ± 41.8* | 145.8 ± 29.9* |
| % variation | — | −76 | −75 | −85 |

Results are expressed as mean ± sem
n = 10 rats per group
Day 0 (D0): Induction of Chronic arthritis by administration of CFA
Vehicle: saline
911 (10 mg/kg) was intravenously administered at D14 or D17 and pain measurement was performed at D18.
Indomethacin (10 mg/kg) was orally given at D18 and pain measurement was performed one hour after dosing.
Dunnett's test: *indicates a significant difference in comparison with the vehicle-treated group for P < 0.05

As shown in Table 10, anti-NGF antibody 911 significantly reduced pain in a rat model of rheumatoid arthritis 24 hours or 4 days after a single administration of the antibody.

Example 7

Pharmacological Effects of Anti-NGF Antagonist Antibody E3 and 911 in a Rat Model of Rheumatoid Arthritis Pharmacological effects (anti-inflammatory and analgesic effects) of anti-NGF antagonist antibody E3 and 911 were investigated in a model of complete Freund's adjuvant (CFA)-induced chronic arthritis in rats in comparison with indomethacin used as an internal positive control substance. Analgesic effects of E3 and 911 were evaluated by the measurement of nociceptive response. Anti-inflammatory effects were evaluated by paw volume, arthritis index (inflammation score), body and hindpaws weight. Paw cytokine levels (IL-6, IL-1β, TNF-α and TGF-β1), circulating TGF-β1 in serum, E3 and 911 plasma concentrations, biological parameters and X-ray radiographies were performed at the end of experiment.

Experimental Protocol

1. Study Design 80 male Lewis rats (LEWIS Lew/Ico) (Charles River Laboratories-Belgium) 5-weeks old were included in this study. They were housed in a temperature (19.5-24.5° C.) and relative humidity (45-65%) controlled room with a 12-h light/dark cycle, with ad libitum access to filtered tap-water and standard pelleted laboratory chow (SAFE, France) throughout the study. Upon receipt at animal facilities, they were housed 5 per cage and a 10-day acclimatization period were observed before any testing. Animals were individually identified on the tail.

Five groups of 10 animals (5-weeks old male Lewis rats—LEWIS Lew/Ico, from Charles River Laboratories—Belgium) each were included in this study: Group 1: non arthritic rats/saline (vehicle), i.v. bolus, n=10; Group 2: arthritic rats/saline (vehicle), i.v. bolus, n=10; Group 3: arthritic rats/Indomethacin 3 mg/kg, p.o daily over 10 days, n=10; Group 4: arthritic rats/E3, 1 mg/kg, i.v. bolus, n=10; Group 5: arthritic rats/911, 10 mg/kg, i.v. bolus, n=10. The doses were expressed in terms of free active substance (mg/kg). E3 and 911 were extemporaneously prepared in saline from the stock solution to the desired concentration. E3, 1 mg/kg: 3.41 mL of the stock solution (0.88 mg/ml) q.s.p. 15 mL of saline. 911 10 mg/kg: 12 mL of the stock solution (2.5 mg/ml) q.s.p. 15 mL of saline. All diluted solutions (before i.v. injection) were sterilized using a sterile filter unit of 0.20 μm. pH and osmolarity values of diluted solutions were measured before each i.v. injection. Before the first i.v., osmolarity (mosm/L) for saline, E3, and 911 were 278, 269, and 308 respectively; pH for saline, E3, and 911 were 5.93, 6.76, 6.71 respectively. Before the second i.v., osmolarity (mosm/L) for saline, E3, and 911 were 280, 270, and 309 respectively; pH for saline, E3, and 911 were 5.86, 6.72, and 6.59 respectively.

E3 or 911 or saline were administered by i.v. bolus injection on Day 14 and Day 19 after arthritis induction in a coded and random order with a volume of 5 mL/kg. The non arthritic group was given by i.v. bolus injection of saline on Day 14 and Day 19 with a volume of 5 mL/kg. Indomethacin was extemporaneously prepared in 1% methylcellulose. Indomethacin was administered by oral route (p.o.) once daily over 10 days from Day 14 to Day 23 after arthritis induction in a coded and random order with a volume of 10 mL/kg.

2. Induction of Arthritis

On Day 0 (D 0), arthritis was induced in 70 rats by intradermal injection into the tail of 0.05 ml of a *Mycobacterium butyricum* suspension. A group of 10 rats did not receive any intradermal injection (non arthritic rats). On Day 14 (D14), the arthritic rats were included in the study using the following criteria: all included rats displayed an increase of mean paw volume (mean of the left and right paw volume) of at least 0.30 ml compared to the mean paw volume (mean of the left and right paw volume) in the non arthritic group (paw volume measurement as described below); all included rats displayed a vocalization upon gentle flexion (nociceptive response measurement as described below); and all included rats displayed a score of arthritis index of 2-3 on each hindpaw (arthritis index measurement as described below) (the animals with a score of 0, 1 or 4 were discarded).

3. Body Weight

The animals were weighed once daily from Day 0 to Day 24 (except during the week-end days before the treatment: D 1, D 2, D 8, D 9, D10). All measurements were performed between 9:00 and 12:00 am except at D14 (7:30-9:00 am) and D 24 (7:30-8:00 am).

3. Paw Volume Measurement

The right and left hindpaw volume of each rat (arthritic and non arthritic rats) was measured using a plethysmometer. The measurements were performed at the following times (after induction of arthritis): Day 14 (before i.v. bolus or p.o. administration); and Day 24 (5 days after the last i.v. bolus injection or 24 h after the last p.o. administration). All measurements were performed between 9:00 and 12:00 am. All the data were collected and stored by the WinDas software.

4. Arthritis Index

Arthritis index was evaluated using an inflammation score for each hind and forepaw (arthritic rats): Score 0: normal aspect; Score 1: erythema; Score 2: erythema with slight edema; Score 3: strong inflammation without ankylosis; Score 4: ankylosis. This evaluation was performed at the following times (after induction of arthritis): Day 14 (before i.v. bolus or p.o. administration); and Day 24 (5 days after the last i.v. bolus injection or 24 h after the last p.o. administration). All measurements were performed between 2:00 and 3:00 pm (D14), 8:00 and 9:00 am (D 24). All the data were collected and stored by the WinDas software.

5. Measurement of Nociceptive Response (Vocalization Test)

The nociceptive response was evaluated by gentle flexion of the right and left hindpaw repeatedly 2 times at intervals of 4 to 5 sec with a finger of the operator (arthritic rats). The intensity of the level of vocalization was recorded for each animal for each hindpaw (2 times: on right hindpaw: s1 and s3; 2 times: on left hindpaw: s2 and s4). This evaluation was performed at the following times (after induction of arthritis): Day 14 (before i.v. bolus or p.o. administration); Day 18 (before the second i.v. bolus injection or 1 hr after p.o. administration); and Day 24 (5 days after the last i.v. bolus injection or 24 h after the last p.o. administration). All measurements were performed between 9:00 and 12:00 am except at D 14 (7:30-9:00 am) and D 24 (7:30-9:00 am).

6. Blood Collection for Measurement of E3 or 911 Concentration and Circulating TGF-β1 and Hematological Parameters On Day 24 (after paw volume and arthritis index measurements and test vocalization), under general anaesthesia using isoflurane (in a mixture of oxygen and nitrous oxide), the blood samples (about 800-1000 μl) was collected by capillary action with a micropipette from retroorbital sinus.

Measurement of E3 or 911 concentration (groups 2, 4 and 5): A part of blood sample was collected in tubes containing L1-Heparin (maintained on ice) and centrifuged at 2500-3000 g for 10 min. Plasma samples (at least 100 μL) were obtained, frozen in liquid nitrogen, stored at −80° C. One sample was slightly hemolyzed (vehicle-treated arthritic rat #36).

Measurement of circulating TGF-β1 (groups 1-2-3-4-5): A part of blood sample was collected in micro tubes for serum preparation at ambient temperature. Following sample collection, blood was mixed and allowed to clot for 30 minutes prior to the centrifugation. The tubes were centrifuged at about 6000 g for 3 minutes. Each serum sample (at least 100 μL except for rat #52 and #53) was aliquoted and stored at −20° C. until sample activation for TGF-β1 analysis. These aliquots (50 vials) were kept for a period of 6 months starting from the end of the study. Some samples were slightly hemolyzed (vehicle-treated non arthritic rat: #2, #5, #9, #10; vehicle treated arthritic rat: #53, #63; E3-treated arthritic rat #31, #51; 911-treated arthritic rat: #52, 62, #64). TGF-β1 levels were measured using human TGF-β1 ELISA kit (ref. DB100, Batch 212258 and 213610, R&D Systems—France).

Blood collection for hematological parameters (groups 1-2-3-4-5: 50 vials): A part of blood sample was collected in tubes containing K3-EDTA (at least 100 μL). The determination of parameters were performed on the day of the collection and the samples were not stored. The hematological parameters including red blood cells, white blood cells, platelets, hemoglobin, hematocrit were measured with a hematology cell counter (D 24). Some hematological parameters were not measured due to the clotted samples (vehicle-treated non arthritic rat: #10; E3-treated arthritic rats: #59, #67; 911-treated arthritic rats: #16).

7. Paw Cytokines Levels

On Day 24 (5 days after the last i.v. bolus injection or 24 hours after the last p.o. administration) (after X-rays radiographies), each animal hindpaw (arthritic and non arthritic rats) was weighed and was collected in a labelled polyethylene vial. Tissue samples were frozen in liquid nitrogen and stored at −80° C.

Preparation of Joint Homogenates:

Frozen Hind Paws were Pulverized Using a Bio-Pulverizer. The powdered hind paws were then placed into a 50 ml conical centrifuge tube containing 3 ml PBS supplemented with 50 μl of anti-protease cocktail and homogenized on ice using Ultra-Turrax homogenizer (50% of the maximal speed). Homogenates were then centrifuged at 2000×g for 15 minutes at 4° C. and supernatants were filtered through 0.2 μm Sartorius filters, aliquoted and stored at −80° C. until use.

Cytokine Levels Measurement:

Cytokine levels of TNF-α (Rat TNF-α ELISA kit, ref. RTA00, Batch 213718, R&D Systems, France), IL-1βRat IL-1β ELISA kit, ref. RLB00, Batch 212435, R&D Systems, France), IL-6 Rat IL-6 ELISA kit, ref. R6000, Batch 211773, 214008 and 214362, R&D Systems, France), and TGF-β1 Human TGF-β1 ELISA kit, ref. DB100, Batch 212258 and 213610, R&D Systems, France) were determined in duplicate, according to the manufacturer's procedure. Aliquots of hind paw homogenates were stored at −80° C.

8. X-Ray Analysis

On Day 24, after blood collecting the animals were sacrificed and X-ray radiographies (hindpaws) were obtained for assessment of joint lesions. X-ray analysis was focused on articular erosions, articular space, periosteum abnormalities on both hindpaws. All the radiographies were analyzed by looking at seven different items: the soft tissue damage, deformity, demineralization, joint space, erosions, osteogenesis and periostal reaction. For each animal, the first six items were analyzed independently by looking at the worse hind foot. The periostal reaction was analyzed by looking at the tail. For each item, the score goes from 0 (normal) to 4 (maximal damage). Therefore the total score goes from 0 to 28. The radiographic interpretation was done by the same reader without knowing anything about the animals (treated or not treated).

9. Observations

One animal (#65) died at D 23 after indomethacin administration (before the administration at D 23) due to an unknown cause.

10. Analysis and Expression of Results

All results were reported as Mean±S.E.M. of 10 rats in each group at each time point. Paw volume was expressed in ml calculated from the mean value of the right and left paw volume. Arthritis index was calculated from the sum of the score obtained for each of the 4 paws. The nociceptive response was evaluated by the intensity of the level of vocalization recorded for each animal (mean of 4 values: 2 times/paw) in mV. The percentage inhibition of the nociceptive response was calculated from the mean value of the vehicle-treated arthritic group [(mean value of vehicle-treated arthritic group−mean value of treated arthritic group/mean value of vehicle-treated arthritic group)*100]. Body weight was expressed in grams. Hindpaws (left and right) weight was expressed in grams. Cytokine levels (IL-6, IL-1β, TNF-α and TGF-β1) of each hind paw was expressed in pg/ml. Circulating levels of TGF-β1 was expressed in pg/ml. Radiological index for each parameter (demineralization, erosions, periostal reaction, soft tissue damage, space joint, osteogenesis deformity) and total radiological index (total score) were calculated from the sum of the scores obtained for each parameter. The inter-group significances of the deviations between the values of vehicle-treated group (arthritic rats) and vehicle-treated group (non arthritic rats) were assessed by the Student t test or Mann-Whitney Rank Sum Test when equal variance or normality test failed. The inter-group significances of the deviations between the values of vehicle-treated group (arthritic rats) and E3- and 911- and Indomethacin-treated groups were assessed by the 1-way analysis of variance ANOVA followed by the non-paired Dunnett t test. A probability of P≤0.05 was considered as significant. All statistical analysis was performed by the Sigmastat™ software.

Results

1. Nociceptive Response (Vocalization Test)

Figure 18:
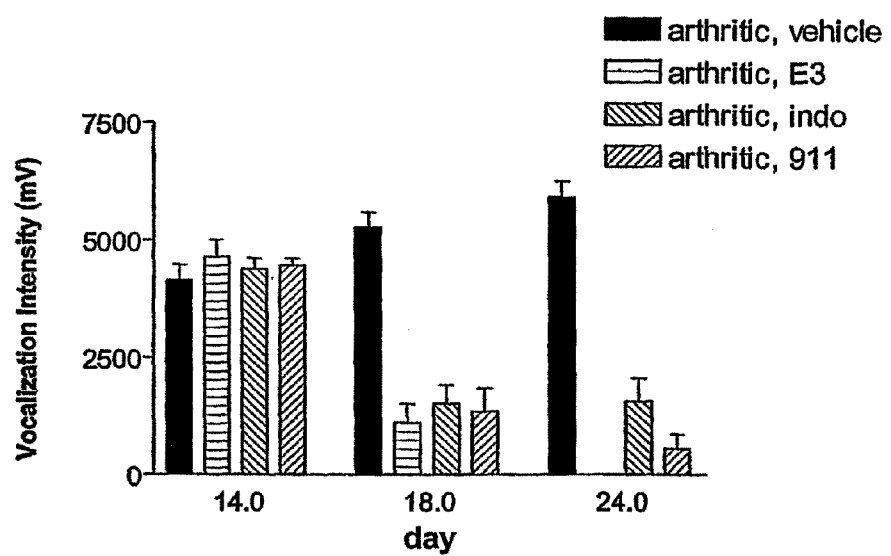
FIG. 18: is a graph demonstrating nociceptive response in arthritic rats (rheumatoid arthritis model) after administration of anti-NGF antibodies (E3 and 911) on D14 and D19. E3 (1 mg/kg, i.v. on day 14 and day 19), 911 (10 mg/kg, i.v. on day 14 and day 19), or indo (indomethacin 3 mg/kg, p.o. daily over 10 days) were administered to arthritic mice. Vocalization intensity values are expressed in mV as means±s.e.m.

As shown in Table 11 and FIG. 18, on D 14, the nociceptive response was 4147±331, 4386±235, 4644±367 and 4468±143 in vehicle-, indomethacin-, E3-, and 911-treated arthritic groups, respectively. Indomethacin strongly and significantly decreased the nociceptive response after 3 mg/kg/day p.o. (for 10 days) by about −3768 mV (% inhibition: 71%) and −4353 mV (% inhibition: 74%) at D18 and D 24, respectively compared to the vehicle-treated arthritic group (D18: 1511±398 vs 5279±326 mV; D 24: 1552±508 vs 5905±345 mV). E3 (1 mg/kg i.v. at D14 and D19) strongly and significantly decreased the nociceptive response by about −4167 mV (% inhibition: 79%) and −5905 mV (% inhibition: 100%) at D18 and D 24, respectively compared to the vehicle-treated arthritic group (D18: 1112±401 vs 5279±326 mV; D 24:0±0 vs 5905±345 mV). 911 (10 mg/kg i.v. 2 days at D14 and D19) strongly and significantly decreased the nociceptive response by about −3932 (% inhibition: 74%) and −5358 mV (% inhibition: 91%) at D18 and D 24, respectively compared to the vehicle-treated arthritic group (D18: 1347±492 vs 5279±326 mV; D 24: 547±307 vs 5905±345 mV).

TABLE 11

Effects of E3 and 911 after i.v. injection (2 days: D14-D19) on nociceptive response in rheumatoid arthritis in rats

| | | Day | | |
|---|---|---|---|---|
| | | D14 | D18 | D24 |
| Arthritic Rats | vehicle i.v. | 4147 ± 331 | 5279 ± 326 | 5905 ± 345 |
| | E3 1 mg/kg i.v. | 4644 ± 367 | 1112 ± 401* | 0 ± 0* |

TABLE 11-continued

Effects of E3 and 911 after i.v. injection (2 days: D14-D19) on nociceptive response in rheumatoid arthritis in rats

| | Day | | |
|---|---|---|---|
| | D14 | D18 | D24 |
| % inhibition | 0 | 79 | 100 |
| 911 10 mg/kg i.v. | 4468 ± 143 | 1347 ± 492* | 547 ± 307* |
| % inhibition | 0 | 74 | 91 |
| Indomethacin 3 mg/kg p.o. (over 10 days) | 4386 ± 235 | 1511 ± 398* | 1552 ± 508 |
| % inhibition | 0 | 71 | 74 |

Figure 19:
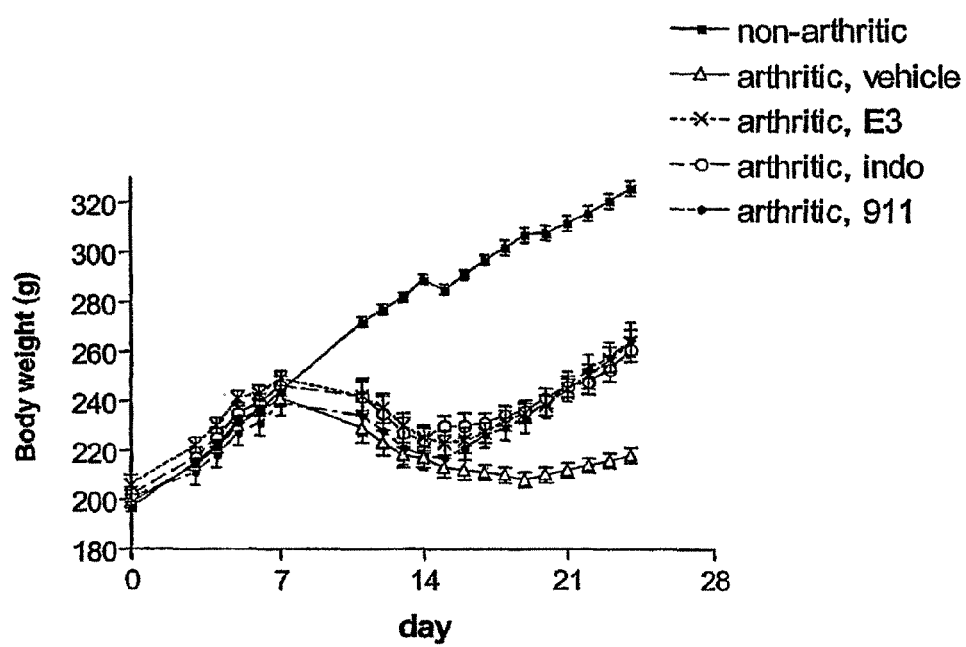
FIG. 19: is a graph demonstrating effects of anti-NGF antibodies on body weight in arthritis in rats (rheumatoid arthritis model) after administration of anti-NGF antibodies on D14 and D19. E3 (1 mg/kg, i.v. on day 14 and day 19), 911 (10 mg/kg, i.v. on day 14 and day 19), or indo (indomethacin 3 mg/kg, p.o. daily over 10 days) were administered to arthritic mice. Body weight values are expressed in grams as mean±s.e.m.

Values are expressed in mV as Mean ± S.E.M.
n = 10 animals per group except at D24 for Indomethacin (n = 9)
Dunnett t test: *P ≤ 0.05 vs vehicle-treated arthritic rats 2. Body Weight As shown in Table 12 and FIG. 19, a marked decrease in the body weight gain was observed in arthritic rats in comparison to non arthritic rats from D 0 to D14 due to arthritis establishment. At D14 (selection day) the arthritic rats displayed a significant decrease in weight compared to the non arthritic rats (289±2 vs 217±4 g) (Student t test P<0.05). However, no significant difference in weight (D14) was detected in all arthritic groups (Dunnett t test P>0.05). The body weight moderately and significantly increased in Indomethacin-treated group (3 mg/kg/day for 10 days) from D17 to D 24 with a maximum of about 43 g at D 24 compared to the vehicle-treated arthritic group (261±5 vs 218±3 g). After E3 treatment (1 mg/kg i.v. at D14 and D19), the body weight moderately and significantly increased from D17 to D 24 with a maximum of about 46 g at D 24 compared to the vehicle-treated arthritic group (264±5 g vs 218±3 g). After 911 treatment (10 mg/kg i.v. at D14 and D19), the body weight moderately and significantly increased from D18 to D 24 with a maximum of about 47 g at D 24 compared to the vehicle-treated arthritic (265±7 vs 218±3 g).

TABLE 12

Effects of E3 and 911 after i.v. injection (2 days: D 14-D 19) on body weight in rheumatoid arthritis in rats

| | Day | D 0 | D 3 | D 4 | D 5 | D 6 | D 7 | D 11 | D 12 | D 13 | D 14 |
|---|---|---|---|---|---|---|---|---|---|---|---|
| Non Arthritic Rats | vehicle i.v. | 197 ± 2 | 215 ± 2 | 222 ± 2 | 232 ± 2 | 236 ± 2 | 244 ± 2 | 272 ± 2 | 277 ± 2 | 282 ± 2 | 289 ± 2 |
| Arthritic Rats | vehicle i.v. | 199 ± 2 | 214 ± 2 | 221 ± 2 | 230 ± 2 | 236 ± 2 | 241 ± 3 | 229 ± 6 | 223 ± 5 | 218 ± 5 | 217 ± 4 |
| | E3 1 mg/kg i.v. | 206 ± 4 | 222 ± 3 | 230 ± 3 | 241 ± 3 | 243 ± 3 | 249 ± 3 | 242 ± 6 | 237 ± 6 | 230 ± 5 | 225 ± 5 |
| | 911 10 mg/kg i.v. | 201 ± 2 | 211 ± 5 | 218 ± 5 | 227 ± 5 | 231 ± 5 | 239 ± 5 | 234 ± 8 | 228 ± 7 | 221 ± 7 | 218 ± 6 |
| | Indomethacin 3 mg/kg p.o. over 10 days | 202 ± 3 | 217 ± 4 | 225 ± 4 | 235 ± 4 | 239 ± 4 | 246 ± 4 | 242 ± 7 | 235 ± 7 | 227 ± 6 | 224 ± 5 |

| | Day | D 15 | D 16 | D 17 | D 18 | D 19 | D 20 | D 21 | D 22 | D 23 | D 24 |
|---|---|---|---|---|---|---|---|---|---|---|---|
| Non Athritic Rats | vehicle i.v. | 285 ± 2 | 291 ± 2 | 297 ± 2 | 302 ± 3 | 307 ± 3 | 308 ± 3 | 312 ± 3 | 316 ± 3 | 321 ± 3 | 326 ± 3 |
| Arthritic Rats | vehicle i.v. | 213 ± 4 | 212 ± 4 | 211 ± 3 | 210 ± 3 | 208 ± 3 | 210 ± 3 | 212 ± 3 | 214 ± 3 | 216 ± 3 | 218 ± 3 |
| | E3 1 mg/kg i.v. | 223 ± 5 | 224 ± 5 | 227 ± 4 * | 232 ± 4 * | 235 ± 4 * | 238 ± 4 * | 245 ± 4 * | 250 ± 5 * | 257 ± 5 * | 264 ± 5 * |
| | 911 10 mg/kg i.v. | 217 ± 5 | 221 ± 5 | 226 ± 5 | 229 ± 5 * | 233 ± 6 * | 239 ± 6 * | 246±6 * | 253 ± 6 * | 258 ± 6 * | 265 ± 7 * |
| | Indomethacin 3 mg/kg p.o. over 10 days | 230 ± 4 | 230 ± 5 | 231 ± 4 * | 234 ± 4 * | 236 ± 4 * | 241 ± 4 * | 246 ± 4 * | 248 ± 5 * | 253 ± 5 * | 261 ± 5 * |

Values are expressed in grams as Mean ± S.E.M. n = 10 animals per group except at D 23 and D 24 (n = 9) for Indomethacin
Dunnett t test:
* P ≤ 0.05 vs vehicle-treated arthritic rats

3. Paw Volume

On D14, a randomization was performed in order to obtain homogenous groups in terms of paw volume. As shown in Table 13, on D14, the hindpaw volume (mean of the right and left paw volume) was significantly greater in arthritic group than that in non arthritic group (2.10±0.05 vs 1.44±0.02 mL (Student t test P<0.05)). Indomethacin (3 mg/kg/day p.o. for 10 days) significantly decreased the paw volume by about −0.75 mL (D 24) compared to the vehicle-treated arthritic group (1.59±0.03 mL vs 2.34±0.08 mL). E3 (1 mg/kg i.v. on D14 and D19) slightly and significantly increased the paw volume by about 0.37 mL compared to the vehicle-treated arthritic group (2.71±0.09 mL vs 2.34±0.08 mL). 911 (10 mg/kg i.v. on D14 and D19) slightly and significantly increased the paw volume by about 0.36 mL compared to the vehicle-treated arthritic group (2.70±0.11 mL vs 2.34±0.08 mL).

TABLE 13

Effects of E3 and 911 after i.v. injection (2 days: D14-D19) on paw volume in rheumatoid arthritis in rats

| | | Day | |
|---|---|---|---|
| | | D14 | D24 |
| Non Arthritic Rats | vehicle i.v. | 1.44 ± 0.02 | 1.47 ± 0.02 |
| Arthritic Rats | vehicle i.v. | 2.10 ± 0.05 | 2.34 ± 0.08 |
| | E3 1 mg/kg i.v. | 2.06 ± 0.03 | 2.71 ± 0.09* |
| | 911 10 mg/kg i.v. | 2.02 ± 0.07 | 2.70 ± 0.11* |
| | Indomethacin 3 mg/kg p.o. over 10 days | 2.08 ± 0.06 | 1.59 ± 0.03* |

Values are expressed in mL as Mean ± S.E.M.
n = 10 animals per group except at D24 for Indomethacin (n = 9)
Dunnett t test: *P ≤ 0.05 vs vehicle-treated arthritic rats

4. Arthritis Index

As shown in Table 14, on D14, the arthritis index was 10.1±0.8, 8.7E 0.6, 10.2±0.4 and 9.4±0.7 and in vehicle-, indomethacin-, E3-, and 911-treated arthritic groups, respectively. Indomethacin strongly and significantly decreased the arthritis index after 3 mg/kg/day p.o. (for 10 days) by a maximum of about −8.0 compared to the vehicle-treated arthritic group (2.7±0.7 vs 10.7±0.6). E3 (1 mg/kg i.v. on D14 and D 19) did not affect the arthritis index compared to the vehicle-treated arthritic group (11.4±0.4 vs 10.7±0.6). 911 (10 mg/kg i.v. on D14 and D19) did not affect the arthritis index compared to the vehicle-treated arthritic group (10.9±0.7 vs 10.7±0.6).

TABLE 14

Effects of E3 and 911 after i.v. injection (2 days: D14-D19) on arthritis index in rheumatoid arthritis in rats

| | | Day | |
|---|---|---|---|
| | | D14 | D24 |
| Arthritic Rats | vehicle i.v. | 10.1 ± 0.8 | 10.7 ± 0.6 |
| | E3 1 mg/kg i.v. | 10.2 ± 0.4 | 11.4 ± 0.4 |
| | 911 10 mg/kg i.v. | 9.4 ± 0.7 | 10.9 ± 0.7 |
| | Indomethacin 3 mg/kg p.o. over 10 days | 8.7 ± 0.6 | 2.7 ± 0.7* |

Values are expressed as Mean ± S.E.M. (score)
n = 10 animals per group except for Indomethacin (n = 9)
Dunnett t test: *P ≤ 0.05 vs vehicle-treated arthritic rats

5. Paw Cytokines Levels

As shown in Table 15, on D 24, the left and right paws cytokine levels were increased in arthritic vehicle-treated group by a maximum of about 3.5 (IL-1β), 4 (TNF-α) and 1.8 (TGF-β1) fold compared to the non-arthritic vehicle-treated group. No significant difference was observed for IL-6 levels, in right and left paw, between the two groups: The cytokines levels of arthritic group were similar in left and right paw: 259.7±38.5 vs 219.2±32.4, 4802.8 365.5 vs 4007.1±380.4, 17.8±1.6 vs 18.6±1.9 and 9735.0±1219.8 vs 9161.4±846.1 pg/ml for IL-6, IL-1β, TNF-α and TGF-β1 respectively. Indomethacin slightly, but significantly, decreased the TGF-β1 level in right paw after 3 mg/kg/day p.o. (for 10 days) by about 1.3 times, compared to the vehicle-treated arthritic group (7057.4±335.6 vs 9161.4±846.1), whereas it did not modify IL-6, TNF-α or IL-1 levels. A similar but not significant effect was observed in the left paw. E3 (1 mg/kg i.v. on D14 and D19) did not affect the IL-6, IL-1β, TNF-α or TGF-β1 levels, in both paws, compared to the vehicle-treated arthritic group. 911 (10 mg/kg i.v. on D14 and D19) increased the IL-1β level in right paw compared to the vehicle-treated arthritic group (6215.3±666.7 vs 4007.1±380.4). It had no effect on others cytokine levels in both paws.

TABLE 15

Effect of E3 and 911 after i.v. injection (2 days on D 14 and D 19) on paw cytokines levels in rheumatoid arthritic rats

| | Non-arthritic Rats vehicle i.v. | Arthritic Rats | | | |
|---|---|---|---|---|---|
| | | vehicle i.v. | E3 1 mg/kg i.v. | 911 10 mg/kg i.v. | Indomethacin 3 mg/kg p.o. |
| Left paw cytokines levels | | | | | |
| IL-6 | 298.6 ± 35.6 | 259.7 ± 38.5 | 234.4 ± 35.2 | 262.5 ± 42.5 | 249.7 ± 60.4 |
| IL-1β | 1383.0 ± 57.9 | 4802.8 ± 365.5 | 5060.0 ± 473.5 | 5500.8 ± 625.3 | 4029.1 ± 449.9 |
| TNF-α | 4.3 ± 2.9 | 17.8 ± 1.6 | 23.6 ± 2.5 | 29.9 ± 4.8 | 29.9 ± 3.6 |
| TGF-β1 | 5264.7 ± 209.2 | 9735.0 ± 1219.8 | 9796.7 ± 491.2 | 11053.5 ± 713.3 | 7708.2 ± 293.9 |

TABLE 15-continued

Effect of E3 and 911 after i.v. injection (2 days on D 14 and D 19) on paw cytokines levels in rheumatoid arthritic rats

|  | Non-arthritic Rats vehicle i.v. | Arthritic Rats | | | |
|---|---|---|---|---|---|
|  |  | vehicle i.v. | E3 1 mg/kg i.v. | 911 10 mg/kg i.v. | Indomethacin 3 mg/kg p.o. |
|  | Right paw cytokines levels | | | | |
| IL-6 | 286.4 ± 76.1 | 219.2 ± 32.4 | 214.6 ± 47.2 | 284.9 ± 38.9 | 295.9 ± 47.8 |
| IL-1β | 1342.1 ± 86.1 | 4007.1 ± 380.4 | 4853.5 ± 605.0 | 6215.3 ± 666.7 * | 3884.4 ± 534.4 |
| TNF-α | 15.7 ± 4.8 | 18.6 ± 1.9 | 21.5 ± 2.5 | 33.4 ± 5.7 | 30.6 ± 5.7 |
| TGF-β1 | 5024.8 ± 148.4 | 9161.4 ± 846.1 | 9362.7 ± 423.4 | 10861.2 ± 604.6 | 7057.4 ± 335.6 * |

Values are expressed in pg/ml, as Mean ± S.E.M.
n = 10 animals per group except for Non-arthritic/vehicle (Right paw), Arthritic/vehicle (Left paw) and Indomethacin (n = 9)
Dunnett t test:
* P ≤ 0.05 vs vehicle-treated arthritic rats 6. Measurement of Circulating TGF-β1

As shown in Table 16, on D 24, the serum TGF-β1 level was increased in arthritic vehicle-treated group compared to the non arthritic vehicle-treated group (81715.7±1984.1 vs 60269.9±2142.8). Indomethacin significantly decreased the serum TGF-β1 level after 3 mg/kg/day p.o. (for 10 days) by about 1.5 times, compared to the vehicle-treated arthritic group (57222.2±3194.1 vs 81715.7±1984.1). E3 (1 mg/kg i.v. on D14 and D19) and 911 (10 mg/kg i.v. on D14 and D19) significantly decreased the serum TGF-β1 level so that the cytokine level in E3- and 911-treated groups were comparable with those observed in vehicle-treated non arthritic group (69408.8±3926.7 and 67214.5±3649.4 respectively, vs 60269.9±2142.8).

TABLE 16

Effect of E3 and 911 after i.v. injection (2 days on D 14 and D 19) on serum TGF-β1 levels in rheumatoid arthritic rats

|  | Non-arthritic Rats vehicle i.v. | Arthritic Rats | | | |
|---|---|---|---|---|---|
|  |  | vehicle i.v. | E3 1 mg/kg i.v. | 911 10 mg/kg i.v. | Indomethacin 3 mg/kg p.o. |
| TGF-β1 | 60269.9 ± 2142.8 | 81715.7 ± 1984.1 | 69408.8 ± 3926.7 * | 67214.5 ± 3649.4 * | 57222.2 ± 3194.1 * |

Values are expressed in pg/ml, as Mean ± S.E.M.
n = 10 animals per group except for Non-arthritic/vehicle (Right paw), Arthritic/vehicle (Left paw) and Indomethacin (n = 9)
Dunnett t test:
* P ≤ 0.05 vs vehicle-treated arthritic rats 7. Hematological Parameters As shown in Table 17, the hematological parameters such as white blood cells and platelets were greater in vehicle-treated arthritic rats in comparison to vehicle-treated non arthritic rats (Student t test P<0.05), whereas the red blood cells, hemoglobin and hematocrit (Student t test P>0.05) were unchanged. Indomethacin did not affect the blood parameters after 3 mg/kg/day p.o. (for 10 days) compared to the vehicle-treated arthritic group. E3 (1 mg/kg i.v. on D14 and D19) did not affect the blood parameters compared to the vehicle-treated arthritic group. 911 (10 mg/kg i.v. on D14 and D19) did not affect the blood parameters compared to the vehicle-treated arthritic group.

TABLE 17

Effects of E3 and 911 after i.v. injection (2 days on D 14 and D 19) on blood parameters in rheumatoid arthritis in rats (Measurement at D 24)

|  | Day | White blood cells $10^3/mm^3$ | Red blood cells $10^6/mm^3$ | Hemoglobin g/dl | Hematocrit % | Platelets $10^3/mm^3$ |
|---|---|---|---|---|---|---|
| Non Arthritic Rats | vehicle i.v. | 8.7 ± 0.9 n = 9 | 7.98 ± 0.31 n = 9 | 15.1 ± 0.7 n = 9 | 42.6 ± 1.6 n = 9 | 322 ± 89 n = 9 |

TABLE 17-continued

Effects of E3 and 911 after i.v. injection (2 days on D 14 and D 19) on blood parameters in rheumatoid arthritis in rats (Measurement at D 24)

|  | Day | White blood cells $10^3/mm^3$ | Red blood cells $10^6/mm^3$ | Hemoglobin g/dl | Hematocrit % | Platelets $10^3/mm^3$ |
|---|---|---|---|---|---|---|
| Arthritic Rats | vehicle i.v. | 19.0 ± 0.9 n = 10 | 7.54 ± 0.31 n = 10 | 13.2 ± 0.7 n = 10 | 37.4 ± 1.6 n = 10 | 10.43 ± 89 n = 10 |
|  | E3 1 mg/kg i.v. | 19.1 ± 1.2 n = 7 | 7.74 ± 0.17 n = 8 | 12.9 ± 0.3 n = 8 | 38.5 ± 1.0 n = 8 | 827 ± 77 n = 8 |
|  | 911 10 mg/kg i.v. | 22.6 ± 2.9 n = 8 | 7.30 ± 0.40 n = 9 | 12.1 ± 0.7 n = 9 | 36.5 ± 2.1 n = 9 | 799 ± 121 n = 9 |
|  | Indomethacin 3 mg/kg p.o. over 10 days | 21.7 ± 2.5 n = 9 | 6.93 ± 0.31 n = 9 | 11.8 ± 0.6 n = 9 | 35.0 ± 1.5 n = 9 | 705 ± 111 n = 9 |

Values are expressed as Mean ± S.E.M.
Anova: P > 0.05 vs vehicle-treated arthritic rats

7. Hindpaw Weight

As shown in Table 18, the left and right hindpaw weight was greater in vehicle-treated arthritic rats than in vehicle-treated non arthritic rats (3.43±0.11 vs 1.98±0.01 and 3.32±0.12 vs 1.99±0.02 μg, respectively) (Student t test or Mann-Withney P<0.05). Indomethacin significantly decreased the hindpaws weight after 3 mg/kg/day p.o. (for 10 days) compared to the vehicle-treated arthritic group (left hindpaw: 2.23±0.04 vs 3.43±0.11 g; right hindpaw: 2.20±0.05 vs 3.32±0.12 g). E3 (1 mg/kg i.v. on D14 and D19) only significantly increased the left hindpaw weight compared to the vehicle-treated arthritic group (left hindpaw: 3.86±0.14 vs 3.43±0.11 g; right hindpaw: 3.72±0.13 vs 3.32±0.12 g). 911 (10 mg/kg i.v. on D14 and D19) only significantly increased the right hindpaw weight compared to the vehicle-treated arthritic group (left hindpaw: 3.73±0.12 vs 3.43±0.11 g; right hindpaw: 3.83±0.15 vs 3.32±0.12 g).

TABLE 18

Effects of E3 and 911 after i.v. injection (2 days on D14 and D19) on hindpaws weight in rheumatoid arthritis in rats (Measurement at D24)

|  |  | Left paw | Right paw |
|---|---|---|---|
| Non Arthritic Rats | vehicle i.v | 1.98 ± 0.01 | 1.99 ± 0.02 |
| Arthritic Rats | vehicle i.v. | 3.43 ± 0.11 | 3.32 ± 0.12 |
|  | E3 1 mg/kg i.v. | 3.86 ± 0.14* | 3.72 ± 0.13 |
|  | 911 10 mg/kg i.v. | 3.73 ± 0.12 | 3.83 ± 0.15* |
|  | Indomethacin 3 mg/kg p.o. over 10 days | 2.23 ± 0.04* | 2.20 ± 0.05* |

Values are expressed in grams as Mean ± S.E.M.
n = 10 animals per group except for Indomethacin (n = 9)
Dunnett t test: *P ≤ 0.05 vs vehicle-treated arthritic rats

8. X-Ray Analysis

As shown in Table 19, a total score of 0.0±0.0 was observed in the vehicle-treated non arthritic rats. The vehicle-treated arthritic rats have a total score of 15.1±1.3 with high scores for demineralization (2.4±0.3), erosions (2.7±0.3), soft tissue damage (3.1±0.2) and space joint (3.3±0.2), a moderate score for periostal reaction (1.0±0.3), osteogenesis (0.8±0.2) and deformity (1.8±0.2). Indomethacin (3 mg/kg/day p.o. for 10 days) strongly and significantly decreased the total score by about 10.7 in comparison to vehicle-treated arthritic rats (4.4±0.9 vs 15.1±1.3). E3 (1 mg/kg i.v. on D14 and D19) did not affect the total score compared to the vehicle-treated arthritic group (14.2±1.3 vs 15.1±1.3). 911 (10 mg/kg i.v. on D14 and D19) did not affect the total score compared to the vehicle-treated arthritic group (15.4±1.0 vs 15.1±1.3).

TABLE 19

Effects of E3 and 911 after i.v. injection (2 days on D 14 and D 19) on X-ray parameters in rheumatoid arthritis in rats

|  | Day | Demineralization | Erosions | Periostal reaction | Soft tissue damage | Space joint | osteogenesis | Deformity | TOTAL score |
|---|---|---|---|---|---|---|---|---|---|
| Non Arthritic Rats | vehicle i.v. | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 |
| Arthritic Rats | vehicle i.v. | 2.4 ± 0.3 | 2.7 ± 0.3 | 1.0 ± 0.3 | 3.1 ± 0.2 | 3.3 ± 0.2 | 0.8 ± 0.2 | 1.8 ± 0.2 | 15.1 ± 1.3 |
|  | E3 1 mg/kg i.v. | 2.0 ± 0.2 | 2.4 ± 0.3 | 0.8 ± 0.2 | 3.3 ± 0.3 | 2.7 ± 0.2 | 1.2 ± 0.2 | 1.8 ± 0.2 | 14.2 ± 1.3 |
|  | 911 10 mg/kg i.v. | 2.3 ± 0.3 | 2.5 ± 0.2 | 1.0 ± 0.3 | 3.4 ± 0.2 | 3.3 ± 0.2 | 0.9 ± 0.2 | 2.0 ± 0.2 | 15.4 ± 1.0 |
|  | Indomethacin 3 mg/kg p.o. | 0.3 ± 0.2 * | 0.9 ± 0.2 * | 0.7 ± 0.3 | 1.0 ± 0.2 * | 1.0 ± 0.2 * | 0.1 ± 0.1 | 0.4 ± 0.2 * | 4.4 ± 0.9 * |

Values are expressed as Mean ± S.E.M (score).
n = 10 animals per group except for Indomethacin (n = 9)
Dunnett t test:
* P ≤ 0.05 vs vehicle-treated arthritic rats Conclusion Under experimental conditions described above, E3 (1 mg/kg i.v. 2 days: D14-D19) and 911 (10 mg/kg i.v. 2 days: D14-D19) showed strong analgesic effects, but did not show significant anti-inflammatory effects in this arthritis model.

Example 8

Effects of Different Doses of Anti-NGF Antibody E3 in a Rat Model of Rheumatoid Arthritis The ability of E3 to produce reduction in pain in arthritic rats was further investigated by examining the dose response relationship between E3 administration and pain reduction. Rats were treated with adjuvant to induce arthritis as described above. Ten rats not injected with adjuvant were used as non-arthritic controls. Fourteen days after adjuvant injection, animals were qualified into the study based on the criteria stated above, randomized into eight groups of ten rats and tested for the intensity of their vocalization response. They were then dosed on day 14 with saline, or 0.003 mg/kg, 0.01 mg/kg, 0.03 mg/kg, 0.1 mg/kg, 0.3 mg/kg, 1 mg/kg or 5 mg/kg of E3 antibody as described above. Animals were tested for their vocalization response on days 16, 18, 20, and 24. Animals were redosed with saline or the same dose of E3 on day 18 after the vocalization testing. Animals were also weighed each day, starting at day 14. Thus, animals were dosed twice with a given dose of antibody or saline on days 14 and 18, and assessed for pain five times, on days 14, 16, 18, 20 and 24. Data are shown in Tables 20-22 and in FIGS. 20-22.

TABLE 20

Effects of different doses of E3 on nociceptive response (vocalization intensity) in rheumatoid arthritic rats. Vocalization intensity values are expressed in mV as mean ± s.e.m.

| | | vehicle | 0.003 mg/kg | 0.01 mg/kg | 0.03 mg/kg | 0.1 mg/kg | 0.3 mg/kg | 1.0 mg/kg | 5.0 mg/kg |
|---|---|---|---|---|---|---|---|---|---|
| day 14 | mean | 1129.25 | 981.75 | 1007.28 | 963.18 | 1159.30 | 1191.58 | 1067.00 | 896.25 |
| | s.e.m | 143.06 | 71.00 | 66.50 | 62.12 | 132.76 | 123.44 | 69.73 | 57.53 |
| day 16 | mean | 1042.85 | 825.60 | 576.88 | 448.43 | 283.71 | 151.85 | 98.62 | 79.18 |
| | s.e.m | 130.51 | 57.94 | 49.71 | 81.01 | 60.00 | 26.08 | 29.17 | 27.30 |
| day 18 | mean | 968.10 | 427.43 | 334.45 | 292.52 | 262.96 | 194.19 | 174.13 | 200.42 |
| | s.e.m | 117.85 | 48.55 | 35.10 | 52.36 | 62.32 | 53.56 | 88.61 | 120.15 |
| day 20 | mean | 942.18 | 448.00 | 313.13 | 209.48 | 79.74 | 66.27 | 71.23 | 63.57 |
| | s.e.m | 100.69 | 33.73 | 61.98 | 24.43 | 33.18 | 31.34 | 42.37 | 23.47 |
| day 24 | mean | 913.68 | 724.50 | 596.38 | 513.60 | 432.45 | 176.32 | 19.21 | 12.35 |
| | s.e.m | 131.29 | 115.90 | 44.76 | 63.67 | 70.38 | 66.61 | 10.14 | 12.35 |

The effect of treating animals with various doses of anti-NGF antibody E3 on pain induced vocalization (data shown in Table 20) was statistically analyzed by using two-way ANOVA to compare the results obtained pairwise between arthritic animals treated with vehicle with those treated with a given dose of antibody E3. There was a highly significant effect at all levels of E3 tested ($p<0.0001$). Even at the lowest dose tested (0.003 mg/kg of E3), the difference in vocalization was significant ($p<0.0001$).

Figure 20:
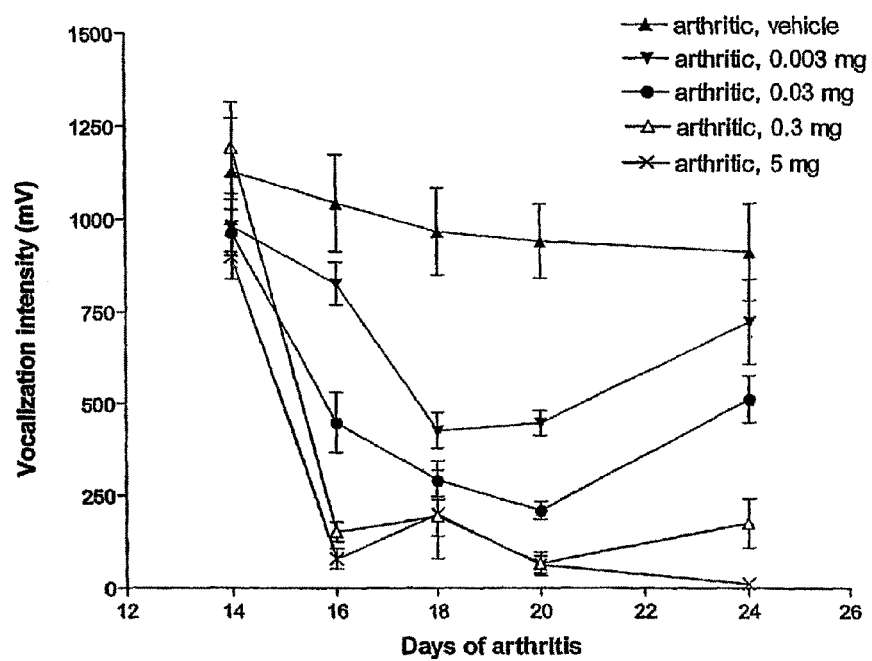
FIG. 20: is a graph demonstrating nociceptive response in arthritic rats (rheumatoid arthritis model) after administration of different doses of anti-NGF antibody E3 (0.003 mg/kg, 0.03 mg/kg, 0.3 mg/kg, and 5 mg/kg) on D14 and D18. Vocalization intensity values are expressed in mV as means±s.e.m.
Figure 21:
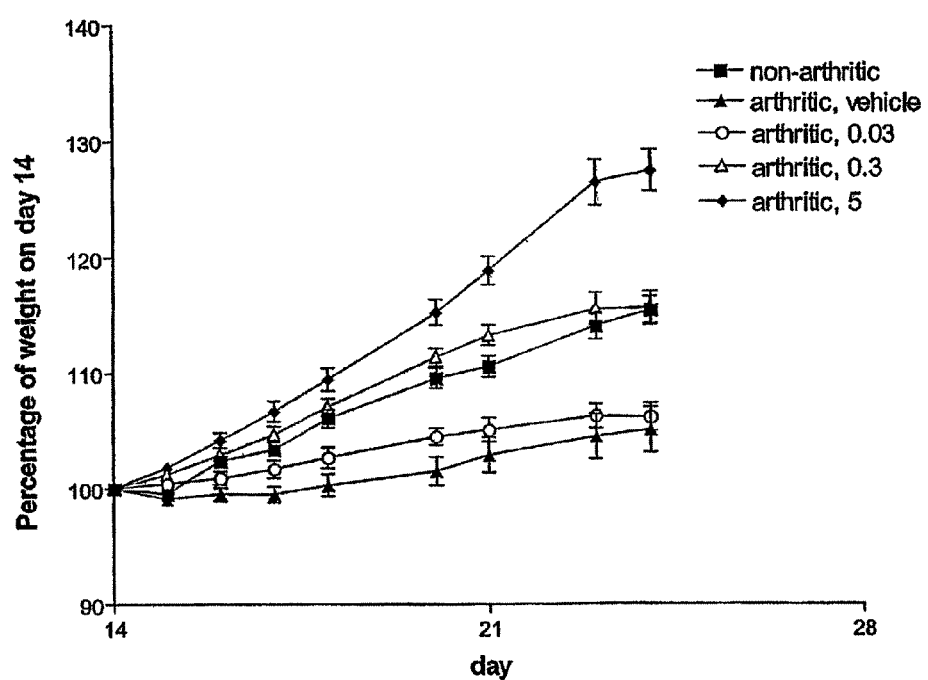
FIG. 21: is a graph demonstrating effects of anti-NGF antibody E3 on percentage of weight on Day 14 (normalized to Day 14) in arthritic rats (rheumatoid arthritis model) after administration of different doses of anti-NGF antibody E3 (0.03 mg/kg, 0.3 mg/kg, and 5 mg/kg) on D14 and D18.

As shown in Table 20 and FIG. 20, in agreement with the above experiments, treatment with antibody E3 at 1 mg/kg showed a rapid and robust relief of pain. Within two days (the earliest time point tested) the vocalization intensity fell by 90%. Treatment with lower concentrations of E3 also provided robust pain relief, although at lower doses the pain relief took somewhat longer to manifest. It is likely that the apparent decrease in efficacy on day 24 of all but the highest doses tested is due to a decrease in the actual level of plasma E3 level secondary to an immune response by the subject rats. It is apparent that doses as low as 0.003 mg/kg provide at least partial pain relief in this model.

TABLE 21

Effects of different doses of E3 on body weight in rheumatoid arthritic rats (normalized to day 14).

| | Non-Arthritic | | vehicle | | 0.003 mg/kg | | 0.01 mg/kg | | 0.03 mg/kg | |
|---|---|---|---|---|---|---|---|---|---|---|
| Day | Mean | S.E.M | Mean | S.E.M | Mean | S.E.M | Mean | S.E.M | Mean | S.E.M |
| 14 | 100.00 | 0.00 | 100.00 | 0.00 | 100.00 | 0.00 | 100.00 | 0.00 | 100.00 | 0.00 |
| 15 | 99.53 | 0.30 | 99.14 | 0.37 | 99.20 | 0.48 | 99.18 | 0.43 | 100.34 | 0.36 |
| 16 | 102.52 | 0.45 | 99.57 | 0.60 | 99.58 | 0.79 | 99.33 | 0.72 | 100.89 | 0.57 |
| 17 | 103.31 | 0.41 | 99.50 | 0.64 | 100.46 | 0.77 | 99.69 | 0.73 | 101.80 | 0.82 |
| 18 | 106.11 | 0.72 | 100.26 | 0.93 | 100.90 | 1.19 | 100.69 | 0.72 | 102.70 | 0.92 |

TABLE 21-continued

Effects of different doses of E3 on body weight in rheumatoid arthritic rats (normalized to day 14).

| 20 | 109.62 | 0.85 | 101.46 | 1.22 | 102.26 | 1.58 | 102.70 | 1.07 | 104.51 | 0.75 |
|---|---|---|---|---|---|---|---|---|---|---|
| 21 | 110.52 | 0.93 | 102.73 | 1.49 | 103.16 | 1.87 | 102.63 | 1.18 | 105.08 | 0.98 |
| 23 | 114.28 | 1.19 | 104.54 | 1.92 | 106.09 | 1.67 | 104.41 | 1.33 | 106.14 | 1.06 |
| 24 | 115.44 | 1.15 | 105.12 | 1.92 | 106.16 | 1.90 | 104.23 | 1.46 | 106.23 | 1.26 |

|  | 0.1 mg/kg | | 0.3 mg/kg | | 1.0 mg/kg | | 5.0 mg/kg | |
|---|---|---|---|---|---|---|---|---|
| Day | Mean | S.E.M | Mean | S.E.M | Mean | S.E.M | Mean | S.E.M |
| 14 | 100.00 | 0.00 | 100.00 | 0.00 | 100.00 | 0.00 | 100.00 | 0.00 |
| 15 | 99.83 | 0.59 | 101.05 | 0.38 | 100.53 | 0.37 | 101.61 | 0.41 |
| 16 | 101.07 | 0.82 | 102.88 | 0.50 | 102.95 | 0.56 | 104.09 | 0.60 |
| 17 | 101.89 | 1.12 | 104.76 | 0.70 | 105.74 | 0.76 | 106.85 | 0.79 |
| 18 | 103.69 | 1.47 | 107.11 | 0.78 | 108.46 | 0.82 | 109.53 | 1.00 |
| 20 | 107.36 | 1.78 | 111.26 | 0.77 | 113.57 | 0.83 | 115.32 | 1.11 |
| 21 | 108.50 | 2.01 | 113.31 | 0.87 | 116.71 | 0.92 | 119.11 | 1.21 |
| 23 | 109.25 | 2.15 | 115.59 | 1.38 | 123.35 | 1.13 | 126.36 | 1.94 |
| 24 | 108.77 | 2.08 | 115.58 | 1.43 | 124.41 | 1.00 | 127.25 | 1.79 |

TABLE 22

Effects of different doses of E3 on body weight in rheumatoid arthritic rats (normalized to day 0).

|  | Non-Arthritic | | vehicle | | 0.003 mg/kg | | 0.01 mg/kg | | 0.03 mg/kg | |
|---|---|---|---|---|---|---|---|---|---|---|
| Day | Mean | S.E.M | Mean | S.E.M | Mean | S.E.M | Mean | S.E.M | Mean | S.E.M |
| 0 | 100.00 | 0.00 | 100.00 | 0.00 | 100.00 | 0.00 | 100.00 | 0.00 | 100.00 | 0.00 |
| 1 | 100.45 | 0.19 | 98.34 | 0.48 | 98.37 | 0.35 | 98.86 | 0.33 | 98.67 | 0.34 |
| 2 | 105.94 | 0.33 | 101.75 | 0.71 | 102.47 | 0.59 | 102.61 | 0.40 | 102.05 | 0.53 |
| 3 | 109.29 | 0.33 | 105.04 | 1.04 | 106.54 | 0.99 | 106.29 | 0.60 | 105.31 | 0.85 |
| 4 | 113.13 | 0.46 | 109.14 | 1.15 | 110.09 | 0.72 | 110.61 | 0.41 | 109.24 | 0.82 |
| 7 | 124.15 | 0.70 | 119.90 | 1.39 | 121.29 | 1.32 | 121.59 | 0.72 | 117.15 | 1.36 |
| 8 | 127.82 | 0.80 | 123.38 | 1.52 | 124.44 | 1.43 | 124.47 | 1.24 | 118.52 | 1.89 |
| 9 | 132.40 | 0.80 | 125.50 | 1.59 | 125.91 | 1.69 | 125.82 | 1.95 | 118.60 | 2.62 |
| 10 | 135.91 | 0.83 | 123.51 | 1.77 | 123.30 | 2.47 | 123.87 | 2.59 | 115.26 | 3.19 |
| 11 | 140.42 | 1.13 | 119.82 | 1.98 | 119.55 | 2.76 | 121.20 | 2.99 | 112.94 | 3.48 |
| 14 | 152.59 | 1.72 | 111.79 | 1.40 | 111.50 | 1.87 | 111.80 | 1.65 | 108.37 | 2.75 |
| 15 | 151.87 | 1.87 | 110.82 | 1.41 | 110.63 | 2.05 | 110.85 | 1.44 | 108.68 | 2.45 |
| 16 | 156.47 | 2.25 | 111.33 | 1.74 | 111.08 | 2.32 | 110.98 | 1.31 | 109.21 | 2.16 |
| 17 | 157.65 | 2.08 | 111.24 | 1.62 | 112.06 | 2.36 | 111.42 | 1.66 | 110.16 | 2.03 |
| 18 | 161.98 | 2.71 | 112.16 | 2.21 | 112.60 | 2.78 | 112.54 | 1.64 | 111.14 | 2.11 |
| 20 | 167.36 | 2.93 | 113.49 | 2.37 | 114.17 | 3.24 | 114.82 | 2.12 | 113.17 | 2.49 |
| 21 | 168.73 | 3.07 | 114.93 | 2.62 | 115.25 | 3.68 | 114.76 | 2.30 | 113.80 | 2.68 |
| 23 | 174.51 | 3.54 | 116.96 | 3.02 | 118.48 | 3.49 | 116.76 | 2.51 | 114.93 | 2.62 |
| 24 | 176.27 | 3.50 | 117.63 | 3.13 | 118.58 | 3.71 | 116.56 | 2.57 | 114.99 | 2.51 |

|  | 0.1 mg/kg | | 0.3 mg/kg | | 1.0 mg/kg | | 5.0 mg/kg | |
|---|---|---|---|---|---|---|---|---|
| Day | Mean | S.E.M | Mean | S.E.M | Mean | S.E.M | Mean | S.E.M |
| 0 | 100.00 | 0.00 | 100.00 | 0.00 | 100.00 | 0.00 | 100.00 | 0.00 |
| 1 | 99.31 | 0.61 | 99.26 | 0.28 | 98.81 | 0.27 | 98.25 | 0.58 |
| 2 | 102.87 | 0.73 | 102.98 | 0.43 | 103.18 | 0.50 | 101.82 | 0.53 |
| 3 | 106.26 | 0.82 | 106.95 | 0.50 | 106.52 | 0.55 | 105.47 | 0.58 |
| 4 | 110.20 | 0.64 | 110.50 | 0.58 | 110.52 | 0.67 | 109.29 | 0.58 |
| 7 | 120.50 | 1.20 | 120.03 | 0.82 | 121.54 | 1.15 | 119.77 | 1.19 |
| 8 | 123.48 | 1.58 | 121.38 | 1.31 | 124.28 | 1.59 | 121.96 | 1.72 |
| 9 | 125.46 | 2.47 | 121.57 | 2.09 | 125.60 | 2.23 | 123.04 | 2.42 |
| 10 | 123.95 | 3.38 | 118.27 | 3.07 | 124.11 | 2.97 | 120.00 | 2.81 |
| 11 | 121.98 | 3.93 | 116.02 | 3.32 | 121.27 | 3.42 | 117.97 | 2.98 |
| 14 | 113.90 | 2.14 | 108.43 | 1.94 | 111.72 | 2.27 | 111.58 | 2.59 |
| 15 | 113.66 | 1.91 | 109.59 | 2.12 | 112.30 | 2.23 | 113.33 | 2.37 |
| 16 | 115.06 | 2.00 | 111.54 | 2.02 | 115.00 | 2.36 | 116.06 | 2.30 |
| 17 | 115.99 | 2.18 | 113.57 | 2.04 | 118.08 | 2.32 | 119.14 | 2.42 |
| 18 | 118.01 | 2.29 | 116.13 | 2.14 | 121.16 | 2.55 | 122.14 | 2.61 |
| 20 | 122.17 | 2.57 | 120.62 | 2.20 | 126.90 | 2.87 | 128.60 | 2.77 |
| 21 | 123.49 | 2.90 | 122.88 | 2.49 | 130.41 | 2.98 | 132.82 | 2.84 |
| 23 | 124.35 | 3.02 | 125.36 | 2.83 | 137.81 | 3.09 | 140.79 | 2.83 |
| 24 | 123.77 | 2.80 | 125.33 | 2.75 | 138.93 | 2.76 | 141.77 | 2.61 |

The effect of treating animals with various doses of anti-NGF antibody E3 on body weight was statistically analyzed by using two-way ANOVA to compare the results obtained pairwise between arthritic animals treated with vehicle with those treated with a given dose of antibody E3. Using data normalized to weight on day 14 (Table 21), doses of 0.03 mg/kg of E3 resulted in a significant change in body weight ($p<0.005$). At all higher dose of E3, the difference between treated and untreated arthritic animals was significant ($p=$ or $<0.0001$). Using data normalized to weight on day 0 (Table 22), dose of 0.03 mg/kg of E3 resulted in a significant change in body weight ($p<0.002$). At all higher dose of E3, the difference between treated and untreated arthritic animals was significant ($p<0.0001$).

Figure 22:
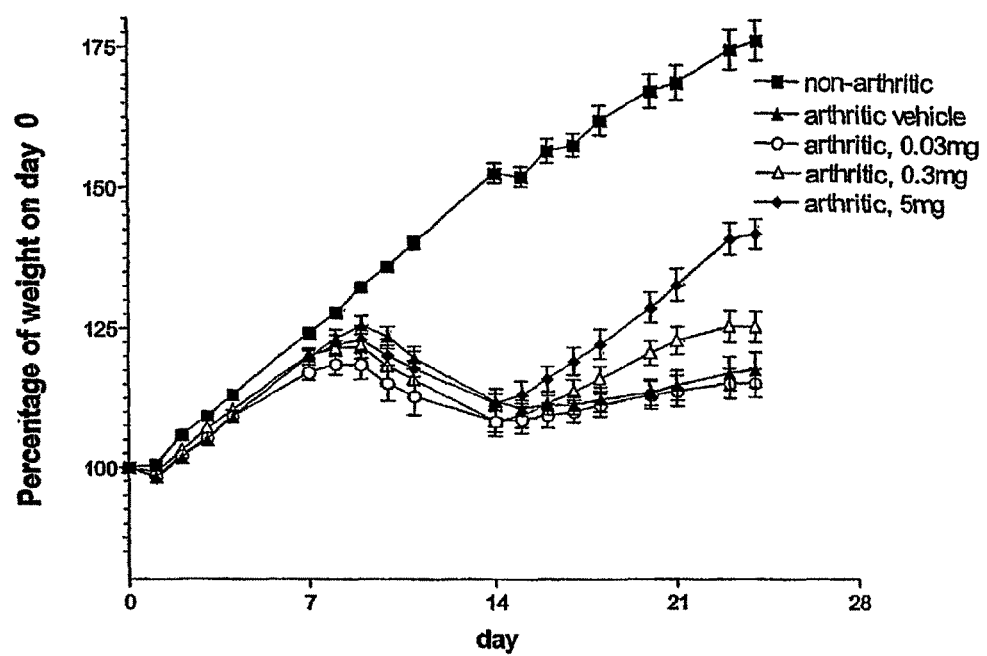
FIG. 22: is a graph demonstrating effects of anti-NGF antibody E3 on weight loss in arthritic rats (rheumatoid arthritis model) after administration of different doses of anti-NGF antibody E3 (0.03 mg/kg, 0.3 mg/kg, and 5 mg/kg) on D14 and D18. Body weight values were normalized to Day 0.

Again in agreement with earlier studies, rats treated with E3 showed less apparent weight loss than saline treated arthritic rats (Table 22 and FIG. 22). In fact, rats treated with high doses of antibody E3 were recovering the earlier weight loss, and actually gaining weight faster than their non-arthritic cohorts (Table 21 and FIG. 21).

Example 9

Analgesic Effects of Anti-NGF Antibody E3 in Patients with Moderate to Severe Pain from Osteoarthritis of the Knee In this randomized, placebo-controlled, double-blind, dose-escalation study, analgesic effects of single intravenous doses (3 μg/kg, 10 μg/kg, 30 μg/kg, 100 μg/kg, or 300 μg/kg) of anti-NGF antibody E3 were compared with placebo in patients with moderate to severe pain from osteoarthritis of the knee. Adult males and females (ages between 35 to 65) who were experiencing moderate-to-severe pain from osteoarthritis of the knee, but were in otherwise overall good health were enrolled in the study. During the screening period, patients were required to discontinue arthritis medications such as NSAIDs, cyclooxygenase type-2 (COX-2) inhibitors, and opiates at least 14 days prior to administration of anti-NGF antibody E3. Patients were allowed to use rescue medications of acetaminophen or ibuprofen with some restrictions based on laboratory findings or past medical history. Some patients took rescue medications during the study, but rescue medications were not consumed for 2 days before and after administration of anti-NGF antibody E3.

Thirty-four patients were admitted to the study and assessed as inpatients for on Study Days −1, 1 and 2. Anti-NGF antibody E3 administration occurred on the morning of Day 1. Electronic diaries were used to record index knee pain and rescue medication usage in clinic and at home. Ten patients were treated with placebo. Twenty-four patients were treated with anti-NGF antibody E3: four patients per dose level for 3 μg/kg (cohort 1), 10 μg/kg (cohort 2), and 30 μg/kg (cohort 3); and six patients per dose level for 100 μg/kg (cohort 4) and 300 μg/kg (cohort 5). The placebo used was sterile 0.9% Sodium Chloride Injection, USP (normal saline). Anti-NGF antibody E3 was a frozen liquid formulation consisting of 10 mg/ml antibody in an aqueous solution of 10 mM histidine, 275 mM sucrose, 0.01% polysorbate 20, pH 6.0. One hour prior to IV administration, frozen antibody was thawed and diluted into Sodium Chloride Injection, USP. The volume for each patient was calculated based on the subject's Day −1 weight and assigned dose level, ranging from 3-6 cc for cohort 1, 10-20 cc for cohort 2, 30-60 cc for cohort 3, and 109 cc for cohort 4 and cohort 5. For cohorts 1 and 2, antibody E3 was administered by a slow IV bolus over 3 to 5 minutes, followed with an IV flush of 5 cc Sodium Chloride Injection, USP. For cohorts 3-5, antibody E3 was administered at 100 cc/hour via infusion pump, followed with an IV flush of 5 cc Sodium Chloride. Injection, USP and discontinuation of the IV. Within each cohort, the placebo (Sodium Chloride Injection, USP) was administered by slow bolus or continuous infusion in the same fashion as the antibody E3.

After two in-patient days, patients were discharged home. Depending of the dose level cohort, they continued to be assessed for pain levels for 28 days after antibody E3 administration (Cohorts 1, 2, and 3) or up to 181 days after antibody E3 administration (Cohorts 4 and 5). Periodic safety assessments was performed for 181 days in all patients.

Analgesic effects were assessed before dosing and at multiple times after administration of antibody E3. Validated electronic VAS ranging from 0-100 with 101 point resolution was used for current index knee pain. Patients were cued 4 times daily and instructed to indicate the level of arthritis pain in the index knee at that moment. Validated electronic VAS ranging from 0-100 with 101 point resolution was also used for index knee pain during walking. VAS for index knee pain during walking was completed daily, concurrent with the fourth current index knee pain VAS.

Electronic diary for data collection was issued on day −8 and a 7-day screening assessment of electronic diary compliance was performed from day −8 to day −2 to determine success in using the electronic diaries for a given subject. Subjects were instructed to complete 4 diaries per day. The mean VAS recorded during the screening period is used as baseline for assessment of efficacy.

WOMAC (Western Ontario and McMaster Universities Arthritis Scale) 3.1 Osteoarthritis Index Version VA.1© was also used for assessing arthritis pain. WOMAC 3.1™ consists of 24 questions divided into 3 domains: pain (5 questions), stiffness (2 questions), and physical function (17 questions). Bellamy et al., *J. Rheumatol* 15:1833-40 (1988); and Bellamy, *Semin. Arthritis Rheum.* 18:14-7 (1989). The physical function domain provides information of the ability to perform activities of daily living. Patients performed the test directly on the electronic diary during designated clinic visits, using validated electronic VAS ranging from 0-100 with 101 point resolution. Each domain was scored by determining the means of the VAS scores of the component questions. The total WOMAC 3.1™ was scored by determining the means of the scores from each of the 3 domains. Patients were also required to report rescue medication used via the electronic diary.

Outcome was assessed as change from baseline (pain level during screening period), expressed as pain intensity difference (PID) or summed pain intensity difference (SPID) for different dose levels. Changes from baseline in the activity measurements were analyzed using an analysis of covariance (ANCOVA) model with treatment as the main factor and baseline pain as a covariate. For means and mean changes, comparisons of antibody E3 with placebo was made using Dunnett's test. Tukey-Ciminera-Heyse trend test was used to assess the dose-response relationship.

As shown in FIG. 24, decrease of mean daily pain intensity after the single administration of anti-NGF antibody E3 was observed in every dose tested. Generally, the effect in reducing pain intensity lasted longer in the higher dose (30 μg/kg, 100 μg/kg and 300 μg/kg) treated group than the lower dose (3 μg/kg and 10 μg/kg) treated group. As shown in FIG. 25, the pain intensity reductions lasted for at least 80 days after administration of 100 μg/kg of E3.

Table 23 below shows the summed pain intensity differences (SPID) for each dosing of E3 for days 2-8, days 2-14, days 2-21, and days 2-28 as compared to baseline levels.

ANCOVA was used for statistically analysis. Table 23 indicates that pain reduction was statistically significant (p<0.05) after single administration of anti-NGF antibody E3.

TABLE 23

Summed pain intensity differences for varying time intervals as compared to baseline.

|  | Days 2-8 | Days 2-14 | Days 2-21 | Days 2-28 |
|---|---|---|---|---|
| Placebo | −269 | −486 | −758 | −1055 |
| 3 µg/kg | −572 | −956 | −1048 | −1067 |
|  | (0.11) | (0.18) | (0.63) | (0.99) |
|  | (0.43) | (0.62) | (0.99) | (1.00) |
| 10 µg/kg | −671 | −1174 | −1623 | −2020 |
|  | (0.04) | (0.05) | (0.15) | (0.29) |
|  | (0.17) | (0.24) | (0.55) | (0.81) |
| 30 µg/kg | −733 | −1371 | −2042 | −2566 |
|  | (0.02) | (0.02) | (0.04) | (0.10) |
|  | (0.09) | (0.08) | (0.17) | (0.40) |
| 100 µg/kg | −766 | −1403 | −1996 | −2726 |
|  | (<0.01) | (<0.01) | (0.02) | (0.04) |
|  | (0.02) | (0.02) | (0.10) | (0.17) |
| 300 µg/kg | −769 | −1340 | −1869 | −2521 |
|  | (<0.01) | (<0.01) | (0.04) | (0.07) |
|  | (0.02) | (0.04) | (0.17) | (0.29) |
| All | −713 | −1269 | −1752 | −2254 |
|  | (<0.01) | (<0.01) | (0.01) | (0.04) |
|  | (<0.01) | (<0.01) | (0.06) | (0.18) |

Statistically analysis was performed with no adjustment and with adjustment for multiple comparisons. The first row of the p values in parenthesis for each time interval was without adjustment; the second row of p values in parenthesis was with Dunnett's adjustment.

Figure 26:
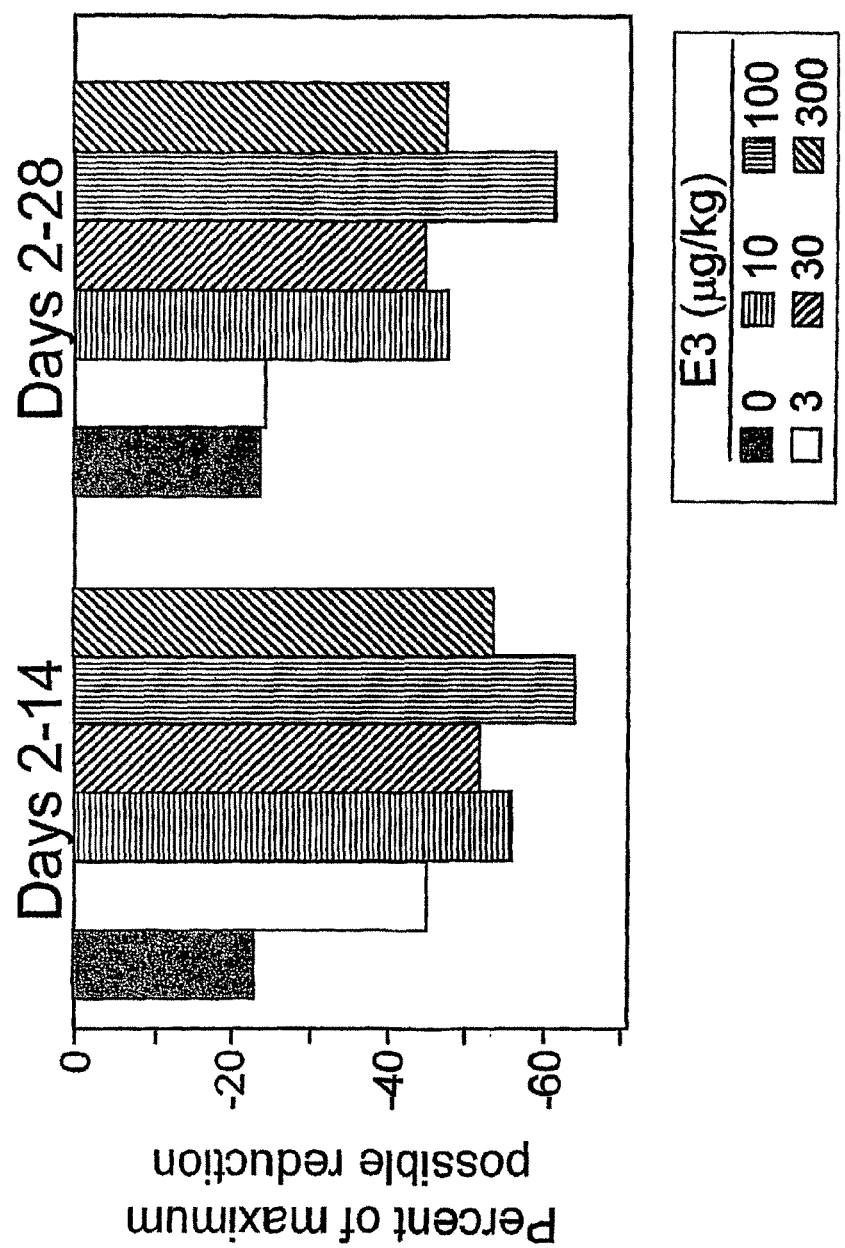
FIG. 26 depicts percent maximal reduction in summed pain intensity difference (SPID) from day 2 to day 14 and from day 2 to day 28 after administration of anti-NGF antibody E3.

As shown in FIG. 26, percent of maximal reduction in SPID by the single administration of anti-NGF antibody E3 reached about 45% to about 65% from day 2 to day 14 for every E3 dose tested, and reached about 45% to about 60% from day 2 to day 28 for 10 µg/kg, 30 µg/kg, 100 µg/kg, and 300 µg/kg E3 dose.

Figure 27:
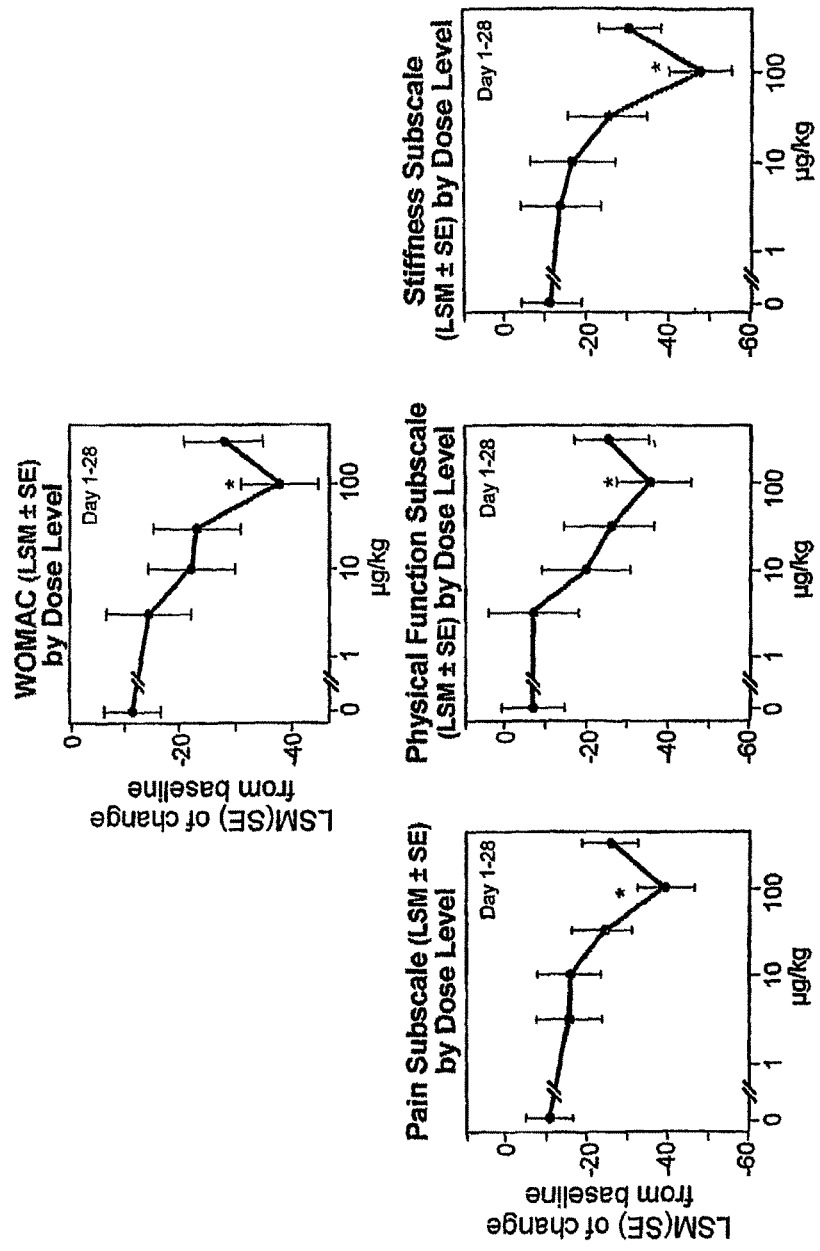
FIG. 27 depicts least square mean (LSM) response for WOMAC, pain subscale, physical function subscale, and stiffness subscale from day 1 to day 28 after administration of different doses (3 µg/kg, 10 µg/kg, 30 µg/kg, 100 µg/kg, and 300 µg/kg) of anti-NGF antibody E3. "SE" refers to standard error. X axes correspond to dose of anti-NGF antibody E3 administered. "*" indicates P<0.05 as compared to baseline under Dunnett's test.

As shown in FIG. 27, administration of anti-NGF antibody E3 also reduced WOMAC score from day 1 to day 28. Pain, physical function and stiffness score were reduced significantly at 100 µg/kg dose of E3. These data indicate that single administration of anti-NGF antibody not only reduces pain, but also improves physical function and stiffness in patients having osteoarthritis.

Deposit of Biological Material

The following materials have been deposited with the American Type Culture Collection, 10801 University Boulevard, Manassas, Va., USA (ATCC):

| Material | | ATCC Accession No. | Date of Deposit |
|---|---|---|---|
| Eb.911.3E | E3 light chain | PTA-4893 | Jan. 8, 2003 |
| Eb.pur.911.3E | E3 light chain | PTA-4894 | Jan. 8, 2003 |
| Db.911.3E | E3 heavy chain | PTA-4895 | Jan. 8, 2003 |

Vector Eb.911.3E is a polynucleotide encoding the E3 light chain variable region; vector Eb.pur.911.3E is a polynucleotide encoding E3 light chain variable region, and vector Db.911.3E is a polynucleotide encoding the E3 heavy chain variable region.

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Rinat Neuroscience Corp. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC Section 122 and the Commissioner's rules pursuant thereto (including 37 CFR Section 1.14 with particular reference to 8860G 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Antibody Sequences

Heavy chain variable region (Kabat CDRs are underlined; Chothia CDRs are BOLD AND ITALICIZED)

(SEQ ID NO: 1)
QVQLQESGPGLVICPSETLSLTCTVS<u>GFSLI*GYDL*</u>NWIRQPPGKGLEW

IG<u>I*IWGDGTTD*</u>*YNSAVKS*RVTISKDTSKNQFSLKLSSVTAADTAVY

YCAR*GGYWYATSYYFDY*WGQGTLVTVS

Light chain variable region (Kabat CDRs are underlined; Chothia CDRs are BOLD AND ITALICIZED)

(SEQ ID NO: 2)
DIQMTQSPSSLSASVGDRVTITC<u>R*ASQSIS*NNLN</u>WYQQKPGKAPKLL

IY<u>*YTSRFHS*</u>GVPSRFSGSGSGTDFTFTISSLQPEDIATYYC

<u>*QQEHTLPYT*</u>FGQGTKLEIKRT

E3 heavy chain extended CDRs (SEQ ID NO: 3)
CDRH1: GFSLIGYDLN (SEQ ID NO: 4)
CDRH2: IIWGDGTTDYNSAVKS (SEQ ID NO: 5)
CDRH3: GGYWYATSYYFDY E3 light chain extended CDRs (SEQ ID NO: 6)
CDRL1: RASQSISNNLN (SEQ ID NO: 7)
CDRL2: YTSRFHS (SEQ ID NO: 8)
CDRL3: QQEHTLPYT Mouse monoclonal antibody 911 extended CDRs
911 heavy chain extended CDRs (SEQ ID NO: 9)
CDRH1: GFSLIGYDIN (SEQ ID NO: 10)
CDRH2: MIWGDGTTDYNSALKS (SEQ ID NO: 11)
CDRH3: GGYYYGTSYYFDY 911 light chain extended CDRs (SEQ ID NO: 12)
CDRL1: RASQDISNIALN

CDRL2: YISRFHS (SEQ ID NO: 13)

CDRL3: QQSKTLPYT (SEQ ID NO: 14)

E3 heavy chain amino acid sequence (full)
(SEQ ID NO: 16)
QVQLQESGPGLVKPSETLSLTCTVSGFSLIGYDLNWIRQPPGKGLEWIGI
IWGDGTTDYNSAVKSRVTISKDTSKNQFSLKLSSVTAADTAVYYCARGGY
WYATSYYFDYWGQGTLVTVSSASTKGPSVFPLAPCSRSTSESTAALGCLV
KDYFPEPVTVSWNSGALTSGVHTFPAVLQSSGLYSLSSVVTVPSSNFGTQ
TYTCNVDHKPSNTKVDKTVERKCCVECPPCPAPPVAGPSVFLFPPKPKDT
LMISRTPEVTCVVVDVSHEDPEVQFNWYVDGVEVHNAKTKPREEQFNSTF
RVVSVLTVVHQDWLNGKEYKCKVSNKGLPSSIEKTISKTKGQPREPQVYT
LPPSREEMTKNQVSLTCLVKGFYPSDIAVEWESNGQPENNYKTTPPMLDS
DGSFFLYSKLTVDKSRWQQGNVFSCSVMHEALHNHYTQKSLSLSPGK 3E light chain amino acid sequence (full antibody)
(SEQ ID NO: 17)
DIQMTQSPSSLSASVGDRVTITCRASQSISNNLNWYQQKPGKAPKLLIYY
TSRFHSGVPSRFSGSGSGTDFTFTISSLQPEDIATYYCQQEHTLPYTFGQ
GTKLEIIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC 3E heavy chain nucleotide sequence (full antibody)
(SEQ ID NO: 65)
CAGGTGCAGCTGCAGGAGTCTGGCCCAGGACTGGTGAAGCCTTCCGAGAC
CCTGTCCCTCACCTGCACTGTCTCTGGGTTCTCACTTATCGGCTATGATC
TTAACTGGATCCGACAGCCTCCAGGGAAGGGACTGGAGTGGATTGGGATT
ATCTGGGGTGATGGAACCACAGACTATAATTCAGCTGTCAAATCCCGCGT
CACCATCTCAAAAGACACCTCCAAGAACCAGTTCTCCCTGAAGCTGAGCT
CTGTGACCGCCGCGGACACGGCCGTGTATTACTGTGCGAGAGGAGGTTAT
TGGTACGCCACTAGCTACTACTTTGACTACTGGGGCCAGGGCACCCTGGT
CACCGTCTCCTCAGCCTCCACCAAGGGCCCATCTGTCTTCCCACTGGCCC
CATGCTCCCGCAGCACCTCCGAGAGCACAGCCGCCCTGGGCTGCCTGGTC
AAGGACTACTTCCCAGAACCTGTGACCGTGTCCTGGAACTCTGGCGCTCT
GACCAGCGGCGTGCACACCTTCCCAGCTGTCCTGCAGTCCTCAGGTCTCT
ACTCCCTCAGCAGCGTGGTGACCGTGCCATCCAGCAACTTCGGCACCCAG
ACCTACACCTGCAACGTAGATCACAAGCCAAGCAACACCAAGGTCGACAA
GACCGTGGAGAGAAAGTGTTGTGTGGAGTGTCCACCTTGTCCAGCCCCTC
CAGTGGCCGGACCATCCGTGTTCCTGTTCCCTCCAAAGCCAAAGGACACC
CTGATGATCTCCAGAACCCCAGAGGTGACCTGTGTGGTGGTGGACGTGTC
CCACGAGGACCCAGAGGTGCAGTTCAACTGGTATGTGGACGGAGTGGAGG
TGCACAACGCCAAGACCAAGCCAAGAGAGGAGCAGTTCAACTCCACCTTC
AGAGTGGTGAGCGTGCTGACCGTGGTGCACCAGGACTGGCTGAACGGAAA
GGAGTATAAGTGTAAGGTGTCCAACAAGGGACTGCCATCCAGCATCGAGA
AGACCATCTCCAAGACCAAGGGACAGCCAAGAGAGCCACAGGTGTATACC CTGCCACCATCCAGAGGAGGAGATGACCAAGAACCAGGTGTCCCTGACCTG
TCTGGTGAAGGGATTCTATCCATCCGACATCGCCGTGGAGTGGGAGTCCA
ACGGACAGCCAGAGAACAACTATAAGACCACCCCTCCAATGCTGGACTCC
GACGGATCCTTCTTCCTGTATTCCAAGCTGACCGTGGACAAGTCCAGATG
GCAGCAGGGAAACGTGTTCTCTTGTTCCGTGATGCACGAGGCCCTGCACA
ACCACTATACCCAGAAGAGCCTGTCCCTGTCTCCAGGAAAGTAA 3E heavy chain variable domain nucleotide sequence
(SEQ ID NO: 66)
CAGGTGCAGCTGCAGGAGTCTGGCCCAGGACTGGTGAAGCCTTCCGAGAC
CCTGTCCCTCACCTGCACTGTCTCTGGGTTCTCACTTATCGGCTATGATC
TTAACTGGATCCGACAGCCTCCAGGGAAGGGACTGGAGTGGATTGGGATT
ATCTGGGGTGATGGAACCACAGACTATAATTCAGCTGTCAAATCCCGCGT
CACCATCTCAAAAGACACCTCCAAGAACCAGTTCTCCCTGAAGCTGAGCT
CTGTGACCGCCGCGGACACGGCCGTGTATTACTGTGCGAGAGGAGGTTAT
TGGTACGCCACTAGCTACTACTTTGACTACTGGGGCCAGGGCACCCTGGT
CACCGTCTCCTCA 3E light chain nucleotide sequence (full antibody)
(SEQ ID NO: 67)
GATATCCAGATGACACAGTCCCCATCCTCCCTGTCTGCCTCTGTGGGTGA
CCGCGTCACCATCACCTGCCGCGCATCTCAGTCCATTAGCAATAATCTGA
ACTGGTATCAGCAGAAGCCAGGCAAAGCCCCAAAACTCCTGATCTACTAC
ACCTCACGCTTCCACTCAGGTGTCCCATCACGCTTCAGTGGCAGTGGCTC
TGGTACAGATTTCACCTTCACCATTAGCAGCCTGCAACCAGAAGATATTG
CCACTTATTACTGCCAACAGGAGCATACCCTTCCATATACCTTCGGTCAA
GGCACCAAGCTGGAGATCAAACGCACTGTGGCTGCACCATCTGTCTTCAT
CTTTCCTCCATCTGATGAGCAGTTGAAATCCGGAACTGCCTCTGTTGTGT
GCCTGCTGAATAACTTCTATCCACGCGAGGCCAAAGTACAGTGGAAGGTG
GATAACGCCCTCCAATCCGGTAACTCCCAGGAGAGTGTCACAGAGCAGGA
CAGCAAGGACAGCACCTACAGCCTCAGCAGCACCCTGACCCTGAGCAAAG
CAGACTACGAGAAACACMAAGTCTACGCCTGCGAAGTCACCCATCAGGGC
CTGAGTTCTCCAGTCACAAAGAGCTTCAACCGCGGTGAGTGCTAA 3E light chain variable domain nucleotide sequence
(SEQ ID NO: 68)
GATATCCAGATGACACAGTCCCCATCCTCCCTGTCTGCCTCTGTGGGTGA
CCGCGTCACCATCACCTGCCGCGCATCTCAGTCCATTAGCAATAATCTGA
ACTGGTATCAGCAGAAGCCAGGCAAAGCCCCAAAACTCCTGATCTACTAC
ACCTCACGCTTCCACTCAGGTGTCCCATCACGCTTCAGTGGCAGTGGCTC
TGGTACAGATTTCACCTTCACCATTAGCAGCCTGCAACCAGAAGATATTG
CCACTTATTACTGCCAACAGGAGCATACCCTTCCATATACCTTCGGTCAA
GGCACCAAGCTGGAGATCAAACGC It is understood that the examples and embodiments described herein are for illustrative purposes only and that various modifications or changes in light thereof will be suggested to persons skilled in the art and are to be included within the spirit and purview of this application.

The following is claimed:

1. A method for reducing stiffness in an individual having osteoarthritis comprising administering an effective amount of a monoclonal anti-NGF antagonist antibody to the individual, wherein the anti-NGF antagonist antibody blocks the interaction of human NGF with p75 and trkA,
wherein the anti-NGF antagonist antibody: (a) binds NGF with a $K_D$ of less than about 2 nM; (b) inhibits human NGF-dependent survival of mouse E13.5 trigeminal neurons with an IC50 of about 100 pM or less, wherein the IC50 is measured in the presence of about 15 pM human NGF; and (c) inhibits human NGF-dependent survival of mouse E 13.5 trigeminal neurons with an IC50 of about 10 pM or less, wherein the IC50 is measured in the presence of about 1.5 pM of NGF.

2. The method of claim 1, wherein the individual is a human.

3. The method of claim 1, wherein the anti-NGF antagonist antibody is administered at a dosing frequency in a range from once every week to once every twelve weeks.

4. The method of claim 1, wherein the anti-NGF antagonist antibody is administered once every month, once every two months, once every three months, once every four months, once every five months, or once every six months.

5. The method of claim 1, wherein the anti-NGF antagonist antibody is administered once every three months.

6. The method of claim 1, wherein the anti-NGF antagonist antibody is administered at a dose in a range from about 3 μg/kg to about 1 mg/kg.

7. The method of claim 6, wherein the anti-NGF antagonist antibody is administered at a dose of about 100 μg/kg.

8. The method of claim 6, wherein the anti-NGF antagonist antibody is administered at a dose of about 300 μg/kg.

9. The method of claim 1, wherein the anti-NGF antagonist antibody is administered intravenously.

10. The method of claim 1, wherein the anti-NGF antagonist antibody is administered subcutaneously.

11. The method of claim 1, wherein the anti-NGF antagonist antibody is a humanized antibody.

12. The method of claim 1, wherein the anti-NGF antagonist antibody binds human NGF.

13. The method of claim 12, wherein the anti-NGF antagonist antibody further binds rodent NGF.

14. The method of claim 1, wherein the anti-NGF antagonist antibody comprises a heavy chain variable region comprising: (a) a CDR1 region shown in SEQ ID NO: 3; (b) a CDR2 region shown in SEQ ID NO:4; and (c) a CDR3 region shown in SEQ ID NO:5, and a light chain variable region comprising: (a) a CDR1 region shown in SEQ ID NO:6; (b) a CDR2 region shown in SEQ ID NO:7; and (c) a CDR3 region shown in SEQ ID NO:8.

15. The method of claim 14, wherein the anti-NGF antagonist antibody is an antibody comprising the amino acid sequences shown in SEQ ID NOS: 1 and 2.

16. The method of claim 15, wherein the anti-NGF antagonist antibody is an antibody comprising the amino acid sequences shown in SEQ ID NOS: 16 and 17.

17. The method of claim 1, wherein the anti-NGF antagonist antibody competes for binding to human NGF with an antibody comprising the amino acid sequences shown in SEQ ID NOS: 1 and 2.

18. The method of claim 1, wherein the anti-NGF antagonist antibody binds essentially the same epitope as an antibody comprising the amino acid sequences shown in SEQ ID NOS: 1 and 2.

19. The method of claim 1, wherein the anti-NGF antagonist antibody binds to an epitope comprising: residues K32, K34 and E35 within variable region 1 of human NGF (hNGF); residues F79 and T81 within variable region 4 of hNGF; residues H84 and K88 within variable region 4 of hNGF; and/or residue R103 between variable region 5 of hNGF and the C-terminus.

20. A method for reducing stiffness in an individual having osteoarthritis comprising administering an effective amount of a monoclonal anti-NGF antagonist antibody to the individual, wherein the anti-NGF antagonist antibody blocks the interaction of human NGF with p75 and trkA,
wherein the anti-NGF antagonist antibody binds to an epitope comprising: residues K32, K34 and E35 within variable region 1 of human NGF (hNGF); residues F79 and T81 within variable region 4 of hNGF; residues H84 and K88 within variable region 4 of hNGF; and/or residue R103 between variable region 5 of hNGF and the C-terminus.

21. The method of claim 20, wherein the individual is a human.

22. The method of claim 20, wherein the anti-NGF antagonist antibody is administered at a dosing frequency in a range from once every week to once every twelve weeks.

23. The method of claim 20, wherein the anti-NGF antagonist antibody is administered once every month, once every two months, once every three months, once every four months, once every five months, or once every six months.

24. The method of claim 20, wherein the anti-NGF antagonist antibody is administered once every three months.

25. The method of claim 20, wherein the anti-NGF antagonist antibody is administered at a dose in a range from about 3 μg/kg to about 1 mg/kg.

26. The method of claim 25, wherein the anti-NGF antagonist antibody is administered at a dose of about 100 μg/kg.

27. The method of claim 25, wherein the anti-NGF antagonist antibody is administered at a dose of about 300 μg/kg.

28. The method of claim 20, wherein the anti-NGF antagonist antibody is administered intravenously.

29. The method of claim 20, wherein the anti-NGF antagonist antibody is administered subcutaneously.

30. The method of claim 20, wherein the anti-NGF antagonist antibody is a humanized antibody.

31. The method of claim 20, wherein the anti-NGF antagonist antibody binds human NGF.

32. The method of claim 20, wherein the anti-NGF antagonist antibody further binds rodent NGF.

33. The method of claim 20, wherein the anti-NGF antagonist antibody: (a) binds NGF with a $K_D$ of less than about 2 nM; (b) inhibits human NGF-dependent survival of mouse E13.5 trigeminal neurons with an IC50 of about 100 pM or less, wherein the IC50 is measured in the presence of about 15 pM human NGF; and (c) inhibits human NGF-dependent survival of mouse E 13.5 trigeminal neurons with an IC50 of about 10 pM or less, wherein the IC50 is measured in the presence of about 1.5 pM of NGF.

34. The method of claim 20, wherein the anti-NGF antagonist antibody comprises a heavy chain variable region comprising: (a) a CDR1 region shown in SEQ ID NO: 3; (b) a CDR2 region shown in SEQ ID NO:4; and (c) a CDR3 region shown in SEQ ID NO:5, and a light chain variable region comprising: (a) a CDR1 region shown in SEQ ID NO:6; (b) a CDR2 region shown in SEQ ID NO:7; and (c) a CDR3 region shown in SEQ ID NO:8.

35. The method of claim 34, wherein the anti-NGF antagonist antibody is an antibody comprising the amino acid sequences shown in SEQ ID NOS: 1 and 2.

36. The method of claim 35, wherein the anti-NGF antagonist antibody is an antibody comprising the amino acid sequences shown in SEQ ID NOS: 16 and 17.

37. The method of claim 20, wherein the anti-NGF antagonist antibody competes for binding to human NGF with an antibody comprising the amino acid sequences shown in SEQ ID NOS: 1 and 2.

38. The method of claim 20, wherein the anti-NGF antagonist antibody binds essentially the same epitope as an antibody comprising the amino acid sequences shown in SEQ ID NOS: 1 and 2.

* * * * *

UNITED STATES PATENT AND TRADEMARK OFFICE
CERTIFICATE OF CORRECTION

| | | |
|---|---|---|
| PATENT NO. | : 8,540,990 B2 | Page 1 of 1 |
| APPLICATION NO. | : 11/911305 | |
| DATED | : September 24, 2013 | |
| INVENTOR(S) | : Rosenthal et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1272 days.

Signed and Sealed this
Tenth Day of February, 2015

Michelle K. Lee
*Deputy Director of the United States Patent and Trademark Office*